United States Patent
Wang et al.

(10) Patent No.: US 11,447,542 B2
(45) Date of Patent: Sep. 20, 2022

(54) ANTI-O2 ANTIBODIES AND USES THEREOF

(71) Applicants: MEDIMMUNE, LLC, Gaithersburg, MD (US); Humabs BioMed SA, Bellinzona (CH)

(72) Inventors: Qun Wang, Gaithersburg, MD (US); Charles K. Stover, Gaithersburg, MD (US); Meghan Pennini, Gaithersburg, MD (US); Xiaodong Xiao, Gaithersburg, MD (US); Davide Corti, Bellinzona (CH); Elisabetta Cameroni, Bellinzona (CH); Martina Beltramello, Bellinzona (CH); Gilad Kaplan, Gaithersburg, MD (US); Anna DeMarco, Bellinzona (CH)

(73) Assignees: MEDIMMUNE, LLC, Gaithersburg, MD (US); HUMABS BIOMED SA, Bellinzona (CH)

( * ) Notice: Subject to any disclaimer, the term of this patent is extended or adjusted under 35 U.S.C. 154(b) by 550 days.

(21) Appl. No.: 16/323,185

(22) PCT Filed: Aug. 4, 2017

(86) PCT No.: PCT/US2017/045480
§ 371 (c)(1),
(2) Date: Feb. 4, 2019

(87) PCT Pub. No.: WO2018/027124
PCT Pub. Date: Feb. 8, 2018

(65) Prior Publication Data
US 2021/0238263 A1 Aug. 5, 2021

Related U.S. Application Data

(60) Provisional application No. 62/371,402, filed on Aug. 5, 2016.

(51) Int. Cl.
| | |
|---|---|
| *C07K 16/00* | (2006.01) |
| *C12P 21/08* | (2006.01) |
| *A61K 39/395* | (2006.01) |
| *A61K 39/00* | (2006.01) |
| *A61K 39/40* | (2006.01) |
| *A61K 39/108* | (2006.01) |
| *C07K 16/12* | (2006.01) |
| *A61P 31/04* | (2006.01) |
| *A61K 31/407* | (2006.01) |

(52) U.S. Cl.
CPC ........ *C07K 16/1228* (2013.01); *A61K 31/407* (2013.01); *A61K 39/40* (2013.01); *A61P 31/04* (2018.01); *A61K 2039/505* (2013.01); *A61K 2039/545* (2013.01); *C07K 2317/565* (2013.01); *C07K 2317/73* (2013.01); *C07K 2317/76* (2013.01); *C07K 2317/92* (2013.01)

(58) Field of Classification Search
CPC .................................................... C07K 14/26
See application file for complete search history.

(56) References Cited

U.S. PATENT DOCUMENTS

| | | |
|---|---|---|
| 4,474,893 A | 10/1984 | Readinq |
| 4,714,681 A | 12/1987 | Readinq |
| 4,816,567 A | 3/1989 | Cabilly et al. |
| 4,925,648 A | 5/1990 | Hansen et al. |
| 4,946,778 A | 8/1990 | Ladner et al. |
| 5,179,018 A | 1/1993 | Bogard et al. |
| 5,545,806 A | 8/1996 | Lonberg et al. |
| 5,545,807 A | 8/1996 | Surani et al. |
| 5,569,825 A | 10/1996 | Lonberg et al. |
| 5,573,920 A | 11/1996 | Randle |
| 5,601,819 A | 2/1997 | Wonq et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,661,016 A | 8/1997 | Lonberg et al. |
| 5,677,425 A | 10/1997 | Bodmer et al. |
| 5,731,168 A | 3/1998 | Carter et al. |
| 5,750,373 A | 5/1998 | Garrard et al. |

(Continued)

FOREIGN PATENT DOCUMENTS

| | | |
|---|---|---|
| EP | 184187 A2 | 6/1986 |
| EP | 239400 A2 | 9/1987 |

(Continued)

OTHER PUBLICATIONS

Paul, Fundamental Immunology, 3rd Edition, 1993, pp. 292-295 (Year: 1993).*
International Search Report and Written Opinion dated Dec. 14, 2017 for International Application No. PCT/US2017/045480, ISA, United States, 18 pages.
Sahly, H., et al., "Serum antibodies to klebsiella capsular polysaccharides in ankylosing spondylitis," Arthritis & Rheumatology 37(5): 754-759, American College of Rheumatology, United States (1994).

(Continued)

*Primary Examiner* — Gary B Nickol
*Assistant Examiner* — Lakia J Jackson-Tongue
(74) *Attorney, Agent, or Firm* — Sterne, Kessler, Goldstein and Fox P.L.L.C.

(57) ABSTRACT

The present disclosure provides binding proteins (e.g., antibodies or antigen binding fragments thereof) that specifically bind to *Klebsiella pneumoniae* O2 and induce opsonophagocytic killing of *Klebsiella* (e.g., *Klebsiella pneumoniae*) and/or protects mice from a lethal *Klebsiella* challenge. The present disclosure also provides methods of reducing *Klebsiella* (e.g., *Klebsiella pneumoniae*) or treating or preventing *Klebsiella* (e.g., *Klebsiella pneumoniae*) infection in a subject comprising administering the *Klebsiella pneumoniae* O2 binding proteins, (e.g., antibodies or antigen-binding fragments thereof) to the subject.

21 Claims, 15 Drawing Sheets
Specification includes a Sequence Listing.

(56) References Cited

U.S. PATENT DOCUMENTS

| | | | |
|---|---|---|---|
| 5,807,706 | A | 9/1998 | Carter et al. |
| 5,821,333 | A | 10/1998 | Carter et al. |
| 5,869,046 | A | 2/1999 | Presta et al. |
| 5,885,573 | A | 3/1999 | Bluestone et al. |
| 5,885,793 | A | 3/1999 | Griffiths et al. |
| 5,969,108 | A | 10/1999 | McCafferty et al. |
| 6,121,022 | A | 9/2000 | Presta et al. |
| 6,165,745 | A | 12/2000 | Ward et al. |
| 6,172,197 | B1 | 1/2001 | McCafferty et al. |
| 6,180,377 | B1 | 1/2001 | Morgan et al. |
| 6,194,551 | B1 | 2/2001 | Idusogie et al. |
| 6,277,375 | B1 | 8/2001 | Ward |
| 6,300,064 | B1 | 10/2001 | Knappik et al. |
| 6,521,404 | B1 | 2/2003 | Griffiths et al. |
| 6,528,624 | B1 | 3/2003 | Idusogie et al. |
| 6,544,731 | B1 | 4/2003 | Griffiths et al. |
| 6,555,313 | B1 | 4/2003 | Griffiths et al. |
| 6,582,915 | B1 | 6/2003 | Griffiths et al. |
| 6,593,081 | B1 | 7/2003 | Griffiths et al. |
| 6,653,068 | B2 | 11/2003 | Frisch et al. |
| 6,706,484 | B1 | 3/2004 | Knappik et al. |
| 6,737,056 | B1 | 5/2004 | Presta |
| 6,821,505 | B2 | 11/2004 | Ward |
| 7,083,784 | B2 | 8/2006 | Dall'Acqua et al. |
| 7,122,637 | B2 | 10/2006 | Presta |
| 7,183,387 | B1 | 2/2007 | Presta |
| 7,264,963 | B1 | 9/2007 | Knappik et al. |
| 7,317,091 | B2 | 1/2008 | Lazar et al. |
| 7,332,581 | B2 | 2/2008 | Presta |
| 7,335,742 | B2 | 2/2008 | Presta |
| 7,355,008 | B2 | 4/2008 | Stavenhagen et al. |
| 7,371,826 | B2 | 5/2008 | Presta |
| 7,658,921 | B2 | 2/2010 | Dall'Acqua et al. |
| 2002/0155537 | A1 | 10/2002 | Carter et al. |
| 2003/0020734 | A1 | 1/2003 | Yin et al. |
| 2004/0002587 | A1 | 1/2004 | Watkins et al. |
| 2004/0132101 | A1 | 7/2004 | Lazar et al. |
| 2005/0074821 | A1 | 4/2005 | Wild, Jr. et al. |
| 2007/0065444 | A1 | 3/2007 | North et al. |
| 2010/0330078 | A1 | 12/2010 | Bender et al. |
| 2013/0243792 | A1 | 9/2013 | Vogels et al. |
| 2015/0252025 | A1 | 9/2015 | Poyurovsky et al. |
| 2017/0073397 | A1 | 3/2017 | Wang et al. |

FOREIGN PATENT DOCUMENTS

| | | |
|---|---|---|
| GB | 2188638 A | 10/1987 |
| WO | WO-9100360 A1 | 1/1991 |
| WO | WO-92/01047 A1 | 1/1992 |
| WO | WO-9205793 A1 | 4/1992 |
| WO | WO-9208802 A1 | 5/1992 |
| WO | WO-9311161 A1 | 6/1993 |
| WO | WO-9317715 A1 | 9/1993 |
| WO | WO-9413804 A1 | 6/1994 |
| WO | WO-99/058572 A1 | 11/1999 |
| WO | WO-0044788 A1 | 8/2000 |
| WO | WO-0296948 A2 | 12/2002 |
| WO | WO-2011/069164 A2 | 6/2011 |
| WO | WO-2012/006635 A1 | 1/2012 |
| WO | WO-2015/175874 A2 | 11/2015 |
| WO | WO-2016131503 A1 | 8/2016 |
| WO | WO 2017/064258 A1 | 4/2017 |
| WO | WO-2018027124 A1 | 2/2018 |
| WO | WO-2018075375 A1 | 4/2018 |

OTHER PUBLICATIONS

Sahly, H., et al., "Surfactant Protein D Binds selectively to Klebsiella pneumonia Lipopolysaccharides Containing Mannose-Rich O-Antigens," Journal of Immunology 169(6):3267-3274, American Association of Immunologists, United States (2002).

Whitefield, C., et al., "Structural analysis of the O-antigen side chain polysaccharides in the lipopolysaccharides of Klebsiella serotypes O2(2a), O2(2a,2b), and O2(2a,2c)," Journal of Bacteriology, 174(15):4913-4919, American Society for Microbiology, United States (1992).

Hsieh, P-F., et al., "Lipopolysaccharide O1 Antigen Contributes to the Virulence in *Klebsiella pneumoniae* Causing Pyogenic Live Abscess," PLOS One, 7(3):e33155, 13 pages, Public Library of Science, United States (2012).

Hsieh, P-F., et al., "D-galactan II is an immunodominant antigen in O1 lipopolysaccharide and affects virulence in Klebsiella pneumonia: implication in vaccine design," Frontiers in Microbiology, 5(608), 14 pages, Frontiers Media, Switzerland (2014).

Andersen et al., Recombinant protein expression for therapeutic applications, Curr. Opin. Biotechnol., 13(2):117-23 (Apr. 2002).

Barbas et al., In vitro evolution of a neutralizing human antibody to human immunodeficiency virus type 1 to enhance affinity and broaden strain cross-reactivity, Proc. Natl. Acad. Sci. USA, 91(9):3809-13 (Apr. 1994).

Beltramello et al., The human immune response to Dengue virus is dominated by highly cross-reactive antibodies endowed with neutralizing and enhancing activity, Cell Host Microbe, 8(3):271-83 (Sep. 2010).

Bird et al., Single-chain antigen-binding proteins, Science, 242(4877):423-6 (Oct. 1988).

Boerner et al., Production of antigen-specific human monoclonal antibodies from in vitro-primed human splenocytes, J. Immunol., 147(1):86-95 (Jul. 1991).

Brade et al., A monoclonal antibody with specificity for the genus *Klebsiella* binds to a common epitope located in the core region of Klebsiella lipopolysaccharide, J. Endotoxin Res., 7(2):119-24 (2001).

Chadd et al., Therapeutic antibody expression technology, Curr. Opin. Biotechnol., 12(2):188-94 (Apr. 2001).

Cheung et al., Epitope-specific antibody response to the surface antigen of duck hepatitis B virus in infected ducks, Virology, 176(2):546-52 (Jun. 1990).

Chothia et al., Canonical structures for the hypervariable regions of immunoglobulins, J. Mol. Biol., 196(4):901-17 (Aug. 1987).

Clackson et al., Making antibody fragments using phage display libraries, Nature, 352(6336):624-8 (Aug. 1991).

Clarke et al., Molecular cloning of the rfb region of Klebsiella pneumoniae serotype O1:K20: the rfb gene cluster is responsible for synthesis of the D-galactan I O polysaccharide, J. Bacteriol., 174(14):4614-21 (Jul. 1992).

Dall'Acqua et al., Properties of human IgG1s engineered for enhanced binding to the neonatal Fc receptor (FcRn), J. Biol. Chem., 281 (33):23514-24 (Aug. 2006).

Gram et al., In vitro selection and affinity maturation of antibodies from a naive combinatorial immunoglobulin library, Proc. Natl. Acad. Sci. USA, 89(8):3576-80 (Apr. 1992).

Hoogenboom et al., By-passing Immunisation: Human antibodies from synthetic repertoires of germline $V_H$gene segments rearranged in vitro, J. Mol. Biol., 227:381-8 (1992).

Hu et al., Minibody: A novel engineered anti-carcinoembryonic antigen antibody fragment (singlechain Fv-CH3) which exhibits rapid, high-level targeting of xenografts, Cancer Res., 56(13):3055-61 (Jul. 1996).

Huse et al., Generation of a large combinatorial library of the immunoglobulin repertoire in phage lambda, Science, 246(4935):1275-81 (Dec. 1989).

Huston et al., Protein engineering of antibody binding sites: recovery of specific activity in an antidigoxin single-chain Fv analogue produced in *Escherichia coli*, Proc. Natl. Acad. Sci. USA, 85(16):5879-83 (1988).

International Application No. PCT/US2017/045480, International Preliminary Report on Patentability, dated Feb. 5, 2019.

International Application No. PCT/US2017/045480, International Search Report and Written Opinion, dated Dec. 14, 2017.

Iredell et al., Antibiotic resistance in Enterobacteriaceae: mechanisms and clinical implications, BMJ, 352:h6420 (Feb. 2016).

Kirkland et al., Analysis of the fine specificity and cross-reactivity of monoclonal anti-lipid A antibodies, J. Immunol., 137(11):3614-9 (Dec. 1986).

(56) References Cited

OTHER PUBLICATIONS

Knappik et al., Fully synthetic human combinatorial antibody libraries (HuCAL) based on modular consensus frameworks and CDRs randomized with trinucleotides, J. Mol. Biol., 296(1):57-86 (Feb. 2000).
Köhler et al., Continuous cultures of fused cells secreting antibody of predefined specificity, Nature, 256(5517):495-7 (Aug. 1975).
Larrick et al., Producing proteins in transgenic plants and animals, Curr. Opin. Biotechnol., 12(4):411-8 (Aug. 2001).
Ledermann et al., A phase-I study of repeated therapy with radiolabelled antibody to carcinoembryonic antigen using intermittent or continuous administration of cyclosporin A to suppress the immune response, Int. J. Cancer, 47(5):659-64 (Mar. 1991).
Lefranc et al., IMGT unique numbering for immunoglobulin and T cell receptor variable domains and Ig superfamily V-like domains, Dev. Comp. Immunol., 27(1):55-77 (Jan. 2003).
Marks et al., By-passing immunization. Human antibodies from V-gene libraries displayed on phage, J. Mol. Biol., 222(3):581-97 (Dec. 1991).
Marks et al., By-passing immunization: building high affinity human antibodies by chain shuffling, Biotechnology (NY), 10(7):779-83 (Jul. 1992).
McCafferty et al., Phage antibodies: filamentous phage displaying antibody variable domains, Nature, 348(6301):552-4 (Dec. 1990).
Moldenhauer et al., Identity of HML-1 antigen on intestinal intraepithelial T cells and of B-ly7 antigen on hairy cell leukaemia, Scand. J. Immunol., 32(2):77-82 (Aug. 1990).
Morel et al., Monoclonal antibodies to bovine serum albumin: affinity and specificity determinations, Mol. Immunol., 25(1):7-15 (Jan. 1988).
Pinna et al., Clonal dissection of the human memory B-cell repertoire following infection and vaccination, Eur. J. Immunol., 39(5):1260-70 (May 2009).
Reiter et al., Engineering antibody Fv fragments for cancer detection and therapy: disulfide-stabilized Fv fragments, Nat. Biotechnol., 14(10):1239-45 (Oct. 1996).
Rothe et al., The human combinatorial antibody library HuCAL GOLD combines diversification of all six CDRs according to the natural immune system with a novel display method for efficient selection of high-affinity antibodies, J. Mol. Biol., 376(4):1182-200 (Feb. 2008).
Sahly et al., Serum antibodies to Klebsiella capsular polysaccharides in ankylosing spondylitis, Arthritis Rheum., 37(5):754-9 (May 1994).
Sahly et al., Surfactant protein D binds selectively to Klebsiella pneumoniae lipopolysaccharides containing mannose-rich O-antigens, J. Immunol., 169(6):3267-74 (Sep. 2002).
Schier et al., Isolation of picomolar affinity anti-c-erbB-2 single-chain Fv by molecular evolution of the complementarity determining regions in the center of the antibody binding site, J. Mol. Biol., 263(4):551-67 (Nov. 1996).
Sheets et al., Efficient construction of a large nonimmune phage antibody library: the production of high-affinity human single-chain antibodies to protein antigens, Proc. Natl. Acad. Sci. USA, 95(11):6157-62 (May 1998).
Stahli et al., Distinction of epitopes by monoclonal antibodies, Methods Enzymol., 92:242-53 (1983).
Stemmer, Rapid evolution of a protein in vitro by DNA shuffling, Nature, 370(6488):389-91 (Aug. 1994).
Szijártó et al., Both clades of the epidemic KPC-producing Klebsiella pneumoniae clone ST258 share a modified galactan O-antigen type, Int. J. Med. Microbiol., 306(2):89-98 (Feb. 2016).
Traggiai et al., An efficient method to make human monoclonal antibodies from memory B cells: potent neutralization of SARS coronavirus, Nat. Med., 10(8):871-5 (Aug. 2004).
Trautmann et al., O antigen seroepidemiology of Klebsiella clinical isolates and implications for immunoprophylaxis of Klebsiella infections, Vaccine, 22(7):818-21 (Feb. 2004).

Vaughn et al., Human antibodies with sub-nanomolar affinities isolated from a large non-immunized phage display library, Nat. Biotechnol., 14(3):309-14 (Mar. 1996).
Wang et al., Target-Agnostic Identification of Functional Monoclonal Antibodies Against Klebsiella pneumoniae Multimeric MrkA Fimbrial Subunit, J. Infect. Dis., 213(11):1800-8 (Jun. 2016).
Ward et al., Binding activities of a repertoire of single immunoglobulin variable domains secreted from *Escherichia coli*, Nature, 341(6242):544-6 (Oct. 1989).
Whitfield et al., Expression of two structurally distinct D-galactan O antigens in the lipopolysaccharide of Klebsiella pneumoniae serotype O1, J. Bacteriol., 173(4):1420-31 (Feb. 1991).
Whitfield et al., Structural analysis of the O-antigen side chain polysaccharides in the lipopolysaccharides of Klebsiella serotypes O2(2a), O2(2a,2b), and O2(2a,2c), J. Bacteriol., 174(15):4913-9 (Aug. 1992).
Co-Pending U.S. Appl. No. 16/342,688, Int'l filing date Oct. 16, 2017, inventor Wang; Q et al. (Unpublished).
International Search Report and Written Opinion dated Apr. 3, 2018 for International Application No. PCT/US2017/056725, ISA, United States, 14 pages.
Ahmadi, K., et al., "Antibodies to Klebsiella pneumoniae lipopolysaccharide in patients with ankylosing spondylitis." British journal of rheumatology 37(12): 1330-1333, British Society for Rheumatology, United Kingdom (1998).
Goel, M., et al., "Plasticity within the antigen-combining site may manifest as molecular mimicry in the humoral immune response." The Journal of Immunology 173(12): 7358-7367, American Association of Immunologists, United States (2004).
Lloyd, C., et al., "Modelling the human immune response: performance of a 1011 human antibody repertoire against a broad panel of therapeutically relevant antigens." Protein Engineering, Design & Selection 22(3): 159-168, Oxford University Press, United Kingdom (2009).
Sela-Culang, I., et al., "The structural basis of antibody-antigen recognition." Frontiers in Immunology 4:302, 13 pages, Frontiers Publishing, Switzerland (2013).
Bagshawe, K.D., et al., "Antibodyenzyme conjugates can generate cytotoxic drugs from inactive precursors at tumor sites.Antibody," Immunoconjugates and Radiopharmaceuticals 4: 915-22, Mary Ann Liebert Publishers, United Sates (1991).
Holliger, P., et al., "Diabodies": small bivalent and bispecific antibody fragments, Proc. Natl. Acad. Sci. USA, 90(14):6444-8, National Academy of Sciences, United States (Jul. 1993).
Holliger, P., et al., "Engineering bispecific antibodies," Curr. Opin. Biotechnol., 4(4):446-9, Current Biology Ltd., United States (Aug. 1993).
Lowe, D., et al., "Combinatorial protein biochemistry for therapeutics and proteomics," Curr. Pharm. D Biotechnol., 5(1): 17-27, Bentham Science Publishers Ltd., United Kingdom (2004).
Oganesyan, V., et al., "Structural characterization of a human Fc fragment engineered for lack of D effector functions," Acta Crystalloqr. D Biol. Crystalloqr., 64(Pt. 6):700-4, Elsevier, Netherlands (Jun. 2008).
Pluckthun, A., "Antibody engineering: advances from the use of *Escherichia coli* expression systems," Biotechnoloqy(NY):9(6):545-51 (Jun. 1991).
Podschun, R., et al., "*Klebsiella* spp. as nosocomial pathogens: epidemiology, taxonomy, typing methods, and pathogenicity factors," Clin. Microbial. Rev., 11 (4):589-603, American Society for Microbiology, United States (Oct. 1998).
Ridgway, J.B.B., et al., "'Knobs-into-holes' engineering of antibody CH3 domains for heavy chain heterodimerization," Protein Enq., 9(7):617-21, Oxford University Press, United Kingdom (Jul. 1996).
Tutt, A., et al., "Trispecific F(ab')3 derivatives that use cooperative signaling via the TCR/CD3 complex and CO2 to activate and redirect restinq cytotoxic T cells," J. Immunol., 147(1):60-9, American Association of Immunologists, United States (Jul. 1991).
Kostelny, S.A., et al., "Formation of a bispecific antibody by the use of leucine zippers," J Immunol 148(5):1547-53, American Association of Immunologists, United States (Mar. 1992).

(56) References Cited

OTHER PUBLICATIONS

Krebs, B., et al., "High-throughput generation and engineering of recombinant human antibodies," J Immunol Methods 254(1-2):67-84, Elsevier, Netherlands (Aug. 2001).

Trautmann, M., et al., "Evaluation of a competitive ELISA method for the determination of Klebsiella O antigens," J Med Microbiol 44(1):44-51, The Pathological Society of Great Britain and Ireland, United Kingdom (Jan. 1996).

Held, T.K., et al., "Binding to and Opsonophagocytic Activity of O-Antigen-Specific Monoclonal Antibodies against Encapsulated and Nonencapsulated *Klebsiella pneumoniae* Serotype O1 Strains," 68(5):2402-2409, American Society for Microbiology, United States (2000).

Rukavina, T., et al., "Protective effect of antilipopolysaccharide monoclonal antibody in experimental *Klebsiella* infection," Infect Immunology 65(5):1754-1760, American Society for Microbiology, United States (1997).

Van, N.M., et al., "Binding Studies of a Monoclonal Antibody Specific for 3-Deoxy-D-manno-Octulosonic Acid with a Panel of *Klebsiella pneumoniae* Lipopolysaccharides Representing All of the O Serotypes," Infection and Immunity 62(3):1052-1057, American Society for Microbiology, United States (1994).

Trautmann, M., et al., "O-antigen seroepidemiology of *Klebsiella* clinical isolates and implications for immunoprophylaxis of *Klebsiella* infections," *Clinical and Diagnostic Laboratory Immunology* 4(5):550-555, American Society for Microbiology, United States (Sep. 1997).

\* cited by examiner

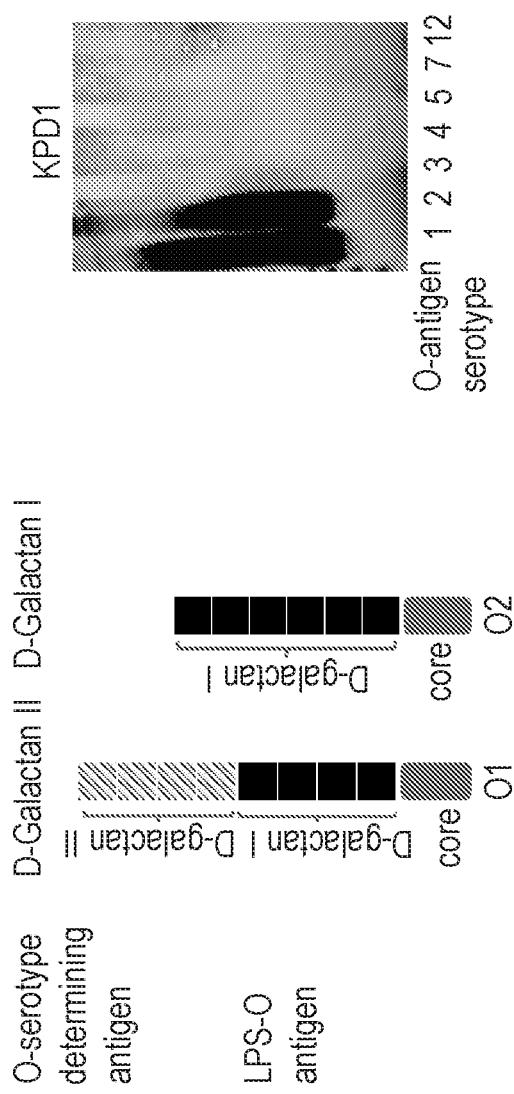

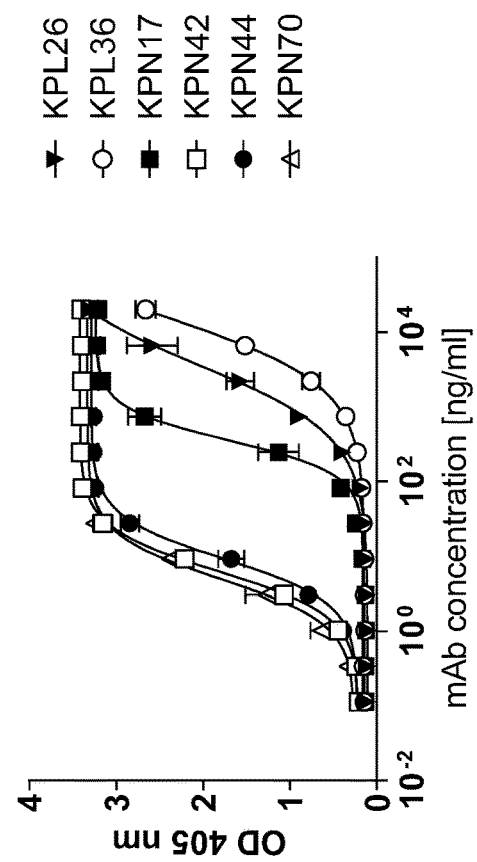
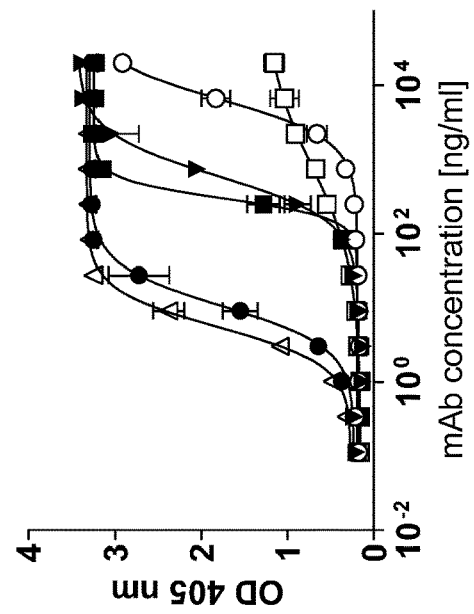

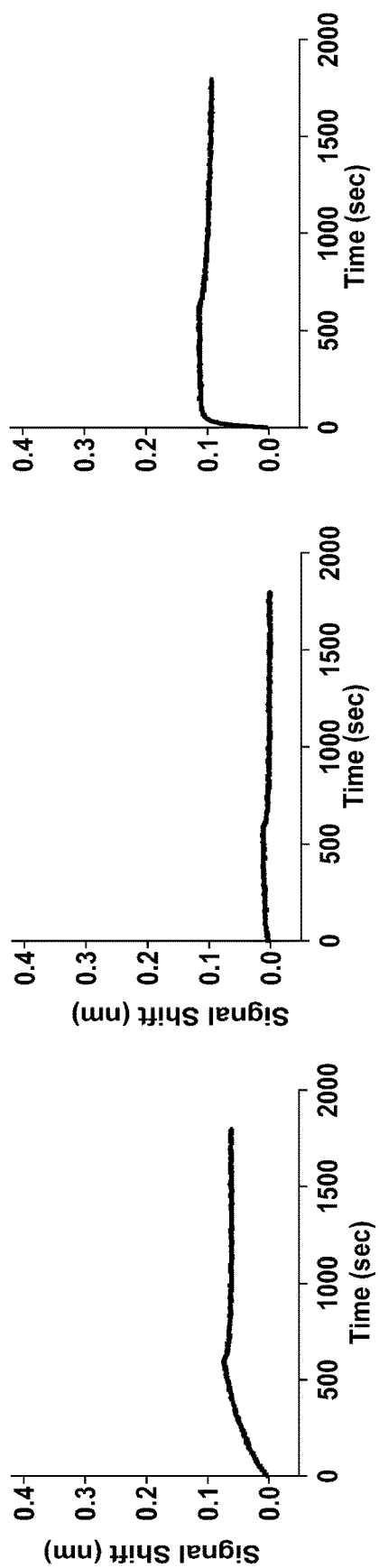
FIG. 3A KPN17-rIgG1
FIG. 3B KPN42-rIgG1
FIG. 3C KPN44-rIgG1
FIG. 3D KPN70-rIgG1
FIG. 3E KPL26 (IgG2)
FIG. 3F KPL36 (IgG2)

KPN17-rIgG1

KPN42-rIgG1

KPN44-rIgG1

KPN70-rIgG1

KPL26 (IgG2)

KPL36 (IgG2)

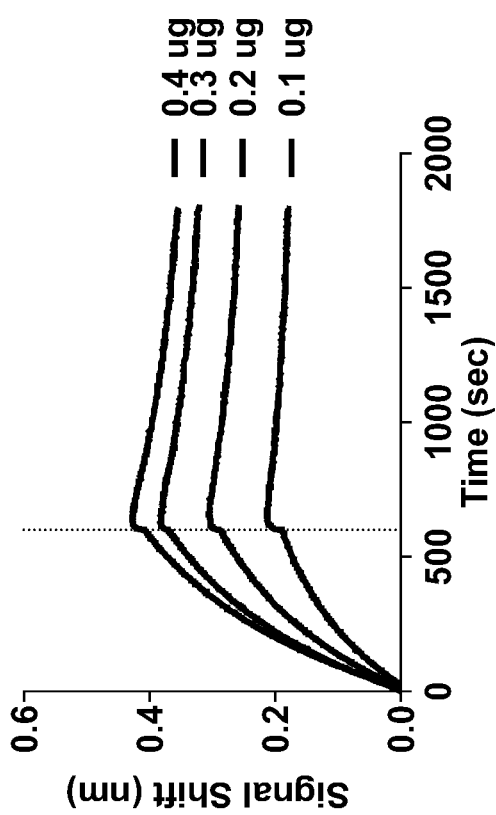
FIG. 3N
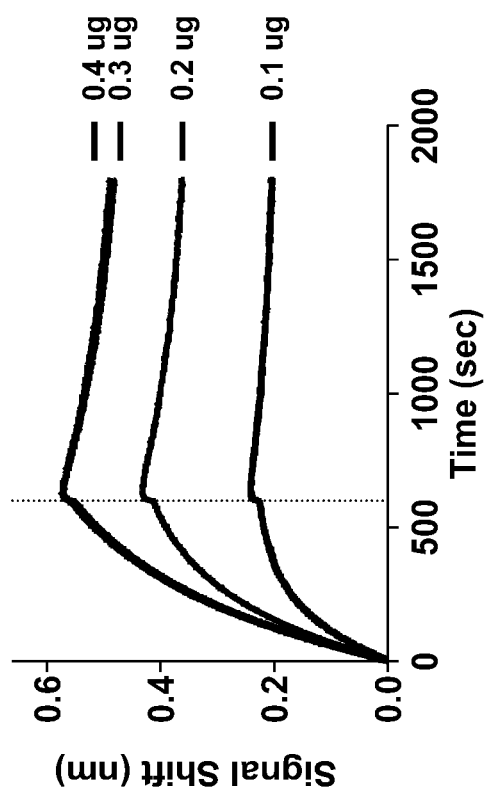
FIG. 3M
| | 0.1 ug | 0.2 ug | 0.3 ug | 0.4 ug |
|---|---|---|---|---|
| KPN42-rIgG1 | 3.23e-009 | 4.68e-009 | 5.17e-009 | 6.03e-009 |
| KPN179-rIgG1 | 8.93e-009 | 7.79e-009 | 6.95e-009 | 8.25e-009 |
FIG. 3O

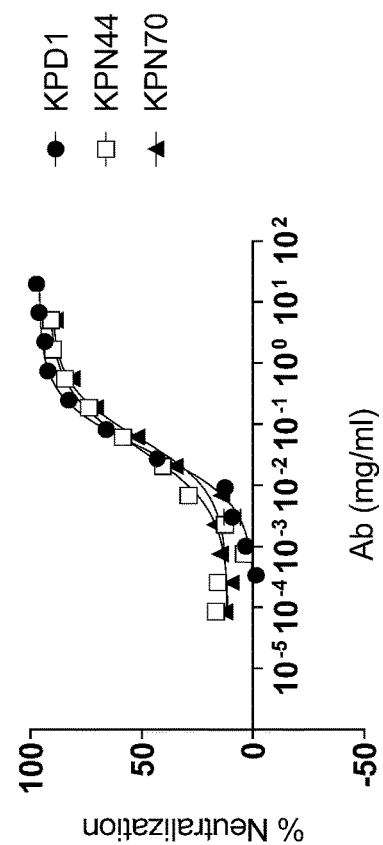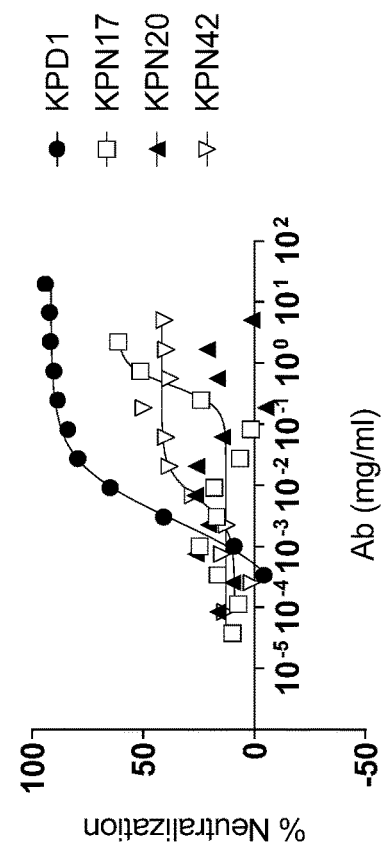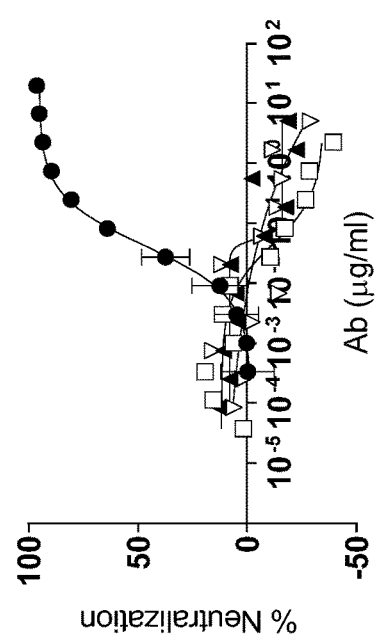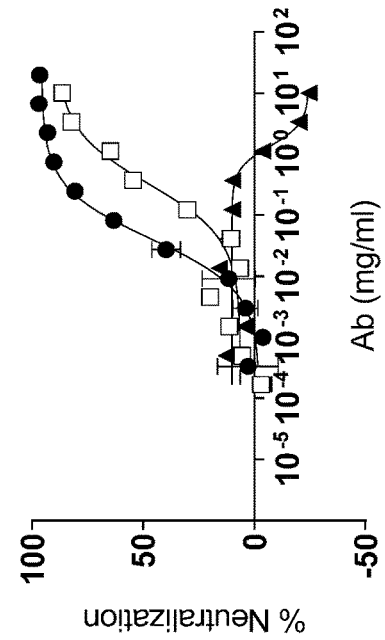

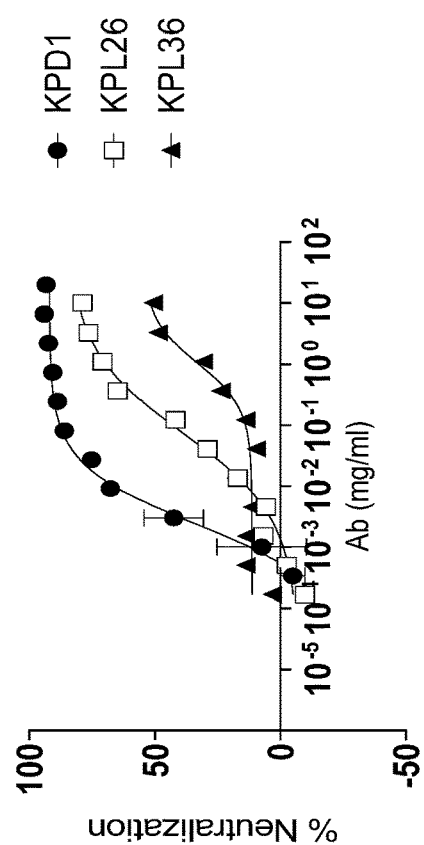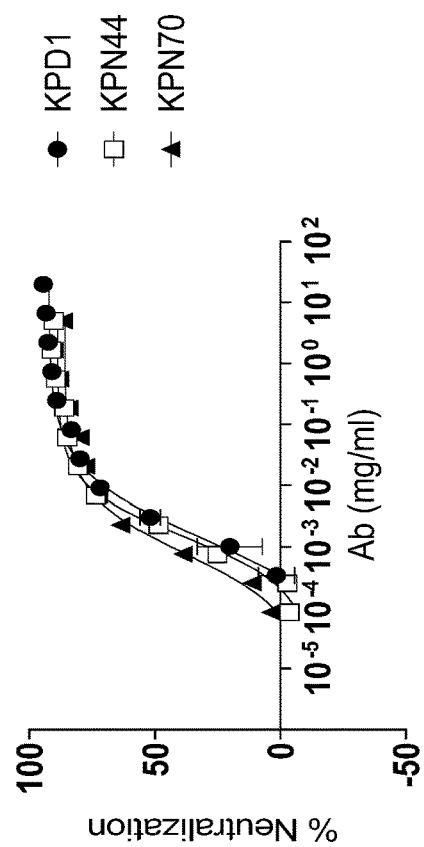

O2_961842 Pneumonia

Challenge = 2e8 CFU/mouse IN at T0
Antibody = 2mpk IV at T+1

Log Rank (Mantel-Cox Test):
p = 0.0001

O2_977778 Pneumonia

Challenge = 3e8 CFU/mouse IN at T0
Antibody = 2mpk IV at T+1

Log Rank (Mantel-Cox Test):
****O2_KPN179 IgG1 and O2_KPN42 p > 0.0001
***O2_KPN179 IgG3 p = 0.0003
α-O2 pIgG p = 0.0004

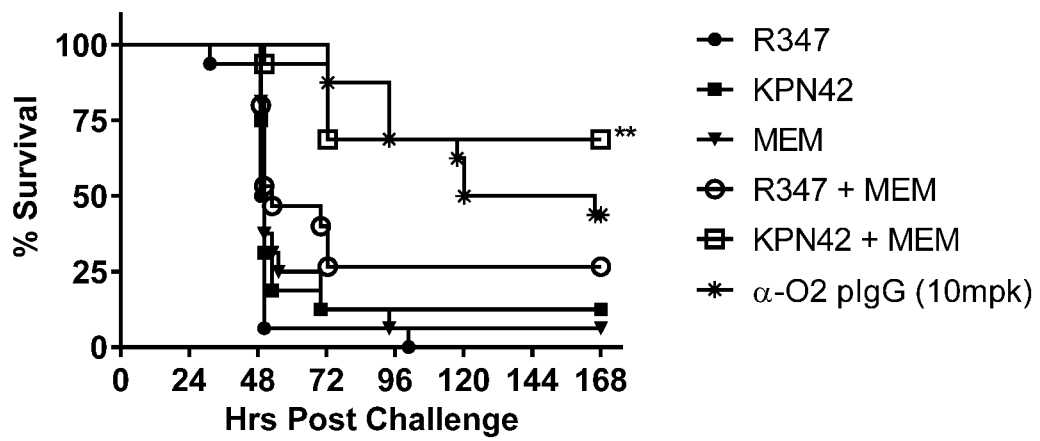
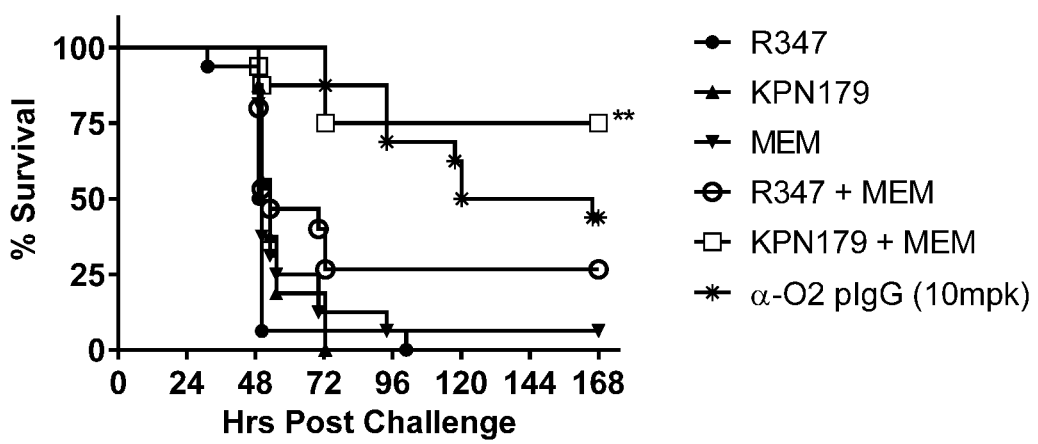

FIG. 9A

KPN42

VH
EVQLVESGGGLVKPGGSLRLSCAASGFTFNDAWMNWVRQAPGKGLEWVARIKKK
HEGVTTDYPASVRGRFTISRDDSKNTVYLQMGRLRIEDTAIYYCTTRIVTTNDYWG
QGTLVTVSS (SEQ ID NO:8)

VL
QSALTQPPSVSGSPGQSVTISCTGTSSDVGAYDYVSWYQQYAGKVPKHIIYDVNER
PSGVPDRFSGSKSGNTAALTISGLQAEDEADYYCCSYAGGDIFVFGTGTQVTVL
(SEQ ID NO:9)

FIG. 9B

KPN179

VH
EVQVVESGGGLVKPGGSLRLSCAASGFTFNNAWMNWVRQAPGKGLEWVGRIKRK
ADGETTDYPASVKGRFTVSRDDSKNTIYLQMNSLKTEDTAIYYCTTRIVTTNDYWG
QGTLVTVSS (SEQ ID NO:53)

VL
QSALTQPPSVSGSPGQSVTISCTGTSSDVGYYDYVSWYQQHHPGKAPKHMIYDVN
KRPSGVPDRFSGSKSGNTASLTISGLQAEDEADYYCCSYAGGDTFVFGTGTKVTVL
(SEQ ID NO:54)

FIG. 9C

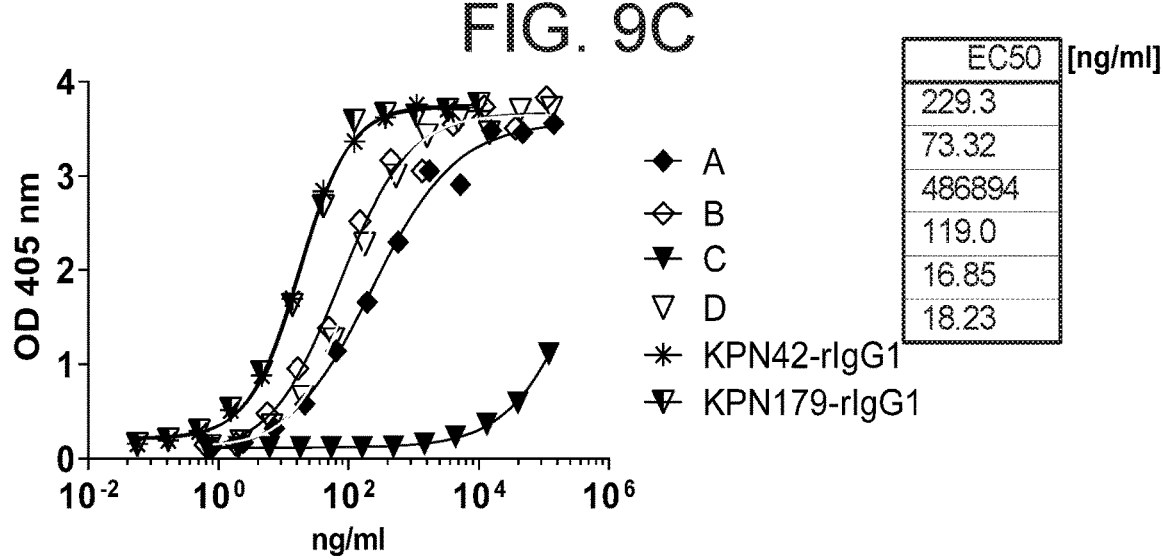

A: KPN42-FR-GL-VH/KPN42-FR-GL-C105A-VL
B: KPN42-FR-1-2-4-GL-VH/KPN42-FR-GL-C105A-VL
C: KPN179-FR-GL-N35S-VH/KPN179-FR-GL-C105A-VL
D: KPN179-FR1-2-4-GL-N35S-VH/KPN179-FR-GL-C105A-VL

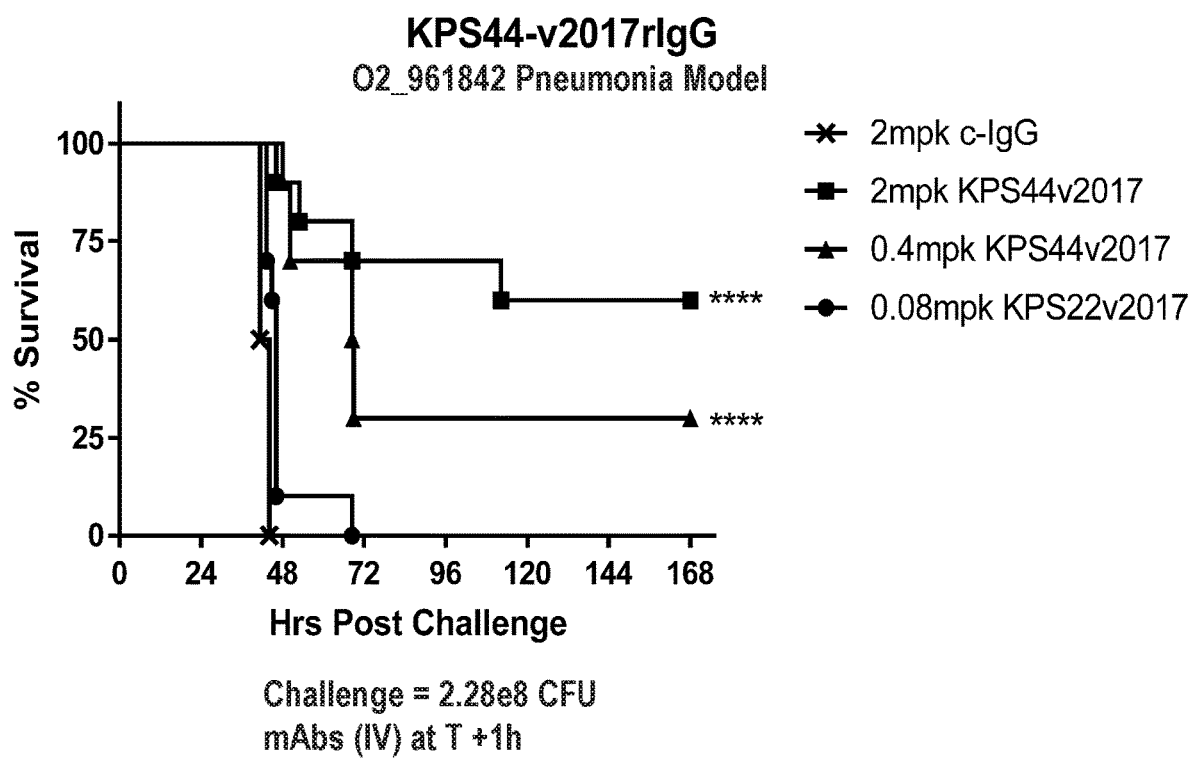

O2 mAbs in Therapy
O2_961842 Pneumonia Model

Challenge = 2.3e8 CFU
mAbs (IV) at T+1h

| Clone name | KD (nM) |
|---|---|
| KPS44 | 2.86 |
| KPS44-v2017 | 3.82 |
| KPS44-G1 | 5.91 |
| KPS44-G2 | 6.51 |
| KPS44-G3 | 2.93; 7.49 |
| KPS44-G4 | 11.20 |
| KPS44-G6 | 5.02 |
| KPS44-G8 | 4.06 |
| KPS44-G10 | 8.06 |
| KPS44-G11 | 1.60 |
| KPS44-G14 | 7.84 |

SEQUENCE LISTING

<160> NUMBER OF SEQ ID NOS: 274

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      KPN42 VH-CDR1 peptide

<400> SEQUENCE: 1

Gly Phe Thr Phe Asn Asp Ala Trp
1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN42 VH-CDR2 peptide

<400> SEQUENCE: 2

Ile Lys Lys Lys His Glu Gly Val Thr Thr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN42 VH-CDR3 peptide

<400> SEQUENCE: 3

Thr Thr Arg Ile Val Thr Thr Asn Asp Tyr
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN42 VL-CDR1 peptide

<400> SEQUENCE: 4

Ser Ser Asp Val Gly Ala Tyr Asp Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      KPN42 VL-CDR2 peptide

<400> SEQUENCE: 5

Asp Val Asn
1

<210> SEQ ID NO 6
<211> LENGTH: 9
<212> TYPE: PRT
<213> ORGANISM: Artificial Sequence
<220> FEATURE:

```
<223> OTHER INFORMATION: Description of Artificial Sequence: Synthetic
      KPN42 VL-CDR2 peptide

<400> SEQUENCE: 6

Ile Ile Tyr Asp Val Asn Glu Arg Pro
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN42 VL-CDR3 peptide

<400> SEQUENCE: 7

Cys Ser Tyr Ala Gly Gly Asp Ile Phe Val
1               5                   10

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      KPN42 VH polypeptide

<400> SEQUENCE: 8

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Asp Ala
            20                  25                  30

Trp Met Asn Trp Val Arg Gln Ala Pro Gly Lys Gly Leu Glu Trp Val
        35                  40                  45

Ala Arg Ile Lys Lys Lys His Glu Gly Val Thr Thr Asp Tyr Pro Ala
    50                  55                  60

Ser Val Arg Gly Arg Phe Thr Ile Ser Arg Asp Asp Ser Lys Asn Thr
65                  70                  75                  80

Val Tyr Leu Gln Met Gly Arg Leu Arg Ile Glu Asp Thr Ala Ile Tyr
                85                  90                  95

Tyr Cys Thr Thr Arg Ile Val Thr Thr Asn Asp Tyr Trp Gly Gln Gly
            100                 105                 110

Thr Leu Val Thr Val Ser Ser
        115

<210> SEQ ID NO 9
<211> LENGTH: 110
<212> TYPE: PRT
<213> ORGANISM: Artificial Sequence
<220> FEATURE:
<223> OTHER INFORMATION: Description of Artificial Sequence: Synthetic
      KPN42 VL polypeptide

<400> SEQUENCE: 9

Gln Ser Ala Leu Thr Gln Pro Pro Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asp Tyr Val Ser Trp Tyr Gln Gln Tyr Ala Gly Lys Val Pro Lys His
        35                  40                  45

Ile Ile Tyr Asp Val Asn Glu Arg Pro Ser Gly Val Pro Asp Arg Phe
    50                  55                  60
```

```
Ser Gly Ser Lys Ser Gly Asn Thr Ala Ala Leu Thr Ile Ser Gly Leu
65                  70                  75                  80

Gln Ala Glu Asp Glu Ala Asp Tyr Tyr Cys Cys Ser Tyr Ala Gly Gly
                85                  90                  95

Asp Ile Phe Val Phe Gly Thr Gly Thr Gln Val Thr Val Leu
            100                 105                 110

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      KPN42--FR-1-2-4-GL-VH/KPN42-FR-GL-C105A-VL (KPN42-v2016)
      VH-CDR1 peptide

<400> SEQUENCE: 10

Gly Phe Thr Phe Asn Asp Ala Trp
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN42--FR-1-2-4-GL-VH/KPN42-FR-GL-C105A-VL
      (KPN42-v2016) VH-CDR2 peptide

<400> SEQUENCE: 11

Ile Lys Lys Lys His Glu Gly Val Thr Thr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN42--FR-1-2-4-GL-VH/KPN42-FR-GL-C105A-VL
      (KPN42-v2016) VH-CDR3 peptide

<400> SEQUENCE: 12

Thr Thr Arg Ile Val Thr Thr Asn Asp Tyr
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN42--FR-1-2-4-GL-VH/KPN42-FR-GL-C105A-VL
      (KPN42-v2016) VL-CDR1 peptide

<400> SEQUENCE: 13

Ser Ser Asp Val Gly Ala Tyr Asp Tyr
1               5

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      KPN42--FR-1-2-4-GL-VH/KPN42-FR-GL-C105A-VL
      (KPN42-v2016) VL-CDR2 peptide
```

<400> SEQUENCE: 14

Asp Val Asn
1

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN42--FR-1-2-4-GL-VH/KPN42-FR-GL-C105A-VL
      (KPN42-v2016) VL-CDR2 peptide

<400> SEQUENCE: 15

Met Ile Tyr Asp Val Asn Lys Arg Pro
1               5

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN42--FR-1-2-4-GL-VH/KPN42-FR-GL-C105A-VL
      (KPN42-v2016) VL-CDR3 peptide

<400> SEQUENCE: 16

Ala Ser Tyr Ala Gly Gly Asp Ile Phe Val
1               5                   10

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      KPN42-v2016 VH polypeptide

<400> SEQUENCE: 17

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Asp Ala
            20                  25                  30

Trp Met Asn Trp Val Arg Gln Ala Pro Gly Lys Gly Leu Glu Trp Val
        35                  40                  45

Gly Arg Ile Lys Lys Lys His Glu Gly Val Thr Thr Asp Tyr Pro Ala
    50                  55                  60

Ser Val Arg Gly Arg Phe Thr Ile Ser Arg Asp Asp Ser Lys Asn Thr
65                  70                  75                  80

Val Tyr Leu Gln Met Gly Arg Leu Arg Ile Glu Asp Thr Ala Ile Tyr
                85                  90                  95

Tyr Cys Thr Thr Arg Ile Val Thr Thr Asn Asp Tyr Trp Gly Gln Gly
            100                 105                 110

Thr Leu Val Thr Val Ser Ser
        115

<210> SEQ ID NO 18
<211> LENGTH: 110
<212> TYPE: PRT
<213> ORGANISM: Artificial Sequence
<220> FEATURE:
<223> OTHER INFORMATION: Description of Artificial Sequence: Synthetic
      KPN42-v2016 VL polypeptide

<400> SEQUENCE: 18

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asp Tyr Val Ser Trp Tyr Gln Gln His Pro Gly Lys Ala Pro Lys Leu
        35                  40                  45

Met Ile Tyr Asp Val Asn Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Gly
                85                  90                  95

Asp Ile Phe Val Phe Gly Thr Gly Thr Lys Val Thr Val Leu
            100                 105                 110

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      KPN42-FR-GL-VH/KPN42-FR-GL-C105A-VL VH-CDR1 peptide

<400> SEQUENCE: 19

Gly Phe Thr Phe Asn Asp Ala Trp
1               5

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN42-FR-GL-VH/KPN42-FR-GL-C105A-VL VH-CDR2 peptide

<400> SEQUENCE: 20

Ile Lys Lys Lys His Glu Gly Val Thr Thr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN42-FR-GL-VH/KPN42-FR-GL-C105A-VL VH-CDR3 peptide

<400> SEQUENCE: 21

Thr Thr Arg Ile Val Thr Thr Asn Asp Tyr
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN42-FR-GL-VH/KPN42-FR-GL-C105A-VL VL-CDR1 peptide

<400> SEQUENCE: 22

Ser Ser Asp Val Gly Ala Tyr Asp Tyr
1               5

```
<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      KPN42-FR-GL-VH/KPN42-FR-GL-C105A-VL VL-CDR2 peptide

<400> SEQUENCE: 23

Asp Val Asn
1

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN42-FR-GL-VH/KPN42-FR-GL-C105A-VL VL-CDR2 peptide

<400> SEQUENCE: 24

Met Ile Tyr Asp Val Asn Lys Arg Pro
1               5

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN42-FR-GL-VH/KPN42-FR-GL-C105A-VL VL-CDR3 peptide

<400> SEQUENCE: 25

Ala Ser Tyr Ala Gly Gly Asp Ile Phe Val
1               5                  10

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic
      KPN42-FR-GL-VH/KPN42-FR-GL-C105A-VL VH polypeptide

<400> SEQUENCE: 26

Glu Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Asn Asp Ala
            20                  25                  30

Trp Met Asn Trp Val Arg Gln Ala Pro Gly Lys Gly Leu Glu Trp Val
        35                  40                  45

Gly Arg Ile Lys Lys Lys His Glu Gly Val Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Arg Ile Val Thr Asn Asp Tyr Trp Gly Gln Gly
            100                 105                 110

Thr Leu Val Thr Val Ser Ser
        115
```

```
<210> SEQ ID NO 27
<211> LENGTH: 110
<212> TYPE: PRT
<213> ORGANISM: Artificial Sequence
<220> FEATURE:
<223> OTHER INFORMATION: Description of Artificial Sequence: Synthetic
      KPN42-FR-GL-VH/KPN42-FR-GL-C105A-VL VL polypeptide

<400> SEQUENCE: 27

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asp Tyr Val Ser Trp Tyr Gln Gln His Pro Gly Lys Ala Pro Lys Leu
        35                  40                  45

Met Ile Tyr Asp Val Asn Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Gly
                85                  90                  95

Asp Ile Phe Val Phe Gly Thr Gly Thr Lys Val Thr Val Leu
            100                 105                 110

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS3 VH-CDR1 peptide

<400> SEQUENCE: 28

Gly Phe Ser Phe Arg Asp Tyr Gly
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS3 VH-CDR2 peptide

<400> SEQUENCE: 29

Ile Ser Tyr Asp Gly Arg Asp Gln
1               5

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      KPS3 VH-CDR3 peptide

<400> SEQUENCE: 30

Gly Pro Phe Tyr Asn Pro Ser Leu Tyr Tyr Pro Pro
1               5                   10

<210> SEQ ID NO 31
<211> LENGTH: 6
<212> TYPE: PRT
<213> ORGANISM: Artificial Sequence
<220> FEATURE:
```

<223> OTHER INFORMATION: Description of Artificial Sequence: Synthetic
      KPS3 VL-CDR1 peptide

<400> SEQUENCE: 31

Gln Ser Ile Ser Ser Gln
1               5

<210> SEQ ID NO 32
<211> LENGTH: 3
<212> TYPE: PRT
<213> ORGANISM: Artificial Sequence
<220> FEATURE:
<223> OTHER INFORMATION: Description of Artificial Sequence: Synthetic
      KPS3 VL-CDR2 peptide

<400> SEQUENCE: 32

Asp Ala Ser
1

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      KPS3 VL-CDR2 peptide

<400> SEQUENCE: 33

Leu Ile His Asp Ala Ser Asn Arg Asp
1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      KPS3 VL-CDR3 peptide

<400> SEQUENCE: 34

Leu Gln Arg Asn Asn Trp Pro Pro Trp Thr
1               5                   10

<210> SEQ ID NO 35
<211> LENGTH: 119
<212> TYPE: PRT
<213> ORGANISM: Artificial Sequence
<220> FEATURE:
<223> OTHER INFORMATION: Description of Artificial Sequence: Synthetic
      KPS3 VH polypeptide

<400> SEQUENCE: 35

Gln Gly Gln Leu Val Asp Ser Gly Gly Val Val Gln Arg Gly Gly
1               5                   10                  15

Ser Gln Arg Leu Ser Cys Ala Ala Ser Gly Phe Ser Phe Arg Asp Tyr
            20                  25                  30

Gly Met His Trp Val Arg Gln Ala Pro Gly Lys Gly Leu Glu Trp Val
        35                  40                  45

Ala Phe Ile Ser Tyr Asp Gly Arg Asp Gln Tyr Tyr Ala Asp Ser Val
    50                  55                  60

Lys Gly Arg Phe Ile Ile Ser Arg Asp Asn Ser Lys Asn Thr Leu Ser
65                  70                  75                  80

Leu Gln Met Asn Ser Leu Arg Pro Glu Asp Thr Ala Val Tyr Tyr Cys
                85                  90                  95

```
Gly Pro Phe Tyr Asn Pro Ser Leu Tyr Tyr Pro Pro Trp Gly His Gly
                100                 105                 110

Leu Pro Val Ile Val Ser Ser
        115
```

<210> SEQ ID NO 36
<211> LENGTH: 108
<212> TYPE: PRT
<213> ORGANISM: Artificial Sequence
<220> FEATURE:
<223> OTHER INFORMATION: Description of Artificial Sequence: Synthetic
      KPS3 VL polypeptide

<400> SEQUENCE: 36

```
Glu Val Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Gln
            20                  25                  30

Leu Ala Trp Tyr Gln Gln Lys Pro Gly Gln Ala Pro Arg Leu Leu Ile
        35                  40                  45

His Asp Ala Ser Asn Arg Asp Thr Gly Val Pro Asp Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Leu Gln Arg Asn Asn Trp Pro Pro
                85                  90                  95

Trp Thr Phe Gly Gln Gly Thr Lys Val Glu Ile Lys
            100                 105
```

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      KPN70 VH-CDR1 peptide

<400> SEQUENCE: 37

```
Gly Gly Ser Ile Ser Thr Tyr Tyr
1               5
```

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      KPN70 VH-CDR2 peptide

<400> SEQUENCE: 38

```
Ile His Gln Ser Gly Thr Thr
1               5
```

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      KPN70 VH-CDR3 peptide

<400> SEQUENCE: 39

```
Ala Arg Glu Ser Asp Asp Gly Tyr Lys Trp Asn Tyr Phe Asp Tyr
1               5                   10                  15
```

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      KPN70 VL-CDR1 peptide

<400> SEQUENCE: 40

Gln Ile Val Thr Asn Tyr
1               5

<210> SEQ ID NO 41
<211> LENGTH: 3
<212> TYPE: PRT
<213> ORGANISM: Artificial Sequence
<220> FEATURE:
<223> OTHER INFORMATION: Description of Artificial Sequence: Synthetic
      KPN70 VL-CDR2 peptide

<400> SEQUENCE: 41

Asp Met Ser
1

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN70 VL-CDR2 peptide

<400> SEQUENCE: 42

Leu Ile Phe Asp Met Ser Ile Arg Ala
1               5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN70 VL-CDR3 peptide

<400> SEQUENCE: 43

Gln His Arg Ser Asn Trp Pro Leu Phe Thr
1               5                   10

<210> SEQ ID NO 44
<211> LENGTH: 121
<212> TYPE: PRT
<213> ORGANISM: Artificial Sequence
<220> FEATURE:
<223> OTHER INFORMATION: Description of Artificial Sequence: Synthetic
      KPN70 VH polypeptide

<400> SEQUENCE: 44

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
            20                  25                  30

Tyr Trp Asn Trp Ile Arg Gln Ser Pro Gly Lys Glu Leu Glu Trp Ile
        35                  40                  45

Ala Asn Ile His Gln Ser Gly Thr Thr Tyr Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Val Ile Ser Val Thr Ala Ala Asp Thr Ala Val Tyr Tyr Cys Ala
                85                  90                  95

Arg Glu Ser Asp Asp Gly Tyr Lys Trp Asn Tyr Phe Asp Tyr Trp Gly
            100                 105                 110

Gln Gly Thr Leu Val Thr Val Ser Ser
        115                 120

<210> SEQ ID NO 45
<211> LENGTH: 108
<212> TYPE: PRT
<213> ORGANISM: Artificial Sequence
<220> FEATURE:
<223> OTHER INFORMATION: Description of Artificial Sequence: Synthetic
      KPN70 VL polypeptide

<400> SEQUENCE: 45

Glu Ile Val Leu Thr Gln Ser Pro Ala Ser Leu Ser Leu Ser Pro Gly
1               5                   10                  15

Glu Arg Ala Thr Leu Ser Cys Arg Ala Ser Gln Ile Val Thr Asn Tyr
            20                  25                  30

Leu Ala Trp Tyr Gln His Lys Pro Gly Gln Ala Pro Arg Leu Leu Ile
        35                  40                  45

Phe Asp Met Ser Ile Arg Ala Ala Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Leu
                85                  90                  95

Phe Thr Phe Gly Pro Gly Thr Lys Val Asp Ile Lys
            100                 105

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      KPN179 VH-CDR1 peptide

<400> SEQUENCE: 46

Gly Phe Thr Phe Asn Asn Ala Trp
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN179 VH-CDR2 peptide

<400> SEQUENCE: 47

Ile Lys Arg Lys Ala Asp Gly Glu Thr Thr
1               5                   10

<210> SEQ ID NO 48
<211> LENGTH: 10
<212> TYPE: PRT
<213> ORGANISM: Artificial Sequence
<220> FEATURE:

```
<223> OTHER INFORMATION: Description of Artificial Sequence: Synthetic
      KPN179 VH-CDR3 peptide

<400> SEQUENCE: 48

Thr Thr Arg Ile Val Thr Thr Asn Asp Tyr
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN179 VL-CDR1 peptide

<400> SEQUENCE: 49

Ser Ser Asp Val Gly Tyr Tyr Asp Tyr
1               5

<210> SEQ ID NO 50
<211> LENGTH: 3
<212> TYPE: PRT
<213> ORGANISM: Artificial Sequence
<220> FEATURE:
<223> OTHER INFORMATION: Description of Artificial Sequence: Synthetic
      KPN179 VL-CDR2 peptide

<400> SEQUENCE: 50

Asp Val Asn
1

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN179 VL-CDR2 peptide

<400> SEQUENCE: 51

Met Ile Tyr Asp Val Asn Lys Arg Pro
1               5

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN179 VL-CDR3 peptide

<400> SEQUENCE: 52

Cys Ser Tyr Ala Gly Gly Asp Thr Phe Val
1               5                   10

<210> SEQ ID NO 53
<211> LENGTH: 119
<212> TYPE: PRT
<213> ORGANISM: Artificial Sequence
<220> FEATURE:
<223> OTHER INFORMATION: Description of Artificial Sequence: Synthetic
      KPN179 VH polypeptide

<400> SEQUENCE: 53

Glu Val Gln Val Val Glu Ser Gly Gly Gly Leu Val Lys Pro Gly Gly
1               5                   10                  15
```

```
Ser Leu Arg Leu Ser Cys Ala Ala Ser Gly Phe Thr Phe Asn Asn Ala
         20                  25                  30

Trp Met Asn Trp Val Arg Gln Ala Pro Gly Lys Gly Leu Glu Trp Val
     35                  40                  45

Gly Arg Ile Lys Arg Lys Ala Asp Gly Glu Thr Thr Asp Tyr Pro Ala
 50                  55                  60

Ser Val Lys Gly Arg Phe Thr Val Ser Arg Asp Asp Ser Lys Asn Thr
 65                  70                  75                  80

Ile Tyr Leu Gln Met Asn Ser Leu Lys Thr Glu Asp Thr Ala Ile Tyr
                 85                  90                  95

Tyr Cys Thr Thr Arg Ile Val Thr Thr Asn Asp Tyr Trp Gly Gln Gly
            100                 105                 110

Thr Leu Val Thr Val Ser Ser
        115
```

```
<210> SEQ ID NO 54
<211> LENGTH: 111
<212> TYPE: PRT
<213> ORGANISM: Artificial Sequence
<220> FEATURE:
<223> OTHER INFORMATION: Description of Artificial Sequence: Synthetic
      KPN179 VL polypeptide

<400> SEQUENCE: 54
```

```
Gln Ser Ala Leu Thr Gln Pro Pro Ser Val Ser Gly Ser Pro Gly Gln
 1               5                  10                  15

Ser Val Thr Ile Ser Cys Thr Gly Thr Ser Ser Asp Val Gly Tyr Tyr
             20                  25                  30

Asp Tyr Val Ser Trp Tyr Gln Gln His Pro Gly Lys Ala Pro Lys
         35                  40                  45

His Met Ile Tyr Asp Val Asn Lys Arg Pro Ser Gly Val Pro Asp Arg
 50                  55                  60

Phe Ser Gly Ser Lys Ser Gly Asn Thr Ala Ser Leu Thr Ile Ser Gly
 65                  70                  75                  80

Leu Gln Ala Glu Asp Glu Ala Asp Tyr Tyr Cys Cys Ser Tyr Ala Gly
                 85                  90                  95

Gly Asp Thr Phe Val Phe Gly Thr Gly Thr Lys Val Thr Val Leu
            100                 105                 110
```

```
<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      KPN44 VH-CDR1 peptide

<400> SEQUENCE: 55
```

```
Gly Gly Ser Thr Ser Ser Tyr Tyr
 1               5
```

```
<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      KPN44 VH-CDR2 peptide
```

```
<400> SEQUENCE: 56

Ile His His Gly Gly Thr Thr
1               5

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      KPN44 VH-CDR3 peptide

<400> SEQUENCE: 57

Ala Arg Glu Ser Asp Asp Gly Tyr Arg Trp Asn Tyr Phe Asp Tyr
1               5                   10                  15

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      KPN44 VL-CDR1 peptide

<400> SEQUENCE: 58

Gln Thr Ile Thr Asn Tyr
1               5

<210> SEQ ID NO 59
<211> LENGTH: 3
<212> TYPE: PRT
<213> ORGANISM: Artificial Sequence
<220> FEATURE:
<223> OTHER INFORMATION: Description of Artificial Sequence: Synthetic
      KPN44 VL-CDR2 peptide

<400> SEQUENCE: 59

Asp Met Ser
1

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN44 VL-CDR2 peptide

<400> SEQUENCE: 60

Leu Ile Phe Asp Met Ser Lys Arg Ala
1               5

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN44 VL-CDR3 peptide

<400> SEQUENCE: 61

Gln His Arg Ser Asn Trp Pro Leu Phe Thr
1               5                   10

<210> SEQ ID NO 62
<211> LENGTH: 121
```

<212> TYPE: PRT
<213> ORGANISM: Artificial Sequence
<220> FEATURE:
<223> OTHER INFORMATION: Description of Artificial Sequence: Synthetic
    KPN44 VH polypeptide

<400> SEQUENCE: 62

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Thr Ser Ser Tyr
            20                  25                  30

Tyr Trp Asn Trp Ile Arg Gln Ala Pro Gly Lys Pro Leu Gln Trp Ile
        35                  40                  45

Ala Asn Ile His His Gly Gly Thr Thr Tyr Tyr Asn Pro Ser Leu Arg
    50                  55                  60

Ser Arg Val Thr Met Ser Leu Asp Thr Ser Asn Asn Gln Phe Ser Leu
65                  70                  75                  80

Lys Leu Thr Ser Val Thr Ala Ala Asp Thr Ala Val Tyr Phe Cys Ala
                85                  90                  95

Arg Glu Ser Asp Asp Gly Tyr Arg Trp Asn Tyr Phe Asp Tyr Trp Gly
            100                 105                 110

Gln Gly Val Leu Val Thr Val Ser Ser
        115                 120

<210> SEQ ID NO 63
<211> LENGTH: 108
<212> TYPE: PRT
<213> ORGANISM: Artificial Sequence
<220> FEATURE:
<223> OTHER INFORMATION: Description of Artificial Sequence: Synthetic
    KPN44 VL polypeptide

<400> SEQUENCE: 63

Glu Ile Val Leu Thr Gln Ser Pro Ala Ser Leu Ser Leu Ser Pro Gly
1               5                   10                  15

Asp Arg Ala Thr Leu Ser Cys Arg Ala Ser Gln Thr Ile Thr Asn Tyr
            20                  25                  30

Leu Ala Trp Tyr Gln His Lys Pro Gly Gln Ala Pro Arg Leu Leu Ile
        35                  40                  45

Phe Asp Met Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Leu
                85                  90                  95

Phe Thr Phe Gly Pro Gly Thr Asn Val Asp Ile Lys
            100                 105

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
    KPN17 VH-CDR1 peptide

<400> SEQUENCE: 64

Gly Phe Thr Phe Ser His Phe Trp
1               5

```
<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      KPN17 VH-CDR2 peptide

<400> SEQUENCE: 65

Ile Asp Gly Ser Val Thr Asn Leu
1               5

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      KPN17 VH-CDR3 peptide

<400> SEQUENCE: 66

Ala Arg Asp Leu Val Gly Ile Gly Thr Pro Ala Gly Tyr Gly Met Asp
1               5                   10                  15

Val

<210> SEQ ID NO 67
<211> LENGTH: 6
<212> TYPE: PRT
<213> ORGANISM: Artificial Sequence
<220> FEATURE:
<223> OTHER INFORMATION: Description of Artificial Sequence: Synthetic
      KPN17 VL-CDR1 peptide

<400> SEQUENCE: 67

Gln Gly Ile Ser Thr Tyr
1               5

<210> SEQ ID NO 68
<211> LENGTH: 3
<212> TYPE: PRT
<213> ORGANISM: Artificial Sequence
<220> FEATURE:
<223> OTHER INFORMATION: Description of Artificial Sequence: Synthetic
      KPN17 VL-CDR2 peptide

<400> SEQUENCE: 68

Ala Ala Ser
1

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN17 VL-CDR2 peptide

<400> SEQUENCE: 69

Leu Ile Tyr Ala Ala Ser Thr Leu Gln
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN17 VL-CDR3 peptide
```

<400> SEQUENCE: 70

Gln Gln Leu Thr Ser His Leu Tyr Thr
1               5

<210> SEQ ID NO 71
<211> LENGTH: 124
<212> TYPE: PRT
<213> ORGANISM: Artificial Sequence
<220> FEATURE:
<223> OTHER INFORMATION: Description of Artificial Sequence: Synthetic
      KPN17 VH polypeptide

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser His Phe
                20                  25                  30

Trp Met His Trp Val Arg Gln Ala Pro Gly Gln Gly Leu Val Trp Val
            35                  40                  45

Ala Arg Ile Asp Gly Ser Val Thr Asn Leu Arg Tyr Ala Gly Ser Val
        50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Asp Leu Val Gly Ile Gly Thr Pro Ala Gly Tyr Gly Met Asp
            100                 105                 110

Val Trp Gly Gln Gly Thr Thr Val Thr Val Ser Ser
        115                 120

<210> SEQ ID NO 72
<211> LENGTH: 107
<212> TYPE: PRT
<213> ORGANISM: Artificial Sequence
<220> FEATURE:
<223> OTHER INFORMATION: Description of Artificial Sequence: Synthetic
      KPN17 VL polypeptide

<400> SEQUENCE: 72

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Thr Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Glu Phe Thr Leu Thr Ile Asn Ser Leu Gln Ser
65                  70                  75                  80

Glu Asp Phe Ala Thr Tyr Tyr Cys Gln Gln Leu Thr Ser His Leu Tyr
                85                  90                  95

Thr Phe Gly Gln Gly Thr Lys Leu Glu Ile Lys
            100                 105

<210> SEQ ID NO 73
<211> LENGTH: 6
<212> TYPE: PRT
<213> ORGANISM: Artificial Sequence
<220> FEATURE:

```
<223> OTHER INFORMATION: Description of Artificial Sequence: Synthetic
      6F6 VH-CDR1 peptide

<400> SEQUENCE: 73

Pro Ile Ala Tyr Met Gly
1               5

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      6F6 VH-CDR2 peptide

<400> SEQUENCE: 74

Asp Ile Leu Pro Asn Ile Gly Arg Thr Ile Tyr Gly Glu Lys Phe Glu
1               5                   10                  15

Asp

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      6F6 VH-CDR3 peptide

<400> SEQUENCE: 75

Arg Gly Thr Ser Gly Ala Met Asp Tyr
1               5

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      6F6 VL-CDR1 peptide

<400> SEQUENCE: 76

Arg Ser Ser Gln Gly Leu Val His Ser Thr Gly Asn Thr Phe Leu His
1               5                   10                  15

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      6F6 VL-CDR2 peptide

<400> SEQUENCE: 77

Lys Val Ser Asn Arg Phe Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      6F6 VL-CDR3 peptide

<400> SEQUENCE: 78

Ser Gln Ser Thr His Ile Pro Tyr Thr
1               5
```

<210> SEQ ID NO 79

<400> SEQUENCE: 79

000

<210> SEQ ID NO 80
<211> LENGTH: 119
<212> TYPE: PRT
<213> ORGANISM: Artificial Sequence
<220> FEATURE:
<223> OTHER INFORMATION: Description of Artificial Sequence: Synthetic
      6F6 VH polypeptide

<400> SEQUENCE: 80

Gln Val His Leu Gln Gln Ser Gly Ser Glu Leu Arg Ser Pro Gly Ser
1               5                   10                  15

Ser Val Lys Leu Ser Cys Lys Asp Phe Asp Ser Asp Val Phe Pro Ile
                20                  25                  30

Ala Tyr Met Gly Trp Ile Arg Gln Gln Pro Gly His Gly Phe Asp Trp
            35                  40                  45

Ile Gly Asp Ile Leu Pro Asn Ile Gly Arg Thr Ile Tyr Gly Glu Lys
        50                  55                  60

Phe Glu Asp Lys Ala Thr Leu Asp Ala Asp Thr Val Ser Asn Thr Ala
65                  70                  75                  80

Tyr Leu Glu Leu Ser Ser Leu Thr Ser Glu Asp Ser Ala Ile Tyr Tyr
                85                  90                  95

Cys Ala Arg Arg Gly Thr Ser Gly Ala Met Asp Tyr Trp Gly Gln Gly
            100                 105                 110

Thr Ser Val Thr Val Ser Ser
        115

<210> SEQ ID NO 81
<211> LENGTH: 112
<212> TYPE: PRT
<213> ORGANISM: Artificial Sequence
<220> FEATURE:
<223> OTHER INFORMATION: Description of Artificial Sequence: Synthetic
      6F6 VL polypeptide

<400> SEQUENCE: 81

Asp Val Val Met Thr Gln Thr Pro Leu Phe Leu Pro Val Ser Leu Gly
1               5                   10                  15

Asp Gln Ala Ser Ile Ser Cys Arg Ser Ser Gln Gly Leu Val His Ser
                20                  25                  30

Thr Gly Asn Thr Phe Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Ile Pro Tyr Thr Phe Gly Gly Gly Thr Lys Leu Glu Ile Lys
            100                 105                 110

<210> SEQ ID NO 82
<211> LENGTH: 8
<212> TYPE: PRT

<213> ORGANISM: Artificial Sequence
<220> FEATURE:
<223> OTHER INFORMATION: Description of Artificial Sequence: Synthetic
      KPL26 VH-CDR1 peptide

<400> SEQUENCE: 82

Gly Phe Ile Phe Gly Ser Ser Trp
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      KPL26 VH-CDR2 peptide

<400> SEQUENCE: 83

Ile Asn Pro Asp Gly Ser Ala Thr
1               5

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      KPL26 VH-CDR3 peptide

<400> SEQUENCE: 84

Thr Arg Asn Lys Ala Tyr Asn Ala Leu Asp Tyr
1               5                   10

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      KPL26 VL-CDR1 peptide

<400> SEQUENCE: 85

Ser Ser Asp Val Gly Gly Asn Asn Tyr
1               5

<210> SEQ ID NO 86
<211> LENGTH: 3
<212> TYPE: PRT
<213> ORGANISM: Artificial Sequence
<220> FEATURE:
<223> OTHER INFORMATION: Description of Artificial Sequence: Synthetic
      KPL26 VL-CDR2 peptide

<400> SEQUENCE: 86

Glu Val Ser
1

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      KPL26 VL-CDR2 peptide

<400> SEQUENCE: 87

Ile Ile Tyr Glu Val Ser Lys Arg Pro
1               5

```
<210> SEQ ID NO 88
<211> LENGTH: 8
<212> TYPE: PRT
<213> ORGANISM: Artificial Sequence
<220> FEATURE:
<223> OTHER INFORMATION: Description of Artificial Sequence: Synthetic
      KPL26 VL-CDR3 peptide

<400> SEQUENCE: 88

Ser Ser Phe Gly Gly Ser Lys Met
1               5

<210> SEQ ID NO 89
<211> LENGTH: 118
<212> TYPE: PRT
<213> ORGANISM: Artificial Sequence
<220> FEATURE:
<223> OTHER INFORMATION: Description of Artificial Sequence: Synthetic
      KPL26 VH polypeptide

<400> SEQUENCE: 89

Glu Val Gln Leu Val Glu Ser Gly Gly Gly Leu Val Gln Ser Gly Gly
1               5                   10                  15

Ser Leu Arg Leu Ser Cys Glu Thr Ser Gly Phe Ile Phe Gly Ser Ser
            20                  25                  30

Trp Met Thr Trp Val Arg Gln Ala Pro Gly Lys Gly Leu Glu Trp Val
        35                  40                  45

Ala Thr Ile Asn Pro Asp Gly Ser Ala Thr Ser Tyr Glu Asp Ser Val
    50                  55                  60

Arg Gly Arg Phe Ala Val Ser Arg Asp Asn Ala Lys Asn Ser Val Tyr
65                  70                  75                  80

Leu Gln Met Asn Ser Leu Arg Ala Glu Asp Thr Ala Val Tyr Phe Cys
                85                  90                  95

Thr Arg Asn Lys Ala Tyr Asn Ala Leu Asp Tyr Trp Gly Gln Gly Thr
            100                 105                 110

Leu Val Thr Val Ser Ser
        115

<210> SEQ ID NO 90
<211> LENGTH: 108
<212> TYPE: PRT
<213> ORGANISM: Artificial Sequence
<220> FEATURE:
<223> OTHER INFORMATION: Description of Artificial Sequence: Synthetic
      KPL26 VL polypeptide

<400> SEQUENCE: 90

Gln Ser Ala Leu Thr Gln Pro Pro Ser Ala Ser Gly Ser Pro Gly Gln
1               5                   10                  15

Ser Val Thr Leu Ser Cys Thr Gly Thr Ser Ser Asp Val Gly Gly Asn
            20                  25                  30

Asn Tyr Val Ser Trp Tyr Gln Gln His Pro Gly Lys Ala Pro Lys Leu
        35                  40                  45

Ile Ile Tyr Glu Val Ser Lys Arg Pro Ser Gly Val Pro Asn Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Phe Gly Gly Ser
                85                  90                  95
```

Lys Met Phe Gly Gly Gly Thr Lys Leu Thr Val Leu
            100                 105

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS18 VH-CDR1 peptide

<400> SEQUENCE: 91

Gly Phe Thr Phe Lys Asn Ala Trp
1               5

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      KPS18 VH-CDR2 peptide

<400> SEQUENCE: 92

Val Lys Asn Glu Val Asp Gly Gly Thr Ile
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS18 VH-CDR3 peptide

<400> SEQUENCE: 93

Arg Ala Phe Trp Ser Gly Phe Pro Ala Gly Tyr
1               5                   10

<210> SEQ ID NO 94
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS18 VL-CDR1 peptide

<400> SEQUENCE: 94

Arg Ser Asn Ile Gly Ser Asp Ser
1               5

<210> SEQ ID NO 95
<211> LENGTH: 3
<212> TYPE: PRT
<213> ORGANISM: Artificial Sequence
<220> FEATURE:
<223> OTHER INFORMATION: Description of Artificial Sequence: Synthetic
      KPS18 VL-CDR2 peptide

<400> SEQUENCE: 95

Asp Asn Asn
1

<210> SEQ ID NO 96
<211> LENGTH: 9
<212> TYPE: PRT
<213> ORGANISM: Artificial Sequence
<220> FEATURE:

```
<223> OTHER INFORMATION: Description of Artificial Sequence: Synthetic
      KPS18 VL-CDR2 peptide

<400> SEQUENCE: 96

Leu Met Tyr Asp Asn Asn Lys Arg Pro
1               5

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS18 VL-CDR3 peptide

<400> SEQUENCE: 97

Ala Thr Trp Asp Ser Ser Leu Ser Ala Tyr Val
1               5                   10

<210> SEQ ID NO 98
<211> LENGTH: 120
<212> TYPE: PRT
<213> ORGANISM: Artificial Sequence
<220> FEATURE:
<223> OTHER INFORMATION: Description of Artificial Sequence: Synthetic
      KPS18 VH polypeptide

<400> SEQUENCE: 98

Glu Val Arg Leu Val Glu Ser Gly Gly Gly Leu Val Lys Pro Gly Gly
1               5                   10                  15

Ser Leu Arg Leu Ser Cys Ala Ala Ser Gly Phe Thr Phe Lys Asn Ala
            20                  25                  30

Trp Met Ser Trp Ile Arg Gln Ala Pro Gly Lys Gly Leu Glu Trp Val
        35                  40                  45

Gly Arg Val Lys Asn Glu Val Asp Gly Gly Thr Ile Asp Tyr Gly Val
    50                  55                  60

Pro Val Arg Gly Arg Phe Thr Ile Ser Arg Asp Asp Ser Gln Gly Thr
65                  70                  75                  80

Leu Ser Leu Glu Met Asn Ser Leu Arg Glu Asp Asp Thr Gly Ile Tyr
                85                  90                  95

Tyr Cys Arg Ala Phe Trp Ser Gly Phe Pro Ala Gly Tyr Trp Gly Gln
            100                 105                 110

Gly Thr Leu Val Ser Val Ser Ser
        115                 120

<210> SEQ ID NO 99
<211> LENGTH: 110
<212> TYPE: PRT
<213> ORGANISM: Artificial Sequence
<220> FEATURE:
<223> OTHER INFORMATION: Description of Artificial Sequence: Synthetic
      KPS18 VL polypeptide

<400> SEQUENCE: 99

Gln Ser Val Leu Thr Gln Pro Pro Ser Leu Ser Ala Ala Pro Gly Gln
1               5                   10                  15

Thr Val Thr Ile Ala Cys Ser Gly Ser Arg Ser Asn Ile Gly Ser Asp
            20                  25                  30

Ser Val Ser Trp Phe Gln Gln Phe Pro Gly Thr Ala Pro Arg Val Leu
        35                  40                  45

Met Tyr Asp Asn Asn Lys Arg Pro Ser Gly Ile Ser Asp Arg Phe Ser
    50                  55                  60
```

Gly Ser Lys Ser Gly Thr Ser Val Thr Leu Asp Ile Thr Gly Leu Gln
65                  70                  75                  80

Thr Gly Asp Glu Ala Asp Tyr Tyr Cys Ala Thr Trp Asp Ser Ser Leu
                85                  90                  95

Ser Ala Tyr Val Phe Gly Ser Gly Thr Lys Val Thr Val Leu
            100                 105                 110

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS24 VH-CDR1 peptide

<400> SEQUENCE: 100

Gly Phe Thr Phe Lys Asn Ala Trp
1               5

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      KPS24 VH-CDR2 peptide

<400> SEQUENCE: 101

Val Lys Ser Glu Val Asp Gly Gly Thr Thr
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS24 VH-CDR3 peptide

<400> SEQUENCE: 102

Arg Ala Phe Trp Ser Asp Phe Gln Thr Gly Tyr
1               5                   10

<210> SEQ ID NO 103
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS24 VL-CDR1 peptide

<400> SEQUENCE: 103

Ser Ser Asn Ile Gly Ser Asp Ser
1               5

<210> SEQ ID NO 104
<211> LENGTH: 3
<212> TYPE: PRT
<213> ORGANISM: Artificial Sequence
<220> FEATURE:
<223> OTHER INFORMATION: Description of Artificial Sequence: Synthetic
      KPS24 VL-CDR2 peptide

<400> SEQUENCE: 104

Glu Asn Asn
1

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      KPS24 VL-CDR2 peptide

<400> SEQUENCE: 105

Leu Met Tyr Glu Asn Asn Lys Arg Pro
1               5

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS24 VL-CDR3 peptide

<400> SEQUENCE: 106

Ala Ala Trp Asp Ser Ser Leu Arg Ala Tyr Val
1               5                   10

<210> SEQ ID NO 107
<211> LENGTH: 120
<212> TYPE: PRT
<213> ORGANISM: Artificial Sequence
<220> FEATURE:
<223> OTHER INFORMATION: Description of Artificial Sequence: Synthetic
      KPS24 VH polypeptide

<400> SEQUENCE: 107

Glu Leu His Leu Val Glu Ser Gly Gly Gly Leu Val Lys Pro Gly Gly
1               5                   10                  15

Ser Leu Arg Leu Ser Cys Ala Ala Ser Gly Phe Thr Phe Lys Asn Ala
            20                  25                  30

Trp Met Ser Trp Ile Arg Gln Ala Pro Gly Lys Gly Leu Glu Trp Val
        35                  40                  45

Gly Arg Val Lys Ser Glu Val Asp Gly Gly Thr Thr Asp Tyr Gly Val
    50                  55                  60

Pro Val Arg Gly Arg Phe Thr Ile Ser Arg Asp Asp Ser Gln Ser Thr
65                  70                  75                  80

Leu Ser Leu Glu Met Ser Ser Leu Gln Asp Asp Thr Gly Val Tyr
                85                  90                  95

Tyr Cys Arg Ala Phe Trp Ser Asp Phe Gln Thr Gly Tyr Trp Gly Gln
                100                 105                 110

Gly Thr Leu Val Thr Val Ser Ser
        115                 120

<210> SEQ ID NO 108
<211> LENGTH: 110
<212> TYPE: PRT
<213> ORGANISM: Artificial Sequence
<220> FEATURE:
<223> OTHER INFORMATION: Description of Artificial Sequence: Synthetic
      KPS24 VL polypeptide

<400> SEQUENCE: 108

Gln Ser Val Leu Thr Gln Pro Pro Ser Val Ser Ala Ala Pro Gly Gln
1               5                   10                  15

```
Thr Val Thr Ile Ala Cys Ser Gly Ser Ser Asn Ile Gly Ser Asp
            20                  25                  30

Ser Val Ser Trp Phe Gln Gln Leu Pro Gly Thr Ala Pro Arg Val Leu
    35                  40                  45

Met Tyr Glu Asn Asn Lys Arg Pro Ser Gly Ile Ser Asp Arg Phe Ser
50                  55                  60

Gly Ser Lys Ser Gly Thr Ser Val Thr Leu Gly Ile Thr Gly Leu Gln
65                  70                  75                  80

Thr Gly Asp Glu Ala Asp Tyr Tyr Cys Ala Ala Trp Asp Ser Ser Leu
                85                  90                  95

Arg Ala Tyr Val Phe Gly Ser Gly Thr Lys Val Thr Val Leu
            100                 105                 110

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS44 VH-CDR1 peptide

<400> SEQUENCE: 109

Gly Phe Thr Phe Lys Asn Ala Trp
1               5

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      KPS44 VH-CDR2 peptide

<400> SEQUENCE: 110

Val Lys Ser Glu Val Asp Gly Gly Thr Ile
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44 VH-CDR3 peptide

<400> SEQUENCE: 111

Arg Ala Phe Trp Ser Gly Phe Pro Thr Gly Tyr
1               5                   10

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS44 VL-CDR1 peptide

<400> SEQUENCE: 112

Ser Ser Asn Ile Gly Ser Asp Ser
1               5

<210> SEQ ID NO 113
<211> LENGTH: 3
<212> TYPE: PRT
```

```
<213> ORGANISM: Artificial Sequence
<220> FEATURE:
<223> OTHER INFORMATION: Description of Artificial Sequence: Synthetic
      KPS44 VL-CDR2 peptide

<400> SEQUENCE: 113

Glu Asn Asn
1

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      KPS44 VL-CDR2 peptide

<400> SEQUENCE: 114

Leu Ile Tyr Glu Asn Asn Lys Arg Pro
1               5

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44 VL-CDR3 peptide

<400> SEQUENCE: 115

Ala Thr Trp Asp Ser Ser Leu Ser Ala Tyr Val
1               5                   10

<210> SEQ ID NO 116
<211> LENGTH: 120
<212> TYPE: PRT
<213> ORGANISM: Artificial Sequence
<220> FEATURE:
<223> OTHER INFORMATION: Description of Artificial Sequence: Synthetic
      KPS44/KPS44-G1 VH polypeptide

<400> SEQUENCE: 116

Glu Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Lys Asn Ala
            20                  25                  30

Trp Met Ser Trp Ile Arg Gln Ala Pro Gly Lys Gly Leu Glu Trp Val
        35                  40                  45

Gly Arg Val Lys Ser Glu Val Asp Gly Gly Thr Ile Asp Tyr Gly Val
    50                  55                  60

Pro Val Arg Gly Arg Phe Thr Ile Ser Arg Asp Asp Ser Gln Gly Thr
65                  70                  75                  80

Leu Ser Leu Glu Met Asn Ser Leu Lys Asp Asp Asp Thr Gly Val Tyr
                85                  90                  95

Tyr Cys Arg Ala Phe Trp Ser Gly Phe Pro Thr Gly Tyr Trp Gly Gln
            100                 105                 110

Gly Ala Leu Val Ser Val Ser Ser
        115                 120

<210> SEQ ID NO 117
<211> LENGTH: 110
<212> TYPE: PRT
<213> ORGANISM: Artificial Sequence
<220> FEATURE:
```

```
<223> OTHER INFORMATION: Description of Artificial Sequence: Synthetic
      KPS44 VL polypeptide

<400> SEQUENCE: 117

Gln Ser Val Leu Thr Gln Pro Pro Ser Leu Ser Ala Ala Pro Gly Gln
1               5                   10                  15

Thr Ile Thr Ile Ala Cys Ser Gly Thr Ser Ser Asn Ile Gly Ser Asp
            20                  25                  30

Ser Val Ser Trp Phe Gln Gln Phe Pro Gly Thr Ala Pro Arg Val Leu
        35                  40                  45

Ile Tyr Glu Asn Asn Lys Arg Pro Ser Gly Ile Ser Asp Arg Phe Ser
    50                  55                  60

Gly Ser Lys Ser Gly Thr Ser Val Thr Leu Gly Ile Thr Gly Leu Gln
65                  70                  75                  80

Thr Gly Asp Glu Ala Asp Tyr Tyr Cys Ala Thr Trp Asp Ser Ser Leu
                85                  90                  95

Ser Ala Tyr Val Phe Gly Ser Gly Thr Lys Val Thr Val Leu
            100                 105                 110

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS30 VH-CDR1 peptide

<400> SEQUENCE: 118

Gly Phe Ser Phe Ser Thr Ser Trp
1               5

<210> SEQ ID NO 119
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS30 VH-CDR2 peptide

<400> SEQUENCE: 119

Ile Asp Pro Asp Gly Ser Thr Arg
1               5

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS30 VH-CDR3 peptide

<400> SEQUENCE: 120

Ala Arg Asp Tyr Ala Tyr Asn Arg Phe Asp Tyr
1               5                   10

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      KPS30 VL-CDR1 peptide
```

<400> SEQUENCE: 121

Ser Ser Asp Ile Gly Ala Asn Asn Tyr
1               5

<210> SEQ ID NO 122
<211> LENGTH: 3
<212> TYPE: PRT
<213> ORGANISM: Artificial Sequence
<220> FEATURE:
<223> OTHER INFORMATION: Description of Artificial Sequence: Synthetic
      KPS30 VL-CDR2 peptide

<400> SEQUENCE: 122

Glu Val Asn
1

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      KPS30 VL-CDR2 peptide

<400> SEQUENCE: 123

Leu Leu Tyr Glu Val Asn Lys Arg Pro
1               5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS30 VL-CDR3 peptide

<400> SEQUENCE: 124

Cys Gly Tyr Gly Gly Gly Arg Val
1               5

<210> SEQ ID NO 125
<211> LENGTH: 118
<212> TYPE: PRT
<213> ORGANISM: Artificial Sequence
<220> FEATURE:
<223> OTHER INFORMATION: Description of Artificial Sequence: Synthetic
      KPS30 VH polypeptide

<400> SEQUENCE: 125

Glu Met Gln Leu Val Glu Ser Gly Gly Gly Leu Val Gln Pro Gly Val
1               5                   10                  15

Ser Leu Arg Leu Ser Cys Val Asp Ser Gly Phe Ser Phe Ser Thr Ser
            20                  25                  30

Trp Leu Ala Trp Val Arg Gln Ala Pro Gly Lys Gly Leu Glu Trp Leu
        35                  40                  45

Ala Asn Ile Asp Pro Asp Gly Ser Thr Arg Asn His Val Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Ala Tyr Asn Arg Phe Asp Tyr Trp Gly Gln Gly Thr
            100                 105                 110

```
Met Val Thr Val Ser Ser
        115

<210> SEQ ID NO 126
<211> LENGTH: 108
<212> TYPE: PRT
<213> ORGANISM: Artificial Sequence
<220> FEATURE:
<223> OTHER INFORMATION: Description of Artificial Sequence: Synthetic
      KPS30 VL polypeptide

<400> SEQUENCE: 126

Gln Ser Ala Leu Thr Gln Pro Pro Ser Ala Ser Gly Ser Pro Gly Gln
1               5                   10                  15

Ser Val Val Ile Ser Cys Thr Gly Thr Ser Ser Asp Ile Gly Ala Asn
            20                  25                  30

Asn Tyr Val Ser Trp Tyr Gln Gln His Pro Gly Lys Ala Pro Lys Leu
        35                  40                  45

Leu Leu Tyr Glu Val Asn Lys Arg Pro Ser Gly Val Pro Asp Arg Phe
    50                  55                  60

Ser Ala Ser Lys Ser Gly Asn Thr Ala Ser Leu Thr Val Ser Gly Leu
65                  70                  75                  80

Leu Ala Glu Asp Glu Ala Asp Tyr Tyr Cys Cys Gly Tyr Gly Gly Gly
                85                  90                  95

Arg Val Phe Gly Gly Gly Thr Lys Leu Thr Val Leu
            100                 105

<210> SEQ ID NO 127
<211> LENGTH: 10
<212> TYPE: PRT
<213> ORGANISM: Artificial Sequence
<220> FEATURE:
<223> OTHER INFORMATION: Description of Artificial Sequence: Synthetic
      KPD1 VH-CDR1 peptide

<400> SEQUENCE: 127

Gly Val Ser Ile Thr Ser Asn Thr Tyr Trp
1               5                   10

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      KPD1 VH-CDR2 peptide

<400> SEQUENCE: 128

Leu Ser Tyr Ser Gly Asp Thr
1               5

<210> SEQ ID NO 129
<211> LENGTH: 14
<212> TYPE: PRT
<213> ORGANISM: Artificial Sequence
<220> FEATURE:
<223> OTHER INFORMATION: Description of Artificial Sequence: Synthetic
      KPD1 VH-CDR3 peptide

<400> SEQUENCE: 129

Ala Arg Asp Pro Asp Ile Ile Arg Asn Phe Gln Phe Asp Tyr
1               5                   10
```

```
<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      KPD1 VL-CDR1 peptide

<400> SEQUENCE: 130

Gln Ile Leu Tyr Met Ser His
1               5

<210> SEQ ID NO 131
<211> LENGTH: 3
<212> TYPE: PRT
<213> ORGANISM: Artificial Sequence
<220> FEATURE:
<223> OTHER INFORMATION: Description of Artificial Sequence: Synthetic
      KPD1 VL-CDR2 peptide

<400> SEQUENCE: 131

Gly Ala Ser
1

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      KPD1 VL-CDR2 peptide

<400> SEQUENCE: 132

Leu Ile Tyr Gly Ala Ser Ile Arg Ala
1               5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
      KPD1 VL-CDR3 peptide

<400> SEQUENCE: 133

Gln Gln Tyr Gly Ala Ser Pro Thr
1               5

<210> SEQ ID NO 134
<211> LENGTH: 122
<212> TYPE: PRT
<213> ORGANISM: Artificial Sequence
<220> FEATURE:
<223> OTHER INFORMATION: Description of Artificial Sequence: Synthetic
      KPD1 VH polypeptide

<400> SEQUENCE: 134

Gln Val Gln Leu Gln Glu Ser Asp Pro Arg Leu Val Lys Pro Ser Glu
1               5                   10                  15

Thr Leu Ser Leu Thr Cys Ser Val Ser Gly Val Ser Ile Thr Ser Asn
            20                  25                  30

Thr Tyr Trp Trp Ala Trp Ile Arg Gln Pro Pro Gly Lys Lys Leu Glu
        35                  40                  45

Trp Ile Gly Ser Leu Ser Tyr Ser Gly Asp Thr Tyr Tyr Asn Pro Ser
    50                  55                  60
```

```
Leu Thr Ser Arg Val Thr Ile Ser Arg Asp Ile His Gln Asn Gln Phe
 65                  70                  75                  80

Phe Leu Glu Leu Asn Ser Val Thr Ala Ala Asp Thr Ala Met Tyr Tyr
                 85                  90                  95

Cys Ala Arg Asp Pro Asp Ile Ile Arg Asn Phe Gln Phe Asp Tyr Trp
            100                 105                 110

Gly Arg Gly Thr Leu Val Thr Val Ser Ser
        115                 120

<210> SEQ ID NO 135
<211> LENGTH: 107
<212> TYPE: PRT
<213> ORGANISM: Artificial Sequence
<220> FEATURE:
<223> OTHER INFORMATION: Description of Artificial Sequence: Synthetic
      KPD1 VL polypeptide

<400> SEQUENCE: 135

Glu Ile Val Leu Thr Gln Ser Pro Gly Ile Leu Ser Leu Ser Pro Gly
 1               5                  10                  15

Glu Arg Ala Thr Leu Ser Cys Arg Val Ser Gln Ile Leu Tyr Met Ser
                 20                  25                  30

His Leu Ala Trp Tyr Gln His Lys Pro Gly Gln Ala Pro Arg Leu Leu
             35                  40                  45

Ile Tyr Gly Ala Ser Ile Arg Ala Thr Gly Val Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ala Ser Pro
                 85                  90                  95

Thr Phe Gly Gln Gly Thr Met Val Glu Ile Lys
            100                 105

<210> SEQ ID NO 136
<211> LENGTH: 358
<212> TYPE: DNA
<213> ORGANISM: Artificial Sequence
<220> FEATURE:
<223> OTHER INFORMATION: Description of Artificial Sequence: Synthetic
      KPN42 VH polynucleotide

<400> SEQUENCE: 136
gaggtgcagc tggtggagtc tgggggaggc ttggtaaagc cggggggggtc ccttagactc      60 tcctgtgcag cctctggttt cactttcaat gacgcctgga tgaactgggt ccgccaggct     120
ccaggaaagg ggctggagtg ggtcgcccgc attaaaaaga acatgaagg tgttacgaca      180 gactaccctg catccgtgag aggcagattc accatctcaa gagatgattc taaaaacaca     240
gtgtatctgc agatgggcag actgagaatc gaggacactg ccatatatta ctgtaccaca     300
aggatagtga ctaccaatga ctactggggc cagggaaccc tggtcaccgt ctcctcag      358

<210> SEQ ID NO 137
<211> LENGTH: 357
<212> TYPE: DNA
<213> ORGANISM: Artificial Sequence
<220> FEATURE:
<223> OTHER INFORMATION: Description of Artificial Sequence: Synthetic
      KPN42-v2016 VH polynucleotide

<400> SEQUENCE: 137
```

```
gaggtgcagc tggtcgaatc tggcggggga ctggtgaaac ctggcggctc tctgaggctg      60
agttgcgccg cttcaggctt caccttcaac gacgcatgga tgaattgggt gcgacaggca     120
cctggaaagg gactggagtg ggtcggccgg atcaagaaaa agcacgaagg ggtgaccaca     180
gattaccctg ctagcgtccg gggaagattc actattagca gagacgattc caaaaacacc     240
gtgtatctgc agatgggcag gctgcgcatc gaggacaccg ccatctacta ttgtactacc     300
cgcatcgtga caactaatga ttactggggg cagggaaccc tggtgacagt cagctcc        357
```

<210> SEQ ID NO 138
<211> LENGTH: 357
<212> TYPE: DNA
<213> ORGANISM: Artificial Sequence
<220> FEATURE:
<223> OTHER INFORMATION: Description of Artificial Sequence: Synthetic
      KPN42-FR-GL-VH/KPN42-FR-GL-C105A-VL VH polynucleotide

<400> SEQUENCE: 138

```
gaggtgcagc tggtcgaatc tggcggggga ctggtgaagc ctggcggctc tctgcgactg      60
agttgcgccg cttcaggctt cacctttaac gacgcttgga tgaattgggt gaggcaggca     120
cctggaaaag gactggagtg ggtgggacgc atcaagaaaa agcacgaagg ggtgaccaca     180
gattacgcag cccctgtcaa ggccggttca acaattagca gagacgattc caagaacact     240
ctgtatctgc agatgaatag cctgaaaacc gaggacacag ccgtgtacta ttgtactacc     300
agaatcgtca caactaacga ttactggggg cagggaactc tggtgaccgt cagctcc       357
```

<210> SEQ ID NO 139
<211> LENGTH: 358
<212> TYPE: DNA
<213> ORGANISM: Artificial Sequence
<220> FEATURE:
<223> OTHER INFORMATION: Description of Artificial Sequence: Synthetic
      KPS3 VH polynucleotide

<400> SEQUENCE: 139

```
cagggacagt tggtggactc tgggggaggc gtggtccagc ggggggggtc tcagagactc      60
tcctgcgcag cgtctggatt cagcttcaga gactatggca tgcactgggt ccgccaggct     120
ccaggcaagg ggctggagtg ggtggccttt atatcatatg atgggagaga tcaatactat     180
gcagactccg tgaagggccg attcatcatc tccagagaca attccaagaa cacgctgtct     240
ctgcaaatga acagcctgag acctgaggac acggctgtct attactgtgg gccttttttat     300 aaccccagtc tctactaccc ccctggggc acggacttc cggtcatcgt ctcctcag         358
```

<210> SEQ ID NO 140
<211> LENGTH: 364
<212> TYPE: DNA
<213> ORGANISM: Artificial Sequence
<220> FEATURE:
<223> OTHER INFORMATION: Description of Artificial Sequence: Synthetic
      KPN70 VH polynucleotide

<400> SEQUENCE: 140

```
caggtgcagc tgcaggagtc gggcccggga ctggtgaagc cttcggagac cctgtctctc      60
acctgcactg tctctggtgg ctccatcagt acttactact ggaactggat ccggcagtcc     120
ccagggaagg aattggagtg gattgcaaat atacatcaaa gtgggaccac ctactacaac     180
ccctccctca agagtcgagt caccatgtca gtagacacgt ccaagaacca gttctccctg     240
aaggtgatct ctgtgactgc tgcggacacg gccgtgtatt actgtgcgag agagtccgac     300
```

```
gatggctaca agtggaacta ctttgactac tggggccagg aaccctagt caccgtctcc      360 tcag                                                                  364
```

<210> SEQ ID NO 141
<211> LENGTH: 358
<212> TYPE: DNA
<213> ORGANISM: Artificial Sequence
<220> FEATURE:
<223> OTHER INFORMATION: Description of Artificial Sequence: Synthetic
    KPN179 VH polynucleotide

<400> SEQUENCE: 141

```
gaggtgcagg tggtggagtc tgggggaggc ttggtaaagc cggggggtc ccttagactc      60 tcctgtgcag cctctggttt cactttcaat aacgcctgga tgaactgggt ccgccaggct    120
ccagggaagg ggctggagtg ggtcggccgt attaaaagga aagctgatgg tgagacaaca    180
gactaccctg catccgtgaa aggcagattc accgtctcaa gagatgattc aaaaaacacg    240
atatatctgc agatgaacag cctgaaaacc gaggacacag ccatatatta ctgtaccaca    300
aggatagtga ctaccaatga ctactggggc cagggaaccc tggtcaccgt ctcctcag     358
```

<210> SEQ ID NO 142
<211> LENGTH: 364
<212> TYPE: DNA
<213> ORGANISM: Artificial Sequence
<220> FEATURE:
<223> OTHER INFORMATION: Description of Artificial Sequence: Synthetic
    KPN44 VH polynucleotide

<400> SEQUENCE: 142

```
caggtgcagc tgcaggagtc gggcccggga ctggtgaagc cttcggagac cctgtctctc    60
acctgcactg tgtccggtgg ctccaccagt agttactact ggaactggat ccggcaggcc   120
ccagggaagc cattgcagtg gattgcaaat atacatacg gtgggaccac ttattacaac    180
ccctccctca ggagtcgggt caccatgtct ctggacactt ccataacca gttctccctg    240 aagctgacct ctgtgactgc tgcggacacg gccgtctatt tctgtgcgag agagtccgac    300
gatggctaca gtggaactac ctttgactac tggggccagg gagtcctggt caccgtctcc    360
tcag                                                                 364
```

<210> SEQ ID NO 143
<211> LENGTH: 373
<212> TYPE: DNA
<213> ORGANISM: Artificial Sequence
<220> FEATURE:
<223> OTHER INFORMATION: Description of Artificial Sequence: Synthetic
    KPN17 VH polynucleotide

<400> SEQUENCE: 143

```
gaggtgcagc tggtggagtc cgggggaggc ttggttcagc ctgggggtc cctgagactc     60 tcctgtgcag cctctggatt caccttcagt cacttctgga tgcactgggt ccgccaagct   120
ccagggcagg gctggtgtg gtcgcacgt attgatggtt ctgtgacaaa cttgaggtac    180
gcgggctccg tggagggggcg attcaccatc tccagagaca cgccaagaa cacgctgtat    240 ttgcaaatga acagtctgag agacgaggac acggctgtat attactgtgc aagagatttg    300
gtaggaattg gcacgccggc cgggtacggt atggacgtct ggggccaagg gaccacggtc    360
accgtctcct cag                                                       373
```

<210> SEQ ID NO 144

<211> LENGTH: 357
<212> TYPE: DNA
<213> ORGANISM: Artificial Sequence
<220> FEATURE:
<223> OTHER INFORMATION: Description of Artificial Sequence: Synthetic
      6F6 VH polynucleotide

<400> SEQUENCE: 144
caggttcacc tacaacagtc tggttctgaa ctgaggagtc ctgggtcttc agtaaagctt     60
tcatgcaagg attttgattc agacgtcttc cctattgctt atatgggttg gattaggcag    120
cagcctgggc atggatttga ctggattggg acatactcc caaatattgg tagaacaatc    180
tatggagaga agtttgagga caaagccaca ctggatgcag acacagtgtc caacacagcc    240
tacttggagc tcagcagtct gacatctgag gactctgcta tctactattg tgcaaggagg    300
gggacgtcgg gggctatgga ctactggggt caaggaacct cagtcaccgt ctcctca      357

<210> SEQ ID NO 145
<211> LENGTH: 355
<212> TYPE: DNA
<213> ORGANISM: Artificial Sequence
<220> FEATURE:
<223> OTHER INFORMATION: Description of Artificial Sequence: Synthetic
      KPL26 VH polynucleotide

<400> SEQUENCE: 145
gaggtgcagc tggtggagtc tgggggaggc ttggtccagt cggggggggtc cctgagactc     60 tcctgtgaaa cctctggatt cattttggt agttcttgga tgacctgggt ccgccaggct    120
ccagggaaag gctggagtg gtggccacc ataaaccctg atggaagtgc acaagctat     180 gaggactctg tgaggggccg attcgccgtc tccagagaca cgccaagaa ctcagtgtat    240 ctgcaaatga acagcctgag agccgaggac acggccgtgt acttctgtac aaggaataag    300
gcatacaatg cccttgacta ctggggccag ggaaccctgg tcaccgtctc ctcag         355

<210> SEQ ID NO 146
<211> LENGTH: 361
<212> TYPE: DNA
<213> ORGANISM: Artificial Sequence
<220> FEATURE:
<223> OTHER INFORMATION: Description of Artificial Sequence: Synthetic
      KPS18 VH polynucleotide

<400> SEQUENCE: 146
gaggttcgcc tggtggagtc tggggggaggc ttggtaaagc ctgggggggtc cctaagactc     60 tcctgtgcag cctcaggatt cactttcaaa aacgcctgga tgagctggat ccgccaggct    120
ccagggaagg ggctggagtg ggttggccgt gttaaaaacg aagttgatgg ggggacaata    180
gactacggtg tgcccgtgag aggcagattc accatctcaa gagacgattc acaaggcacg    240
ctgtctctgg agatgaacag cctgagagag gatgacacag ggatttatta ctgtcgggct    300
ttttggagtg gttttcctgc cggatactgg ggccagggaa ccctggtcag cgtctcctca    360
g                                                                    361

<210> SEQ ID NO 147
<211> LENGTH: 361
<212> TYPE: DNA
<213> ORGANISM: Artificial Sequence
<220> FEATURE:
<223> OTHER INFORMATION: Description of Artificial Sequence: Synthetic
      KPS24 VH polynucleotide -continued

<400> SEQUENCE: 147

```
gagctgcacc tggtggagtc tggggggaggc ttggtaaagc ctgggggggtc ccttagactc      60 tcctgtgcag cctcaggatt cactttcaaa aacgcctgga tgagctggat ccgccaggct     120
ccagggaagg ggctggagtg ggttggccgt gttaaaagcg aagttgatgg ggggacaaca     180
gactacggtg tgcccgtgag aggcagattc accatctcaa gagatgattc acaaagcacg     240
ctgtctctgg agatgagcag cctgcaagac gatgacacag cgtttatta ctgtcgggct      300 ttttggagtg attttcaaac cggctactgg ggccagggaa ccctggtcac cgtctcctca     360
g                                                                       361
```

<210> SEQ ID NO 148
<211> LENGTH: 361
<212> TYPE: DNA
<213> ORGANISM: Artificial Sequence
<220> FEATURE:
<223> OTHER INFORMATION: Description of Artificial Sequence: Synthetic
      KPS44 VH polynucleotide

<400> SEQUENCE: 148

```
gaggtgcacc tggtggagtc tggggggaggc ttggtaaagc ctgggggggtc ccttagactc      60 tcctgtgcag cctcaggatt cactttcaaa aacgcctgga tgagctggat ccgccaggct     120
ccagggaagg ggctggagtg ggttggccgt gttaaaagcg aagttgatgg ggggacaata     180
gactacggtg tgcccgtgag aggcagattc accatctcaa gagatgattc acaaggcaca     240
ctgtctctgg agatgaacag cctgaaagac gatgacacag cgtttatta ttgtcgggct      300 ttttggagtg gttttcctac cggatactgg ggccagggag ccctggtcag cgtctcctca     360
g                                                                       361
```

<210> SEQ ID NO 149
<211> LENGTH: 355
<212> TYPE: DNA
<213> ORGANISM: Artificial Sequence
<220> FEATURE:
<223> OTHER INFORMATION: Description of Artificial Sequence: Synthetic
      KPS30 VH polynucleotide

<400> SEQUENCE: 149

```
gagatgcagt tggtagagtc tggggggaggc ttggtccagc ctggggtgtc cctgagactc      60
tcctgtgtag actctggatt cagttttagt acctcttggt tggcctgggt ccgccaggct     120
ccagggaagg ggctggagtg gctggccaac atagatccag atggaagcac agaaaatcat     180
gtggactctg tgaggggccg attcaccatc tccagagaca cgccaagaa ttcactgtat      240 ctccagatga acagcctgag agccgaggac acggccgtct attactgtgc gagagactat     300
gcctacaatc gctttgacta ctggggccag ggaaccatgg tcaccgtctc ctcag           355
```

<210> SEQ ID NO 150
<211> LENGTH: 367
<212> TYPE: DNA
<213> ORGANISM: Artificial Sequence
<220> FEATURE:
<223> OTHER INFORMATION: Description of Artificial Sequence: Synthetic
      KPD1 VH polynucleotide

<400> SEQUENCE: 150

```
caggtgcagc tgcaggagtc ggacccacga ctggtgaagc cttcggagac cctgtccctc      60
acctgtagtg tctctggtgt ctccatcacc agtaacactt actggtgggc ctggatccgc     120
```

```
cagcccccag ggaagaaact ggagtggatt gggagtctct cttacagtgg ggacacctac    180
tacaacccgt ccctcacgag tcgcgtcacc atatcaagag atatccatca gaaccaattt    240
ttcctggagt tgaactctgt gaccgccgcc gacacggcca tgtattactg tgcgagagat    300
cccgacatca ttcgcaattt ccagtttgac tactggggcc ggggaaccct ggtcaccgtc    360
tcctcgg                                                              367
```

```
<210> SEQ ID NO 151
<211> LENGTH: 330
<212> TYPE: DNA
<213> ORGANISM: Artificial Sequence
<220> FEATURE:
<223> OTHER INFORMATION: Description of Artificial Sequence: Synthetic
      KPN42 VL polynucleotide

<400> SEQUENCE: 151
cagtctgccc tgactcagcc tccctcagtg tccgggtctc ctggacagtc agtcaccatc     60
tcctgcactg gaaccagcag tgatgttggt gcttacgact atgtctcctg gtaccaacag    120
tacgcaggca aagtccccaa acacataatt tatgatgtca atgagcggcc ctcaggggtc    180
cctgatcgct tctctggctc caagtctggc aacacggccg ccctgaccat ctctgggctc    240
caggctgagg atgaggctga ttattattgc tgctcatatg caggcggtga catctttgtc    300
ttcggaactg ggactcaggt caccgtccta                                     330
```

```
<210> SEQ ID NO 152
<211> LENGTH: 330
<212> TYPE: DNA
<213> ORGANISM: Artificial Sequence
<220> FEATURE:
<223> OTHER INFORMATION: Description of Artificial Sequence: Synthetic
      KPN42-v2016 VL polynucleotide

<400> SEQUENCE: 152
cagtctgccc tgacccagcc taggtctgtg agtgggtcac ccggacagag tgtcacaatc     60
tcatgcaccg gaacaagctc cgacgtgggc gcttacgatt atgtctcttg gtaccagcag    120
caccccggga aggcacctaa actgatgatc tacgacgtga acaagcggcc aagtggcgtc    180
cccgatagat tcagcggctc caaatctggg aatacagcta gcctgactat ctccggcctg    240
caggcagagg acgaagccga ttactattgt gccagctacg ctggcgggga cattttcgtg    300
tttggaactg gcaccaaggt gaccgtcctg                                     330
```

```
<210> SEQ ID NO 153
<211> LENGTH: 330
<212> TYPE: DNA
<213> ORGANISM: Artificial Sequence
<220> FEATURE:
<223> OTHER INFORMATION: Description of Artificial Sequence: Synthetic
      KPN42-FR-GL-VH/KPN42-FR-GL-C105A-VL VL polynucleotide

<400> SEQUENCE: 153
cagtctgccc tgacccagcc taggtctgtg agtgggtcac ccggacagag tgtcacaatc     60
tcatgcaccg gaacaagctc cgacgtgggc gcttacgatt atgtctcttg gtaccagcag    120
caccccggga aggcacctaa actgatgatc tacgacgtga acaagcggcc aagtggcgtc    180
cccgatagat tcagcggctc caaatctggg aatacagcta gcctgactat ctccggcctg    240
caggcagagg acgaagccga ttactattgt gccagctacg ctggcgggga cattttcgtg    300
tttggaactg gcaccaaggt gaccgtcctg                                     330
```

<210> SEQ ID NO 154
<211> LENGTH: 325
<212> TYPE: DNA
<213> ORGANISM: Artificial Sequence
<220> FEATURE:
<223> OTHER INFORMATION: Description of Artificial Sequence: Synthetic
      KPS3 VL polynucleotide

<400> SEQUENCE: 154

```
gaggttgtct tgacacagtc tccagccact ctgtctttgt ctccagggga aagagccacc      60
ctctcctgta gggccagtca gagcattagc agccaattag cgtggtacca acagaaacct     120
ggccaggctc ccaggctcct catccatgat gcatccaaca gggacactgg cgtcccagac     180
aggttcagtg gcagtgggtc tgggacagac ttcactctca ccatcagcag cctagagcct     240
gaagattttg ctatgtatta ctgtctccag cgtaacaact ggcctccgtg gacgttcggc     300
caagggacca aggtggaaat caaac                                           325
```

<210> SEQ ID NO 155
<211> LENGTH: 325
<212> TYPE: DNA
<213> ORGANISM: Artificial Sequence
<220> FEATURE:
<223> OTHER INFORMATION: Description of Artificial Sequence: Synthetic
      KPN70 VL polynucleotide

<400> SEQUENCE: 155

```
gaaattgtgt tgacacagtc tccagcctcc ctgtctttgt ctccagggga aagagccacc      60
ctctcctgca gggccagtca gattgttacc aactacttag cctggtatca acataaacct     120
ggccaggctc ccaggctcct catctttgat atgtccatta gggccgctgg catcccagcc     180
aggttcagtg gcagtgggtc tgggacagac ttcactctca ccatcagcag ccttgagcct     240
gaagattttg cagtttatta ctgtcaacac cgtagcaact ggcctctatt cactttcggc     300
cctgggacca aagtggatat caaac                                           325
```

<210> SEQ ID NO 156
<211> LENGTH: 334
<212> TYPE: DNA
<213> ORGANISM: Artificial Sequence
<220> FEATURE:
<223> OTHER INFORMATION: Description of Artificial Sequence: Synthetic
      KPN179 VL polynucleotide

<400> SEQUENCE: 156

```
cagtctgccc tgactcagcc tccctcagtg tccgggtctc ctggacagtc agtcaccatc      60
tcctgcactg gaaccagcag tgatgttggt tattacgact atgtctcctg gtaccaacag     120
caccacccag gcaaagcccc caaacacatg atttatgatg tcaataagcg gccctcaggg     180
gtccctgatc gcttctctgg ctccaagtct ggcaacacgg cctccctgac catctctggg     240
ctccaggctg aggatgaggc tgattattat tgctgttcat atgcaggcgg tgacactttt     300
gtcttcggaa ctgggaccaa ggtcaccgtc ctag                                 334
```

<210> SEQ ID NO 157
<211> LENGTH: 325
<212> TYPE: DNA
<213> ORGANISM: Artificial Sequence
<220> FEATURE:
<223> OTHER INFORMATION: Description of Artificial Sequence: Synthetic
      KPN44 VL polynucleotide

<400> SEQUENCE: 157

```
gaaattgtgt tgacacagtc tccagcctcc ctgtctttgt ctccagggga cagagccacc    60
ctctcctgca gggccagtca gacgattacc aactacttag cctggtacca acataaacct   120
ggccaggctc ccagactcct catctttgat atgtcgaaaa gggccactgg catcccagcc   180
aggttcagtg gcagtgggtc tgggacagac ttcactctca ccatcagcag ccttgagcct   240
gaagattttg cagtttacta ctgtcaacac cgtagcaact ggcctctatt cactttcggc   300
cctgggacca acgtggatat caaac                                         325
```

<210> SEQ ID NO 158
<211> LENGTH: 322
<212> TYPE: DNA
<213> ORGANISM: Artificial Sequence
<220> FEATURE:
<223> OTHER INFORMATION: Description of Artificial Sequence: Synthetic
    KPN17 VL polynucleotide

<400> SEQUENCE: 158

```
gacatccagt tgacccagtc tccatccttc ctgtctgcct ctgtaggaga cagagtcacc    60
atcacttgcc gggccagtca gggcattagc acttatttag cctggtatca acaaaaacca   120
gggaaagccc ctaagctcct gatctatgct gcatccactt tgcaaagtgg ggtcccatca   180
aggttcagcg gcagtggatc tgggacagaa ttcactctca caatcaacag cctgcagtct   240
gaagattttg caacttacta ctgtcagcag cttactagtc acctctacac ttttggccag   300
gggaccaagc tggagatcaa ac                                            322
```

<210> SEQ ID NO 159
<211> LENGTH: 336
<212> TYPE: DNA
<213> ORGANISM: Artificial Sequence
<220> FEATURE:
<223> OTHER INFORMATION: Description of Artificial Sequence: Synthetic
    6F6 VL polynucleotide

<400> SEQUENCE: 159

```
gatgttgtga tgacccaaac tccactcttc ctgcctgtca gtcttggaga tcaagcctcc    60
atctcttgca gatctagtca gggccttgta cacagtactg aaacaccttt ttacattgg    120
tacctgcaga agccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggaatt tatttctgct ctcaaagtac acatattccg   300
tacacgttcg gagggggggac caagctggaa ataaaa                            336
```

<210> SEQ ID NO 160
<211> LENGTH: 325
<212> TYPE: DNA
<213> ORGANISM: Artificial Sequence
<220> FEATURE:
<223> OTHER INFORMATION: Description of Artificial Sequence: Synthetic
    KPL26 VL polynucleotide

<400> SEQUENCE: 160

```
cagtctgccc tgactcagcc tccctccgcg tccgggtctc ctggacaatc agtcaccctc    60
tcctgcactg gaaccagcag tgacgttggt ggtaataact atgtctcctg gtaccaacag   120
cacccaggca aagcccccaa actcatcatt tatgaggtca gtaagcggcc ctcagggggtc   180
cctaatcgtt tctctggctc caagtctggc aacacggcct ccctgaccgt ctctgggctc   240
```

```
caggctgagg atgaggctga ttattactgc agctcatttg gaggtagtaa gatgttcggc    300
ggagggacca agctgaccgt cctag                                          325
```

<210> SEQ ID NO 161
<211> LENGTH: 331
<212> TYPE: DNA
<213> ORGANISM: Artificial Sequence
<220> FEATURE:
<223> OTHER INFORMATION: Description of Artificial Sequence: Synthetic
      KPS18 VL polynucleotide

<400> SEQUENCE: 161

```
cagtctgtgt tgacgcagcc gccctcactg tctgcggccc caggacagac ggtcaccatc     60
gcctgctctg gaagtagatc aacattggg agtgattccg tctcctggtt ccagcagttc    120
ccaggaacag cccccagagt cctcatgtat gacaataata gcgaccctc aggcatttct    180 gaccgattct ctggctccaa gtctggcacg tcagtcaccc tggacatcac cggactccag    240
actggggacg aggccgatta ttactgcgca acatgggata gcagcctgag tgcttatgtc    300
ttcggatctg ggaccaaggt caccgtccta a                                  331
```

<210> SEQ ID NO 162
<211> LENGTH: 331
<212> TYPE: DNA
<213> ORGANISM: Artificial Sequence
<220> FEATURE:
<223> OTHER INFORMATION: Description of Artificial Sequence: Synthetic
      KPS24 VL polynucleotide

<400> SEQUENCE: 162

```
cagtctgtgt tgacgcagcc gccctcagtg tctgcggccc caggacagac ggtcaccatc     60
gcctgctctg gaagtagctc aacattggg agtgattccg tatcctggtt ccagcagctc    120
ccaggaacag cccccagagt cctcatgtat gaaaataata gcgaccctc agggatttct    180 gaccgattct ctggctccaa gtctggcacg tcagtcaccc tgggcatcac cggactccag    240
actggggacg aggccgatta ttactgcgca gcatgggata gcagcctacg tgcttatgtc    300
ttcggatctg ggaccaaggt caccgtccta g                                  331
```

<210> SEQ ID NO 163
<211> LENGTH: 331
<212> TYPE: DNA
<213> ORGANISM: Artificial Sequence
<220> FEATURE:
<223> OTHER INFORMATION: Description of Artificial Sequence: Synthetic
      KPS44 VL polynucleotide

<400> SEQUENCE: 163

```
cagtctgtgt tgacgcagcc gccctcactg tctgcggccc ctggacagac gatcaccatc     60
gcctgctctg gaactagttc aacattggg agtgattccg tatcctggtt ccagcaattc    120
ccaggaacag cccccagagt cctcatatat gagaataata gcgaccctc aggcatttct    180 gaccgattct ctggctccaa gtctggcacg tcagtcacac tgggcatcac cggactccag    240
actggggacg aggccgatta ttactgcgca acatgggata gcagcctgag tgcttatgtc    300
ttcggatctg ggaccaaggt caccgtccta g                                  331
```

<210> SEQ ID NO 164
<211> LENGTH: 325
<212> TYPE: DNA
<213> ORGANISM: Artificial Sequence
<220> FEATURE:

<223> OTHER INFORMATION: Description of Artificial Sequence: Synthetic
KPS30 VL polynucleotide

<400> SEQUENCE: 164

```
cagtctgccc tgactcagcc tccctccgcg tccgggtctc ctggacagtc agtcgtcatc    60
tcctgcactg gaaccagcag tgacattggg gctaataact atgtctcctg gtaccaacaa   120
cacccaggca agcccccaa actcttgctt tatgaggtca ataagcggcc ctcaggggtc    180
cctgatcgct tctctgcctc caagtctggc aacacggcct ccctgaccgt ctctgggctc   240
ctggctgagg atgaggctga ttattactgc tgcggatatg gaggcgggag ggtgttcggc   300
ggagggacca agctgaccgt cctac                                        325
```

<210> SEQ ID NO 165
<211> LENGTH: 322
<212> TYPE: DNA
<213> ORGANISM: Artificial Sequence
<220> FEATURE:
<223> OTHER INFORMATION: Description of Artificial Sequence: Synthetic
KPD1 VL polynucleotide

<400> SEQUENCE: 165

```
gaaattgtgt tgacgcagtc tccaggcatc ctgtctttgt ctccagggga gagagccacc    60
ctctcttgca gggtcagtca gattctttac atgtctcatt tggcctggta tcagcataaa   120
cctggacagg ctcccagact cctcatctat ggtgcgtcca tcagggccac tggcgtccca   180
gacaggttca gtggcagtgg gtccgggaca gacttcactc tcaccatcag cagactggag   240
cctgaagatt ttgcagtgta ttactgtcag cagtatggcg cctcaccgac gttcggccaa   300
gggacaatgg tggaaatcaa ac                                           322
```

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
KPN179-FR-1-2-4-GL N35S-VH/KPN179-FR-GL-C105A-VL VH-CDR1 peptide

<400> SEQUENCE: 166

Gly Phe Thr Phe Ser Asn Ala Trp
1               5

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
KPN179-FR-1-2-4-GL N35S-VH/KPN179-FR-GL-C105A-VL VH-CDR2 peptide

<400> SEQUENCE: 167

Ile Lys Arg Lys Ala Asp Gly Glu Thr Thr
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Description of Artificial Sequence: Synthetic
KPN179-FR-1-2-4-GL N35S-VH/KPN179-FR-GL-C105A-VL VH-CDR3 peptide

<400> SEQUENCE: 168

Thr Thr Arg Ile Val Thr Thr Asn Asp Tyr
1               5                   10

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
      KPN179-FR-GL N35S-VH/KPN179-FR-GL-C105A-VL VH-CDR1 peptide

<400> SEQUENCE: 169

Gly Phe Thr Phe Ser Asn Ala Trp
1               5

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN179-FR-GL N35S-VH/KPN179-FR-GL-C105A-VL VH-CDR2 peptide

<400> SEQUENCE: 170

Ile Lys Arg Lys Ala Asp Gly Glu Thr Thr
1               5                   10

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN179-FR-GL N35S-VH/KPN179-FR-GL-C105A-VL VH-CDR3 peptide

<400> SEQUENCE: 171

Thr Thr Arg Ile Val Thr Thr Asn Asp Tyr
1               5                   10

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      KPL36 VH-CDR1 peptide

<400> SEQUENCE: 172

Gly Phe Thr Phe Ile Ser Ser Trp
1               5

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      KPL36 VH-CDR2 peptide

<400> SEQUENCE: 173

Ile Asn Pro Asp Gly Thr Glu Thr
1               5

<210> SEQ ID NO 174
<211> LENGTH: 11

```
<212> TYPE: PRT
<213> ORGANISM: Artificial Sequence
<220> FEATURE:
<223> OTHER INFORMATION: Description of Artificial Sequence: Synthetic
      KPL36 VH-CDR3 peptide

<400> SEQUENCE: 174

Ala Arg Asn Lys Ala Tyr Asn Ala His Asp Phe
1               5                   10

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN179-FR-1-2-4-GL N35S-VH/KPN179-FR-GL-C105A-VL VL-CDR1 peptide

<400> SEQUENCE: 175

Ser Ser Asp Val Gly Tyr Tyr Asp Tyr
1               5

<210> SEQ ID NO 176
<211> LENGTH: 3
<212> TYPE: PRT
<213> ORGANISM: Artificial Sequence
<220> FEATURE:
<223> OTHER INFORMATION: Description of Artificial Sequence: Synthetic
      KPN179-FR-1-2-4-GL N35S-VH/KPN179-FR-GL-C105A-VL VL-CDR2 peptide

<400> SEQUENCE: 176

Asp Val Asn
1

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN179-FR-1-2-4-GL N35S-VH/KPN179-FR-GL-C105A-VL VL-CDR2 peptide

<400> SEQUENCE: 177

Met Ile Tyr Asp Val Asn Lys Arg Pro
1               5

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN179-FR-1-2-4-GL N35S-VH/KPN179-FR-GL-C105A-VL VL-CDR3 peptide

<400> SEQUENCE: 178

Ala Ser Tyr Ala Gly Gly Asp Thr Phe Val
1               5                   10

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN179-FR-GL N35S-VH/KPN179-FR-GL-C105A-VL VL-CDR1 peptide
```

<400> SEQUENCE: 179

Ser Ser Asp Val Gly Tyr Tyr Asp Tyr
1               5

<210> SEQ ID NO 180
<211> LENGTH: 3
<212> TYPE: PRT
<213> ORGANISM: Artificial Sequence
<220> FEATURE:
<223> OTHER INFORMATION: Description of Artificial Sequence: Synthetic
      KPN179-FR-GL N35S-VH/KPN179-FR-GL-C105A-VL VL-CDR2 peptide

<400> SEQUENCE: 180

Asp Val Asn
1

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      KPN179-FR-GL N35S-VH/KPN179-FR-GL-C105A-VL VL-CDR2 peptide

<400> SEQUENCE: 181

Met Ile Tyr Asp Val Asn Lys Arg Pro
1               5

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      KPN179-FR-GL N35S-VH/KPN179-FR-GL-C105A-VL VL-CDR3 peptide

<400> SEQUENCE: 182

Ala Ser Tyr Ala Gly Gly Asp Thr Phe Val
1               5                   10

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      KPL36 VL-CDR1 peptide

<400> SEQUENCE: 183

Ser Ser Asp Val Gly Gly Asn Asn Phe
1               5

<210> SEQ ID NO 184
<211> LENGTH: 3
<212> TYPE: PRT
<213> ORGANISM: Artificial Sequence
<220> FEATURE:
<223> OTHER INFORMATION: Description of Artificial Sequence: Synthetic
      KPL36 VL-CDR2 peptide

<400> SEQUENCE: 184

Glu Val Asn
1

<210> SEQ ID NO 185
<211> LENGTH: 9

```
<212> TYPE: PRT
<213> ORGANISM: Artificial Sequence
<220> FEATURE:
<223> OTHER INFORMATION: Description of Artificial Sequence: Synthetic
      KPL36 VL-CDR2 peptide

<400> SEQUENCE: 185

Ile Ile Tyr Glu Val Asn Lys Arg Pro
1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      KPL36 VL-CDR3 peptide

<400> SEQUENCE: 186

Gly Ala Phe Gly Gly Ser Lys Met
1               5

<210> SEQ ID NO 187
<211> LENGTH: 119
<212> TYPE: PRT
<213> ORGANISM: Artificial Sequence
<220> FEATURE:
<223> OTHER INFORMATION: Description of Artificial Sequence: Synthetic
      KPN179-FR-1-2-4-GL N35S-VH/KPN179-FR-GL-C105A-VL VH
      polypeptide

<400> SEQUENCE: 187

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Arg Lys Ala Asp Gly Glu Thr Thr Asp Tyr Pro Ala
    50                  55                  60

Ser Val Lys Gly Arg Phe Thr Val Ser Arg Asp Asp Ser Lys Asn Thr
65                  70                  75                  80

Ile Tyr Leu Gln Met Asn Ser Leu Lys Thr Glu Asp Thr Ala Ile Tyr
                85                  90                  95

Tyr Cys Thr Thr Arg Ile Val Thr Thr Asn Asp Tyr Trp Gly Gln Gly
            100                 105                 110

Thr Leu Val Thr Val Ser Ser
        115

<210> SEQ ID NO 188
<211> LENGTH: 119
<212> TYPE: PRT
<213> ORGANISM: Artificial Sequence
<220> FEATURE:
<223> OTHER INFORMATION: Description of Artificial Sequence: Synthetic
      KPN179-FR-GL N35S-VH/KPN179-FR-GL-C105A-VL VH
      polypeptide

<400> SEQUENCE: 188

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30
```

Trp Met Asn Trp Val Arg Gln Ala Pro Gly Lys Gly Leu Glu Trp Val
         35                  40                  45

Gly Arg Ile Lys Arg Lys Ala Asp Gly Glu Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Arg Ile Val Thr Thr Asn Asp Tyr Trp Gly Gln Gly
                 100                 105                 110

Thr Leu Val Thr Val Ser Ser
         115

<210> SEQ ID NO 189
<211> LENGTH: 118
<212> TYPE: PRT
<213> ORGANISM: Artificial Sequence
<220> FEATURE:
<223> OTHER INFORMATION: Description of Artificial Sequence: Synthetic
      KPL36 VH polypeptide

<400> SEQUENCE: 189

Glu Val Gln Leu Val Glu Ser Gly Gly Gly Val Val Gln Ser Gly Gly
 1               5                  10                  15

Ser Leu Arg Leu Ser Cys Glu Thr Ser Gly Phe Thr Phe Ile Ser Ser
                 20                  25                  30

Trp Met Ser Trp Val Arg Gln Ala Pro Gly Thr Gly Leu Glu Trp Val
         35                  40                  45

Ala Thr Ile Asn Pro Asp Gly Thr Glu Thr Pro Tyr Ala Asp Ser Leu
 50                  55                  60

Lys Gly Arg Phe Thr Ile Ser Arg Asp Asn Thr Lys Ser Leu Tyr
 65                  70                  75                  80

Leu Gln Ile His Ser Leu Arg Ala Asp Asp Thr Ala Val Tyr Phe Cys
                 85                  90                  95

Ala Arg Asn Lys Ala Tyr Asn Ala His Asp Phe Trp Gly Gln Gly Thr
                 100                 105                 110

Leu Val Met Val Ser Ser
         115

<210> SEQ ID NO 190
<211> LENGTH: 110
<212> TYPE: PRT
<213> ORGANISM: Artificial Sequence
<220> FEATURE:
<223> OTHER INFORMATION: Description of Artificial Sequence: Synthetic
      KPN179-FR-1-2-4-GL N35S-VH/KPN179-FR-GL-C105A-VL VL
      polypeptide

<400> SEQUENCE: 190

Gln Ser Ala Leu Thr Gln Pro Arg Ser Val Ser Gly Ser Pro Gly Gln
 1               5                  10                  15

Ser Val Thr Ile Ser Cys Thr Gly Thr Ser Ser Asp Val Gly Tyr Tyr
                 20                  25                  30

Asp Tyr Val Ser Trp Tyr Gln Gln His Pro Gly Lys Ala Pro Lys Leu
         35                  40                  45

Met Ile Tyr Asp Val Asn Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ala Ser Tyr Ala Gly Gly
                85                  90                  95

Asp Thr Phe Val Phe Gly Thr Gly Thr Lys Val Thr Val Leu
            100                 105                 110

<210> SEQ ID NO 191
<211> LENGTH: 110
<212> TYPE: PRT
<213> ORGANISM: Artificial Sequence
<220> FEATURE:
<223> OTHER INFORMATION: Description of Artificial Sequence: Synthetic
      KPN179-FR-GL N35S-VH/KPN179-FR-GL-C105A-VL VL polypeptide

<400> SEQUENCE: 191

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Tyr Tyr
                20                  25                  30

Asp Tyr Val Ser Trp Tyr Gln Gln His Pro Gly Lys Ala Pro Lys Leu
            35                  40                  45

Met Ile Tyr Asp Val Asn Lys Arg Pro Ser Gly Val Pro Asp Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Ala Gly Gly
                85                  90                  95

Asp Thr Phe Val Phe Gly Thr Gly Thr Lys Val Thr Val Leu
            100                 105                 110

<210> SEQ ID NO 192
<211> LENGTH: 108
<212> TYPE: PRT
<213> ORGANISM: Artificial Sequence
<220> FEATURE:
<223> OTHER INFORMATION: Description of Artificial Sequence: Synthetic
      KPL36 VL polypeptide

<400> SEQUENCE: 192

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Asn
                20                  25                  30

Asn Phe Val Ser Trp Tyr Gln Gln Tyr Pro Gly Lys Ala Pro Lys Leu
            35                  40                  45

Ile Ile Tyr Glu Val Asn Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Gly Ala Phe Gly Gly Ser
                85                  90                  95

Lys Met Phe Gly Gly Gly Thr Lys Leu Thr Val Leu
            100                 105

<210> SEQ ID NO 193
<211> LENGTH: 357
<212> TYPE: DNA
<213> ORGANISM: Artificial Sequence
<220> FEATURE:
<223> OTHER INFORMATION: Description of Artificial Sequence: Synthetic
      KPN179-FR-1-2-4-GL N35S-VH/KPN179-FR-GL-C105A-VL VH polynucleotide

<400> SEQUENCE: 193

```
gaggtgcagc tggtcgaatc cggcggggga ctggtgaaac ctggcggctc tctgcgactg      60
agttgcgccg cttcaggctt cacctttagc aacgcatgga tgaattgggt gagacaggca     120
cctggaaagg gactggagtg gtcggccgg atcaagagaa agctgacgg ggaaaccaca      180
gattaccctg catctgtgaa gggcaggttc acagtcagcc gcgacgattc caaaaacact    240
atctacctgc agatgaatag tctgaagacc gaggacacag ccatctacta ttgtactacc    300
cggattgtga caactaacga ttactggggg cagggaactc tggtgaccgt cagctcc       357
```

<210> SEQ ID NO 194
<211> LENGTH: 357
<212> TYPE: DNA
<213> ORGANISM: Artificial Sequence
<220> FEATURE:
<223> OTHER INFORMATION: Description of Artificial Sequence: Synthetic
KPN179-FR-GL N35S-VH/KPN179-FR-GL-C105A-VL VH polynucleotide

<400> SEQUENCE: 194

```
gaggtgcagc tggtcgaatc tggcggggga ctggtgaaac ctggcggctc tctgcgactg      60
agttgcgccg cttcaggctt cacctttagc aacgcttgga tgaattgggt gagacaggca     120
cctggaaagg gactggagtg gtgggacgg atcaagagaa aagccgacgg ggaaaccaca      180
gattacgcag cccctgtgaa gggcaggttc acaattagcc gcgacgattc caaaaacact    240
ctgtatctgc agatgaatag cctgaagacc gaggacacag ccgtgtacta ttgtactacc    300
cggatcgtca caactaacga ttactggggg cagggaactc tggtgaccgt cagctcc       357
```

<210> SEQ ID NO 195
<211> LENGTH: 355
<212> TYPE: DNA
<213> ORGANISM: Artificial Sequence
<220> FEATURE:
<223> OTHER INFORMATION: Description of Artificial Sequence: Synthetic
KPL36 VH polynucleotide

<400> SEQUENCE: 195

```
gaggtgcagc tggtggagtc tgggggaggc gtggtccagt ctgggggtc cctgagactc      60
tcctgtgaga cttctggatt cacctttata agttcttgga tgagttgggt ccgccaggct    120
ccagggacag gactggagtg gtggccacc attaaccctg atggaactga dacaccctac     180
gcggactcgc tgaagggccg cttcaccatc tccagagaca acaccaagaa gtcactttat   240
ctgcaaatcc atagcctgag agccgacgac acggccgtct atttctgtgc aaggaataag   300
gcatacaatg cccatgactt ctggggccag ggaaccctgg tcaccgtctc ctcag        355
```

<210> SEQ ID NO 196
<211> LENGTH: 330
<212> TYPE: DNA
<213> ORGANISM: Artificial Sequence
<220> FEATURE:
<223> OTHER INFORMATION: Description of Artificial Sequence: Synthetic
KPN179-FR-1-2-4-GL N35S-VH/KPN179-FR-GL-C105A-VL VL polynucleotide

<400> SEQUENCE: 196

```
cagtctgccc tgactcagcc taggtctgtg agtgggtcac ccggacagag tgtcacaatc      60
tcatgcaccg gaacaagctc cgacgtgggc tactatgatt acgtctcttg gtatcagcag    120
caccccggga aggctcctaa actgatgatc tacgacgtga caagcggcc aagtggcgtc     180
cccgatagat tcagcggctc caaatctggg aatacagcaa gcctgactat tccggcctg    240
```

```
caggcagagg acgaagccga ttactattgt gccagctatg ctggcgggga caccttcgtg      300
tttggaactg gcaccaaggt gacagtcctg                                       330

<210> SEQ ID NO 197
<211> LENGTH: 330
<212> TYPE: DNA
<213> ORGANISM: Artificial Sequence
<220> FEATURE:
<223> OTHER INFORMATION: Description of Artificial Sequence: Synthetic
      KPN179-FR-GL N35S-VH/KPN179-FR-GL-C105A-VL VL polynucleotide

<400> SEQUENCE: 197
cagtctgccc tgactcagcc taggtctgtg agtgggtcac ccggacagag tgtcacaatc      60
tcatgcaccg gaacaagctc cgacgtgggc tactatgatt acgtctcttg gtatcagcag      120
caccccggga aggctcctaa actgatgatc tacgacgtga acaagcggcc aagtggcgtc      180
cccgatagat tcagcggctc caaatctggg aatacagcaa gcctgactat ttccggcctg      240
caggcagagg acgaagccga ttactattgt gccagctatg ctggcgggga caccttcgtg      300
tttggaactg gcaccaaggt gacagtcctg                                       330

<210> SEQ ID NO 198
<211> LENGTH: 325
<212> TYPE: DNA
<213> ORGANISM: Artificial Sequence
<220> FEATURE:
<223> OTHER INFORMATION: Description of Artificial Sequence: Synthetic
      KPL36 VL polynucleotide

<400> SEQUENCE: 198
cagtctgccc tgactcagcc tccctccgcg tccgggtctc ctggacaatc agtcaccatc      60
tcctgcactg gaaccagtag tgacgtaggt ggtaataact ttgtctcctg gtaccaacag      120
tatccaggca aagcccccaa actcattatt tatgaggtca ataagcggcc ctcaggggtc      180
cctgatcgtt tctctggctc caagtctggc aacacggcct ccctgaccgt ctctgggctc      240
caggctgagg atgaggctga ttattactgc ggcgcatttg aggtagcaa gatgttcggc       300 ggagggacca agctgaccgt cctag                                            325

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-v2017/KPS-44-G2/KPS-44-G3 VH-CDR3 peptide

<400> SEQUENCE: 199

Arg Ala Phe Phe Ser Gly Phe Pro Thr Gly Tyr
1               5                   10

<210> SEQ ID NO 200
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS44-v2017/KPS-44-G1/KPS-44-G3 VL-CDR1 peptide

<400> SEQUENCE: 200

Ser Ser Asn Ile Gly Ser Asn Tyr
1               5
```

```
<210> SEQ ID NO 201
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-v2017/KPS-44-G1/KPS-44-G2 VL-CDR3 peptide

<400> SEQUENCE: 201

Ala Thr Phe Asp Ser Ser Leu Ser Ala Tyr Val
1               5                   10

<210> SEQ ID NO 202
<211> LENGTH: 120
<212> TYPE: PRT
<213> ORGANISM: Artificial Sequence
<220> FEATURE:
<223> OTHER INFORMATION: Description of Artificial Sequence: Synthetic
      KPS44-v2017/KPS44-G2/KPS44-G3 VH polypeptide

<400> SEQUENCE: 202

Glu Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Lys Asn Ala
            20                  25                  30

Trp Met Ser Trp Ile Arg Gln Ala Pro Gly Lys Gly Leu Glu Trp Val
        35                  40                  45

Gly Arg Val Lys Ser Glu Val Asp Gly Gly Thr Ile Asp Tyr Gly Val
    50                  55                  60

Pro Val Arg Gly Arg Phe Thr Ile Ser Arg Asp Asp Ser Gln Gly Thr
65                  70                  75                  80

Leu Ser Leu Glu Met Asn Ser Leu Lys Asp Asp Asp Thr Gly Val Tyr
                85                  90                  95

Tyr Cys Arg Ala Phe Phe Ser Gly Phe Pro Thr Gly Tyr Trp Gly Gln
            100                 105                 110

Gly Ala Leu Val Ser Val Ser Ser
        115                 120

<210> SEQ ID NO 203
<211> LENGTH: 110
<212> TYPE: PRT
<213> ORGANISM: Artificial Sequence
<220> FEATURE:
<223> OTHER INFORMATION: Description of Artificial Sequence: Synthetic
      KPS44-v2017/KPS44-G1 VL polypeptide

<400> SEQUENCE: 203

Gln Ser Val Leu Thr Gln Pro Pro Ser Leu Ser Ala Ala Pro Gly Gln
1               5                   10                  15

Thr Ile Thr Ile Ala Cys Ser Gly Thr Ser Ser Asn Ile Gly Ser Asn
            20                  25                  30

Tyr Val Ser Trp Phe Gln Gln Phe Pro Gly Thr Ala Pro Arg Val Leu
        35                  40                  45

Ile Tyr Glu Asn Asn Lys Arg Pro Ser Gly Ile Ser Asp Arg Phe Ser
    50                  55                  60

Gly Ser Lys Ser Gly Thr Ser Val Thr Leu Gly Ile Thr Gly Leu Gln
65                  70                  75                  80

Thr Gly Asp Glu Ala Asp Tyr Tyr Cys Ala Thr Phe Asp Ser Ser Leu
                85                  90                  95
```

```
Ser Ala Tyr Val Phe Gly Ser Gly Thr Lys Val Thr Val Leu
            100                 105                 110
```

<210> SEQ ID NO 204
<211> LENGTH: 110
<212> TYPE: PRT
<213> ORGANISM: Artificial Sequence
<220> FEATURE:
<223> OTHER INFORMATION: Description of Artificial Sequence: Synthetic
      KPS44-G2 VL polypeptide

<400> SEQUENCE: 204

```
Gln Ser Val Leu Thr Gln Pro Pro Ser Leu Ser Ala Ala Pro Gly Gln
1               5                   10                  15

Thr Ile Thr Ile Ala Cys Ser Gly Thr Ser Ser Asn Ile Gly Ser Asp
            20                  25                  30

Ser Val Ser Trp Phe Gln Gln Phe Pro Gly Thr Ala Pro Arg Val Leu
        35                  40                  45

Ile Tyr Glu Asn Asn Lys Arg Pro Ser Gly Ile Ser Asp Arg Phe Ser
50                  55                  60

Gly Ser Lys Ser Gly Thr Ser Val Thr Leu Gly Ile Thr Gly Leu Gln
65                  70                  75                  80

Thr Gly Asp Glu Ala Asp Tyr Tyr Cys Ala Thr Phe Asp Ser Ser Leu
                85                  90                  95

Ser Ala Tyr Val Phe Gly Ser Gly Thr Lys Val Thr Val Leu
            100                 105                 110
```

<210> SEQ ID NO 205
<211> LENGTH: 110
<212> TYPE: PRT
<213> ORGANISM: Artificial Sequence
<220> FEATURE:
<223> OTHER INFORMATION: Description of Artificial Sequence: Synthetic
      KPS44-G3 VL polypeptide

<400> SEQUENCE: 205

```
Gln Ser Val Leu Thr Gln Pro Pro Ser Leu Ser Ala Ala Pro Gly Gln
1               5                   10                  15

Thr Ile Thr Ile Ala Cys Ser Gly Thr Ser Ser Asn Ile Gly Ser Asn
            20                  25                  30

Tyr Val Ser Trp Phe Gln Gln Phe Pro Gly Thr Ala Pro Arg Val Leu
        35                  40                  45

Ile Tyr Glu Asn Asn Lys Arg Pro Ser Gly Ile Ser Asp Arg Phe Ser
50                  55                  60

Gly Ser Lys Ser Gly Thr Ser Val Thr Leu Gly Ile Thr Gly Leu Gln
65                  70                  75                  80

Thr Gly Asp Glu Ala Asp Tyr Tyr Cys Ala Thr Trp Asp Ser Ser Leu
                85                  90                  95

Ser Ala Tyr Val Phe Gly Ser Gly Thr Lys Val Thr Val Leu
            100                 105                 110
```

<210> SEQ ID NO 206
<211> LENGTH: 360
<212> TYPE: DNA
<213> ORGANISM: Artificial Sequence
<220> FEATURE:
<223> OTHER INFORMATION: Description of Artificial Sequence: Synthetic
      KPS44-v2017 VH polynucleotide

<400> SEQUENCE: 206

```
gaggtgcacc tggtcgaatc cggcggggga ctggtgaaac caggcgggtc tctgagactg      60
agttgcgccg cttcaggctt caccttcaag aacgcatgga tgagctggat tagacaggca     120
cctgggaagg gactggagtg ggtgggccgc gtcaaatctg aagtggatgg aggcaccatc     180
gactacgggg tgcctgtccg gggaagattc accattagcc gagacgattc ccagggcaca     240
ctgtctctgg agatgaatag tctgaaggac gatgacactg ggtgtactat tgtagagct     300 ttcttttcag gatttcctac cggctattgg ggacagggg cctggtgag cgtcagctcc      360
```

<210> SEQ ID NO 207
<211> LENGTH: 360
<212> TYPE: DNA
<213> ORGANISM: Artificial Sequence
<220> FEATURE:
<223> OTHER INFORMATION: Description of Artificial Sequence: Synthetic
    KPS44-G1 VH polynucleotide

<400> SEQUENCE: 207

```
gaggtacacc ttgtagaaag tggggtggg cttgtcaagc ctgggggaag tttgagactg      60
agttgcgccg caagtggctt cacgtttaag aacgcatgga tgtcctggat tagacaagcc     120
cccggtaaag gtttggaatg ggtaggacga gttaagtctg aggttgacgg ggggacgata     180
gattacggtg ttcccgtgcg cggcagattc acgataagtc gagacgactc tcagggtaca     240
cttagcctcg aaatgaatag cctcaaagac gatgatacag gcgtttatta ttgccgcgca     300
ttctggagtg gcttcccgac tgggtactgg gggcaaggtg ctcttgtctc agtgtcatcc     360
```

<210> SEQ ID NO 208
<211> LENGTH: 360
<212> TYPE: DNA
<213> ORGANISM: Artificial Sequence
<220> FEATURE:
<223> OTHER INFORMATION: Description of Artificial Sequence: Synthetic
    KPS44-G2/KPS44-G3 VH polynucleotide

<400> SEQUENCE: 208

```
gaggtacacc ttgtagaaag tggggtggg cttgtcaagc ctggggaag tttgagactg       60 agttgcgccg caagtggctt cacgtttaag aacgcatgga tgtcctggat tagacaagcc     120
cccggtaaag gtttggaatg ggtaggacga gttaagtctg aggttgacgg ggggacgata     180
gattacggtg ttcccgtgcg cggcagattc acgataagtc gagacgactc tcagggtaca     240
cttagcctcg aaatgaatag cctcaaagac gatgatacag gcgtttatta ttgccgcgca     300
ttctttagtg gcttcccgac tgggtactgg gggcaaggtg ctcttgtctc agtgtcatcc     360
```

<210> SEQ ID NO 209
<211> LENGTH: 330
<212> TYPE: DNA
<213> ORGANISM: Artificial Sequence
<220> FEATURE:
<223> OTHER INFORMATION: Description of Artificial Sequence: Synthetic
    KPS44-v2017 VL polynucleotide

<400> SEQUENCE: 209

```
cagagcgtgc tgacacagcc cccttcactg agcgccgctc ctggacagac catcacaatt      60
gcttgctccg gcactagctc caacatcggg tccaattacg tgtcttggtt ccagcagttt     120
ccaggaaccg cacccagggt cctgatctat gagaacaata gcggccctc aggcattagc      180 gacagattct ccgggtctaa aagtggaact agcgtgaccc tgggaattac cggcctgcag     240
```

```
acaggcgacg aagcagatta ctattgtgcc accttcgatt ctagtctgag tgcctacgtc    300
tttggctctg ggacaaaagt gactgtcctg                                     330
```

<210> SEQ ID NO 210
<211> LENGTH: 330
<212> TYPE: DNA
<213> ORGANISM: Artificial Sequence
<220> FEATURE:
<223> OTHER INFORMATION: Description of Artificial Sequence: Synthetic
      KPS44-G1 VL polynucleotide

<400> SEQUENCE: 210

```
cagtccgttt tgacgcaacc cccgtcactg agtgctgcgc ctgggcagac cataacgatc    60
gcctgctcag ggaccagcag taatataggc tctaattatg tatcatggtt ccagcaattc   120
cctggcacgg cacctcgcgt actgatctac gaaaataata agcggccctc aggcatttca   180
gataggttct ctgggagcaa gagtggtaca agcgtaacgc tcggtatcac cggtctccag   240
acaggtgatg aagctgatta ctactgcgct acttttgata gctctctttc agcttacgtg   300
tttggttccg ggaccaaagt gacagtcctc                                    330
```

<210> SEQ ID NO 211
<211> LENGTH: 330
<212> TYPE: DNA
<213> ORGANISM: Artificial Sequence
<220> FEATURE:
<223> OTHER INFORMATION: Description of Artificial Sequence: Synthetic
      KPS44-G2 VL polynucleotide

<400> SEQUENCE: 211

```
cagtccgttt tgacgcaacc cccgtcactg agtgctgcgc ctgggcagac cataacgatc    60
gcctgctcag ggaccagcag taatataggc tctgattctg tatcatggtt ccagcaattc   120
cctggcacgg cacctcgcgt actgatctac gaaaataata agcggccctc aggcatttca   180
gataggttct ctgggagcaa gagtggtaca agcgtaacgc tcggtatcac cggtctccag   240
acaggtgatg aagctgatta ctactgcgct acttttgata gctctctttc agcttacgtg   300
tttggttccg ggaccaaagt gacagtcctc                                    330
```

<210> SEQ ID NO 212
<211> LENGTH: 330
<212> TYPE: DNA
<213> ORGANISM: Artificial Sequence
<220> FEATURE:
<223> OTHER INFORMATION: Description of Artificial Sequence: Synthetic
      KPS44-G3 VL polynucleotide

<400> SEQUENCE: 212

```
cagtccgttt tgacgcaacc cccgtcactg agtgctgcgc ctgggcagac cataacgatc    60
gcctgctcag ggaccagcag taatataggc tctaattatg tatcatggtt ccagcaattc   120
cctggcacgg cacctcgcgt actgatctac gaaaataata agcggccctc aggcatttca   180
gataggttct ctgggagcaa gagtggtaca agcgtaacgc tcggtatcac cggtctccag   240
acaggtgatg aagctgatta ctactgcgct acttgggata gctctctttc agcttacgtg   300
tttggttccg ggaccaaagt gacagtcctc                                    330
```

<210> SEQ ID NO 213
<211> LENGTH: 120
<212> TYPE: PRT
<213> ORGANISM: Artificial Sequence

```
<220> FEATURE:
<223> OTHER INFORMATION: Description of Artificial Sequence: Synthetic
      KPS44-G4 VH polypeptide

<400> SEQUENCE: 213

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Lys Asn Ala
            20                  25                  30

Trp Met Ser Trp Ile Arg Gln Ala Pro Gly Lys Gly Leu Glu Trp Val
        35                  40                  45

Gly Arg Val Lys Ser Glu Val Asp Ala Gly Thr Ile Asp Tyr Gly Val
    50                  55                  60

Pro Val Arg Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Arg Ala Phe Tyr Ser Gly Phe Pro Thr Gly Tyr Trp Gly Gln
            100                 105                 110

Gly Thr Leu Val Thr Val Ser Ser
        115                 120

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS44-G4 VH-CDR1 peptide

<400> SEQUENCE: 214

Gly Phe Thr Phe Lys Asn Ala Trp
1               5

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      KPS44-G4 VH-CDR2 peptide

<400> SEQUENCE: 215

Val Lys Ser Glu Val Asp Ala Gly Thr Ile
1               5                   10

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-G4 VH-CDR3 peptide

<400> SEQUENCE: 216

Arg Ala Phe Tyr Ser Gly Phe Pro Thr Gly Tyr
1               5                   10

<210> SEQ ID NO 217
<211> LENGTH: 110
<212> TYPE: PRT
<213> ORGANISM: Artificial Sequence
```

```
<220> FEATURE:
<223> OTHER INFORMATION: Description of Artificial Sequence: Synthetic
      KPS44-G4 VL polypeptide

<400> SEQUENCE: 217

Gln Ser Val Leu Thr Gln Pro Pro Ser Val Ala Ala Pro Gly Gln
1               5                   10                  15

Lys Val Thr Ile Ala Cys Ser Gly Thr Ser Ser Asn Ile Gly Ser Asp
            20                  25                  30

Ala Val Ser Trp Phe Gln Gln Leu Pro Gly Thr Ala Pro Lys Leu Leu
        35                  40                  45

Ile Tyr Glu Asn Asn Lys Arg Pro Ser Gly Ile Ser Asp Arg Phe Ser
50                  55                  60

Gly Ser Lys Ser Gly Thr Ser Val Thr Leu Gly Ile Thr Gly Leu Gln
65                  70                  75                  80

Thr Gly Asp Glu Ala Asp Tyr Tyr Cys Ala Thr Phe Glu Ser Ser Leu
                85                  90                  95

Ser Ala Tyr Val Phe Gly Thr Gly Thr Lys Val Thr Val Leu
            100                 105                 110

<210> SEQ ID NO 218
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS44-G4 VL-CDR1 peptide

<400> SEQUENCE: 218

Ser Ser Asn Ile Gly Ser Asp Ala
1               5

<210> SEQ ID NO 219
<211> LENGTH: 3
<212> TYPE: PRT
<213> ORGANISM: Artificial Sequence
<220> FEATURE:
<223> OTHER INFORMATION: Description of Artificial Sequence: Synthetic
      KPS44-G4 VL-CDR2 peptide

<400> SEQUENCE: 219

Glu Asn Asn
1

<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-G4 VL-CDR3 peptide

<400> SEQUENCE: 220

Ala Thr Phe Glu Ser Ser Leu Ser Ala Tyr Val
1               5                   10

<210> SEQ ID NO 221
<211> LENGTH: 360
<212> TYPE: DNA
<213> ORGANISM: Artificial Sequence
<220> FEATURE:
<223> OTHER INFORMATION: Description of Artificial Sequence: Synthetic
      KPS44-G4 VH polynucleotide
```

<400> SEQUENCE: 221

```
caggtacagc ttgtagaaag tggggtggg cttgtcaagc ctgggggaag tttgagactg      60
agttgcgccg caagtggctt cacgtttaag aacgcatgga tgtcctggat tagacaagcc    120
cccggtaaag gtttggaatg ggtaggacga gttaagtctg aggttgacgc cgggacgata    180
gattacggtg ttcccgtgcg cggcagattc acgataagtc gagacgactc taagaataca    240
ctttacctcc agatgaatag cctcaaaacc gaggatacag ccgtttatta ttgccgcgca    300
ttctatagtg gcttcccgac tgggtactgg gggcaaggta ctcttgtcac agtgtcatcc    360
```

<210> SEQ ID NO 222
<211> LENGTH: 330
<212> TYPE: DNA
<213> ORGANISM: Artificial Sequence
<220> FEATURE:
<223> OTHER INFORMATION: Description of Artificial Sequence: Synthetic
KPS44-G4 VL polynucleotide

<400> SEQUENCE: 222

```
cagtccgttt tgacgcaacc cccgtcagtg agtgctgcgc ctgggcagaa ggtgacgatc      60
gcctgctcag ggaccagcag taatataggc tctgatgctg tatcatggtt ccagcaactg    120
cctggcacgg cacctaaact gctgatctac gaaataata agcggccctc aggcatttca    180
gataggttct ctgggagcaa gagtggtaca agctaacgc tcggtatcac cggtctccag    240
acaggtgatg aagctgatta ctactgcgct acttttgaga gctctctttc agcttacgtg    300
tttggtaccg ggaccaaagt gacagtcctc                                     330
```

<210> SEQ ID NO 223
<211> LENGTH: 120
<212> TYPE: PRT
<213> ORGANISM: Artificial Sequence
<220> FEATURE:
<223> OTHER INFORMATION: Description of Artificial Sequence: Synthetic
KPS44-G6 VH polypeptide

<400> SEQUENCE: 223

```
Gln Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Lys Asn Ala
            20                  25                  30

Trp Met Ser Trp Ile Arg Gln Ala Pro Gly Lys Gly Leu Glu Trp Val
        35                  40                  45

Gly Arg Val Lys Ser Glu Val Asp Ala Gly Thr Ile Asp Tyr Gly Val
    50                  55                  60

Pro Val Arg Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Arg Ala Phe Tyr Ser Gly Phe Pro Thr Gly Tyr Trp Gly Gln
            100                 105                 110

Gly Thr Leu Val Thr Val Ser Ser
        115                 120
```

<210> SEQ ID NO 224
<211> LENGTH: 8
<212> TYPE: PRT
<213> ORGANISM: Artificial Sequence
<220> FEATURE:

```
<223> OTHER INFORMATION: Description of Artificial Sequence: Synthetic
      KPS44-G6 VH-CDR1 peptide

<400> SEQUENCE: 224

Gly Phe Thr Phe Lys Asn Ala Trp
1               5

<210> SEQ ID NO 225
<211> LENGTH: 10
<212> TYPE: PRT
<213> ORGANISM: Artificial Sequence
<220> FEATURE:
<223> OTHER INFORMATION: Description of Artificial Sequence: Synthetic
      KPS44-G6 VH-CDR2 peptide

<400> SEQUENCE: 225

Val Lys Ser Glu Val Asp Ala Gly Thr Ile
1               5                   10

<210> SEQ ID NO 226
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-G6 VH-CDR3 peptide

<400> SEQUENCE: 226

Arg Ala Phe Tyr Ser Gly Phe Pro Thr Gly Tyr
1               5                   10

<210> SEQ ID NO 227
<211> LENGTH: 110
<212> TYPE: PRT
<213> ORGANISM: Artificial Sequence
<220> FEATURE:
<223> OTHER INFORMATION: Description of Artificial Sequence: Synthetic
      KPS44-G6 VL polypeptide

<400> SEQUENCE: 227

Gln Ser Val Leu Thr Gln Pro Pro Ser Val Ser Ala Ala Pro Gly Gln
1               5                   10                  15

Lys Val Thr Ile Ala Cys Ser Gly Thr Ser Ser Asn Ile Gly Ser Glu
            20                  25                  30

Ser Val Ser Trp Phe Gln Gln Leu Pro Gly Thr Ala Pro Lys Leu Leu
        35                  40                  45

Ile Tyr Glu Asn Asn Lys Arg Pro Ser Gly Ile Ser Asp Arg Phe Ser
    50                  55                  60

Gly Ser Lys Ser Gly Thr Ser Val Thr Leu Gly Ile Thr Gly Leu Gln
65                  70                  75                  80

Thr Gly Asp Glu Ala Asp Tyr Tyr Cys Ala Thr Phe Glu Ser Ser Leu
                85                  90                  95

Ser Ala Tyr Val Phe Gly Thr Gly Thr Lys Val Thr Val Leu
            100                 105                 110

<210> SEQ ID NO 228
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS44-G6 VL-CDR1 peptide
```

-continued

<400> SEQUENCE: 228

Ser Ser Asn Ile Gly Ser Glu Ser
1               5

<210> SEQ ID NO 229
<211> LENGTH: 3
<212> TYPE: PRT
<213> ORGANISM: Artificial Sequence
<220> FEATURE:
<223> OTHER INFORMATION: Description of Artificial Sequence: Synthetic
      KPS44-G6 VL-CDR2 peptide

<400> SEQUENCE: 229

Glu Asn Asn
1

<210> SEQ ID NO 230
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-G6 VL-CDR3 peptide

<400> SEQUENCE: 230

Ala Thr Phe Glu Ser Ser Leu Ser Ala Tyr Val
1               5                   10

<210> SEQ ID NO 231
<211> LENGTH: 360
<212> TYPE: DNA
<213> ORGANISM: Artificial Sequence
<220> FEATURE:
<223> OTHER INFORMATION: Description of Artificial Sequence: Synthetic
      KPS44-G6 VH polynucleotide

<400> SEQUENCE: 231
caggtacagc ttgtagaaag tgggggtggg cttgtcaagc ctgggggaag tttgagactg      60
agttgcgccg caagtggctt cacgtttaag aacgcatgga tgtcctggat tagacaagcc    120
cccggtaaag gtttggaatg ggtaggacga gttaagtctg aggttgacgc cgggacgata    180
gattacggtg ttcccgtgcg cggcagattc acgataagtc gagacgactc taagaataca    240
ctttacctcc agatgaatag cctcaaaacc gaggatacag ccgtttatta ttgccgcgca    300
ttctatagtg gcttcccgac tgggtactgg gggcaaggta ctcttgtcac agtgtcatcc    360

<210> SEQ ID NO 232
<211> LENGTH: 330
<212> TYPE: DNA
<213> ORGANISM: Artificial Sequence
<220> FEATURE:
<223> OTHER INFORMATION: Description of Artificial Sequence: Synthetic
      KPS44-G6 VL polynucleotide

<400> SEQUENCE: 232
cagtccgttt tgacgcaacc cccgtcagtg agtgctgcgc ctgggcagaa ggtgacgatc      60
gcctgctcag ggaccagcag taatataggc tctgagtctg tatcatggtt ccagcaactg    120
cctggcacgg cacctaaact gctgatctac gaaaataata gcggccctc aggcatttca    180 gataggttct ctgggagcaa gagtggtaca agcgtaacgc tcggtatcac cggtctccag    240
acaggtgatg aagctgatta ctactgcgct acttttgaga gctctctttc agcttacgtg    300
tttggtaccg ggaccaaagt gacagtcctc                                     330

<210> SEQ ID NO 233
<211> LENGTH: 120
<212> TYPE: PRT
<213> ORGANISM: Artificial Sequence
<220> FEATURE:
<223> OTHER INFORMATION: Description of Artificial Sequence: Synthetic
      KPS44-G8 VH polypeptide

<400> SEQUENCE: 233

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Lys Asn Ala
            20                  25                  30

Trp Met Ser Trp Ile Arg Gln Ala Pro Gly Lys Gly Leu Glu Trp Val
        35                  40                  45

Gly Arg Val Lys Ser Glu Val Asp Ala Gly Thr Ile Asp Tyr Gly Val
    50                  55                  60

Pro Val Arg Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Arg Ala Phe Tyr Ser Gly Phe Pro Thr Gly Tyr Trp Gly Gln
            100                 105                 110

Gly Thr Leu Val Thr Val Ser Ser
        115                 120

<210> SEQ ID NO 234
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS44-G8 VH-CDR1 peptide

<400> SEQUENCE: 234

Gly Phe Thr Phe Lys Asn Ala Trp
1               5

<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence: Synthetic
      KPS44-G8 VH-CDR2 peptide

<400> SEQUENCE: 235

Val Lys Ser Glu Val Asp Ala Gly Thr Ile
1               5                   10

<210> SEQ ID NO 236
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-G8 VH-CDR3 peptide

<400> SEQUENCE: 236

Arg Ala Phe Tyr Ser Gly Phe Pro Thr Gly Tyr
1               5                   10

```
<210> SEQ ID NO 237
<211> LENGTH: 110
<212> TYPE: PRT
<213> ORGANISM: Artificial Sequence
<220> FEATURE:
<223> OTHER INFORMATION: Description of Artificial Sequence: Synthetic
      KPS44-G8 VL polypeptide

<400> SEQUENCE: 237

Gln Ser Val Leu Thr Gln Pro Pro Ser Val Ala Ala Pro Gly Gln
1               5                   10                  15

Lys Val Thr Ile Ala Cys Ser Gly Thr Ser Ser Asn Ile Gly Ser Asp
            20                  25                  30

Ser Val Ser Trp Phe Gln Gln Leu Pro Gly Thr Ala Pro Lys Leu Leu
        35                  40                  45

Ile Tyr Glu Asn Asn Lys Arg Pro Ser Gly Ile Ser Asp Arg Phe Ser
    50                  55                  60

Gly Ser Lys Ser Gly Thr Ser Val Thr Leu Gly Ile Thr Gly Leu Gln
65              70                  75                  80

Thr Gly Asp Glu Ala Asp Tyr Tyr Cys Ala Thr Phe Glu Ser Ser Leu
                85                  90                  95

Ser Ala Tyr Val Phe Gly Thr Gly Thr Lys Val Thr Val Leu
            100                 105                 110

<210> SEQ ID NO 238
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS44-G8 VL-CDR1 peptide

<400> SEQUENCE: 238

Ser Ser Asn Ile Gly Ser Asp Ser
1               5

<210> SEQ ID NO 239
<211> LENGTH: 3
<212> TYPE: PRT
<213> ORGANISM: Artificial Sequence
<220> FEATURE:
<223> OTHER INFORMATION: Description of Artificial Sequence: Synthetic
      KPS44-G8 VL-CDR2 peptide

<400> SEQUENCE: 239

Glu Asn Asn
1

<210> SEQ ID NO 240
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-G8 VL-CDR3 peptide

<400> SEQUENCE: 240

Ala Thr Phe Glu Ser Ser Leu Ser Ala Tyr Val
1               5                   10

<210> SEQ ID NO 241
<211> LENGTH: 360
<212> TYPE: DNA
<213> ORGANISM: Artificial Sequence
<220> FEATURE:
```

<223> OTHER INFORMATION: Description of Artificial Sequence: Synthetic
KPS44-G8 VH polynucleotide

<400> SEQUENCE: 241

```
caggtacagc ttgtagaaag tggggtggg cttgtcaagc ctgggggaag tttgagactg      60
agttgcgccg caagtggctt cacgtttaag aacgcatgga tgtcctggat tagacaagcc    120
cccggtaaag gtttggaatg ggtaggacga gttaagtctg aggttgacgc cgggacgata    180
gattacggtg ttcccgtgcg cggcagattc acgataagtc gagacgactc taagaataca    240
ctttacctcc agatgaatag cctcaaaacc gaggatacag ccgtttatta ttgccgcgca    300
ttctatagtg gcttcccgac tgggtactgg gggcaaggta ctcttgtcac agtgtcatcc    360
```

<210> SEQ ID NO 242
<211> LENGTH: 330
<212> TYPE: DNA
<213> ORGANISM: Artificial Sequence
<220> FEATURE:
<223> OTHER INFORMATION: Description of Artificial Sequence: Synthetic
KPS44-G8 VL polynucleotide

<400> SEQUENCE: 242

```
cagtccgttt tgacgcaacc cccgtcagtg agtgctgcgc tgggcagaa ggtgacgatc      60
gcctgctcag ggaccagcag taatataggc tctgattctg tatcatggtt ccagcaactg    120
cctggcacgg cacctaaact gctgatctac gaaaataata gcggccctc aggcatttca    180
gataggttct ctgggagcaa gagtggtaca agcgtaacgc tcggtatcac cggtctccag    240
acaggtgatg aagctgatta ctactgcgct acttttgaga gctctctttc agcttacgtg    300
tttggtaccg ggaccaaagt gacagtcctc                                      330
```

<210> SEQ ID NO 243
<211> LENGTH: 120
<212> TYPE: PRT
<213> ORGANISM: Artificial Sequence
<220> FEATURE:
<223> OTHER INFORMATION: Description of Artificial Sequence: Synthetic
KPS44-G10 VH polypeptide

<400> SEQUENCE: 243

```
Glu Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Lys Asn Ala
            20                  25                  30

Trp Met Ser Trp Ile Arg Gln Ala Pro Gly Lys Gly Leu Glu Trp Val
        35                  40                  45

Gly Arg Val Lys Ser Glu Val Asp Ala Gly Thr Ile Asp Tyr Gly Val
    50                  55                  60

Pro Val Arg Gly Arg Phe Thr Ile Ser Arg Asp Asp Ser Gln Gly Thr
65                  70                  75                  80

Leu Ser Leu Glu Met Asn Ser Leu Lys Asp Asp Thr Gly Val Tyr
                85                  90                  95

Tyr Cys Arg Ala Phe Tyr Ser Gly Phe Pro Thr Gly Tyr Trp Gly Gln
            100                 105                 110

Gly Ala Leu Val Ser Val Ser Ser
        115                 120
```

<210> SEQ ID NO 244
<211> LENGTH: 8
<212> TYPE: PRT

```
<213> ORGANISM: Artificial Sequence
<220> FEATURE:
<223> OTHER INFORMATION: Description of Artificial Sequence: Synthetic
      KPS44-G10 VH-CDR1 peptide

<400> SEQUENCE: 244

Gly Phe Thr Phe Lys Asn Ala Trp
1               5

<210> SEQ ID NO 245
<211> LENGTH: 10
<212> TYPE: PRT
<213> ORGANISM: Artificial Sequence
<220> FEATURE:
<223> OTHER INFORMATION: Description of Artificial Sequence: Synthetic
      KPS44-G10 VH-CDR2 peptide

<400> SEQUENCE: 245

Val Lys Ser Glu Val Asp Ala Gly Thr Ile
1               5                   10

<210> SEQ ID NO 246
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-G10 VH-CDR3 peptide

<400> SEQUENCE: 246

Arg Ala Phe Tyr Ser Gly Phe Pro Thr Gly Tyr
1               5                   10

<210> SEQ ID NO 247
<211> LENGTH: 110
<212> TYPE: PRT
<213> ORGANISM: Artificial Sequence
<220> FEATURE:
<223> OTHER INFORMATION: Description of Artificial Sequence: Synthetic
      KPS44-G10 VL polypeptide

<400> SEQUENCE: 247

Gln Ser Val Leu Thr Gln Pro Pro Ser Leu Ser Ala Ala Pro Gly Gln
1               5                   10                  15

Thr Ile Thr Ile Ala Cys Ser Gly Thr Ser Ser Asn Ile Gly Ser Asp
            20                  25                  30

Ser Val Ser Trp Phe Gln Gln Phe Pro Gly Thr Ala Pro Arg Val Leu
        35                  40                  45

Ile Tyr Glu Asn Asn Lys Arg Pro Ser Gly Ile Ser Asp Arg Phe Ser
    50                  55                  60

Gly Ser Lys Ser Gly Thr Ser Val Thr Leu Gly Ile Thr Gly Leu Gln
65                  70                  75                  80

Thr Gly Asp Glu Ala Asp Tyr Tyr Cys Ala Thr Phe Glu Ser Ser Leu
                85                  90                  95

Ser Ala Tyr Val Phe Gly Ser Gly Thr Lys Val Thr Val Leu
            100                 105                 110

<210> SEQ ID NO 248
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS44-G10 VL-CDR1 peptide
```

```
<400> SEQUENCE: 248

Ser Ser Asn Ile Gly Ser Asp Ser
1               5

<210> SEQ ID NO 249
<211> LENGTH: 3
<212> TYPE: PRT
<213> ORGANISM: Artificial Sequence
<220> FEATURE:
<223> OTHER INFORMATION: Description of Artificial Sequence: Synthetic
      KPS44-G10 VL-CDR2 peptide

<400> SEQUENCE: 249

Glu Asn Asn
1

<210> SEQ ID NO 250
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-G10 VL-CDR3 peptide

<400> SEQUENCE: 250

Ala Thr Phe Glu Ser Ser Leu Ser Ala Tyr Val
1               5                   10

<210> SEQ ID NO 251
<211> LENGTH: 360
<212> TYPE: DNA
<213> ORGANISM: Artificial Sequence
<220> FEATURE:
<223> OTHER INFORMATION: Description of Artificial Sequence: Synthetic
      KPS44-G10 VH polynucleotide

<400> SEQUENCE: 251
gaggtacacc ttgtagaaag tgggggtggg cttgtcaagc tgggggaag tttgagactg      60 agttgcgccg caagtggctt cacgtttaag aacgcatgga tgtcctggat tagacaagcc    120
cccggtaaag gtttggaatg ggtaggacga gttaagtctg aggttgacgc ggggacgata    180
gattacggtg ttcccgtgcg cggcagattc acgataagtc gagacgactc tcagggtaca    240
cttagcctcg aaatgaatag cctcaaagac gatgatacag gcgttattat tgccgcgca    300 ttctacagtg gcttcccgac tgggtactgg gggcaaggtg ctcttgtctc agtgtcatcc    360

<210> SEQ ID NO 252
<211> LENGTH: 330
<212> TYPE: DNA
<213> ORGANISM: Artificial Sequence
<220> FEATURE:
<223> OTHER INFORMATION: Description of Artificial Sequence: Synthetic
      KPS44-G10 VL polynucleotide

<400> SEQUENCE: 252
cagtccgttt tgacgcaacc cccgtcactg agtgctgcgc ctgggcagac cataacgatc     60
gcctgctcag ggaccagcag taatataggc tctgattctg tatcatggtt ccagcaattc    120
cctggcacgg cacctcgcgt actgatctac gaaaataata gcggccctc aggcatttca    180 gataggttct ctgggagcaa gagtggtaca agcgtaacgc tcggtatcac cggtctccag    240
acaggtgatg aagctgatta ctactgcgct acttttgaga gctctctttc agcttacgtg    300
tttggttccg ggaccaaagt gacagtcctc                                    330
```

<210> SEQ ID NO 253
<211> LENGTH: 120
<212> TYPE: PRT
<213> ORGANISM: Artificial Sequence
<220> FEATURE:
<223> OTHER INFORMATION: Description of Artificial Sequence: Synthetic
      KPS44-G11 VH polypeptide

<400> SEQUENCE: 253

Glu Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Lys Asn Ala
            20                  25                  30

Trp Met Ser Trp Ile Arg Gln Ala Pro Gly Lys Gly Leu Glu Trp Val
        35                  40                  45

Gly Arg Val Lys Ser Glu Val Asp Ala Gly Thr Ile Asp Tyr Gly Val
50                  55                  60

Pro Val Arg Gly Arg Phe Thr Ile Ser Arg Asp Asp Ser Gln Gly Thr
65                  70                  75                  80

Leu Ser Leu Glu Met Asn Ser Leu Lys Asp Asp Asp Thr Gly Val Tyr
                85                  90                  95

Tyr Cys Arg Ala Phe Tyr Ser Gly Phe Pro Thr Gly Tyr Trp Gly Gln
            100                 105                 110

Gly Ala Leu Val Ser Val Ser Ser
        115                 120

<210> SEQ ID NO 254
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS44-G11 VH-CDR1 peptide

<400> SEQUENCE: 254

Gly Phe Thr Phe Lys Asn Ala Trp
1               5

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      KPS44-G11 VH-CDR2 peptide

<400> SEQUENCE: 255

Val Lys Ser Glu Val Asp Ala Gly Thr Ile
1               5                   10

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-G11 VH-CDR3 peptide

<400> SEQUENCE: 256

Arg Ala Phe Tyr Ser Gly Phe Pro Thr Gly Tyr
1               5                   10

<210> SEQ ID NO 257

```
<211> LENGTH: 110
<212> TYPE: PRT
<213> ORGANISM: Artificial Sequence
<220> FEATURE:
<223> OTHER INFORMATION: Description of Artificial Sequence: Synthetic
      KPS44-G11 VL polypeptide

<400> SEQUENCE: 257

Gln Ser Val Leu Thr Gln Pro Pro Ser Val Ser Ala Ala Pro Gly Gln
1               5                   10                  15

Lys Val Thr Ile Ala Cys Ser Gly Thr Ser Ser Asn Ile Gly Ser Asp
            20                  25                  30

Ser Val Ser Trp Phe Gln Gln Leu Pro Gly Thr Ala Pro Lys Leu Leu
        35                  40                  45

Ile Tyr Glu Asn Asn Lys Arg Pro Ser Gly Ile Ser Asp Arg Phe Ser
    50                  55                  60

Gly Ser Lys Ser Gly Thr Ser Val Thr Leu Gly Ile Thr Gly Leu Gln
65                  70                  75                  80

Thr Gly Asp Glu Ala Asp Tyr Tyr Cys Ala Thr Phe Glu Ser Ser Leu
                85                  90                  95

Ser Ala Tyr Val Phe Gly Thr Gly Thr Lys Val Thr Val Leu
            100                 105                 110

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS44-G11 VL-CDR1 peptide

<400> SEQUENCE: 258

Ser Ser Asn Ile Gly Ser Asp Ser
1               5

<210> SEQ ID NO 259
<211> LENGTH: 3
<212> TYPE: PRT
<213> ORGANISM: Artificial Sequence
<220> FEATURE:
<223> OTHER INFORMATION: Description of Artificial Sequence: Synthetic
      KPS44-G11 VL-CDR2 peptide

<400> SEQUENCE: 259

Glu Asn Asn
1

<210> SEQ ID NO 260
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-G11 VL-CDR3 peptide

<400> SEQUENCE: 260

Ala Thr Phe Glu Ser Ser Leu Ser Ala Tyr Val
1               5                   10

<210> SEQ ID NO 261
<211> LENGTH: 360
<212> TYPE: DNA
<213> ORGANISM: Artificial Sequence
<220> FEATURE:
```

<223> OTHER INFORMATION: Description of Artificial Sequence: Synthetic
KPS44-G11 VH polynucleotide

<400> SEQUENCE: 261

```
gaggtacacc ttgtagaaag tggggtggg cttgtcaagc ctgggggaag tttgagactg    60
agttgcgccg caagtggctt cacgtttaag aacgcatgga tgtcctggat tagacaagcc   120
cccggtaaag gtttggaatg ggtaggacga gttaagtctg aggttgacgc ggggacgata   180
gattacggtg ttcccgtgcg cggcagattc acgataagtc gagacgactc tcagggtaca   240
cttagcctcg aaatgaatag cctcaaagac gatgatacag gcgtttatta ttgccgcgca   300
ttctacagtg gcttcccgac tgggtactgg gggcaaggtg ctcttgtctc agtgtcatcc   360
```

<210> SEQ ID NO 262
<211> LENGTH: 330
<212> TYPE: DNA
<213> ORGANISM: Artificial Sequence
<220> FEATURE:
<223> OTHER INFORMATION: Description of Artificial Sequence: Synthetic
KPS44-G11 VL polynucleotide

<400> SEQUENCE: 262

```
cagtccgttt tgacgcaacc cccgtcagtg agtgctgcgc ctgggcagaa ggtgacgatc    60
gcctgctcag ggaccagcag taatataggc tctgattctg tatcatggtt ccagcaactg   120
cctggcacgg cacctaaact gctgatctac gaaaataata gcggccctc aggcatttca   180
gataggttct ctgggagcaa gagtggtaca agcgtaacgc tcggtatcac cggtctccag   240
acaggtgatg aagctgatta ctactgcgct acttttgaga gctctctttc agcttacgtg   300
tttggtaccg ggaccaaagt gacagtcctc                                    330
```

<210> SEQ ID NO 263
<211> LENGTH: 120
<212> TYPE: PRT
<213> ORGANISM: Artificial Sequence
<220> FEATURE:
<223> OTHER INFORMATION: Description of Artificial Sequence: Synthetic
KPS44-G14 VH polypeptide

<400> SEQUENCE: 263

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Lys Asn Ala
            20                  25                  30

Trp Met Ser Trp Ile Arg Gln Ala Pro Gly Lys Gly Leu Glu Trp Val
        35                  40                  45

Gly Arg Val Lys Ser Glu Val Asp Ala Gly Thr Ile Asp Tyr Gly Val
    50                  55                  60

Pro Val Arg Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Arg Ala Phe Tyr Ser Gly Phe Pro Thr Gly Tyr Trp Gly Gln
            100                 105                 110

Gly Thr Leu Val Thr Val Ser Ser
        115                 120
```

<210> SEQ ID NO 264
<211> LENGTH: 8
<212> TYPE: PRT

```
<213> ORGANISM: Artificial Sequence
<220> FEATURE:
<223> OTHER INFORMATION: Description of Artificial Sequence: Synthetic
      KPS44-G14 VH-CDR1 peptide

<400> SEQUENCE: 264

Gly Phe Thr Phe Lys Asn Ala Trp
1               5

<210> SEQ ID NO 265
<211> LENGTH: 10
<212> TYPE: PRT
<213> ORGANISM: Artificial Sequence
<220> FEATURE:
<223> OTHER INFORMATION: Description of Artificial Sequence: Synthetic
      KPS44-G14 VH-CDR2 peptide

<400> SEQUENCE: 265

Val Lys Ser Glu Val Asp Ala Gly Thr Ile
1               5                   10

<210> SEQ ID NO 266
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-G14 VH-CDR3 peptide

<400> SEQUENCE: 266

Arg Ala Phe Tyr Ser Gly Phe Pro Thr Gly Tyr
1               5                   10

<210> SEQ ID NO 267
<211> LENGTH: 110
<212> TYPE: PRT
<213> ORGANISM: Artificial Sequence
<220> FEATURE:
<223> OTHER INFORMATION: Description of Artificial Sequence: Synthetic
      KPS44-G14 VL polypeptide

<400> SEQUENCE: 267

Gln Ser Val Leu Thr Gln Pro Pro Ser Leu Ser Ala Ala Pro Gly Gln
1               5                   10                  15

Thr Ile Thr Ile Ala Cys Ser Gly Thr Ser Ser Asn Ile Gly Ser Asp
            20                  25                  30

Ser Val Ser Trp Phe Gln Gln Phe Pro Gly Thr Ala Pro Arg Val Leu
        35                  40                  45

Ile Tyr Glu Asn Asn Lys Arg Pro Ser Gly Ile Ser Asp Arg Phe Ser
    50                  55                  60

Gly Ser Lys Ser Gly Thr Ser Val Thr Leu Gly Ile Thr Gly Leu Gln
65                  70                  75                  80

Thr Gly Asp Glu Ala Asp Tyr Tyr Cys Ala Thr Phe Glu Ser Ser Leu
                85                  90                  95

Ser Ala Tyr Val Phe Gly Ser Gly Thr Lys Val Thr Val Leu
            100                 105                 110

<210> SEQ ID NO 268
<211> LENGTH: 8
<212> TYPE: PRT
<213> ORGANISM: Artificial Sequence
<220> FEATURE:
<223> OTHER INFORMATION: Description of Artificial Sequence: Synthetic
      KPS44-G14 VL-CDR1 peptide
```

```
<400> SEQUENCE: 268

Ser Ser Asn Ile Gly Ser Asp Ser
1               5

<210> SEQ ID NO 269
<211> LENGTH: 3
<212> TYPE: PRT
<213> ORGANISM: Artificial Sequence
<220> FEATURE:
<223> OTHER INFORMATION: Description of Artificial Sequence: Synthetic
      KPS44-G14 VL-CDR2 peptide

<400> SEQUENCE: 269

Glu Asn Asn
1

<210> SEQ ID NO 270
<211> LENGTH: 11
<212> TYPE: PRT
<213> ORGANISM: Artificial Sequence
<220> FEATURE:
<223> OTHER INFORMATION: Description of Artificial Sequence: Synthetic
      KPS44-G14 VL-CDR3 peptide

<400> SEQUENCE: 270

Ala Thr Phe Glu Ser Ser Leu Ser Ala Tyr Val
1               5                   10

<210> SEQ ID NO 271
<211> LENGTH: 360
<212> TYPE: DNA
<213> ORGANISM: Artificial Sequence
<220> FEATURE:
<223> OTHER INFORMATION: Description of Artificial Sequence: Synthetic
      KPS44-G14 VH polynucleotide

<400> SEQUENCE: 271
caggtacagc ttgtagaaag tgggggtggg cttgtcaagc ctgggggaag tttgagactg      60
agttgcgccg caagtggctt cacgtttaag aacgcatgga tgtcctggat tagacaagcc     120
cccggtaaag gtttggaatg ggtaggacga gttaagtctg aggttgacgc cgggacgata     180
gattacggtg ttcccgtgcg cggcagattc acgataagtc gagacgactc taagaataca     240
ctttacctcc agatgaatag cctcaaaacc gaggatacag ccgttttatta ttgccgcgca     300 ttctatagtg gcttcccgac tgggtactgg gggcaaggta ctcttgtcac agtgtcatcc     360

<210> SEQ ID NO 272
<211> LENGTH: 330
<212> TYPE: DNA
<213> ORGANISM: Artificial Sequence
<220> FEATURE:
<223> OTHER INFORMATION: Description of Artificial Sequence: Synthetic
      KPS44-G14 VL polynucleotide

<400> SEQUENCE: 272
cagtccgttt tgacgcaacc cccgtcactg agtgctgcgc ctgggcagac cataacgatc      60
gcctgctcag ggaccagcag taatataggc tctgattctg tatcatggtt ccagcaattc     120
cctggcacgg cacctcgcgt actgatctac gaaaataata gcggccctc aggcatttca      180 gataggttct ctgggagcaa gagtggtaca agcgtaacgc tcggtatcac cggtctccag     240
acaggtgatg aagctgatta ctactgcgct acttttgaga ctctctttc agcttacgtg      300 tttggttccg ggaccaaagt gacagtcctc                                      330
```

<210> SEQ ID NO 273
<211> LENGTH: 120
<212> TYPE: PRT
<213> ORGANISM: Artificial Sequence
<220> FEATURE:
<223> OTHER INFORMATION: Description of Artificial Sequence: Synthetic
      KPS44-G8-HCvFW1 polypeptide

<400> SEQUENCE: 273

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Lys Asn Ala
            20                  25                  30

Trp Met Ser Trp Ile Arg Gln Ala Pro Gly Lys Gly Leu Glu Trp Val
        35                  40                  45

Gly Arg Val Lys Ser Glu Val Asp Ala Gly Thr Ile Asp Tyr Gly Val
    50                  55                  60

Pro Val Arg Gly Arg Phe Thr Ile Ser Arg Asp Asp Ser Gln Gly Thr
65                  70                  75                  80

Leu Tyr Leu Gln Met Asn Ser Leu Lys Thr Glu Asp Thr Gly Val Tyr
                85                  90                  95

Tyr Cys Arg Ala Phe Tyr Ser Gly Phe Pro Thr Gly Tyr Trp Gly Gln
            100                 105                 110

Gly Thr Leu Val Thr Val Ser Ser
        115                 120

<210> SEQ ID NO 274
<211> LENGTH: 120
<212> TYPE: PRT
<213> ORGANISM: Artificial Sequence
<220> FEATURE:
<223> OTHER INFORMATION: Description of Artificial Sequence: Synthetic
      KPS44-G8-HCvFW2 polypeptide

<400> SEQUENCE: 274

Gln Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Lys Asn Ala
            20                  25                  30

Trp Met Ser Trp Ile Arg Gln Ala Pro Gly Lys Gly Leu Glu Trp Val
        35                  40                  45

Gly Arg Val Lys Ser Glu Val Asp Ala Gly Thr Ile Asp Tyr Gly Val
    50                  55                  60

Pro Val Arg Gly Arg Phe Thr Ile Ser Arg Asp Asp Ser Gln Gly Thr
65                  70                  75                  80

Leu Tyr Leu Gln Met Asn Ser Leu Lys Thr Glu Asp Thr Gly Val Tyr
                85                  90                  95

Tyr Cys Arg Ala Phe Tyr Ser Gly Phe Pro Thr Gly Tyr Trp Gly Gln
            100                 105                 110

Gly Thr Leu Val Thr Val Ser Ser
        115                 120

ANTI-O2 ANTIBODIES AND USES THEREOF

CROSS-REFERENCE TO RELATED APPLICATIONS

This application is a U.S. National Stage application of International Application No. PCT/US2017/045480, filed on Aug. 4, 2017, said International Application No. PCT/US2017/045480 claims benefit under 35 U.S.C. § 119(e) of the U.S. Provisional Application No. 62/371,402, filed Dec. 19, 2014 Aug. 5, 2016. Each of the above listed applications is incorporated by reference herein in its entirety for all purposes.

REFERENCE TO THE SEQUENCE LISTING

This application incorporates by reference a Sequence Listing submitted with the International Application and published as part of the description.

REFERENCE TO SEQUENCE LISTING SUBMITTED ELECTRONICALLY

The content of the electronically submitted sequence listing in ASCII text file KLEB-100-WO-PCT_SL.txt (Size: 138,288 bytes; and Date of Creation: Aug. 4, 2017) filed with the application is incorporated herein by reference in its entirety.

BACKGROUND OF THE INVENTION

Field of the Invention

The field of the invention generally relates to antigen binding proteins (e.g., antibodies and antigen-binding fragments thereof) that specifically bind to *Klebsiella pneumoniae* O2 antigen and the use of those binding proteins for prevention or treatment of *Klebsiella* infections.

Background of the Invention

*Klebsiella* is a Gram negative bacterium that is rapidly gaining clinical importance as a causative agent for opportunistic and nosocomial infection, including pneumonia, urinary tract infection, neonatal septicemia, and surgery wound infection. In addition, there are emerging syndromes associated with *Klebsiella* infections such as pyogenic liver abscesses (PLA), endophthalmitis, meningitis, and necrotizing meningitis. (See Iredell et al. *BMJ* 351: h6420 (2015).)

Antibiotic resistance has emerged as one of the major challenges in the fight against bacterial infections. While some progress has been made against drug resistant *Staphylococcus aureus*, Gram negative opportunistic infections are most problematic. Among these, *Klebsiella pneumoniae* has become particularly challenging with multi-drug resistant strains widely circulating. Antibiotic resistances such as Extended-Spectrum Beta Lactamase (ESBL), *K. pneumoniae* carbapenemase (KPC), and New Delhi metallo-beta-lactamase 1 (NDM-1) have spread worldwide and rendered current antibiotic classes largely inadequate. This reality coupled with the dwindling antibiotics pipeline leaves few therapeutic alternatives. Several recent high profile outbreaks underscore the urgency associated with *K. pneumoniae* antibiotic resistance. It is therefore critical to develop strategies to complement antibiotics therapies.

Multiple virulence factors have been implicated in *K. pneumoniae* pathogenesis, including capsular polysaccharides (CPS) and lipopolysaccharides (LPS). Polyclonal antibodies directed against LPS and CPS are protective in preclinical models of lethal *K. pneumoniae* infections. However targeting these two antigens with antibodies poses a significant challenge with respect to strain coverage. There are more than seventy-seven known capsule serotypes and eight O-antigen serotypes, and it is not clear which are the most prevalent or associated with pathogenesis. In addition, the limited number of monoclonal antibodies targeting conserved epitopes within LPS have no reported protective effect (Brade et al. 2001, J Endotoxin Res, 7(2):119-24).

Thus, there is a great need to identify and develop antibodies that have protective effect against *Klebsiella*, (e.g., *K. pneumoniae*), especially antibiotic resistant *Klebsiella*, infections.

BRIEF SUMMARY OF THE INVENTION

The present disclosure provides *K. pneumoniae* O2 binding proteins, e.g., antibodies or antigen binding fragments thereof, and methods of treating *Klebsiella* infections using *K. pneumoniae* O2 binding proteins.

In one instance provided herein is an isolated antigen binding protein that specifically binds to *Klebsiella pneumoniae* O2 antigen, wherein the antigen binding protein induces opsonophagocytic killing (OPK) of *Klebsiella*. In one instance, the antigen binding protein induces OPK of O1 serotype *Klebsiella* and O2 serotype *Klebsiella*. In one instance, the antigen binding protein induces OPK of O2 serotype *Klebsiella*, but does not induce OPK of O1 serotype *Klebsiella*.

In one instance, the antigen binding protein that specifically binds to *Klebsiella pneumoniae* O2 antigen protects mice from a lethal *Klebsiella* challenge.

In one instance, the antigen binding protein that specifically binds to *Klebsiella pneumoniae* O2 antigen neutralizes lipopolysaccharide (LPS). In one instance, the antigen binding protein that specifically binds to *Klebsiella pneumoniae* O2 antigen inhibits, reduces, or prevents NF-kB activation induced by LPS. In one instance, the antigen binding protein inhibits, reduces, or prevents NF-kB activation induced by both *Klebsiella pneumoniae* O1 LPS and *Klebsiella pneumoniae* O2 LPS. In one instance, the antigen binding protein inhibits, reduces, or prevents NF-kB activation induced by *Klebsiella pneumoniae* O2 LPS, but does not inhibit, reduce, or prevent NF-kB activation induced by *Klebsiella pneumoniae* O1 LPS.

In one instance, the antigen binding protein that specifically binds to *Klebsiella pneumoniae* O2 antigen: (i) neutralizes O1 and/or O2 LPS and induces OPK of O2 serotype *Klebsiella* but does not induce OPK of O1 serotype *Klebsiella*; (ii) neutralizes O1 and/or O2 LPS and induces OPK of O1 serotype *Klebsiella* and O2 serotype *Klebsiella*; or (iii) does not neutralize O1 LPS and induces OPK of O2 serotype *Klebsiella* but does not induce OPK of O1 serotype *Klebsiella*.

In one instance, the antigen binding protein that specifically binds to *Klebsiella pneumoniae* O2 antigen induces OPK of *K. pneumoniae, K. oxytoca, K. granulomatis, K. ozaenae, K. rhinoscleromatis* and/or *K. planticola*. In one instance, the antigen binding protein induces OPK of *K. pneumoniae*.

In one instance, the antigen binding protein that specifically binds to *Klebsiella pneumoniae* O2 antigen also binds to *Klebsiella pneumoniae* O1 antigen.

In one instance, the antigen binding protein that specifically binds to *Klebsiella pneumoniae* O2 antigen a) induces OPK in a multi-drug resistant *Klebsiella*, b) protects mice from a lethal multi-drug resistant *Klebsiella* challenge, or c) induces OPK of a multi-drug resistant *Klebsiella* and protects mice from a lethal multi-drug resistant *Klebsiella* challenge. In one instance, the multi-drug resistant *Klebsiella* is strain Kp961842 or Kp977778 (both of which are ST258 strains). In one instance, the multi-drug resistant *Klebsiella* is a strain listed in one of rows 1-226 of Table 8.

In one instance, the antigen binding protein that specifically binds to *Klebsiella pneumoniae* O2 antigen renders a multi-drug resistant *K. pneumoniae* strain sensitive to at least one antibiotic.

In one instance, the antigen binding protein that specifically binds to *Klebsiella pneumoniae* O2 antigen a) induces OPK in a *Klebsiella* that is susceptible to antibiotics, b) protects mice from a lethal *Klebsiella* challenge, wherein the *Klebsiella* is susceptible to antibiotics, or c) induces OPK in a *Klebsiella* that is susceptible to antibiotics and protects mice from a lethal *Klebsiella* challenge, wherein the *Klebsiella* is susceptible to antibiotics. In one instance, the *Klebsiella* is a strain listed in one of rows 227-254 of Table 8.

In one instance, the antigen binding protein that specifically binds to *Klebsiella pneumoniae O*2 antigen binds to gml− *Klebsiella*. In one instance, the antigen binding protein that specifically binds to *Klebsiella pneumoniae O*2 antigen binds to gml+ *Klebsiella.*

In one instance, the antigen binding protein that specifically binds to *Klebsiella pneumoniae O*2 antigen binds to the D-Galactan I domain of *K. pneumoniae O*2 antigen.

In one instance, provided herein is an isolated antigen binding protein that specifically binds to *Klebsiella pneumoniae O*2 antigen comprising a set of Complementarity-Determining Regions (CDRs): HCDR1, HCDR2, HCDR3, LCDR1, LCDR2, and LCDR3 wherein: HCDR1 has the amino acid sequence of SEQ. ID. NO:1; HCDR2 has the amino acid sequence of SEQ. ID. NO: 2; HCDR3 has the amino acid sequence of SEQ. ID. NO: 3; LCDR1 has the amino acid sequence of SEQ. ID. NO: 4; LCDR2 has the amino acid sequence of SEQ. ID. NO: 5 or 6; and LCDR3 has the amino acid sequence of SEQ. ID. NO: 7.

In one instance, provided herein is an isolated antigen binding protein that specifically binds to *Klebsiella pneumoniae O*2 antigen comprising a set of Complementarity-Determining Regions (CDRs): HCDR1, HCDR2, HCDR3, LCDR1, LCDR2, and LCDR3 wherein: HCDR1 has the amino acid sequence of SEQ. ID. NO:109; HCDR2 has the amino acid sequence of SEQ. ID. NO: 110; HCDR3 has the amino acid sequence of SEQ. ID. NO: 199; LCDR1 has the amino acid sequence of SEQ. ID. NO: 200; LCDR2 has the amino acid sequence of SEQ. ID. NO: 113 or 114; and LCDR3 has the amino acid sequence of SEQ. ID. NO: 201

In one instance, provided herein is an isolated antigen binding protein that specifically binds *Klebsiella pneumoniae O*2 antigen, wherein the antigen binding protein comprises a heavy chain variable region (VH) at least 95%, 96%, 97%, 98% or 99% identical to SEQ ID NO:8 and/or a light chain variable region (VL) at least 95%, 96%, 97%, 98% or 99% identical to SEQ ID NO:9. In one instance, the antigen binding protein thereof comprises a VH comprising SEQ ID NO:8 and a VL comprising SEQ ID NO:9.

In one instance, provided herein is an isolated antigen binding protein that specifically binds *Klebsiella pneumoniae O*2 antigen, wherein the antigen binding protein comprises a heavy chain variable region (VH) at least 95%, 96%, 97%, 98% or 99% identical to SEQ ID NO:202 and/or a light chain variable region (VL) at least 95%, 96%, 97%, 98% or 99% identical to SEQ ID NO:203. In one instance, the antigen binding protein thereof comprises a VH comprising SEQ ID NO:202 and a VL comprising SEQ ID NO:203.

In one instance, provided herein is an isolated antigen binding protein that specifically binds to *Klebsiella pneumoniae O*2 antigen comprising a VH comprising SEQ ID NO:8.

In one instance, provided herein is an isolated antigen binding protein that specifically binds to *Klebsiella pneumoniae O*2 antigen comprising a VH comprising SEQ ID NO:202.

In one instance, provided herein is an isolated antigen binding protein that specifically binds to *Klebsiella pneumoniae O*2 antigen comprising a VL comprising SEQ ID NO:9.

In one instance, provided herein is an isolated antigen binding protein that specifically binds to *Klebsiella pneumoniae O*2 antigen comprising a VL comprising SEQ ID NO:203.

In one instance, provided herein is an isolated antigen binding protein that specifically binds to the same epitope in the *Klebsiella pneumoniae O*2 antigen as an antibody comprising a VH comprising SEQ ID NO:8 and a VL comprising SEQ ID NO:9.

In one instance, provided herein is an isolated antigen binding protein that specifically binds to the same epitope in the *Klebsiella pneumoniae O*2 antigen as an antibody comprising a VH comprising SEQ ID NO:202 and a VL comprising SEQ ID NO:203.

In one instance, provided herein is an isolated antigen binding protein that competitively inhibits the binding to *Klebsiella pneumoniae O*2 antigen of an antibody comprising a VH comprising SEQ ID NO:8 and a VL comprising SEQ ID NO:9.

In one instance, provided herein is an isolated antigen binding protein that competitively inhibits the binding to *Klebsiella pneumoniae O*2 antigen of an antibody comprising a VH comprising SEQ ID NO:202 and a VL comprising SEQ ID NO:203.

In one instance, provided herein is an isolated antigen binding protein that specifically binds to *Klebsiella pneumoniae O*2 antigen comprising a set of Complementarity-Determining Regions (CDRs): HCDR1, HCDR2, HCDR3, LCDR1, LCDR2, and LCDR3 wherein the HCDR1, HCDR2, HCDR3, LCDR1, LCDR2, and LCDR3 comprise the amino acid sequences of: SEQ. ID. NOs: 10-13, 14 or 15, and 16, respectively; SEQ. ID. NOs: 19-22, 23 or 24, and 25, respectively; SEQ. ID. NOs: 28-31, 32 or 33, and 34, respectively; SEQ. ID. NOs: 37-40, 41 or 42, and 43, respectively; SEQ. ID. NOs: 46-49, 50 or 51, and 52, respectively; SEQ. ID. NOs: 166-168, 175, 176 or 177, and 178, respectively; SEQ. ID. NOs: 169-171, 179, 180 or 181, and 182, respectively; SEQ. ID. NOs: 55-58, 59 or 60, and 61, respectively; SEQ. ID. NOs: 64-67, 68 or 69, and 70, respectively; SEQ. ID. NOs: 73-78, respectively; SEQ. ID. NOs: 82-85, 86 or 87, and 88, respectively; SEQ. ID. NOs: 91-94, 95 or 96, and 97, respectively; SEQ. ID. NOs: 100-103, 104 or 105, and 106, respectively; SEQ. ID. NOs: 109-112, 113 or 114, and 115, respectively; SEQ. ID. NOs: 118-121, 122 or 123, and 124, respectively; SEQ. ID. NOs: 127-130, 131 or 132, and 133, respectively; SEQ. ID. NOs: 172-174, 183, 184 or 185, and 186, respectively; or SEQ ID NOs: 109-111, 199, 112-115, 200 and 201.

In one instance, provided herein is an isolated antigen binding protein that specifically binds to *Klebsiella pneumoniae O*2 antigen, wherein the antigen binding protein comprises a VH and VL at least 95%, 96%, 97%, 98%, or 99% identical to: SEQ. ID. NO: 17 and SEQ ID NO:18, respectively; SEQ. ID. NO: 26 and SEQ ID NO:27, respectively; SEQ. ID. NO: 35 and SEQ ID NO:36, respectively; SEQ. ID. NO: 44 and SEQ ID NO:45, respectively; SEQ. ID. NO: 53 and SEQ ID NO:54, respectively; SEQ. ID. NO: 187 and SEQ ID NO:190, respectively; SEQ. ID. NO: 188 and SEQ ID NO:191, respectively; SEQ. ID. NO: 62 and SEQ ID NO:63, respectively; SEQ. ID. NO: 71 and SEQ ID NO:72, respectively; SEQ. ID. NO: 80 and SEQ ID NO:81, respectively; SEQ. ID. NO: 89 and SEQ ID NO:90, respectively; SEQ. ID. NO: 98 and SEQ ID NO:99, respectively; SEQ. ID. NO: 107 and SEQ ID NO:108, respectively; SEQ. ID. NO: 116 and SEQ ID NO:117, respectively; SEQ. ID. NO: 125 and SEQ ID NO:126, respectively; SEQ. ID. NO: 134 and SEQ ID NO:135, respectively; SEQ. ID. NO:189 and SEQ ID NO:192, respectively; or SEQ ID NOs 116 and 202-205.

In one instance, the antigen binding protein comprises a VH and a VL comprising: SEQ. ID. NO: 17 and SEQ ID NO:18, respectively; SEQ. ID. NO: 26 and SEQ ID NO:27, respectively; SEQ. ID. NO: 35 and SEQ ID NO:36, respectively; SEQ. ID. NO: 44 and SEQ ID NO:45, respectively; SEQ. ID. NO: 53 and SEQ ID NO:54, respectively; SEQ. ID. NO: 187 and SEQ ID NO:190, respectively; SEQ. ID. NO: 188 and SEQ ID NO:191, respectively; SEQ. ID. NO: 62 and SEQ ID NO:63, respectively; SEQ. ID. NO: 71 and SEQ ID NO:72, respectively; SEQ. ID. NO: 80 and SEQ ID NO:81, respectively; SEQ. ID. NO: 89 and SEQ ID NO:90, respectively; SEQ. ID. NO: 98 and SEQ ID NO:99, respectively; SEQ. ID. NO: 107 and SEQ ID NO:108, respectively; SEQ. ID. NO: 116 and SEQ ID NO:117, respectively; SEQ. ID. NO: 125 and SEQ ID NO:126, respectively; SEQ. ID. NO: 134 and SEQ ID NO:135, respectively; SEQ. ID. NO: 189 and SEQ ID NO:192, respectively; SEQ ID NOs 116 and 202-205; SEQ ID NO:273 and SEQ ID NO:247, respectively; SEQ ID NO:273 and SEQ ID NO:257, respectively; SEQ ID NO:273 and SEQ ID NO:217, respectively; SEQ ID NO:273 and SEQ ID NO:227, respectively; SEQ ID NO:274 and SEQ ID NO:247, respectively; SEQ ID NO:274 and SEQ ID NO:257, respectively; SEQ ID NO:274 and SEQ ID NO:217, respectively; and SEQ ID NO:274 and SEQ ID NO:227, respectively.

In one instance, provided herein is an isolated antigen binding protein that specifically binds to *Klebsiella pneumoniae* O2 antigen comprising a VH comprising SEQ ID NO:17, SEQ ID NO:26, SEQ ID NO: 35, SEQ ID NO:44, SEQ ID NO:53, SEQ ID NO:187, SEQ ID NO:188, SEQ ID NO:62, SEQ ID NO:71, SEQ ID NO:80, SEQ ID NO:89, SEQ ID NO:98, SEQ ID NO:107, SEQ ID NO:116, SEQ ID NO:125, SEQ ID NO:134, SEQ ID NO:189; or SEQ ID NO: 116; SEQ ID NO:202; SEQ ID NO:213; SEQ ID NO:223; SEQ ID NO:233; SEQ ID NO:243; SEQ ID NO:253; SEQ ID NO:263; SEQ ID NO:273; or SEQ ID NO:274.

In one instance, provided herein is an isolated antigen binding protein that specifically binds to *Klebsiella pneumoniae* O2 antigen comprising a VL comprising SEQ ID NO:18, SEQ ID NO:27, SEQ ID NO: 36, SEQ ID NO:45, SEQ ID NO:54, SEQ ID NO:190, SEQ ID NO:191, SEQ ID NO:63, SEQ ID NO:72, SEQ ID NO:81, SEQ ID NO:90, SEQ ID NO:99, SEQ ID NO:108, SEQ ID NO:117, SEQ ID NO:126, SEQ ID NO:135, SEQ ID NO:192; SEQ ID NO: 203; SEQ ID NO:204; SEQ ID NO:205; SEQ ID NO:217; SEQ ID NO:227; SEQ ID NO:237; SEQ ID NO:247; SEQ ID NO:257; or SEQ ID NO:267.

In one instance, provided herein is an isolated antigen binding protein that specifically binds to the same epitope in the *Klebsiella pneumoniae* O2 antigen as an antibody comprising a VH and a VL comprising: SEQ. ID. NO: 17 and SEQ ID NO:18, respectively; SEQ. ID. NO: 26 and SEQ ID NO:27, respectively; SEQ. ID. NO: 35 and SEQ ID NO:36, respectively; SEQ. ID. NO: 44 and SEQ ID NO:45, respectively; SEQ. ID. NO: 53 and SEQ ID NO:54, respectively; SEQ. ID. NO: 187 and SEQ ID NO:190, respectively; SEQ. ID. NO: 188 and SEQ ID NO:191, respectively; SEQ. ID. NO: 62 and SEQ ID NO:63, respectively; SEQ. ID. NO: 71 and SEQ ID NO:72, respectively; SEQ. ID. NO: 80 and SEQ ID NO:81, respectively; SEQ. ID. NO: 89 and SEQ ID NO:90, respectively; SEQ. ID. NO: 98 and SEQ ID NO:99, respectively; SEQ. ID. NO: 107 and SEQ ID NO:108, respectively; SEQ. ID. NO: 116 and SEQ ID NO:117, respectively; SEQ. ID. NO: 125 and SEQ ID NO:126, respectively; SEQ. ID. NO: 134 and SEQ ID NO:135, respectively; SEQ. ID. NO: 189 and SEQ ID NO:192; or SEQ ID NOs 116 and 202-205.

In one instance, provided herein is an isolated antigen binding protein that competitively inhibits the binding to *Klebsiella pneumoniae* O2 antigen of an antibody comprising a VH and a VL comprising: SEQ. ID. NO: 17 and SEQ ID NO:18, respectively; SEQ. ID. NO: 26 and SEQ ID NO:27, respectively; SEQ. ID. NO: 35 and SEQ ID NO:36, respectively; SEQ. ID. NO: 44 and SEQ ID NO:45, respectively; SEQ. ID. NO: 53 and SEQ ID NO:54, respectively; SEQ. ID. NO: 187 and SEQ ID NO:190, respectively; SEQ. ID. NO: 188 and SEQ ID NO:191, respectively; SEQ. ID. NO: 62 and SEQ ID NO:63, respectively; SEQ. ID. NO: 71 and SEQ ID NO:72, respectively; SEQ. ID. NO: 80 and SEQ ID NO:81, respectively; SEQ. ID. NO: 89 and SEQ ID NO:90, respectively; SEQ. ID. NO: 98 and SEQ ID NO:99, respectively; SEQ. ID. NO: 107 and SEQ ID NO:108, respectively; SEQ. ID. NO: 116 and SEQ ID NO:117, respectively; SEQ. ID. NO: 125 and SEQ ID NO:126, respectively; SEQ. ID. NO: 134 and SEQ ID NO:135, respectively; SEQ. ID. NO: 189 and SEQ ID NO:192; or SEQ ID NOs 116 and 202-205.

In one instance, the antigen binding protein that specifically binds to *Klebsiella pneumoniae* O2 antigen is murine, non-human, humanized, chimeric, resurfaced, or human.

In one instance, the antigen binding protein that specifically binds to *Klebsiella pneumoniae* O2 antigen is an antibody. In one instance, the antigen binding protein that specifically binds to *Klebsiella pneumoniae* O2 antigen is an antigen binding fragment of an antibody. In one instance, the antigen binding protein that specifically binds to *Klebsiella pneumoniae* O2 antigen is a monoclonal antibody, a recombinant antibody, a human antibody, a humanized antibody, a chimeric antibody, or an antigen binding fragment thereof. In one instance, the antigen binding protein that specifically binds to *Klebsiella pneumoniae* O2 antigen comprises a Fab, Fab', F(ab')2, Fd, single chain Fv or scFv, disulfide linked Fv, V-NAR domain, IgNar, intrabody, IgGACH2, minibody, F(ab')3, single-domain antibody, DVD-Ig, Fcab, mAb2, (scFv)2, or scFv-Fc.

In one instance, the antigen binding protein (e.g. an antibody or antigen-binding fragment thereof that specifically binds to *Klebsiella pneumoniae* O2 antigen) binds to *Klebsiella* O2 antigen with an affinity constant of about 4.5E-09 or about 7.8E-09M. In one instance, the binding affinity is measured by octet binding, flow cytometry, Biacore, KinExa, or radioimmunoassay. In one instance, the antigen binding protein (e.g. an antibody or antigen-binding fragment thereof that specifically binds to *Klebsiella pneumoniae* O2 antigen) induces OPK of *Klebsiella*. In one instance, the antigen binding protein (e.g. an antibody or antigen-binding fragment thereof that specifically binds to

*Klebsiella pneumoniae* O2 antigen) induces OPK of O1 serotype *Klebsiella* and O2 serotype *Klebsiella*. In one instance, the antigen binding protein (e.g. an antibody or antigen-binding fragment thereof that specifically binds to *Klebsiella pneumoniae* O2 antigen) induces OPK of O2 serotype *Klebsiella*, but does not induce OPK of O1 serotype *Klebsiella*. In one instance, the antigen binding protein (e.g. an antibody or antigen-binding fragment thereof that specifically binds to *Klebsiella pneumoniae* O2 antigen) protects mice from a lethal *Klebsiella* challenge.

In one instance, the antigen binding protein (e.g. an antibody or antigen-binding fragment thereof that specifically binds to *Klebsiella pneumoniae* O2 antigen) neutralizes LPS. In one instance, the antigen binding protein (e.g. an antibody or antigen-binding fragment thereof) inhibits, reduces, or prevents NF-kB activation induced by LPS. In one instance, the antigen binding protein (e.g. an antibody or antigen-binding fragment thereof that specifically binds to *Klebsiella pneumoniae* O2 antigen) inhibits, reduces, or prevents NF-kB activation induced by both *Klebsiella pneumoniae* O1 LPS and *Klebsiella pneumoniae* O2 LPS. In one instance, the antigen binding protein (e.g. an antibody or antigen-binding fragment thereof that specifically binds to *Klebsiella pneumoniae* O2 antigen) inhibits, reduces, or prevents NF-kB activation induced by *Klebsiella pneumoniae* O2 LPS, but does not inhibit, reduce, or prevent NF-kB activation induced by *Klebsiella pneumoniae* O1 LPS. In one instance, the antigen binding protein (e.g. an antibody or antigen-binding fragment thereof that specifically binds to *Klebsiella pneumoniae* O2 antigen) does not neutralize O1 LPS and induces OPK of O2 serotype *Klebsiella* but does not induce OPK of O1 serotype *Klebsiella*.

In one instance, the antigen binding protein (e.g. an antibody or antigen-binding fragment thereof that specifically binds to *Klebsiella pneumoniae* O2 antigen): (i) neutralizes O1 and/or O2 LPS and induces OPK of O2 serotype *Klebsiella* but does not induce OPK of O1 serotype *Klebsiella*; (ii) neutralizes O1 and/or O2 LPS and induces OPK of O1 serotype *Klebsiella* and O2 serotype *Klebsiella*; or (iii) does not neutralize O1 LPS and induces OPK of O2 serotype *Klebsiella* but does not induce OPK of O1 serotype *Klebsiella*.

In one instance, the antigen binding protein (e.g. an antibody or antigen-binding fragment thereof that specifically binds to *Klebsiella pneumoniae* O2 antigen) induces OPK of *K. pneumoniae, K oxytoca, K. granulomatis, K. ozaenae, K. rhinosclermoatis* and/or *K. planticola*. In one instance, the antigen binding protein (e.g. an antibody or antigen-binding fragment thereof that specifically binds to *Klebsiella pneumoniae* O2 antigen) induces OPK of *K. pneumoniae*.

In one instance, the antigen binding protein (e.g. an antibody or antigen-binding fragment thereof that specifically binds to *Klebsiella pneumoniae* O2 antigen) binds to *Klebsiella pneumoniae* O1 antigen. In one instance, the antigen binding protein (e.g. an antibody or antigen-binding fragment thereof that specifically binds to *Klebsiella pneumoniae* O2 antigen): a) induces OPK in a multi-drug resistant *Klebsiella*, b) protects mice from a lethal multi-drug resistant *Klebsiella* challenge, or c) induces OPK of a multi-drug resistant *Klebsiella* and protects mice from a lethal multi-drug resistant *Klebsiella* challenge. In one instance, the multi-drug resistant *Klebsiella* is strain Kp961842 or Kp977778. In one instance, the multi-drug resistant *Klebsiella* is a strain listed in one of rows 1-226 of Table 8. In one instance, the antigen binding protein (e.g. an antibody or antigen-binding fragment thereof that specifically binds to *Klebsiella pneumoniae* O2 antigen) renders a multi-drug resistant *K. pneumoniae* strain sensitive to at least one antibiotic.

In one instance, the antigen binding protein (e.g. an antibody or antigen-binding fragment thereof that specifically binds to *Klebsiella pneumoniae* O2 antigen): a) induces OPK in a *Klebsiella* that is susceptible to antibiotics, b) protects mice from a lethal *Klebsiella* challenge, wherein the *Klebsiella* is susceptible to antibiotics, or c) induces OPK in a *Klebsiella* that is susceptible to antibiotics and protects mice from a lethal *Klebsiella* challenge, wherein the *Klebsiella* is susceptible to antibiotics. In one instance, the *Klebsiella* is a strain listed in one of rows 227-254 of Table 8.

In one instance, the antigen binding protein (e.g. an antibody or antigen-binding fragment thereof that specifically binds to *Klebsiella pneumoniae* O2 antigen) binds to gml– *Klebsiella*. In one instance, the antigen binding protein (e.g. an antibody or antigen-binding fragment thereof that specifically binds to *Klebsiella pneumoniae* O2 antigen) binds to gml+ *Klebsiella*. In one instance, the antigen binding protein (e.g. an antibody or antigen-binding fragment thereof that specifically binds to *Klebsiella pneumoniae* O2 antigen) binds to the D-Galactan I domain of *K. pneumoniae* O2 antigen.

In one instance, the antigen binding protein (e.g. an antibody or antigen-binding fragment thereof that specifically binds to *Klebsiella pneumoniae* O2 antigen) comprises a heavy chain immunoglobulin constant domain selected from the group consisting of: (a) an IgA constant domain; (b) an IgD constant domain; (c) an IgE constant domain; (d) an IgG1 constant domain; (e) an IgG2 constant domain; (f) an IgG3 constant domain; (g) an IgG4 constant domain; and (h) an IgM constant domain.

In one instance, the antigen binding protein (e.g. an antibody or antigen-binding fragment thereof that specifically binds to *Klebsiella pneumoniae* O2 antigen) comprises a light chain immunoglobulin constant domain selected from the group consisting of: (a) an Ig kappa constant domain; and (b) an Ig lambda constant domain.

In one instance, the antigen binding protein (e.g. an antibody or antigen-binding fragment thereof that specifically binds to *Klebsiella pneumoniae* O2 antigen) comprises a human IgG1 constant domain and a human lambda constant domain.

In one instance, provided herein is an isolated nucleic acid molecule encoding an antigen binding protein provided herein, including e.g., an antibody or antigen-binding fragment thereof that specifically binds to *Klebsiella pneumoniae* O2 antigen. In one instance, the nucleic acid molecule is operably linked to a control sequence.

In one instance, provided herein is a vector comprising a nucleic acid molecule provided herein.

In one instance, provided herein is a host cell transformed with a nucleic acid molecule provided herein or a vector provided herein. In one instance, the host cell is a mammalian host cell. In one instance, the host cell is a HEK293 cell, CHO cell, COS-7 cell, a HeLa cell, a NS0 murine myeloma cell, or a PER.C6® human cell.

In one instance, provided herein is a hybridoma producing an antigen binding protein provided herein, including e.g., an antibody or antigen-binding fragment thereof that specifically binds to *Klebsiella pneumoniae* O2 antigen. In one instance provided herein is an isolated host cell producing an antigen binding protein provided herein, including e.g., an antibody or antigen-binding fragment thereof that specifically binds to *Klebsiella pneumoniae* O2 antigen. In one instance, provided herein is a method of making an antigen binding protein provided herein (e.g. an antibody or antigen-binding fragment thereof that specifically binds to *Klebsiella pneumoniae* O2 antigen) comprising (a) culturing a host cell expressing the antigen binding protein or culturing a host cell provided herein or a hybridoma provided herein; and (b) isolating the antigen binding protein thereof from the cultured host cell or hybridoma. In one instance, provided herein is an antigen binding protein (e.g. an antibody or antigen-binding fragment thereof that specifically binds to *Klebsiella pneumoniae* O2 antigen) produced using a method provided herein.

In one instance, provided herein is a pharmaceutical composition comprising an antigen binding provided herein (e.g. an antibody or antigen-binding fragment thereof that specifically binds to *Klebsiella pneumoniae* O2 antigen) and a pharmaceutically acceptable excipient. In one instance, the pharmaceutically acceptable excipient is a preservative, stabilizer, or antioxidant. In one instance, the pharmaceutical composition is for use as a medicament.

In one instance, the antigen binding protein provided herein or the pharmaceutical composition provided herein (e.g. an antibody or antigen-binding fragment thereof that specifically binds to *Klebsiella pneumoniae* O2 antigen) further comprises a labeling group or an effector group. In one instance, the labeling group is selected from the group consisting of: isotopic labels, magnetic labels, redox active moieties, optical dyes, biotinylated groups, fluorescent moieties such as biotin signaling peptides, Green Fluorescent Proteins (GFPs), blue fluorescent proteins (BFPs), cyan fluorescent proteins (CFPs), yellow fluorescent proteins (YFPs), polypeptide epitopes recognized by a secondary reporter such as histidine peptide (his), hemagglutinin (HA), gold binding peptide, and Flag. In one instance, the effector group is selected from the group consisting of a radioisotope, radionuclide, a toxin, a therapeutic and a chemotherapeutic agent.

In one instance, provided herein is the use of an antigen binding protein or pharmaceutical composition provided herein (e.g. an antibody or antigen-binding fragment thereof that specifically binds to *Klebsiella pneumoniae* O2 antigen) for treating a condition associated with a *Klebsiella* infection.

In one instance, provided herein is a method for treating, preventing, or ameliorating a condition associated with a *Klebsiella* infection in a subject in need thereof comprising administering to the subject an effective amount of an antigen binding protein provided herein or a pharmaceutical composition provided herein (e.g. an antibody or antigen-binding fragment thereof that specifically binds to *Klebsiella pneumoniae* O2 antigen).

In one instance, provided herein is a method for inhibiting the growth of *Klebsiella*, or reducing the number of *Klebsiella* in a subject infected with *Klebsiella* comprising administering to a subject in need thereof an antigen binding protein provided herein or a pharmaceutical composition provided herein.

In one instance, provided herein is a method for treating, preventing, or ameliorating a condition associated with a *Klebsiella* infection in a subject in need thereof comprising administering to the subject an effective amount of antigen binding protein that that specifically binds to *Klebsiella pneumoniae* O2 antigen.

In one instance, provided herein is a method for inhibiting the growth of *Klebsiella*, or reducing the number of *Klebsiella* in a subject infected with *Klebsiella* comprising administering to a subject an effective amount of an antigen binding protein that specifically binds to *Klebsiella pneumoniae* O2 antigen.

In one instance, the *Klebsiella* is antibiotic-resistant. In one instance, the *Klebsiella* is resistant to cephalosporin, quinolone, carbapnem, meroprem, fluoroquinolone, tetracycline, chloramphenicol, trimethoprim, sulfonamide, and/or colistin.

In one instance, provided herein is a method for sensitizing an antibiotic-resistant *Klebsiella* strain to antibiotics comprising contacting the antibody-resistant *Klebsiella* strain with an antigen binding protein that that specifically binds to *Klebsiella pneumoniae* O2 antigen.

In one instance, the method further comprises administering an antibiotic. In one instance, the antigen binding protein and the antibiotic provide a synergistic therapeutic effect.

In one instance, provided herein is a method of preventing or treating a condition associated with a *Klebsiella* infection in a subject infected with an antibiotic-resistant *Klebsiella* strain, comprising co-administering to a subject an antibiotic and an antigen binding protein that specifically binds to *Klebsiella pneumoniae* O2 antigen, wherein the co-administration provides a therapeutic effect greater than the sum of the individual effects of administration of equal molar quantities of the antigen binding protein (e.g. an antibody or antigen-binding fragment thereof) or the antibiotic. In one instance, the therapeutic effect results in greater percent survival than the additive percent survival of subjects to which only one of the antigen binding protein (e.g. an antibody or antigen-binding fragment thereof that specifically binds to *Klebsiella pneumoniae* O2 antigen) or the antibiotic was administered. In one instance, the antibiotic is meropenem, carbapenems, fluoroquinolone, tetracycline, chloramphenicol, trimethoprim, sulfonamide, and/or colistin. In one instance, the antigen binding protein also specifically binds *Klebsiella pneumoniae* O1 antigen.

In one instance, the antigen binding protein that specifically binds to *Klebsiella pneumoniae* O2 antigen is an antibody or antigen binding fragment thereof. In one instance, the antigen binding protein that specifically binds to *Klebsiella pneumoniae* O2 antigen is an antigen binding protein provided herein or a pharmaceutical composition provided herein.

In one instance, the *Klebsiella* is *K. pneumoniae*, *K. oxytoca*, *K. planticola*, *K. ozaenae*, *K. rhinoscleromatis* and/or *K. granulomatis*. In one instance, the *Klebsiella* is *K. pneumoniae*.

In one instance, the condition is selected from the group consisting of pneumonia, urinary tract infection, septicemia/sepsis, neonatal septicemia/sepsis, diarrhea, soft tissue infection, infection following an organ transplant, surgery infection, wound infection, lung infection, pyogenic liver abscesses (PLA), endophthalmitis, meningitis, necrotizing meningitis, ankylosing spondylitis, and spondyloarthropathies. In one instance, the condition is a nosocomial infection.

BRIEF DESCRIPTION OF THE DRAWINGS/FIGURES

FIGS. 1A-B show the expansion of the O2 LPS serotype in multi-drug resistant (MDR) strains of *Klebsiella pneumoniae*. FIG. 1A shows O serotype determining antigens for *Klebsiella pneumoniae* O1/O2 LPS and a western blot analysis of seven purified *Klebsiella* LPS serotypes probed with an isolated anti-O2 monoclonal antibody (mAb). FIG.

1B shows the prevalence of the O1 and O2 serotypes in recent *Klebsiella pneumoniae* clinical isolates.

FIGS. 2A-C show the characterization of anti-O2 LPS monoclonal antibodies (mAbs) by enzyme-linked immunosorbent assay (ELISA). FIG. 2A shows the binding of representative mAbs from each antibody class to O1 LPS. FIG. 2B shows the binding of representative mAbs from each class to O2 LPS. FIG. 2C shows the half maximal effective concentration ($EC_{50}$) of each mAb binding to LPS-O1 or LPS-O2.

FIGS. 3A-3O show the results of an octet binding assay with anti-O2 monoclonal antibodies (mAbs). FIGS. 3A-3F show sensorgram traces of anti-O2 mAbs interacting with O1 LPS. FIGS. 3G-3L show sensorgram traces of anti-O2 mAbs interacting with O2 LPS. FIGS. 3M-3O show affinity measurements of the Class III mAbs KPN42 and KPN179.

FIGS. 4A-4F show LPS neutralization assays performed with selected monoclonal antibodies (mAbs). The % neutralization of the mAbs against LPS-O1 is shown in FIGS. 4A-4C, and the % neutralization of the mAbs against LPS-O2 is shown in FIGS. 4D-4F.

FIGS. 7A-7B show shows that the anti-O2 LPS monoclonal antibodies (mAbs) KPN42 and KPN179 have strong synergy with meropenem in a lethal pneumonia model, as measured by the % survival of mice at various time points post challenge.

Figure 8A:
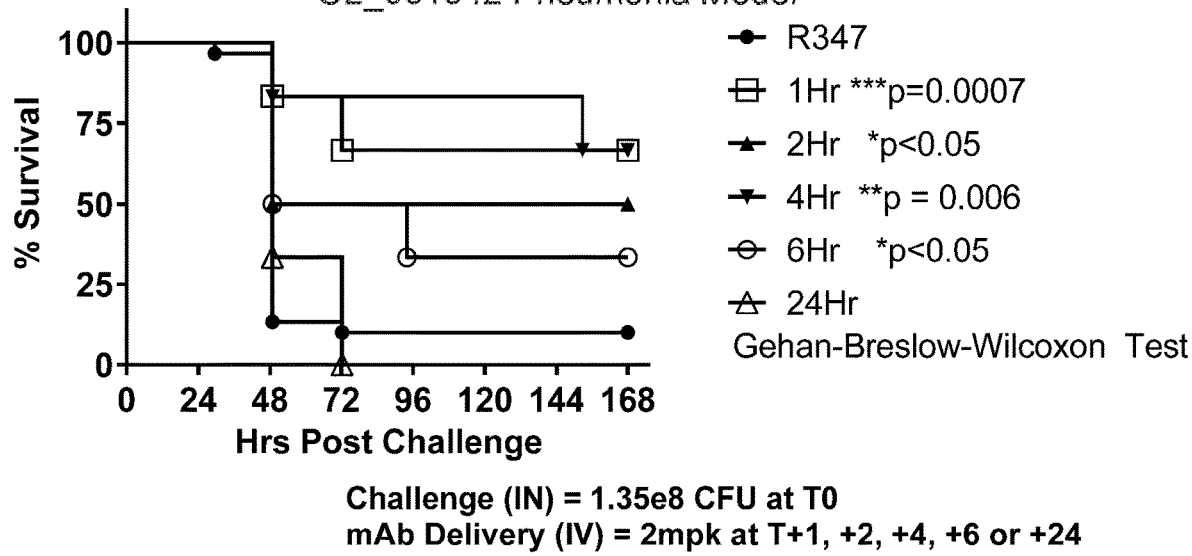
Figure 8B:
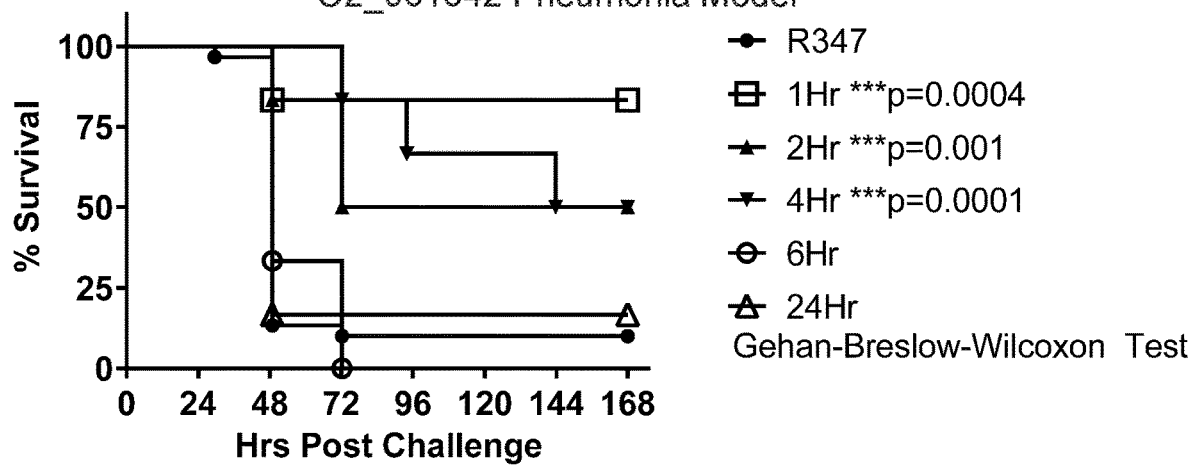

FIGS. 8A-8B show that select anti-O2 monoclonal antibodies (mAbs) protect mice for up to 6 hours post infection in conjunction with Meropenem. For mice treated with KPN42 in conjunction with meropenem, the % survival at various time points post challenge is shown in FIG. 8A. For mice treated with KPN179 in conjunction with meropenem, the % survival at various time points post challenge is shown in FIG. 8B.

FIGS. 9A-9C show the sequence optimization of KPN42 and KPN179. The binding of optimized versions of KPN42 and KPN179 to O2 LPS is shown in the graph in FIG. 9C.

Figure 10B:
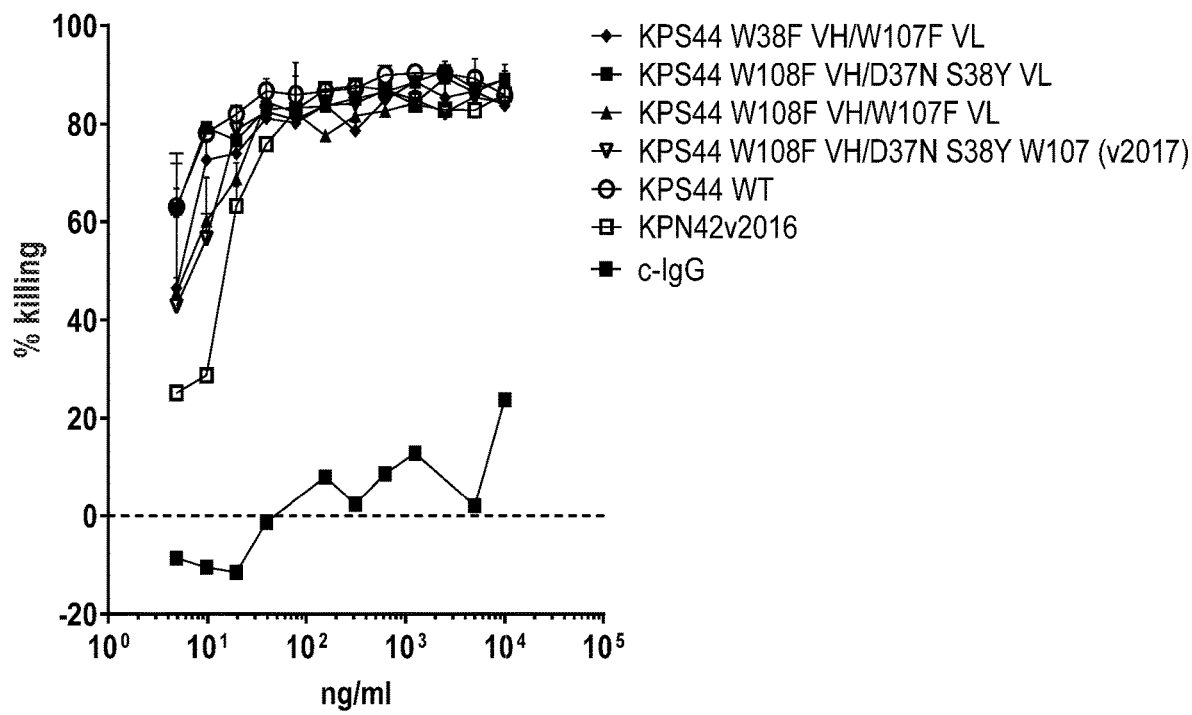
Figure 10C:
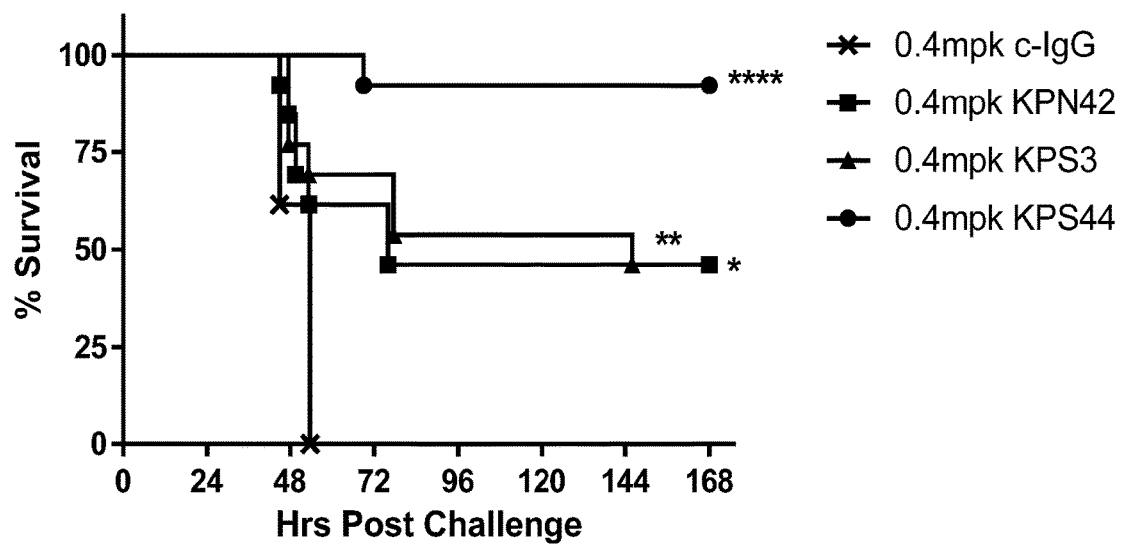

FIGS. 10A-C shows the protection conferred by Class III monoclonal antibodies KPS44 and KPS44v2017 in an opsonophagocytic killing (OPK) assay against an O2 strain of *K. pneumoniae* (FIG. 10B) and lethal pneumonia models against the KPS ST258 O2 strain 961842 (FIGS. 10A and 10C).

Figures 11A, 11B:
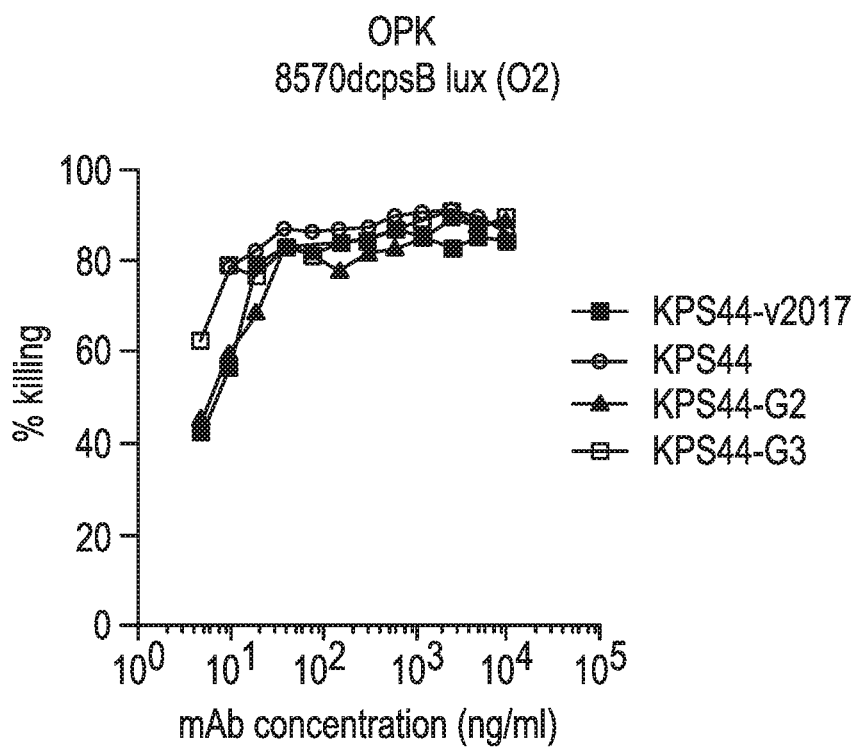

FIG. 11A shows the binding affinities from an octet binding assay with anti-O2 monoclonal antibodies (mAbs). FIG. 11B shows the protection conferred by Class III monoclonal antibodies KPS44, KPS44v2017, KPS44-G2, and KPS44-G3 in an opsonophagocytic killing (OPK) assay against an O2 strain of *K. pneumoniae*

DETAILED DESCRIPTION OF THE INVENTION

The data provided herein shows that a high prevalence of multidrug resistant *Klebsiella pneumoniae* strains are of the O2 serotype (see Example 1). Thus, there is a particularly great need to identify and develop antibodies that have protective effect against *Klebsiella* of the O2 serotype. Accordingly, the present disclosure provides isolated binding proteins, including antibodies or antigen binding fragments thereof, that bind to *Klebsiella pneumoniae* O2 antigen. Related polynucleotides, vectors, host cells, and pharmaceutical compositions comprising the *Klebsiella pneumoniae* O2 binding proteins, including antibodies or antigen binding fragments thereof, are also provided. Also provided are methods of making and using the O2 binding proteins, including antibodies or antigen binding fragments, disclosed herein. The present disclosure also provides methods of preventing and/or treating a condition associated with a *Klebsiella* infection (e.g., *K. pneumoniae* such as O2 serotype *K. pneumoniae*) by administering the O2 binding proteins, including antibodies or antigen binding fragments, disclosed herein.

In order that the present disclosure can be more readily understood, certain terms are first defined. Additional definitions are set forth throughout the detailed description.

I. Definitions

The terms "a," "an," and "the" include plural referents unless the context clearly dictates otherwise. For example, "an antigen binding protein" is understood to represent one or more antigen binding proteins. The terms "a" (or "an"), as well as the terms "one or more," and "at least one" can be used interchangeably herein. Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "comprise" is generally used in the sense of include, that is to say permitting the presence of one or more features or components. Wherever aspects are described herein with the language "comprising," otherwise analogous aspects described in terms of "consisting of," and/or "consisting essentially of" are also provided.

The term "about" as used in connection with a numerical value throughout the specification and the claims denotes an interval of accuracy, familiar and acceptable to a person skilled in the art. In general, such interval of accuracy is ±10%.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

The term "antigen binding protein" refers to a molecule comprised of one or more polypeptides that recognizes and specifically binds to a target, e.g., *K. pneumoniae* O2 antigen, such as an anti-O2 antibody or antigen-binding fragment thereof.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" or "antibody fragment thereof" refers to a portion of an intact antibody. An "antigen-binding fragment" or "antigen-binding fragment thereof" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, scFvs, and single chain antibodies.

It is possible to take monoclonal and other antibodies or fragments thereof and use techniques of recombinant DNA technology to produce other antibodies or chimeric molecules or fragments thereof that retain the specificity of the original antibody or fragment. Such techniques can involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A, or EP-A-239400, and a large body of subsequent literature. A hybridoma or other cell producing an antibody can be subject to genetic mutation or other changes, which may or may not alter the binding specificity of antibodies or fragments thereof produced.

Further techniques available in the art of antibody engineering have made it possible to isolate human and humanized antibodies or fragments thereof. For example, human hybridomas can be made as described by Kontermann and Sefan. Antibody Engineering, Springer Laboratory Manuals (2001). Phage display, another established technique for generating antigen binding proteins has been described in detail in many publications such as Kontermann and Sefan. Antibody Engineering, Springer Laboratory Manuals (2001) and WO92/01047. Transgenic mice in which the mouse antibody genes are inactivated and functionally replaced with human antibody genes while leaving intact other components of the mouse immune system, can be used for isolating human antibodies to human antigens.

Synthetic antibodies or fragments thereof can be created by expression from genes generated by means of oligonucleotides synthesized and assembled within suitable expression vectors, for example as described by Knappik et al. J. Mol. Biol. (2000) 296, 57-86 or Krebs et al. Journal of Immunological Methods 254 2001 67-84.

It has been shown that fragments of a whole antibody can perform the function of binding antigens. Examples of binding fragments are (i) the Fab fragment consisting of VL, VH, CL, and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989), McCafferty et al (1990) Nature, 348, 552-554) which consists of a VH domain; (v) isolated CDR regions; (vi) F(ab')2 fragments, a bivalent fragment comprising two linked Fab fragments; and (vii) single chain Fv molecules (scFv), wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); Fv or scFv molecules may be stabilized by the incorporation of disulphide bridges linking the VH and VL domains (Y. Reiter et al, Nature Biotech, 14, 1239-1245, 1996). Minibodies comprising a scFv joined to a CH3 domain may also be made (S. Hu et al, Cancer Res., 56, 3055-3061, 1996).

The phrase "effector function" refers to the activities of antibodies that result from the interactions of their Fc components with Fc receptors or components of complement. These activities include, for example, antibody-dependent cell-mediated cytotoxicity (ADCC), complement-dependent cytotoxicity (CDC), and antibody-dependent cell phagocytosis (ADCP). Thus an antigen binding protein (e.g., an antibody or antigen binding fragment thereof) with altered effector function refers to an antigen binding protein (e.g., an antibody or antigen binding fragment thereof) that contains an alteration in an Fc region (e.g., amino acid substitution, deletion, or addition or change in oligosaccharide) that changes the activity of at least one effector function (e.g., ADCC, CDC, and/or ADCP). An antigen binding protein (e.g., an antibody or antigen binding fragment thereof) with improved effector function refers to an antigen binding protein (e.g., an antibody or antigen binding fragment thereof) that contains an alteration in an Fc region (e.g., amino acid substitution, deletion, or addition or change in oligosaccharide) that increases the activity of at least one effector function (e.g., ADCC, CDC, and/or ADCP).

The term "specific" can be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the antigen binding protein carrying the antigen binding domain will be able to bind to the various antigens carrying the epitope.

By "specifically binds" it is generally meant that an antigen binding protein including an antibody or antigen binding fragment thereof binds to an epitope via its antigen binding domain, and that the binding entails some complementarity between the antigen binding domain and the epitope. According to this definition, an antibody is said to "specifically bind" to an epitope when it binds to that epitope via its antigen binding domain more readily than it would bind to a random, unrelated epitope. As used herein, an antigen binding protein that "specifically binds" to *Kleb-*

*siella pneumoniae* O2 antigen may or may not also bind to other *Klebsiella pneumoniae* O antigens, including, for example, *Klebsiella pneumoniae* O1 antigen. In some embodiments, the antigen binding proteins disclosed herein specifically bind both *Klebsiella pneumoniae* O2 antigen and *Klebsiella pneumoniae* O1 antigen, while in other embodiments the antigen binding proteins disclosed herein specifically bind *Klebsiella pneumoniae* O2 antigen but do not specifically bind *Klebsiella pneumoniae* O1 antigen.

"Affinity" is a measure of the intrinsic binding strength of a ligand binding reaction. For example, a measure of the strength of the antibody (Ab)-antigen (Ag) interaction is measured through the binding affinity, which may be quantified by the dissociation constant, $k_d$. The dissociation constant is the binding affinity constant and is given by:

$$K_d = \frac{[Ab][Ag]}{[AbAg\ \text{complex}]}$$

Affinity may, for example, be measured using a BIAcore®, a KinExA affinity assay, flow cytometry, and/or radioimmunoassay.

"Potency" is a measure of pharmacological activity of a compound expressed in terms of the amount of the compound required to produce an effect of given intensity. It refers to the amount of the compound required to achieve a defined biological effect; the smaller the dose required, the more potent the drug. Potency of an antigen binding protein that binds O2 can, for example, be determined using an OPK assay, as described herein.

"Opsonophagocytic killing" or "OPK" refers to the death of a cell, e.g., a *Klebsiella*, that occurs as a result of phagocytosis by an immune cell. OPK activity is measured according to the bioluminescent assay used in Example 8. An antigen binding protein (e.g., an antibody or antigen-binding fragment thereof) can induce OPK where the percentage of killing is 40% or greater. An antigen binding protein (e.g., an antibody or antigen-binding fragment thereof) can strongly induce OPK where the percentage of killing is 80% or greater.

An antigen binding protein including an antibody or antigen binding fragment thereof is said to competitively inhibit binding of a reference antibody or antigen binding fragment thereof to a given epitope or "compete" with a reference antibody or antigen binding fragment if it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope or compete with a reference antibody or antigen binding fragment thereof by at least 90%, at least 80%, at least 70%, at least 60%, or at least 50%.

The term "compete" when used in the context of antigen binding proteins (e.g., neutralizing antigen binding proteins or neutralizing antibodies) means competition between antigen binding proteins as determined by an assay in which the antigen binding protein (e.g., antibody or immunologically functional fragment thereof) under test prevents or inhibits specific binding of a reference antigen binding protein (e.g., a ligand, or a reference antibody) to a common antigen (e.g., an O2 polysaccharide or a fragment thereof). Numerous types of competitive binding assays can be used, for example: solid phase direct or indirect radioimmunoassay (RIA), solid phase direct or indirect enzyme immunoassay (EIA), sandwich competition assay (see, e.g., Stahli et al., 1983, Methods in Enzymology 92:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabeled test antigen binding protein and a labeled reference antigen binding protein.

Competitive inhibition can be measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Usually, when a competing antigen binding protein is present in excess, it will inhibit specific binding of a reference antigen binding protein to a common antigen by at least 40%, 45%, 50%, 55%, 60%, 65%, 70% or 75%. In some instance, binding is inhibited by at least 80%, 85%, 90%, 91%, 92%, 93%, 94%, 95%, 96%, 97%, 98%, 99% or more.

Antigen binding proteins, antibodies or antigen binding fragments thereof disclosed herein can be described or specified in terms of the epitope(s) or portion(s) of an antigen, e.g., a target polypeptide that they recognize or specifically bind. For example, the portion of O2 that specifically interacts with the antigen binding domain of the antigen binding polypeptide or fragment thereof disclosed herein is an "epitope". Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. A conformational epitope can be composed of discontinuous sections of the antigen's amino acid sequence. A linear epitope is formed by a continuous sequence of amino acids from the antigen. Epitope determinants may include chemically active surface groupings of molecules such as amino acids, sugar side chains, phosphoryl or sulfonyl groups, and can have specific three dimensional structural characteristics, and/or specific charge characteristics. An epitope typically includes at least 3, 4, 5, 6, 3, 4, 5, 6, 7, 8, 9, 10, 11, 12, 13, 14, 15, 16, 17, 18, 19, 20, 25, 30, 35 amino acids in a unique spatial conformation. Epitopes can be determined using methods known in the art.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

As used herein, the term "polypeptide" refers to a molecule composed of monomers (amino acids) linearly linked by amide bonds (also known as peptide bonds). The term "polypeptide" refers to any chain or chains of two or more amino acids, and does not refer to a specific length of the product. As used herein the term "protein" is intended to encompass a molecule comprised of one or more polypeptides, which can in some instances be associated by bonds other than amide bonds. On the other hand, a protein can also be a single polypeptide chain. In this latter instance the single polypeptide chain can in some instances comprise two or more polypeptide subunits fused together to form a protein. The terms "polypeptide" and "protein" also refer to the products of post-expression modifications, including without limitation glycosylation, acetylation, phosphorylation, amidation, derivatization by known protecting/blocking groups, proteolytic cleavage, or modification by non-naturally occurring amino acids. A polypeptide or protein can be derived from a natural biological source or produced by recombinant technology, but is not necessarily translated from a designated nucleic acid sequence. It can be generated in any manner, including by chemical synthesis.

The term "isolated" refers to the state in which antigen binding proteins of the disclosure, or nucleic acid encoding such binding proteins, will generally be in accordance with the present disclosure. Isolated proteins and isolated nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practiced in vitro or in vivo. Proteins and nucleic acid may be formulated with diluents or adjuvants and still for practical purposes be isolated—for example the proteins will normally be mixed with gelatin or other carriers if used to coat microtitre plates for use in immunoassays, or will be mixed with pharmaceutically acceptable carriers or diluents when used in diagnosis or therapy. Antigen binding proteins may be glycosylated, either naturally or by systems of heterologous eukaryotic cells (e.g. CHO or NS0 (ECACC 85110503) cells, or they may be (for example if produced by expression in a prokaryotic cell) unglycosylated.

A polypeptide, antigen binding protein, antibody, polynucleotide, vector, cell, or composition which is "isolated" is a polypeptide, antigen binding protein, antibody, polynucleotide, vector, cell, or composition which is in a form not found in nature. Isolated polypeptides, antigen binding proteins, antibodies, polynucleotides, vectors, cells, or compositions include those which have been purified to a degree that they are no longer in a form in which they are found in nature. In some embodiments, an antigen binding protein, antibody, polynucleotide, vector, cell, or composition which is isolated is substantially pure.

A "recombinant" polypeptide, protein or antibody refers to a polypeptide or protein or antibody produced via recombinant DNA technology. Recombinant polypeptides, proteins and antibodies expressed in host cells are considered isolated for the purpose of the present disclosure, as are native or recombinant polypeptides which have been separated, fractionated, or partially or substantially purified by any suitable technique.

Also included in the present disclosure are fragments, variants, or derivatives of polypeptides, and any combination thereof. The term "fragment" when referring to polypeptides and proteins of the present disclosure include any polypeptides or proteins which retain at least some of the properties of the reference polypeptide or protein. Fragments of polypeptides include proteolytic fragments, as well as deletion fragments.

The term "variant" as used herein refers to an antibody or polypeptide sequence that differs from that of a parent antibody or polypeptide sequence by virtue of at least one amino acid modification. Variants of antibodies or polypeptides of the present disclosure include fragments, and also antibodies or polypeptides with altered amino acid sequences due to amino acid substitutions, deletions, or insertions. Variants can be naturally or non-naturally occurring. Non-naturally occurring variants can be produced using art-known mutagenesis techniques. Variant polypeptides can comprise conservative or non-conservative amino acid substitutions, deletions or additions.

The term "derivatives" as applied to antibodies or polypeptides refers to antibodies or polypeptides which have been altered so as to exhibit additional features not found on the native polypeptide or protein. An example of a "derivative" antibody is a fusion or a conjugate with a second polypeptide or another molecule (e.g., a polymer such as PEG, a chromophore, or a fluorophore) or atom (e.g., a radioisotope).

The terms "polynucleotide" or "nucleotide" as used herein are intended to encompass a singular nucleic acid as well as plural nucleic acids, and refers to an isolated nucleic acid molecule or construct, e.g., messenger RNA (mRNA), complementary DNA (cDNA), or plasmid DNA (pDNA). In certain aspects, a polynucleotide comprises a conventional phosphodiester bond or a non-conventional bond (e.g., an amide bond, such as found in peptide nucleic acids (PNA)).

The term "nucleic acid" refers to any one or more nucleic acid segments, e.g., DNA, cDNA, or RNA fragments, present in a polynucleotide. When applied to a nucleic acid or polynucleotide, the term "isolated" refers to a nucleic acid molecule, DNA or RNA, which has been removed from its native environment, for example, a recombinant polynucleotide encoding an antigen binding protein contained in a vector is considered isolated for the purposes of the present disclosure. Further examples of an isolated polynucleotide include recombinant polynucleotides maintained in heterologous host cells or purified (partially or substantially) from other polynucleotides in a solution. Isolated RNA molecules include in vivo or in vitro RNA transcripts of polynucleotides of the present disclosure. Isolated polynucleotides or nucleic acids according to the present disclosure further include such molecules produced synthetically. In addition, a polynucleotide or a nucleic acid can include regulatory elements such as promoters, enhancers, ribosome binding sites, or transcription termination signals.

As used herein, the term "host cell" refers to a cell or a population of cells harboring or capable of harboring a recombinant nucleic acid. Host cells can be a prokaryotic cells (e.g., *E. coli*), or alternatively, the host cells can be eukaryotic, for example, fungal cells (e.g., yeast cells such as *Saccharomyces cerivisiae, Pichia pastoris*, or *Schizosaccharomyces pombe*), and various animal cells, such as insect cells (e.g., Sf-9) or mammalian cells (e.g., HEK293F, CHO, COS-7, NIH-3T3, a NS0 murine myeloma cell, a PER.C6® human cell, a Chinese hamster ovary (CHO) cell or a hybridoma).

The term "amino acid substitution" refers to replacing an amino acid residue present in a parent sequence with another amino acid residue. An amino acid can be substituted in a parent sequence, for example, via chemical peptide synthesis or through recombinant methods known in the art. Accordingly, references to a "substitution at position X" or "substitution at position X" refer to the substitution of an amino acid present at position X with an alternative amino acid residue. In some embodiments, substitution patterns can described according to the schema AXY, wherein A is the single letter code corresponding to the amino acid naturally present at position X, and Y is the substituting amino acid residue. In other aspects, substitution patterns can described according to the schema XY, wherein Y is the single letter code corresponding to the amino acid residue substituting the amino acid naturally present at position X.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

Non-conservative substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala, Ser) or no side chain (e.g., Gly).

Other substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

The term "amino acid insertion" refers to introducing a new amino acid residue between two amino acid residues present in the parent sequence. An amino acid can be inserted in a parent sequence, for example, via chemical peptide synthesis or through recombinant methods known in the art. Accordingly as used herein, the phrases "insertion between positions X and Y," "insertion between IMGT positions X and Y," or "insertion between Kabat positions X and Y," wherein X and Y correspond to amino acid positions (e.g., a cysteine amino acid insertion between positions 239 and 240), refers to the insertion of an amino acid between the X and Y positions, and also to the insertion in a nucleic acid sequence of a codon encoding an amino acid between the codons encoding the amino acids at positions X and Y. Insertion patterns can be described according to the schema AXins, wherein A is the single letter code corresponding to the amino acid being inserted, and X is the position preceding the insertion.

The term "percent sequence identity" or "percent identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software programs. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

"Specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. The present disclosure is concerned with antigen-antibody type reactions.

The term "IgG" as used herein refers to a polypeptide belonging to the class of antibodies that are substantially encoded by a recognized immunoglobulin gamma gene. In humans this class comprises IgG1, IgG2, IgG3, and IgG4. In mice this class comprises IgG1, IgG2a, IgG2b, and IgG3.

The term "antigen binding domain" describes the part of an antibody that comprises the area which specifically binds to and is complementary to part or all of an antigen. Where an antigen is large, an antibody may only bind to a particular part of the antigen, which part is termed an epitope. An antigen binding domain may be provided by one or more antibody variable domains (e.g. a so-called Fd antibody fragment consisting of a VH domain). An antigen binding domain may comprise an antibody light chain variable region (VL) and an antibody heavy chain variable region (VH).

The term "antigen binding protein fragment" or "antibody fragment" refers to a portion of an intact antigen binding protein or antibody and refers to the antigenic determining variable regions of an intact antigen binding protein or antibody. It is known in the art that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

The term "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')$_2$, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides. The term "humanized antibody" refers to an antibody derived from a non-human (e.g., murine) immunoglobulin, which has been engineered to contain minimal non-human (e.g., murine) sequences.

The term "chimeric antibody" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

The term "antibody binding site" refers to a region in the antigen (e.g., O2) comprising a continuous or discontinuous site (i.e., an epitope) to which a complementary antibody specifically binds. Thus, the antibody binding site can contain additional areas in the antigen which are beyond the epitope and which can determine properties such as binding affinity and/or stability, or affect properties such as antigen enzymatic activity or dimerization. Accordingly, even if two antibodies bind to the same epitope within an antigen, if the antibodies establish distinct intermolecular contacts with amino acids outside of the epitope, such antibodies are considered to bind to distinct antibody binding sites.

The IMGT numbering system is generally used when referring to a residue in the variable domain (approximately residues 1-107 of the light chain and residues 1-113 of the heavy chain) (e.g. Lefranc, M.-P. et al. Dev. Comp. Immunol. 27: 55-77 (2003)).

The phrases "amino acid position numbering as in Kabat," "Kabat position," and grammatical variants thereof refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The IMGT (Lefranc, M.-P. et al. Dev. Comp. Immunol. 27: 55-77 (2003)) classification of CDRs can also be used.

The term "EU index as in Kabat" refers to the numbering system of the human IgG1 EU antibody described in Kabat et al., Sequences of Immunological Interest, 5th Ed. Public Health Service, National Institutes of Health, Bethesda, Md. (1991). All amino acid positions referenced in the present application refer to IMGT unique numbering unless indicated otherwise. For example, C105 is defined according to IMGT unique numbering. For example, KPN42-C105 and KPN179-C105 correspond to Kabat position 89.

The terms "Fc domain," "Fc Region," and "IgG Fc domain" as used herein refer to the portion of an immunoglobulin, e.g., an IgG molecule, that correlates to a crystallizable fragment obtained by papain digestion of an IgG molecule. The Fc region comprises the C-terminal half of two heavy chains of an IgG molecule that are linked by disulfide bonds. It has no antigen binding activity but contains the carbohydrate moiety and binding sites for complement and Fc receptors, including the FcRn receptor. For example, an Fc domain contains the entire second constant domain CH2 (residues at EU positions 231-340 of human IgG1) and the third constant domain CH3 (residues at EU positions 341-447 of human IgG1).

Fc can refer to this region in isolation, or this region in the context of an antibody, antibody fragment, or Fc fusion protein. Polymorphisms have been observed at a number of positions in Fc domains, including but not limited to EU positions 270, 272, 312, 315, 356, and 358. Thus, a "wild type IgG Fc domain" or "WT IgG Fc domain" refers to any naturally occurring IgG Fc region (i.e., any allele). Myriad Fc mutants, Fc fragments, Fc variants, and Fc derivatives are described, e.g., in U.S. Pat. Nos. 5,624,821; 5,885,573; 5,677,425; 6,165,745; 6,277,375; 5,869,046; 6,121,022; 5,624,821; 5,648,260; 6,528,624; 6,194,551; 6,737,056; 7,122,637; 7,183,387; 7,332,581; 7,335,742; 7,371,826; 6,821,505; 6,180,377; 7,317,091; 7,355,008; U.S. Patent publication 2004/0002587; and PCT Publication Nos. WO 99/058572, WO 2011/069164 and WO 2012/006635.

The sequences of the heavy chains of human IgG1, IgG2, IgG3 and IgG4 can be found in a number of sequence databases, for example, at the Uniprot database (www.uniprot.org) under accession numbers P01857 (IGHG1_HUMAN), P01859 (IGHG2_HUMAN), P01860 (IGHG3_HUMAN), and P01861 (IGHG1_HUMAN), respectively.

The terms "YTE" or "YTE mutant" refer to a set of mutations in an IgG1 Fc domain that results in an increase in the binding to human FcRn and improves the serum half-life of the antibody having the mutation. A YTE mutant comprises a combination of three "YTE mutations": M252Y, S254T, and T256E, wherein the numbering is according to the EU index as in Kabat, introduced into the heavy chain of an IgG. See U.S. Pat. No. 7,658,921, which is incorporated by reference herein. The YTE mutant has been shown to increase the serum half-life of antibodies compared to wild-type versions of the same antibody. See, e.g., Dall'Acqua et al., J. Biol. Chem. 281:23514-24 (2006) and U.S. Pat. No. 7,083,784, which are hereby incorporated by reference in their entireties. A "Y" mutant comprises only the M256Y mutations; similarly a "YT" mutation comprises only the M252Y and S254T; and a "YE" mutation comprises only the M252Y and T256E. It is specifically contemplated that other mutations may be present at EU positions 252 and/or 256. In certain aspects, the mutation at EU position 252 may be M252F, M252S, M252W or M252T and/or the mutation at EU position 256 may be T256S, T256R, T256Q or T256D.

The term "N3" or "N3 mutant" refers to a set of mutations in an IgG1 Fc domain that results in an increase in the binding to FcRn and improves the serum half-life of the antibody having the mutation. The N3 mutant comprises the sequence Cys-Ser-Trp-His-Leu-Cys at positions 432-437 (no insertion between positions 437 and 438), incorporated into a wild type IgG1 constant domain base structure. See WO2015175874, which is hereby incorporated by reference.

The term "naturally occurring O2" generally refers to a state in which the O2 polysaccharide or a fragment thereof can occur. Naturally occurring O2 means O2 polysaccharide which is naturally produced by a cell, without prior introduction of encoding nucleic acid using recombinant technology. Thus, naturally occurring O2 can be as produced naturally by for example *K. pneumoniae* and/or as isolated from different members of the *Klebsiella* genus.

The term "recombinant O2" refers to a state in which the O2 polysaccharide or fragments thereof may occur. Recombinant O2 means O2 polysaccharide or fragments thereof produced by recombinant DNA, e.g., in a heterologous host.

Recombinant proteins expressed in prokaryotic bacterial expression systems are not glycosylated while those expressed in eukaryotic systems such as mammalian or insect cells are glycosylated. Proteins expressed in insect cells however differ in glycosylation from proteins expressed in mammalian cells.

The terms "half-life" or "in vivo half-life" as used herein refer to the biological half-life of a particular type of antibody, antigen binding protein, or polypeptide of the present disclosure in the circulation of a given animal and is represented by a time required for half the quantity administered in the animal to be cleared from the circulation and/or other tissues in the animal.

The term "subject" as used herein refers to any animal (e.g., a mammal), including, but not limited to humans, non-human primates, rodents, sheep, dogs, cats, horses, cows, bears, chickens, amphibians, reptiles, and the like, which is to be the recipient of a particular treatment. The terms "subject" and "patient" as used herein refer to any subject, particularly a mammalian subject, for whom diagnosis, prognosis, or therapy of a condition associated with a *Klebsiella* infection. As used herein, phrases such as "a patient having a condition associated with a *Klebsiella* infection" includes subjects, such as mammalian subjects, that would benefit from the administration of a therapy, imaging or other diagnostic procedure, and/or preventive treatment for that condition associated with a *Klebsiella* infection.

"*Klebsiella*" refers to a genus of gram-negative, facultatively anaerobic, rod-shaped bacteria in the Enterobacteriaceae family. *Klebsiella* include, for example, *K. pneumoniae, K oxytoca, K. planticola K. granulomatis, K. ozaenae,* and *K. rhinoscleromatis.*

Members of the *Klebsiella* genus typically express 2 types of antigens on their cell surface: an O antigen and a K antigen. The O antigen is a lipopolysaccharide, and the K antigen is a capsular polysaccharide. The structural variability of these antigens forms the basis for their classification in into *Klebsiella* "serotypes." Thus, the ability of an O2 binding protein (e.g., an antibody or an antigen binding fragment thereof) to bind to multiple serotypes refers to its ability to bind to *Klebsiella* with different 0 and/or K antigens. In some embodiments, provided herein, the *Klebsiella* is of the O2 serotype. In some embodiments, provided herein, the *Klebsiella* is of the O1 serotype.

The term "pharmaceutical composition" as used herein refers to a preparation which is in such form as to permit the biological activity of the active ingredient to be effective, and which contains no additional components which are unacceptably toxic to a subject to which the composition would be administered. Such composition can be sterile.

An "effective amount" of an antigen binding protein (including an antibody or antigen binding fragment thereof), as disclosed herein is an amount sufficient to carry out a specifically stated purpose. An "effective amount" can be determined empirically and in a routine manner, in relation to the stated purpose. The term "therapeutically effective amount" as used herein refers to an amount of a polypeptide, e.g., an antigen binding protein including an antibody, or other drug effective to "treat" a disease or condition in a subject or mammal and provides some improvement or benefit to a subject having a *Klebsiella*-mediated disease or condition. Thus, a "therapeutically effective" amount is an amount that provides some alleviation, mitigation, and/or decrease in at least one clinical symptom of the *Klebsiella*-mediated disease or condition. Clinical symptoms associated with the *Klebsiella*-mediated disease or condition that can be treated by the methods and systems of the disclosure are well known to those skilled in the art. Further, those skilled in the art will appreciate that the therapeutic effects need not be complete or curative, as long as some benefit is provided to the subject. In some embodiments, the term "therapeutically effective" refers to an amount of a therapeutic agent that is capable of reducing *Klebsiella* (e.g., *K. pneumoniae*) or *Klebsiella* (e.g., *K. pneumoniae*) activity in a patient in need thereof. The actual amount administered and rate and time-course of administration, will depend on the nature and severity of what is being treated. Prescription of treatment, e.g. decisions on dosage etc., is within the responsibility of general practitioners and other medical doctors. Appropriate doses of antibodies and antigen binding fragments thereof are well known in the art; see Ledermann J. A. et al. (1991) Int. J. Cancer 47: 659-664; Bagshawe K. D. et al. (1991) Antibody, Immunoconjugates and Radiopharmaceuticals 4: 915-922.

As used herein, a "sufficient amount" or "an amount sufficient to" achieve a particular result in a patient having a *Klebsiella*-mediated disease or condition refers to an amount of a therapeutic agent (e.g., an antigen binding protein including an antibody, as disclosed herein) that is effective to produce a desired effect, which is optionally a therapeutic effect (i.e., by administration of a therapeutically effective amount). In some embodiments, such particular result is a reduction in *Klebsiella* (e.g., *K. pneumoniae*) or *Klebsiella* (e.g., *K. pneumoniae*) activity in a patient in need thereof.

The term "label" when used herein refers to a detectable compound or composition which is conjugated directly or indirectly to a polypeptide, e.g., an antigen binding protein including an antibody, so as to generate a "labeled" polypeptide or antibody. The label can be detectable by itself (e.g., radioisotope labels or fluorescent labels) or, in the case of an enzymatic label, can catalyze chemical alteration of a substrate compound or composition which is detectable.

Terms such as "treating" or "treatment" or "to treat" or "alleviating" or "to alleviate" or "ameliorating" or "or ameliorate" refer to therapeutic measures that cure, slow down, lessen symptoms of, and/or halt progression of a diagnosed pathologic condition or disorder. Terms such as "preventing" refer to prophylactic or preventative measures that prevent and/or slow the development of a targeted pathologic condition or disorder. Thus, those in need of treatment include those already with the disease or condition. Those in need of prevention include those prone to have the disease or condition and those in whom the disease or condition is to be prevented. For example, the phrase "treating a patient having a *Klebsiella*-mediated disease or condition" refers to reducing the severity of the *Klebsiella*-mediated disease or condition, preferably, to an extent that the subject no longer suffers discomfort and/or altered function due to it (for example, a relative reduction in asthma exacerbations when compared to untreated patients). The phrase "preventing a *Klebsiella*-mediated disease or condition" refers to reducing the potential for a *Klebsiella*-mediated disease or condition and/or reducing the occurrence of the *Klebsiella*-mediated disease or condition.

As used herein, the term "a condition associated with a *Klebsiella* infection" refers to any pathology caused by (alone or in association with other mediators), exacerbated by, associated with, or prolonged by *Klebsiella* infection (e.g. infection with *K. pneumoniae, K. oxytoca, K. planticola, K. ozaenae, K. rhinosclermoatis* and/or *K. granulomatis*) in the subject having the disease or condition. Non-limiting examples of conditions associated with a *Klebsiella* infection include pneumonia, urinary tract infection, septicemia/sepsis, neonatal septicemia, diarrhea, soft tissue infections, infections following an organ transplant, surgery infection, wound infection, lung infection, pyogenic liver abscesses, endophthalmitis, meningitis, necrotizing meningitis, ankylosing spondylitis and spondyloarthropathies. In some embodiments, the *Klebsiella* infection is a nosocomial infection. In some embodiments, the *Klebsiella* infection is an opportunistic infection. In some embodiments, the *Klebsiella* infection follows an organ transplant. In some embodiments, the subject is exposed to a *Klebsiella* contaminated medical device, including, e.g., a ventilator, a catheter, or an intravenous catheter.

The structure for carrying a CDR or a set of CDRs will generally be of an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat, E. A. et al, Sequences of Proteins of Immunological Interest. 4th Edition. (US Department of Health and Human Services. 1987, and updates thereof, now available on the Internet (http://immuno.bme.nwu.edu or find "Kabat" using any search engine), herein incorporated by reference. CDRs can also be carried by other scaffolds such as fibronectin or cytochrome B.

A CDR amino acid sequence substantially as set out herein can be carried as a CDR in a human variable domain or a substantial portion thereof. The HCDR3 sequences substantially as set out herein represent embodiments of the present disclosure and each of these may be carried as a HCDR3 in a human heavy chain variable domain or a substantial portion thereof.

Variable domains employed in the disclosure can be obtained from any germ-line or rearranged human variable domain, or can be a synthetic variable domain based on consensus sequences of known human variable domains. A CDR sequence (e.g. CDR3) can be introduced into a repertoire of variable domains lacking a CDR (e.g. CDR3), using recombinant DNA technology.

For example, Marks et al. (Bio/Technology, 1992, 10:779-783; which is incorporated herein by reference) provide methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire can be combined with a CDR3 of a particular antibody. Using analogous techniques, the CDR3-derived sequences of the present disclosure can be shuffled with repertoires of VH or VL domains lacking a CDR3, and the shuffled complete VH or VL domains combined with a cognate VL or VH domain to provide antigen binding proteins. The repertoire can then be displayed in a suitable host system such as the phage display system of WO92/01047 or any of a subsequent large body of literature, including Kay, B. K., Winter, J., and McCafferty, J. (1996) Phage Display of Peptides and Proteins: A Laboratory Manual, San Diego: Academic Press, so that suitable antigen binding proteins may be selected. A repertoire can consist of from anything from 104 individual members upwards, for example from 106 to 108 or 1010 members. Other suitable host systems include yeast display, bacterial display, T7 display, ribosome display and so on. For a review of ribosome display for see Lowe D and Jermutus L, 2004, Curr. Pharm, Biotech, 517-27, also WO92/01047, which are herein incorporated by reference.

Analogous shuffling or combinatorial techniques are also disclosed by Stemmer (Nature, 1994, 370:389-391, which is herein incorporated by reference), who describes the technique in relation to a β-lactamase gene but observes that the approach may be used for the generation of antibodies.

A further alternative is to generate novel VH or VL regions carrying CDR-derived sequences of the disclosure using random mutagenesis of one or more selected VH and/or VL genes to generate mutations within the entire variable domain. Such a technique is described by Gram et al (1992, Proc. Natl. Acad. Sci., USA, 89:3576-3580), who used error-prone PCR. In some embodiments, one or two amino acid substitutions are made within a set of HCDRs and/or LCDRs.

Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567).

The methods and techniques of the present disclosure are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), all of which are herein incorporated by reference.

The skilled person will be able to use such techniques described above to provide antigen binding proteins of the present disclosure using routine methodology in the art.

II. O2 Antigen Binding Molecules

The present disclosure provides O2 antigen binding molecules, e.g., antigen binding proteins, antibodies, and antigen binding fragments thereof, that specifically bind $K.$ $pneumoniae$ $O2$ antigen. Collectively, these agents are referred to herein as "O2 binding molecules" or "O2 binding agents." In some instances, an O2 binding agent (e.g., an antibody or antigen-binding fragment thereof) binds to $K.$ $pneumoniae$ $O1$ antigen in addition to binding to $K.$ $pneumoniae$ $O2$ antigen. In some instances, an O2 binding agent (e.g., an antibody or antigen-binding fragment thereof) binds to $K.$ $pneumoniae$ $O1$ antigen, but binds preferentially to $K.$ $pneumoniae$ $O2$ antigen. In some instances, an O2 binding agent (e.g., an antibody or antigen-binding fragment thereof) binds to $K.$ $pneumoniae$ $O2$ antigen but does not bind $K.$ $pneumoniae$ $O1$ antigen.

The O2 antigen of $Klebsiella$ lipopolysaccharide (LPS) contains repeating D-galactan I (D-Gal I) units as major structural components. In the O2 antigen, the D-Gal I polymers are directly linked to the core oligosaccharide and are composed of repeat units of the structure→3)-β-D-Galf-(1→3)-α-D-Galp-(1→. In contrast, the O1 antigen of $Klebsiella$ lipopolysaccharide (LPS) contains two structural domains composed of the repeat units D-galactan I and D-galactan II. For both the O1 antigen and the O2 antigen of $Klebsiella$, O-antigen biosynthesis is performed by products of the wb (rfb) gene cluster, which is composed of six genes (wzm, wzt, glf, wbbM, wbbN, and wbbO) (Whitfield, C. et al. 1991. Expression of two structurally distinct D-Galactan O antigens in the lipopolysaccharide of $Klebsiella$ $pneumoniae$ serotype O2. J. Bacteriology. 1420-1431; Clarke, B. R. and Whitfield C. 1992. Molecular cloning of the rfb region of $Klebsiella$ $pneumoniae$ serotype O2:K20. J. Bacteriology. 174: 4614-4621). D-Gal I domain is also the major 0-antigen component for $Klebsiella$ $O2$ LPS. See FIG. 1A.

Several O2 sub-serotypes have been discussed in the literature. (Kelly, R. F., et al. 1996. Clonally diverse rfb gene clusters are involved in expression of a family of related D-Galactan O antigens in $Klebsiella$ species. J. Bacteriology. 5205-5214.) Structural analyses showed that sub-serotype O2 (2a) expresses only the D-Gal I moiety, while other sub-serotypes, such as O2 (2a, 2c), O2 (2a, 2e), O2 (2a, 2e, 2 h), etc. contain additional modifications on the D-Gal I backbone. Recently, →3)-β-D-Galf-(1→3)-[α-D-Galp-(1→4)]-α-D-Galp-(1→trisaccharide repeating unit of sub-serotype O2 (2a, 2f, 2g) were defined as D-Galactan III domain that was expressed in a subset of highly resistant CRE strains (clonal complex 258). The Galactan I modifying locus (gml) gene was responsible for the Galactan III domain, which has an additional galactose attached to D-galactopyranose on D-Gal I repeating units. (Szijarto, V. et. al. $Int$ $J$ $Med$ $Microbiol.$ 306(2):89-98 (2016)).

As used herein, the phrase "O2 antigen" includes both gml+ and gml− O2 LPS and does not include the D-galactose side chain of D-galactan III (D-Gal III) units. Accordingly, an "O2 binding agent" (e.g., an antibody or antigen-binding fragment thereof) as defined herein does not bind specifically to D-Gal III. Thus, in some embodiments, an O2 binding agent (e.g., an antibody or antigen-binding fragment thereof) can bind to an O2 antigen regardless of D-Gal III expression (Table 8). In some embodiments, an O2 binding agent (e.g., an antibody or antigen-binding fragment thereof) can bind to an O2 antigen that contains both D-Gal I and D-Gal III, e.g., by binding to the common carbohydrate moieties expressed in all O2 strains.

In some embodiments, the disclosure provides an isolated antigen binding protein that is an antibody or polypeptide that specifically binds to $K.$ $pneumoniae$ $O2$ antigen. In some embodiments, the antigen binding protein is an antigen binding fragment of an antibody that specifically binds to $K.$ $pneumoniae$ $O2$ antigen.

In certain embodiments, the O2 binding molecules are antibodies or polypeptides. In some embodiments, the disclosure provides an isolated antigen binding protein that is a murine, non-human, humanized, chimeric, resurfaced, or human antigen binding protein that specifically binds to $K.$ $pneumoniae$ $O2$ antigen. In some embodiments, the O2 binding molecules are humanized antibodies or antigen binding fragment thereof. In some embodiments, the O2 binding molecule is a human antibody or antigen binding fragment thereof.

The disclosure provides an isolated antigen binding protein (including an antibody or antigen binding fragment thereof) that specifically binds to $K.$ $pneumoniae$ $O2$ antigen, wherein said antigen binding protein (e.g., an antibody or antigen binding fragment thereof): a) induces opsonophagocytic killing (OPK) of a $Klebsiella$, b) protects mice from a lethal $Klebsiella$ challenge or c) induces OPK of a $Klebsiella$ and protects mice from a lethal $Klebsiella$ challenge. In certain embodiments, the isolated antigen binding protein (including an antibody or antigen binding fragment thereof) does not have LPS neutralization activity (e.g., as determined using the assay described in Example 7). In certain embodiments, the isolated antigen binding protein (including an antibody or antigen binding fragment thereof) has LPS neutralization activity against O2 LPS (e.g., as determined using the assay described in Example 7). In certain embodiments, the isolated antigen binding protein (including an antibody or antigen binding fragment thereof) has LPS neutralization activity against both O1 and O2 LPS (e.g., as determined using the assay described in Example 7). In certain embodiments, the isolated antigen binding protein (including an antibody or antigen binding fragment thereof) does not inhibit, reduce, or prevent NF-kB activation induced by LPS. In certain embodiments, the isolated antigen binding protein (including an antibody or antigen binding fragment thereof) inhibits, reduces, or prevents NF-kB activation induced by O2 LPS. In certain embodiments, the isolated antigen binding protein (including an antibody or antigen binding fragment thereof) inhibits, reduces, or prevents NF-kB activation induced by both O1 and O2 LPS.

The O2-binding agents include anti-O2 antigen antibodies KPN42, KPN42-FR-1-2-4-GL-VH/KPN42-FR-GL-C105A-VL (KPN42-v2016), KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, KPD1, and antigen-binding fragments thereof. The O2-binding agents also include O2-binding agents (e.g., anti-O2 antigen antibodies or antigen-binding fragments thereof) that specifically bind to the same *K. pneumoniae* O2 epitope as KPN42, KPN42-FR-1-2-4-GL-VH/KPN42-FR-GL-C105A-VL, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1. In some embodiments, the O2-binding agents disclosed herein include anti-O2 antigen antibodies or antigen binding fragments thereof that bind to the D-Galactan I domain of *K. pneumoniae* O2 antigen.

The O2-binding agents (e.g. anti-O2 antigen antibodies or antigen binding fragments thereof) also include O2-binding agents that competitively inhibit binding of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 to *K. pneumoniae* O2 antigen. In some embodiments, an anti-O2 antibody or antigen-binding fragment thereof competitively inhibits binding of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 to *K. pneumoniae* O2 antigen in a competition ELISA assay. In some embodiments, an anti-O2 antibody or antigen-binding fragment thereof competitively inhibits binding of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 to *K. pneumoniae* in a competition ELISA assay.

The O2-binding agents (e.g. anti-O2 antigen antibodies or antigen binding fragments thereof) also include O2-binding agents that bind *Klebsiella* of the O2 serotype, independent of gml gene expression. The effect of gml gene expression can be assessed, for example, using the methods provided in Szijártó et al., International Journal of Medical Microbiology 306: 89-98 (2016), which is herein incorporated by reference in its entirety. In some embodiments, the O2-binding agents disclosed herein include anti-O2 antigen antibodies or antigen binding fragments thereof that bind *Klebsiella* of the O2 serotype that do not express the gml gene (i.e., gml– *Klebsiella*). In some embodiments, the O2-binding agents disclosed herein include anti-O2 antigen antibodies or antigen binding fragments thereof that bind *Klebsiella* of the O2 serotype that express the gml gene (i.e., gml+ *Klebsiella*).

The O2-binding agents (e.g. anti-O2 antigen antibodies or antigen binding fragments thereof) also include O2-binding agents that comprise the heavy and light chain complementarity determining region (CDR) sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1. The CDR sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS30, and KPD1 are described in Tables 1 and 2 below.

TABLE 1

| Variable heavy chain CDR amino acid sequences | | | |
| --- | --- | --- | --- |
| Antibody | VH-CDR1 | VH-CDR2 | VH-CDR3 |
| KPN42 | GFTFNDAW (SEQ ID NO: 1) | IKKKHEGVTT (SEQ ID NO: 2) | TTRIVTTNDY (SEQ ID NO: 3) |

TABLE 1-continued

Variable heavy chain CDR amino acid sequences

| Antibody | VH-CDR1 | VH-CDR2 | VH-CDR3 |
|---|---|---|---|
| KPN42-FR-1-2-4-GL-VH/KPN42-FR-GL-C105A-VL (KPN42-v2016) | GFTFNDAW (SEQ ID NO: 10) | IKKKHEGVTT (SEQ ID NO: 11) | TTRIVTTNDY (SEQ ID NO: 12) |
| KPN42-FR-GL-VH/KPN42-FR-GL-C105A-VL | GFTFNDAW (SEQ ID NO: 19) | IKKKHEGVTT (SEQ ID NO: 20) | TTRIVTTNDY (SEQ ID NO: 21) |
| KPS3 | GFSFRDYG (SEQ ID NO: 28) | ISYDGRDQ (SEQ ID NO: 29) | GPFYNPSLYYPP (SEQ ID NO: 30) |
| KPN70 | GGSISTYY (SEQ ID NO: 37) | IHQSGTT (SEQ ID NO: 38) | ARESDDGYKWNYFDY (SEQ ID NO: 39) |
| KPN179 | GFTFNNAW (SEQ ID NO: 46) | IKRKADGETT (SEQ ID NO: 47) | TTRIVTTNDY (SEQ ID NO: 48) |
| KPN179-FR-1-2-4-GL-N35S-VH/KPN179-FR-GL-C105A-VL | GFTFSNAW (SEQ ID NO: 166) | IKRKADGETT (SEQ ID NO: 167) | TTRIVTTNDY (SEQ ID NO: 168) |
| KPN179-FR-GL N35S-VH/KPN179-FR-GL-C105A-VL | GFTFSNAW (SEQ ID NO: 169) | IKRKADGETT (SEQ ID NO: 170) | TTRIVTTNDY (SEQ ID NO: 171) |
| KPN44 | GGSTSSYY (SEQ ID NO: 55) | IHHGGTT (SEQ ID NO: 56) | ARESDDGYRWNYFDY (SEQ ID NO: 57) |
| KPN17 | GFTFSHFW (SEQ ID NO: 64) | IDGSVTNL (SEQ ID NO: 65) | ARDLVGIGTPAGYGMDV (SEQ ID NO: 66) |
| 6F6 | PIAYMG (SEQ ID NO: 73) | DILPNIGRTIYGEKFED (SEQ ID NO: 74) | RGTSGAMDY (SEQ ID NO: 75) |
| KPL26 | GFIFGSSW (SEQ ID NO: 82) | INPDGSAT (SEQ ID NO: 83) | TRNKAYNALDY (SEQ ID NO: 84) |
| KPS18 | GFTFKNAW (SEQ ID NO: 91) | VKNEVDGGTI (SEQ ID NO: 92) | RAFWSGFPAGY (SEQ ID NO: 93) |
| KPS24 | GFTFKNAW (SEQ ID NO: 100) | VKSEVDGGTT (SEQ ID NO: 101) | RAFWSDFQTGY (SEQ ID NO: 102) |
| KPS44 | GFTFKNAW (SEQ ID NO: 109) | VKSEVDGGTI (SEQ ID NO: 110) | RAFWSGFPTGY (SEQ ID NO: 111) |
| KPS44-v2017 | GFTFKNAW (SEQ ID NO: 109) | VKSEVDGGTI (SEQ ID NO: 110) | RAFFSGFPTGY (SEQ ID NO: 199) |
| KPS44-G1 | GFTFKNAW (SEQ ID NO: 109) | VKSEVDGGTI (SEQ ID NO: 110) | RAFWSGFPTGY (SEQ ID NO: 111) |
| KPS44-G2 | GFTFKNAW (SEQ ID NO: 109) | VKSEVDGGTI (SEQ ID NO: 110) | RAFFSGFPTGY (SEQ ID NO: 199) |
| KPS44-G3 | GFTFKNAW (SEQ ID NO: 109) | VKSEVDGGTI (SEQ ID NO: 110) | RAFFSGFPTGY (SEQ ID NO: 199) |
| KPS30 | GFSFSTSW (SEQ ID NO: 118) | IDPDGSTR (SEQ ID NO: 119) | ARDYAYNRFDY (SEQ ID NO: 120) |
| KPD1 | GVSITSNTYW (SEQ ID NO: 127) | LSYSGDT (SEQ ID NO: 128) | ARDPDIIRNFQFDY (SEQ ID NO: 129) |

TABLE 1-continued

Variable heavy chain CDR amino acid sequences

| Antibody | VH-CDR1 | VH-CDR2 | VH-CDR3 |
|---|---|---|---|
| KPL36 | GFTFISSW (SEQ ID NO: 172) | INPDGTET (SEQ ID NO: 173) | ARNKAYNAHDF (SEQ ID NO: 174) |
| KPS44-G4 | GFTFKNAW (SEQ ID NO: 109) | VKSEVDAGTI (SEQ ID NO: 215) | RAFYSGFPTGY (SEQ ID NO: 216) |
| KPS44-G6 | GFTFKNAW (SEQ ID NO: 109) | VKSEVDAGTI (SEQ ID NO: 215) | RAFYSGFPTGY (SEQ ID NO: 216) |
| KPS44-G8 | GFTFKNAW (SEQ ID NO: 109) | VKSEVDAGTI (SEQ ID NO: 215) | RAFYSGFPTGY (SEQ ID NO: 216) |
| KPS44-G10 | GFTFKNAW (SEQ ID NO: 109) | VKSEVDAGTI (SEQ ID NO: 215) | RAFYSGFPTGY (SEQ ID NO: 216) |
| KPS44-G11 | GFTFKNAW (SEQ ID NO: 109) | VKSEVDAGTI (SEQ ID NO: 215) | RAFYSGFPTGY (SEQ ID NO: 216) |
| KPS44-G14 | GFTFKNAW (SEQ ID NO: 109) | VKSEVDAGTI (SEQ ID NO: 215) | RAFYSGFPTGY (SEQ ID NO: 216) |

TABLE 2

Variable light chain CDR amino acid sequences

| Antibody | VL-CDR1 | VL-CDR2 | VL-CDR3 |
|---|---|---|---|
| KPN42 | SSDVGAYDY (SEQ ID NO: 4) | DVN (SEQ ID NO: 5) or IIYDVNERP (SEQ ID NO: 6) | CSYAGGDIFV (SEQ ID NO: 7) |
| KPN42-FR-1-2-4-GL-VH/KPN42-FR-GL-C105A-VL (KPN42-v2016) | SSDVGAYDY (SEQ ID NO: 13) | DVN (SEQ ID NO: 14) or MIYDVNKRP (SEQ ID NO: 15) | ASYAGGDIFV (SEQ ID NO: 16) |
| KPN42-FR-GL-VH/KPN42-FR-GL-C105A-VL | SSDVGAYDY (SEQ ID NO: 22) | DVN (SEQ ID NO: 23) or MIYDVNKRP (SEQ ID NO: 24) | ASYAGGDIFV (SEQ ID NO: 25) |
| KPS3 | QSISSQ (SEQ ID NO: 31) | DAS (SEQ ID NO: 32) or LIHDASNRD (SEQ ID NO: 33) | LQRNNWPPWT (SEQ ID NO: 34) |
| KPN70 | QIVTNY (SEQ ID NO: 40) | DMS (SEQ ID NO: 41) or LIFDMSIRA (SEQ ID NO: 42) | QHRSNWPLFT (SEQ ID NO: 43) |
| KPN179 | SSDVGYYDY (SEQ ID NO: 49) | DVN (SEQ ID NO: 50) or MIYDVNKRP (SEQ ID NO: 51) | CSYAGGDTFV (SEQ ID NO: 52) |
| KPN179-FR-1-2-4-GL-N35S-VH/KPN179-FR-GL-C105A-VL | SSDVGYYDY (SEQ ID NO: 175) | DVN (SEQ ID NO: 176) or MIYDVNKRP (SEQ ID NO: 177) | ASYAGGDTFV (SEQ ID NO: 178) |
| KPN179-FR-GL N35S-VH/KPN179-FR-GL-C105A-VL | SSDVGYYDY (SEQ ID NO: 179) | DVN (SEQ ID NO: 180) or MIYDVNKRP (SEQ ID NO: 181) | ASYAGGDTFV (SEQ ID NO: 182) |

TABLE 2-continued

Variable light chain CDR amino acid sequences

| Antibody | VL-CDR1 | VL-CDR2 | VL-CDR3 |
|---|---|---|---|
| KPN44 | QTITNY (SEQ ID NO: 58) | DMS (SEQ ID NO: 59) or LIFDMSKRA (SEQ ID NO: 60) | QHRSNWPLFT (SEQ ID NO: 61) |
| KPN17 | QGISTY (SEQ ID NO: 67) | AAS (SEQ ID NO: 68) or LIYAASTLQ (SEQ ID NO: 69) | QQLTSHLYT (SEQ ID NO: 70) |
| 6F6 | RSSQGLVHSTGNTFLH (SEQ ID NO: 76) | KVSNRFS (SEQ ID NO: 77) | SQSTHIPYT (SEQ ID NO: 78) |
| KPL26 | SSDVGGNNY (SEQ ID NO: 85) | EVS (SEQ ID NO: 86) or IIYEVSKRP (SEQ ID NO: 87) | SSFGGSKM (SEQ ID NO: 88) |
| KPS18 | RSNIGSDS (SEQ ID NO: 94) | DNN (SEQ ID NO: 95) or LMYDNNKRP (SEQ ID NO: 96) | ATWDSSLSAYV (SEQ ID NO: 97) |
| KPS24 | SSNIGSDS (SEQ ID NO: 103) | ENN (SEQ ID NO: 104) or LMYENNKRP (SEQ ID NO: 105) | AAWDSSLRAYV (SEQ ID NO: 106) |
| KPS44 | SSNIGSDS (SEQ ID NO: 112) | ENN (SEQ ID NO: 113) or LIYENNKRP (SEQ ID NO: 114) | ATWDSSLSAYV (SEQ ID NO: 115) |
| KPS44-v2017 | SSNIGSNY (SEQ ID NO: 200) | ENN (SEQ ID NO: 113) or LIYENNKRP (SEQ ID NO: 114) | ATFDSSLSAYV (SEQ ID NO: 201) |
| KPS44-G1 | SSNIGSNY (SEQ ID NO: 200) | ENN (SEQ ID NO: 113) or LIYENNKRP (SEQ ID NO: 114) | ATFDSSLSAYV (SEQ ID NO: 201) |
| KPS44-G2 | SSNIGSDS (SEQ ID NO: 112) | ENN (SEQ ID NO: 113) or LIYENNKRP (SEQ ID NO: 114) | ATFDSSLSAYV (SEQ ID NO: 201) |
| KPS44-G3 | SSNIGSNY (SEQ ID NO: 200) | ENN (SEQ ID NO: 113) or LIYENNKRP (SEQ ID NO: 114) | ATWDSSLSAYV (SEQ ID NO: 115) |
| KPS30 | SSDIGANNY (SEQ ID NO: 121) | EVN (SEQ ID NO: 122) or LLYEVNKRP (SEQ ID NO: 123) | CGYGGGRV (SEQ ID NO: 124) |
| KPD1 | QILYMSH (SEQ ID NO: 130) | GAS (SEQ ID NO: 131) or LIYGASIRA (SEQ ID NO: 132) | QQYGASPT (SEQ ID NO: 133) |
| KPL36 | SSDVGGNNF (SEQ ID NO: 183) | EVN (SEQ ID NO: 184) or IIYEVNKRP (SEQ ID NO: 185) | GAFGGSKM (SEQ ID NO: 186) |
| KPS44-G4 | SSNIGSDA (SEQ ID NO: 218) | ENN (SEQ ID NO: 113) or LIYENNKRP (SEQ ID NO: 114) | ATFESSLSAYV (SEQ ID NO: 230) |
| KPS44-G6 | SSNIGSES (SEQ ID NO: 228) | ENN (SEQ ID NO: 113) or LIYENNKRP (SEQ ID NO: 114) | ATFESSLSAYV (SEQ ID NO: 230) |
| KPS44-G8 | SSNIGSDS (SEQ ID NO: 238) | ENN (SEQ ID NO: 113) or LIYENNKRP (SEQ ID NO: 114) | ATFESSLSAYV (SEQ ID NO: 230) |
| KPS44-G10 | SSNIGSDS (SEQ ID NO: 238) | ENN (SEQ ID NO: 113) or LIYENNKRP (SEQ ID NO: 114) | ATFESSLSAYV (SEQ ID NO: 230) |
| KPS44-G11 | SSNIGSDS (SEQ ID NO: 238) | ENN (SEQ ID NO: 113) or LIYENNKRP (SEQ ID NO: 114) | ATFESSLSAYV (SEQ ID NO: 230) |

TABLE 2-continued

Variable light chain CDR amino acid sequences

| Antibody | VL-CDR1 | VL-CDR2 | VL-CDR3 |
|---|---|---|---|
| KPS44-G14 | SSNIGSDS (SEQ ID NO: 238) | ENN (SEQ ID NO: 113) or LIYENNKRP (SEQ ID NO: 114) | ATFESSLSAYV (SEQ ID NO: 230) |

Antigen binding proteins (including anti-O2 antigen antibodies or antigen binding fragments thereof) described herein can comprise one of the individual variable light chains or variable heavy chains described herein. Antigen binding proteins (including anti-O2 antigen antibodies or antigen binding fragments thereof) described herein can also comprise both a variable light chain and a variable heavy chain. The variable light chain and variable heavy chain sequences of anti-O2 antigen KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, and KPD1 antibodies are provided in Tables 3 and 4 below.

TABLE 3

Variable heavy chain amino acid sequences

| Antibody | VH Amino Acid Sequence (SEQ ID NO) |
|---|---|
| KPN42 | EVQLVESGGGLVKPGGSLRLSCAASGFTFNDAWMNWVRQAPGKGLEWVARIKKKHEGVTTDYPASVRGRFTISRDDSKNTVYLQMGRLRIEDTAIYYCTTRIVTTNDYWGQGTLVTVSS (SEQ ID NO: 8) |
| KPN42-v2016 | EVQLVESGGGLVKPGGSLRLSCAASGFTFNDAWMNWVRQAPGKGLEWVGRIKKKHEGVTTDYPASVRGRFTISRDDSKNTVYLQMGRLRIEDTAIYYCTTRIVTTNDYWGQGTLVTVSS (SEQ ID NO: 17) |
| KPN42-FR-GL-VH/KPN42-FR-GL-C105A-VL | EVQLVESGGGLVKPGGSLRLSCAASGFTFNDAWMNWVRQAPGKGLEWVGRIKKKHEGVTTDYAAPVKGRFTISRDDSKNTLYLQMNSLKTEDTAVYYCTTRIVTTNDYWGQGTLVTVSS (SEQ ID NO: 26) |
| KPS3 | QGQLVDSGGGVVQRGGSQRLSCAASGFSFRDYGMHWVRQAPGKGLEWVAFISYDGRDQYYADSVKGRFIISRDNSKNTLSLQMNSLRPEDTAVYYCGPFYNPSLYYPPWGHGLPVIVSS (SEQ ID NO: 35) |
| KPN70 | QVQLQESGPGLVKPSETLSLTCTVSGGSISTYYWNWIRQSPGKELEWIANIHQSGTTYYNPSLKSRVTMSVDTSKNQFSLKVISVTAADTAVYYCARESDDGYKWNYFDYWGQGTLVTVSS (SEQ ID NO: 44) |
| KPN179 | EVQVVESGGGLVKPGGSLRLSCAASGFTFNNAWMNWVRQAPGKGLEWVGRIKRKADGETTDYPASVKGRFTVSRDDSKNTIYLQMNSLKTEDTAIYYCTTRIVTTNDYWGQGTLVTVSS (SEQ ID NO: 53) |
| KPN179-FR-1-2-4-GL-N35S-VH/KPN179-FR-GL-C105A-VL | EVQLVESGGGLVKPGGSLRLSCAASGFTFSNAWMNWVRQAPGKGLEWVGRIKRKADGETTDYPASVKGRFTVSRDDSKNTIYLQMNSLKTEDTAIYYCTTRIVTTNDYWGQGTLVTVSS (SEQ ID NO: 187) |
| KPN179-FR-GL N35S-VH/KPN179-FR-GL-C105A-VL | EVQLVESGGGLVKPGGSLRLSCAASGFTFSNAWMNWVRQAPGKGLEWVGRIKRKADGETTDYAAPVKGRFTISRDDSKNTLYLQMNSLKTEDTAVYYCTTRIVTTNDYWGQGTLVTVSS (SEQ ID NO: 188) |
| KPN44 | QVQLQESGPGLVKPSETLSLTCTVSGGSTSSYYWNWIRQAPGKPLQWIANIHHGGTTYYNPSLRSRVTMSLDTSNNQFSLKLTSVTAADTAVYFCARESDDGYRWNYFDYWGQGVLVTVSS (SEQ ID NO: 62) |

TABLE 3-continued

Variable heavy chain amino acid sequences

| Antibody | VH Amino Acid Sequence (SEQ ID NO) |
|---|---|
| KPN17 | EVQLVESGGGLVQPGGSLRLSCAASGFTFSHFWMHWVRQAPGQGLVWVARIDGS VTNLRYAGSVEGRFTISRDNAKNTLYLQMNSLRDEDTAVYYCARDLVGIGTPAGY GMDVWGQGTTVTVSS (SEQ ID NO: 71) |
| 6F6 | QVHLQQSGSELRSPGSSVKLSCKDFDSDVFPIAYMGWIRQQPGHGFDWIGDILPNI GRTIYGEKFEDKATLDADTVSNTAYLELSSLTSEDSAIYYCARRGTSGAMDYWGQ GTSVTVSS (SEQ ID NO: 80) |
| KPL26 | EVQLVESGGGLVQSGGSLRLSCETSGFIFGSSWMTWVRQAPGKGLEWVATINPDG SATSYEDSVRGRFAVSRDNAKNSVYLQMNSLRAEDTAVYFCTRNKAYNALDYW GQGTLVTVSS (SEQ ID NO: 89) |
| KPS18 | EVRLVESGGGLVKPGGSLRLSCAASGFTFKNAWMSWIRQAPGKGLEWVGRVKNE VDGGTIDYGVPVRGRFTISRDDSQGTLSLEMNSLREDDTGIYYCRAFWSGFPAGY WGQGTLVSVSS (SEQ ID NO: 98) |
| KPS24 | ELHLVESGGGLVKPGGSLRLSCAASGFTFKNAWMSWIRQAPGKGLEWVGRVKSE VDGGTTDYGVPVRGRFTISRDDSQSTLSLEMSSLQDDDTGVYYCRAFWSDFQTGY WGQGTLVTVSS (SEQ ID NO: 107) |
| KPS44 | EVHLVESGGGLVKPGGSLRLSCAASGFTFKNAWMSWIRQAPGKGLEWVGRVKSE VDGGTIDYGVPVRGRFTISRDDSQGTLSLEMNSLKDDDTGVYYCRAFWSGFPTGY WGQGALVSVSS (SEQ ID NO: 116) |
| KPS44-v2017 | EVHLVESGGGLVKPGGSLRLSCAASGFTFKNAWMSWIRQAPGKGLEWVGRVKSE VDGGTIDYGVPVRGRFTISRDDSQGTLSLEMNSLKDDDTGVYYCRAFFSGFPTGY WGQGALVSVSS (SEQ ID NO: 202) |
| KPS44-G1 | EVHLVESGGGLVKPGGSLRLSCAASGFTFKNAWMSWIRQAPGKGLEWVGRVKSE VDGGTIDYGVPVRGRFTISRDDSQGTLSLEMNSLKDDDTGVYYCRAFWSGFPTGY WGQGALVSVSS (SEQ ID NO: 116) |
| KPS44-G2 | EVHLVESGGGLVKPGGSLRLSCAASGFTFKNAWMSWIRQAPGKGLEWVGRVKSE VDGGTIDYGVPVRGRFTISRDDSQGTLSLEMNSLKDDDTGVYYCRAFFSGFPTGY WGQGALVSVSS (SEQ ID NO: 202) |
| KPS44-G3 | EVHLVESGGGLVKPGGSLRLSCAASGFTFKNAWMSWIRQAPGKGLEWVGRVKSE VDGGTIDYGVPVRGRFTISRDDSQGTLSLEMNSLKDDDTGVYYCRAFFSGFPTGY WGQGALVSVSS (SEQ ID NO: 202) |
| KPS30 | EMQLVESGGGLVQPGVSLRLSCVDSGFSFSTSWLAWVRQAPGKGLEWLANIDPD GSTRNHVDSVRGRFTISRDNAKNSLYLQMNSLRAEDTAVYYCARDYAYNRFDYW GQGTMVTVSS (SEQ ID NO: 125) |
| KPD1 | QVQLQESDPRLVKPSETLSLTCSVSGVSITSNTYWWAWIRQPPGKKLEWIGSLSYS GDTYYNPSLTSRVTISRDIHQNQFFLELNSVTAADTAMYYCARDPDIIRNFQFDYW GRGTLVTVSS (SEQ ID NO: 134) |
| KPL36 | EVQLVESGGGVVQSGGSLRLSCETSGFTFISSWMSWVRQAPGTGLEWVATINPDG TETPYADSLKGRFTISRDNTKKSLYLQIHSLRADDTAVYFCARNKAYNAHDFWGQ GTLVMVSS (SEQ ID NO: 189) |
| KPS44-G4 | QVQLVESGGGLVKPGGSLRLSCAASGFTFKNAWMSWIRQAPGKGLEWVGRVKSE VDAGTIDYGVPVRGRFTISRDDSKNTLYLQMNSLKTEDTAVYYCRAFYSGFPTGY WGQGTLVTVSS (SEQ ID NO: 213) |
| KPS44-G6 | QVQLVESGGGLVKPGGSLRLSCAASGFTFKNAWMSWIRQAPGKGLEWVGRVKSE VDAGTIDYGVPVRGRFTISRDDSKNTLYLQMNSLKTEDTAVYYCRAFYSGFPTGY WGQGTLVTVSS (SEQ ID NO: 223) |
| KPS44-G8 | QVQLVESGGGLVKPGGSLRLSCAASGFTFKNAWMSWIRQAPGKGLEWVGRVKSE VDAGTIDYGVPVRGRFTISRDDSKNTLYLQMNSLKTEDTAVYYCRAFYSGFPTGY WGQGTLVTVSS (SEQ ID NO: 233) |
| KPS44-G10 | EVHLVESGGGLVKPGGSLRLSCAASGFTFKNAWMSWIRQAPGKGLEWVGRVKSE VDAGTIDYGVPVRGRFTISRDDSQGTLSLEMNSLKDDDTGVYYCRAFYSGFPTGY WGQGALVSVSS (SEQ ID NO: 243) |
| KPS44-G11 | EVHLVESGGGLVKPGGSLRLSCAASGFTFKNAWMSWIRQAPGKGLEWVGRVKSE VDAGTIDYGVPVRGRFTISRDDSQGTLSLEMNSLKDDDTGVYYCRAFYSGFPTGY WGQGALVSVSS (SEQ ID NO: 253) |
| KPS44-G14 | QVQLVESGGGLVKPGGSLRLSCAASGFTFKNAWMSWIRQAPGKGLEWVGRVKSE VDAGTIDYGVPVRGRFTISRDDSKNTLYLQMNSLKTEDTAVYYCRAFYSGFPTGY WGQGTLVTVSS (SEQ ID NO: 263) |

TABLE 3-continued

Variable heavy chain amino acid sequences

| Antibody | VH Amino Acid Sequence (SEQ ID NO) |
|---|---|
| KPS44-G8-HCvFW1 | QVQLVESGGGLVKPGGSLRLSCAASGFTFKNAWMSWIRQAPGKGLEWVGRVKSEVDAGTIDYGVPVRGRFTISRDDSQGTLYLQMNSLKTEDTGVYYCRAFYSGFPTGYWGQGTLVTVSS (SEQ ID NO: 273) |
| KPS44-G8-HCvFW2 | QVHLVESGGGLVKPGGSLRLSCAASGFTFKNAWMSWIRQAPGKGLEWVGRVKSEVDAGTIDYGVPVRGRFTISRDDSQGTLYLQMNSLKTEDTGVYYCRAFYSGFPTGYWGQGTLVTVSS (SEQ ID NO: 274) |

TABLE 4

Variable light chain amino acid sequences

| Antibody | VL Amino Acid Sequence (SEQ ID NO) |
|---|---|
| KPN42 | QSALTQPPSVSGSPGQSVTISCTGTSSDVGAYDYVSWYQQYAGKVPKHIIYDVNERPSGVPDRFSGSKSGNTAALTISGLQAEDEADYYCCSYAGGDIFVFGTGTQVTVL (SEQ ID NO: 9) |
| KPN42-v2016 | QSALTQPRSVSGSPGQSVTISCTGTSSDVGAYDYVSWYQQHPGKAPKLMIYDVNKRPSGVPDRFSGSKSGNTASLTISGLQAEDEADYYCASYAGGDIFVFGTGTKVTVL (SEQ ID NO: 18) |
| KPN42-FR-GL-VH/KPN42-FR-GL-C105A-VL | QSALTQPRSVSGSPGQSVTISCTGTSSDVGAYDYVSWYQQHPGKAPKLMIYDVNKRPSGVPDRFSGSKSGNTASLTISGLQAEDEADYYCASYAGGDIFVFGTGTKVTVL (SEQ ID NO: 27) |
| KPS3 | EVVLTQSPATLSLSPGERATLSCRASQSISSQLAWYQQKPGQAPRLLIHDASNRDTGVPDRFSGSGSGTDFTLTISSLEPEDFAMYYCLQRNNWPPWTFGQGTKVEIK (SEQ ID NO: 36) |
| KPN70 | EIVLTQSPASLSLSPGERATLSCRASQIVTNYLAWYQHKPGQAPRLLIFDMSIRAAGIPARFSGSGSGTDFTLTISSLEPEDFAVYYCQHRSNWPLFTFGPGTKVDIK (SEQ ID NO: 45) |
| KPN179 | QSALTQPPSVSGSPGQSVTISCTGTSSDVGYYDYVSWYQQHPGKAPKHMIYDVNKRPSGVPDRFSGSKSGNTASLTISGLQAEDEADYYCCSYAGGDTFVFGTGTKVTVLv (SEQ ID NO: 54) |
| KPN179-FR-1-2-4-GL-N35S-VH/KPN179-FR-GL-C105A-VL | QSALTQPRSVSGSPGQSVTISCTGTSSDVGYYDYVSWYQQHPGKAPKLMIYDVNKRPSGVPDRFSGSKSGNTASLTISGLQAEDEADYYCASYAGGDTFVFGTGTKVTVL (SEQ ID NO: 190) |
| KPN179-FR-GL-N35S-VH/KPN179-FR-GL-C105A-VL | QSALTQPRSVSGSPGQSVTISCTGTSSDVGYYDYVSWYQQHPGKAPKLMIYDVNKRPSGVPDRFSGSKSGNTASLTISGLQAEDEADYYCASYAGGDTFVFGTGTKVTVL (SEQ ID NO: 191) |
| KPN44 | EIVLTQSPASLSLSPGDRATLSCRASQTITNYLAWYQHKPGQAPRLLIFDMSKRATGIPARFSGSGSGTDFTLTISSLEPEDFAVYYCQHRSNWPLFTFGPGTNVDIK (SEQ ID NO: 63) |
| KPN17 | DIQLTQSPSFLSASVGDRVTITCRASQGISTYLAWYQQKPGKAPKLLIYAASTLQSGVPSRFSGSGSGTEFTLTINSLQSEDFATYYCQQLTSHLYTFGQGTKLEIK (SEQ ID NO: 72) |
| 6F6 | DVVMTQTPLFLPVSLGDQASISCRSSQGLVHSTGNTFLHWYLQKPGQSPKLLIYKVSNRFSGVPDRFSGSGSGTDFTLKISRVEAEDLGIYFCSQSTHIPYTFGGGTKLEIK (SEQ ID NO: 81) |

TABLE 4-continued

Variable light chain amino acid sequences

| Antibody | VL Amino Acid Sequence (SEQ ID NO) |
|---|---|
| KPL26 | QSALTQPPSASGSPGQSVTLSCTGTSSDVGGNNYVSWYQQHPGKAPKLIIYEVSKR PSGVPNRFSGSKSGNTASLTVSGLQAEDEADYYCSSFGGSKMFGGGTKLTVL (SEQ ID NO: 90) |
| KPS18 | QSVLTQPPSLSAAPGQTVTIACSGSRSNIGSDSVSWFQQFPGTAPRVLMYDNNKRP SGISDRFSGSKSGTSVTLDITGLQTGDEADYYCATWDSSLSAYVFGSGTKVTVL (SEQ ID NO: 99) |
| KPS24 | QSVLTQPPSVSAAPGQTVTIACSGSSSNIGSDSVSWFQQLPGTAPRVLMYENNKRPS GISDRFSGSKSGTSVTLGITGLQTGDEADYYCAAWDSSLRAYVFGSGTKVTVL (SEQ ID NO: 108) |
| KPS44 | QSVLTQPPSLSAAPGQTITIACSGTSSNIGSDSVSWFQQFPGTAPRVLIYENNKRPSGI SDRFSGSKSGTSVTLGITGLQTGDEADYYCATWDSSLSAYVFGSGTKVTVL (SEQ ID NO: 117) |
| KPS44-v2017 | QSVLTQPPSLSAAPGQTITIACSGTSSNIGSNYVSWFQQFPGTAPRVLIYENNKRPSG ISDRFSGSKSGTSVTLGITGLQTGDEADYYCATFDSSLSAYVFGSGTKVTVL (SEQ ID NO: 203) |
| KPS44-G1 | QSVLTQPPSLSAAPGQTITIACSGTSSNIGSNYVSWFQQFPGTAPRVLIYENNKRPSG ISDRFSGSKSGTSVTLGITGLQTGDEADYYCATFDSSLSAYVFGSGTKVTVL (SEQ ID NO: 203) |
| KPS44-G2 | QSVLTQPPSLSAAPGQTITIACSGTSSNIGSDSVSWFQQFPGTAPRVLIYENNKRPSGI SDRFSGSKSGTSVTLGITGLQTGDEADYYCATFDSSLSAYVFGSGTKVTVL (SEQ ID NO: 204) |
| KPS44-G3 | QSVLTQPPSLSAAPGQTITIACSGTSSNIGSNYVSWFQQFPGTAPRVLIYENNKRPSG ISDRFSGSKSGTSVTLGITGLQTGDEADYYCATWDSSLSAYVFGSGTKVTVL (SEQ ID NO: 205) |
| KPS30 | QSALTQPPSASGSPGQSVVISCTGTSSDIGANNYVSWYQQHPGKAPKLLLYEVNKR PSGVPDRFSASKSGNTASLTVSGLLAEDEADYYCCGYGGGRVFGGGTKLTVL (SEQ ID NO: 126) |
| KPD1 | EIVLTQSPGILSLSPGERATLSCRVSQILYMSHLAWYQHKPGQAPRLLIYGASIRAT GVPDRFSGSGSGTDFTLTISRLEPEDFAVYYCQQYGASPTFGQGTMVEIK (SEQ ID NO: 135) |
| KPL36 | QSALTQPPSASGSPGQSVTISCTGTSSDVGGNNFVSWYQQYPGKAPKLIIYEVNKRP SGVPDRFSGSKSGNTASLTVSGLQAEDEADYYCGAFGGSKMFGGGTKLTVL (SEQ ID NO: 192) |
| KPS44-G4 | QSVLTQPPSVSAAPGQKVTIACSGTSSNIGSDAVSWFQQLPGTAPKLLIYENNKRPS GISDRFSGSKSGTSVTLGITGLQTGDEADYYCATFESSLSAYVFGTGTKVTVL (SEQ ID NO: 217) |
| KPS44-G6 | QSVLTQPPSVSAAPGQKVTIACSGTSSNIGSESVSWFQQLPGTAPKLLIYENNKRPS GISDRFSGSKSGTSVTLGITGLQTGDEADYYCATFESSLSAYVFGTGTKVTVL (SEQ ID NO: 227) |
| KPS44-G8 | QSVLTQPPSVSAAPGQKVTIACSGTSSNIGSDSVSWFQQLPGTAPKLLIYENNKRPS GISDRFSGSKSGTSVTLGITGLQTGDEADYYCATFESSLSAYVFGTGTKVTVL (SEQ ID NO: 237) |
| KPS44-G10 | QSVLTQPPSLSAAPGQTITIACSGTSSNIGSDSVSWFQQFPGTAPRVLIYENNKRPSGI SDRFSGSKSGTSVTLGITGLQTGDEADYYCATFESSLSAYVFGSGTKVTVL (SEQ ID NO: 247) |
| KPS44-G11 | QSVLTQPPSVSAAPGQKVTIACSGTSSNIGSDSVSWFQQLPGTAPKLLIYENNKRPS GISDRFSGSKSGTSVTLGITGLQTGDEADYYCATFESSLSAYVFGTGTKVTVL (SEQ ID NO: 257) |
| KPS44-G14 | QSVLTQPPSLSAAPGQTITIACSGTSSNIGSDSVSWFQQFPGTAPRVLIYENNKRPSGI SDRFSGSKSGTSVTLGITGLQTGDEADYYCATFESSLSAYVFGSGTKVTVL (SEQ ID NO: 267) |

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a heavy chain variable region (VH) at least 95, 96, 97, 98, or 99% identical to SEQ ID NO: 8, 17, 26, 35, 44, 53, 187, 188, 62, 71, 80, 89, 98, 107, 116, 125, 134, or 189 and a light chain variable region (VL) at least 95, 96, 97, 98, or 99% identical to SEQ ID NOs: 9, 18, 27, 36, 45, 54, 190, 191, 63, 72, 81, 90, 99, 108, 117, 126, 135, or 192. In some embodiments, the isolated antigen binding protein (including, e.g., anti-O2 antigen antibodies or antigen-binding fragments thereof) that specifically binds to *K. pneumoniae* O2 antigen comprises a heavy chain variable region comprising the sequences of SEQ ID NO: 8, 17, 26, 35, 44, 53, 187, 188, 62, 71, 80, 89, 98, 107, 116, 125, 134, or 189 and a light chain variable region comprising the sequences of SEQ ID NOs: 9, 18, 27, 36, 45, 54, 190, 191, 63, 72, 81, 90, 99, 108, 117, 126, 135, or 192. In some embodiments, the isolated antigen binding protein (including, e.g., anti-O2 antigen antibodies or antigen-binding fragments thereof) having least 95, 96, 97, 98, or 99% sequence identity to SEQ ID NO: 8, 9, 17, 18, 26, 27, 35, 36, 44, 45, 53, 54, 187, 190, 188, 191, 62, 63, 71, 72, 80, 81, 89, 90, 98, 99, 107, 108, 116, 117, 125, 126, 134, 135, 189, or 192 differs from SEQ ID NO: 8, 9, 17, 18, 26, 27, 35, 36, 44, 45, 53, 54, 187, 190, 188, 191, 62, 63, 71, 72, 80, 81, 89, 90, 98, 99, 107, 108, 116, 117, 125, 126, 134, 135, 189, or 192 by conservative amino acid substitutions only.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 95% identical to SEQ ID NOs:8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135 or 189 and 192, respectively, and wherein the antigen binding protein induces OPK of *Klebsiella* (e.g., *K. pneumoniae*).

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 95% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 95% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*) and protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 95% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192 respectively, and wherein the antigen binding protein act synergistically with an antibiotic (e.g., meropenem, carbapenems, or colistin).

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 96% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*).

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 96% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 96% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*) and protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 96% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein act synergistically with an antibiotic (e.g., meropenem, carbapenems, or colistin).

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 97% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*).

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 97% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 97% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*) and protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 97% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, 189 and 192, respectively, and wherein the antigen binding protein act synergistically with an antibiotic (e.g., meropenem, carbapenems, or colistin).

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 98% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, 189 or 192, respectively, and wherein the antigen binding protein induces OPK of *Klebsiella* (e.g., *K. pneumoniae*).

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 98% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 98% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*) and protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 98% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein act synergistically with an antibiotic (e.g., meropenem, carbapenems, or colistin).

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 99% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*).

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 99% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 99% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein induces OPK of *Klebsiella* (e.g., *K. pneumoniae*) and protects mice from a lethal *Klebsiella* challenge.

In some embodiments, the disclosure provides an isolated antigen binding protein (including, e.g., anti-O2 antigen antibodies or antigen-binding fragments thereof) that specifically binds to *K. pneumoniae* O2 antigen, wherein said antigen binding protein comprises a VH and VL at least 99% identical to SEQ ID NOs: 8 and 9, 17 and 18, 26 and 27, 35 and 36, 44 and 45, 53 and 54, 187 and 190, 188 and 191, 62 and 63, 71 and 72, 80 and 81, 89 and 90, 98 and 99, 107 and 108, 116 and 117, 125 and 126, 134 and 135, or 189 and 192, respectively, and wherein the antigen binding protein act synergistically with an antibiotic (e.g., meropenem, carbapenems, or colistin).

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the K. pneumoniae O2 antigen is a humanized antibody. In certain embodiments, such antibodies are used therapeutically to reduce antigenicity and HAMA (human anti-mouse antibody) responses when administered to a human subject. Humanized antibodies can be produced using various techniques known in the art. In certain alternative embodiments, the antibody to *K. pneumoniae O*2 antigen is a human antibody.

Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2008, J. Mol. Bio., 376: 1182-200 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

According to the present disclosure, techniques can be adapted for the production of single-chain antibodies specific to *K. pneumoniae O*2 antigen (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for O2 antigen, or fragments thereof. Antibody fragments can be produced by techniques in the art including, but not limited to: (a) a F(ab')2 fragment produced by pepsin digestion of an antibody; (b) a Fab fragment generated by reducing the disulfide bridges of an F(ab')2 fragment, (c) a Fab fragment generated by the treatment of the antibody with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Antigen binding proteins of the present disclosure (including, e.g., anti-O2 antigen antibodies or antigen-binding fragments thereof) can further comprise antibody constant regions or parts thereof. For example, a VL domain can be attached at its C-terminal end to antibody light chain constant domains including human Cκ or Cγ chains. Similarly, an antigen binding protein based on a VH domain can be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. For example, the immunoglobulin heavy chain can be derived from the antibody isotype sub-class, IgG1. Any synthetic or other constant region variant that has these properties and stabilizes variable regions is also contemplated for use in embodiments of the present disclosure. The antibody constant region can be an Fc region with a YTE mutation, such that the Fc region comprises the following amino acid substitutions: M252Y/S254T/T256E. This residue numbering is based on Kabat numbering. The YTE mutation in the Fc region increases serum persistence of the antigen-binding protein (see Dall'Acqua, W. F. et al. (2006) The Journal of Biological Chemistry, 281, 23514-23524).

In some embodiments herein, the antigen binding protein, e.g., antibody or antigen-binding fragment thereof, is modified to improve effector function, e.g., so as to enhance antigen-dependent cell-mediated cytotoxicity (ADCC) and/or complement dependent cytotoxicity (CDC). This can be achieved by making one or more amino acid substitutions or by introducing cysteine in the Fc region. Variants of the Fc region (e.g., amino acid substitutions and/or additions and/or deletions) that can enhance or diminish effector function of an antibody and/or alter the pharmacokinetic properties (e.g., half-life) of the antibody are disclosed, for example in U.S. Pat. No. 6,737,056B1, U.S. Patent Application Publication No. 2004/0132101A1, U.S. Pat. Nos. 6,194,551, and 5,624,821 and 5,648,260. One particular set of substitutions, the triple mutation L234F/L235E/P331S ("TM") causes a profound decrease in the binding activity of human IgG1 molecules to human C1q, CD64, CD32A and CD16. See, e.g., Oganesyan et al., *Acta Crystallogr D Biol Crystallogr.* 64:700-704 (2008). In other cases it can be that constant region modifications increase serum half-life. The serum half-life of proteins comprising Fc regions can be increased by increasing the binding affinity of the Fc region for FcRn.

When the antigen-binding protein is an antibody or an antigen-binding fragment thereof, it can further comprise a heavy chain immunoglobulin constant domain selected from the group consisting of: (a) an IgA constant domain; (b) an IgD constant domain; (c) an IgE constant domain; (d) an IgG1 constant domain; (e) an IgG2 constant domain; (f) an IgG3 constant domain; (g) an IgG4 constant domain; and (h) an IgM constant domain. In some embodiments, the antigen-binding protein is an antibody or an antigen-binding fragment thereof that comprises an IgG1 heavy chain immunoglobulin constant domain. In some embodiments, the antigen-binding protein is an antibody or an antigen-binding fragment thereof that comprises an IgG1/IgG3 chimeric heavy chain immunoglobulin constant domain.

The antigen-binding protein of the disclosure (including, e.g., anti-O2 antigen antibodies or antigen-binding fragments thereof) can further comprise a light chain immunoglobulin constant domain selected from the group consisting of: (a) an Ig kappa constant domain; and (b) an Ig lambda constant domain.

The antigen-binding protein of the disclosure (including, e.g., anti-O2 antigen antibodies or antigen-binding fragments thereof) can further comprise a human IgG1 constant domain and a human lambda constant domain. The antigen-binding protein of the disclosure (including, e.g., anti-O2 antigen antibodies or antigen-binding fragments thereof) can further comprise a human IgG2 constant domain and a human lambda constant domain.

The antigen-binding protein of the disclosure can comprise an IgG1 Fc domain containing a mutation at positions 252, 254 and 256, wherein the position numbering is according to the EU index as in Kabat. For example, the IgG1 Fc domain can contain a mutation of M252Y, S254T, and T256E, wherein the position numbering is according to the EU index as in Kabat.

The present disclosure also relates to an isolated VH domain of the antigen-binding protein of the disclosure and/or an isolated VL domain of the antigen-binding protein of the disclosure.

Antigen-binding proteins (including antibodies or antigen binding fragments thereof) of the disclosure can be labeled with a detectable or functional label. Detectable labels include radiolabels such as 131I or 99Tc, which may be attached to antibodies of the present disclosure using conventional chemistry known in the art of antibody imaging. Labels also include enzyme labels such as horseradish peroxidase. Labels further include chemical moieties such as biotin which may be detected via binding to a specific cognate detectable moiety, e.g., labeled avidin. Non-limiting examples of other detectable or functional labels which may be attached to the antigen-binding proteins (including antibodies or antigen binding fragments thereof) of the disclosure include: isotopic labels, magnetic labels, redox active moieties, optical dyes, biotinylated groups, fluorescent moieties such as biotin signaling peptides, Green Fluorescent Proteins (GFPs), blue fluorescent proteins (BFPs), cyan fluorescent proteins (CFPs), and yellow fluorescent proteins (YFPs), and polypeptide epitopes recognized by a secondary reporter such as histidine peptide (his), hemagglutinin (HA), gold binding peptide, Flag; a radioisotope, radionuclide, a toxin, a therapeutic and a chemotherapeutic agent.

III. Pharmaceutical Compositions

The disclosure also provides a pharmaceutical composition comprising one or more of the O2-binding agents (including, e.g., anti-O2 antigen antibodies or antigen binding fragments) described herein. In certain embodiments, the pharmaceutical compositions further comprise a pharmaceutically acceptable vehicle or pharmaceutically acceptable excipient. In certain embodiments, these pharmaceutical compositions find use in treating, preventing or ameliorating a condition associated with a *Klebsiella* (e.g., *K. pneumoniae*) infection in human patients. In certain embodiments, these pharmaceutical compositions find use in inhibiting growth of *Klebsiella* (e.g., *K. pneumoniae*). In some embodiments, the *Klebsiella* (e.g., *K. pneumoniae*) is of the O2 serotype. In some embodiments, the *Klebsiella* (e.g., *K. pneumoniae*) is of the O1 serotype. In some embodiments, the pharmaceutical composition comprising an O2-binding agent include an anti-O2 antigen antibody or antigen binding fragments thereof that comprise the heavy and light chain complementarity determining region (CDR) sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS30, or KPD1. The CDR sequences of KPN42, KPN42-v2016, KPN42-FR-GL-VH/KPN42-FR-GL-C105A-VL, KPS3, KPN70, KPN179, KPN179-FR-1-2-4-GL-N35S-VH/ KPN179-FR-GL-C105A-VL, KPN179-FR-GL N35S-VH/ KPN179-FR-GL-C105A-VL, KPN44, KPN17, 6F6, KPL26, KPS18, KPS24, KPS44, KPS44-W108F-VH/ KPS44-D37N-S38Y-W107F-VL (KPS44-v2017), KPS44-D37N-S38Y-W107F-VL (KPS44-G1), KPS44-W108F-VH/ KPS44-W107F-VL (KPS44-G2), KPS44-W108F-VH/ KPS44-D37N-S38Y-VL (KPS44-G3), KPS30, or KPD1 antibody as described in Tables 1 and 2 or comprise the variable light chain and variable heavy chain sequences of an anti-O2 antigen KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 antibody as described in Tables 3 and 4.

In certain embodiments, formulations are prepared for storage and use by combining an antibody or anti-O2 binding agent described herein with a pharmaceutically acceptable vehicle (e.g., carrier, excipient) (see, e.g., Remington, The Science and Practice of Pharmacy 20th Edition Mack Publishing, 2000, herein incorporated by reference). In some embodiments, the formulation comprises a preservative.

The pharmaceutical compositions of the present disclosure can be administered in any number of ways for either local or systemic treatment.

In some embodiments, a pharmaceutical composition comprising one or more of the O2-binding agents (e.g., anti-O2 antigen antibodies or antigen binding fragments) described herein is used for treating pneumonia, urinary tract infection, septicemia/sepsis, neonatal septicemia/sepsis, diarrhea, soft tissue infection, infection following an organ transplant, surgery infection, wound infection, lung infection, pyogenic liver abscesses (PLA), endophthalmitis, meningitis, necrotizing meningitis, ankylosing spondylitis, or spondyloarthropathies. In some embodiments, a pharmaceutical composition comprising one or more of the O2-binding agents (e.g., anti-O2 antigen antibodies or antigen binding fragments) described herein is useful in nosocomial infections, opportunistic infections, infections following organ transplants, and other conditions associated with a *Klebsiella* infection (e.g. infection with *K. pneumoniae, K. oxytoca, K. planticola, K. ozaenae, K. rhinosclermoatis*, and/or *K. granulomatis*). In some embodiments, a pharmaceutical composition comprising one or more of the O2-binding agents (including, e.g., anti-O2 antigen antibodies or antigen binding fragments) described herein is useful in subjects exposed to a *Klebsiella* contaminated device, including, e.g., a ventilator, a catheter, or an intravenous catheter.

In some embodiments, the pharmaceutical composition comprises an amount of an O2-binding agent (e.g., an anti-O2 antigen antibody or antigen-binding fragment thereof) that is effective to inhibit growth of the *Klebsiella* in a subject. In some embodiments, the *Klebsiella* is *K. pneumoniae, K. oxytoca, K. planticola, K. ozaenae, K. rhinosclermoatis*, and/or *K. granulomatis*. In some embodiments, the *Klebsiella* is *K. pneumoniae, K. oxytoca*, and/or *K. granulomatis*. In some embodiments, the *Klebsiella* is *K. pneumoniae*. In some embodiments, the *Klebsiella* (e.g., *K. pneumoniae*) is of the O2 serotype. In some embodiments, the *Klebsiella* (e.g., *K. pneumoniae*) is of the O1 serotype.

In some embodiments, the methods of treating, preventing and/or ameliorating a condition associated with a *Klebsiella* infection comprises contacting a subject infected with a *Klebsiella* with a pharmaceutical composition comprising an O2-binding agent (e.g., an anti-O2 antigen antibody or antigen-binding fragment thereof) in vivo. In some embodiments, a pharmaceutical composition comprising an O2-binding agent is administered at the same time or shortly after a subject has been exposed to bacteria to prevent infection. In some embodiments, the pharmaceutical composition comprising an O2-binding agent is administered as a therapeutic after infection.

In certain embodiments, the method of treating, preventing, and/or ameliorating *Klebsiella* infections comprises administering to a subject a pharmaceutical composition comprising an O2-binding agent (e.g., an anti-O2 antigen antibody or antigen-binding fragment thereof). In certain embodiments, the subject is a human. In some embodiments, the pharmaceutical composition comprising an O2-binding agent (e.g., an anti-O2 antigen antibody or antigen-binding fragment thereof) is administered before the subject is infected with *Klebsiella*. In some embodiments, the pharmaceutical composition comprising an O2-binding agent (e.g., an anti-O2 antigen antibody or antigen-binding fragment thereof) is administered after the subject is infected with a *Klebsiella*.

In certain embodiments, the pharmaceutical composition comprising an O2-binding agent (e.g., an anti-O2 antigen antibody or antigen-binding fragment thereof) is administered to a subject on a ventilator. In certain embodiments, the subject has a catheter (e.g., a urinary catheter or an intravenous catheter). In certain embodiments, the subject is receiving antibiotics (e.g., meropenem, carbapenems, fluoroquinolone, tetracycline, chloramphenicol, trimethoprim, sulfonamide, and/or colistin).

In certain embodiments, a pharmaceutical composition comprising an O2-binding agent (e.g., an anti-O2 antigen antibody or antigen-binding fragment thereof) is for the treatment or prevention of a nosocomial *Klebsiella* infection. In certain embodiments, a pharmaceutical composition comprising an O2-binding agent (e.g., an anti-O2 antigen antibody or antigen-binding fragment thereof) is for the treatment or prevention of an opportunistic *Klebsiella* infection. In certain embodiments, a pharmaceutical composition comprising an O2-binding agent (e.g., an anti-O2 antigen antibody or antigen-binding fragment thereof) is for the treatment or prevention of a *Klebsiella* infection following an organ transplant.

In certain embodiments, a pharmaceutical composition comprising an O2-binding 9agent (e.g., an anti-O2 antigen antibody or antigen-binding fragment thereof) is for the treatment or prevention of a *Klebsiella* infection, wherein the *Klebsiella* is an extended spectrum beta-lactamase (ESBL) producing *Klebsiella*. In certain embodiments, a pharmaceutical composition comprising an O2-binding agent (e.g., an anti-O2 antigen antibody or antigen-binding fragment thereof) is for the treatment or prevention of a *Klebsiella* infection, wherein the *Klebsiella* is a non-extended spectrum beta-lactamase (ESBL) producing *Klebsiella*. In certain embodiments, a pharmaceutical composition comprising an O2-binding agent (e.g., an anti-O2 antigen antibody or antigen-binding fragment thereof) is for the treatment or prevention of a *Klebsiella* infection, wherein the *Klebsiella* is a *Klebsiella pneumoniae* carbapenemase (KPC) producing *Klebsiella*.

In certain embodiments, a pharmaceutical composition comprising an O2-binding agent (e.g., an anti-O2 antigen antibody or antigen-binding fragment thereof) is for the treatment or prevention of a cephalosporin resistant *Klebsiella* infection. In certain embodiments, a pharmaceutical composition comprising an O2-binding agent (e.g., an anti-O2 antibody or antigen-binding fragment thereof) is for the treatment or prevention of an aminoglycoside resistant *Klebsiella* infection. In certain embodiments, a pharmaceutical composition comprising an O2-binding agent (e.g., an anti-O2 antigen antibody or antigen-binding fragment thereof) is for the treatment or prevention of a quinolone resistant *Klebsiella* infection. In certain embodiments, a pharmaceutical composition comprising an O2-binding agent (e.g., an anti-O2 antigen antibody or antigen-binding fragment thereof) is for the treatment or prevention of a carbapenem resistant *Klebsiella* infection. In certain embodiments, a pharmaceutical composition comprising an O2-binding agent (e.g., an anti-O2 antigen antibody or antigen-binding fragment thereof) is for the treatment or prevention of a colistin resistant *Klebsiella* infection. In certain embodiments, a pharmaceutical composition comprising an O2-binding agent (e.g., an anti-O2 antigen antibody or antigen-binding fragment thereof) is for the treatment or prevention of a cephalosporin, aminoglycoside, quinolone, fluoroquinolone, tetracycline, chloramphenicol, trimethoprim, sulfonamide, carbapenem, and colistin resistant *Klebsiella* infection. In certain embodiments, a pharmaceutical composition comprising an O2-binding agent (e.g., an anti-O2 antigen antibody or antigen-binding fragment thereof) is for the treatment or prevention of an infection with a *Klebsiella* that is susceptible to antibiotics.

For the treatment, prevention and/or amelioration of a condition associated with a *Klebsiella* infection, the appropriate dosage of a pharmaceutical composition, antibody, or anti-O2 binding agent described herein depends on the type of condition, the severity and course of the condition, the responsiveness of the condition, whether the pharmaceutical composition, antibody, or anti-O2 binding agent is administered for therapeutic or preventative purposes, previous therapy, patient's clinical history, and so on all at the discretion of the treating physician. The pharmaceutical composition, antibody, or anti-O2 binding agent can be administered one time or over a series of treatments lasting from several days to several months, or until a cure is effected or a diminution of the condition is achieved. Optimal dosing schedules can be calculated from measurements of drug accumulation in the body of the patient and will vary depending on the relative potency of an individual antibody or agent. The administering physician can easily determine optimum dosages, dosing methodologies and repetition rates. The O2-binding agents and/or pharmaceutical compositions useful to treat, prevent, and/or amelioration of a condition associated with a *Klebsiella* infection include an anti-O2 antigen antibody or antigen binding fragments thereof that comprise the heavy and light chain complementarity determining region (CDR) sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS30, or KPD1. The CDR sequences of KPN42, KPN42-v2016, KPN42-FR-GL-VH/KPN42-FR-GL-C105A-VL, KPS3, KPN70, KPN179, KPN179-FR-1-2-4-GL-N35S-VH/ KPN179-FR-GL-C105A-VL, KPN179-FR-GL N35S-VH/ KPN179-FR-GL-C105A-VL, KPN44, KPN17, 6F6, KPL26, KPS18, KPS24, KPS44, KPS44-W108F-VH/ KPS44-D37N-S38Y-W107F-VL (KPS44-v2017), KPS44-D37N-S38Y-W107F-VL (KPS44-G1), KPS44-W108F-VH/ KPS44-W107F-VL (KPS44-G2), KPS44-W108F-VH/ KPS44-D37N-S38Y-VL (KPS44-G3), KPS30, or KPD1 antibody as described in Tables 1 and 2 or comprise the variable light chain and variable heavy chain sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 antibody as described in Tables 3 and 4.

IV. Methods of Use

The O2-binding agents (including anti-O2 antigen antibodies and antigen-binding fragments thereof) described herein are useful in a variety of applications including, but not limited to, pneumonia, urinary tract infection, septicemia/sepsis, neonatal septicemia/sepsis, diarrhea, soft tissue infection, infection following an organ transplant, surgery infection, wound infection, lung infection, pyogenic liver abscesses (PLA), endophthalmitis, meningitis, necrotizing meningitis, ankylosing spondylitis, and spondyloarthropathies. In some embodiments, the O2-binding agents (including anti-O2 antigen antibodies and antigen-binding fragments thereof) described herein are useful in nosocomial infections, opportunistic infections, infections following organ transplants, and other conditions associated with a *Klebsiella* infection (e.g. infection with *K. pneumoniae*, *K oxytoca*, *K. planticola*, *K. ozaenae*, *K. rhinoscopematis*, and/or *K. granulomatis*). In some embodiments, the O2-binding agents (including anti-O2 antigen antibodies and antigen-binding fragments thereof) described herein are useful in subjects exposed to a *Klebsiella* contaminated device, including, e.g., a ventilator, a catheter, or an intravenous catheter.

In some embodiments, the disclosure provides methods of treating, preventing and/or ameliorating a condition associated with a *Klebsiella* infection comprising administering an effective amount of an O2-binding agent (e.g., an anti-O2 antigen antibody or antigen-binding fragment thereof) to a subject. In some embodiments, the amount is effective to inhibit growth of the *Klebsiella* in the subject. In some embodiments, the *Klebsiella* is *K. pneumoniae*, *K oxytoca*, *K. planticola*, *K. ozaenae*, *K. rhinoscopematis*, and/or *K. granulomatis*. In some embodiments, the *Klebsiella* is *K. pneumoniae*, *K oxytoca*, and/or *K. granulomatis*. In some embodiments, the *Klebsiella* is *K. pneumoniae*. In some embodiments, the *Klebsiella* (e.g., *K. pneumoniae*) is of the O2 serotype. In some embodiments, the *Klebsiella* (e.g., *K. pneumoniae*) is of the O1 serotype. In some embodiments, the subject has been exposed to *Klebsiella*. In some embodiments, *Klebsiella* has been detected in the subject. In some embodiments, the subject is suspected of being infected with *Klebsiella*, e.g., based on symptoms.

In some embodiments, the disclosure further provides methods of inhibiting growth of *Klebsiella* comprising administering an O2-binding agent (e.g., an anti-O2 antigen antibody or antigen-binding fragment thereof) to a subject. In some embodiments, the *Klebsiella* is *K. pneumoniae*, *K. oxytoca*, *K. planticola*, *K. ozaenae*, *K. rhinoscopematis*, and/or *K. granulomatis*. In some embodiments, the *Klebsiella* is *K. pneumoniae*, *K. oxytoca*, and/or *K. granulomatis*. In some embodiments, the *Klebsiella* is *K. pneumoniae*. In some embodiments, the *Klebsiella* (e.g., *K. pneumoniae*) is of the O2 serotype. In some embodiments, the *Klebsiella* (e.g., *K. pneumoniae*) is of the O1 serotype. In some embodiments, the subject has been exposed to *Klebsiella*. In some embodiments, *Klebsiella* has been detected in the subject. In some embodiments, the subject is suspected of being infected with a *Klebsiella*, e.g., based on symptoms.

In some embodiments, the methods of treating, preventing and/or ameliorating a condition associated with a *Klebsiella* infection comprises contacting a subject infected with a *Klebsiella* with the O2-binding agent (e.g., an anti-O2 antigen antibody or antigen-binding fragment thereof) in vivo. In certain embodiments, contacting a cell with an O2-binding agent is undertaken in an animal model. For example, O2-binding agents can be administered to murine *Klebsiella* infection models to reduce bacterial burden. In some embodiments, the O2-binding agent (e.g., an anti-O2 antigen antibody or antigen-binding fragment thereof) is administered before introduction of bacteria to the animal to prevent infections. In some embodiments, the O2-binding agent (e.g., an anti-O2 antigen antibody or antigen-binding fragment thereof) is administered at the same time or shortly after the animal has been exposed to bacteria to prevent infection. In some embodiments, the O2-binding agent (e.g., an anti-O2 antigen antibody or antigen-binding fragment thereof) is administered as a therapeutic after infection.

In certain embodiments, the method of treating, preventing, and/or ameliorating *Klebsiella* infections comprises administering to a subject an effective amount of an O2-binding agent (e.g., an anti-O2 antigen antibody or antigen-binding fragment thereof). In certain embodiments, the subject is a human. In some embodiments, the effective amount of an O2-binding agent (e.g., an anti-O2 antigen antibody or antigen-binding fragment thereof) is administered before the subject is infected with *Klebsiella*. In some embodiments, the effective amount of an O2-binding agent (e.g., an anti-O2 antigen antibody or antigen-binding fragment thereof) is administered after the subject is infected with a *Klebsiella*.

In certain embodiments, the subject is on a ventilator. In certain embodiments, the subject has a catheter (e.g., a urinary catheter or an intravenous catheter). In certain embodiments, the subject is receiving antibiotics (e.g., meropenem, carbapenems, or colistin).

In certain embodiments, the *Klebsiella* infection is a nosocomial infection. In certain embodiments, the *Klebsiella* infection is an opportunistic infection. In certain embodiments, the *Klebsiella* infection follows an organ transplant.

In certain embodiments, the *Klebsiella* is an extended spectrum beta-lactamase (ESBL) producing *Klebsiella*. In certain embodiments, the *Klebsiella* is a non-ESBL producing *Klebsiella*. In certain embodiments, the *Klebsiella* is a *Klebsiella pneumoniae* carbapenemase (KPC) producing *Klebsiella*.

In certain embodiments, the *Klebsiella* is cephalosporin resistant. In certain embodiments, the *Klebsiella* is aminoglycoside resistant. In certain embodiments, the *Klebsiella* is quinolone resistant. In certain embodiments, the *Klebsiella* is carbapenem resistant. In certain embodiments, the *Klebsiella* is cephalosporin, aminoglycoside, quinolone, and carbapenem resistant. In certain embodiments, the *Klebsiella* is cephalosporin, aminoglycoside, and quinolone resistant. In certain embodiments, the *Klebsiella* is susceptible to antibiotics.

In certain embodiments, the method of treating, preventing, and/or ameliorating *Klebsiella* infections comprises administering to a subject an effective amount of an O2-binding agent (e.g., an anti-O2 antigen antibody or antigen-binding fragment thereof) and an antibiotic. The O2-binding agent (e.g., an anti-O2 antigen antibody or antigen-binding fragment thereof) and the antibiotic can be administered simultaneously or sequentially. The O2-binding agent (e.g., an anti-O2 antigen antibody or antigen-binding fragment thereof) and the antibiotic can be administered in the same pharmaceutical composition. The O2-binding agent (e.g., an anti-O2 antigen antibody or antigen-binding fragment thereof) and the antibiotic can be administered in separate pharmaceutical compositions simultaneously or sequentially. In certain embodiments, the antibiotic is an antibiotic suitable to treat a *Klebsiella* infection. In certain embodiments, the antibiotic is meropenem. In certain embodiments, the antibiotic is a carbapanem or colistin. In certain embodiments, the antibiotic is a cephalosporin, aminoglycoside, quinolone, fluoroquinolone, tetracycline, chloramphenicol, trimethoprim, sulfonamide, carbapenem, and/or colistin.

The present disclosure also provides methods of detecting O2 lipopolysaccharide or *Klebsiella* containing O2 antigen. In some embodiments, a method of detecting O2 or *Klebsiella* containing O2 antigen comprises contacting a sample with an O2 binding agent (e.g., an anti-O2 antigen antibody or antigen-binding fragment thereof) provided herein and assaying for binding of the binding agent (e.g., an antibody or antigen-binding fragment thereof) to the sample. Methods of assessing binding are well known in the art. In some embodiments, the methods comprise detecting O1 lipopolysaccharide or *Klebsiella* containing O1 antigen and O2 lipopolysaccharide or *Klebsiella* containing O2 antigen. In some embodiments, a method of detecting O1 and O2 or *Klebsiella* containing O1 or O2 antigen comprises contacting a sample with an O2 binding agent (e.g., an anti-O2 antigen antibody or antigen-binding fragment thereof) provided herein and assaying for binding of the binding agent (e.g., an antibody or antigen-binding fragment thereof) to the sample. Methods of assessing binding are well known in the art.

V. Kits

A kit comprising an isolated antigen-binding protein (e.g. an anti-O2 antigen antibody or antigen-binding fragment thereof) according to any aspect or embodiment of the present disclosure is also provided as an aspect of the present disclosure. In a kit, the antigen-binding protein, antibody, or antigen-binding fragment thereof can be labeled to allow its reactivity in a sample to be determined, e.g., as described further below. Components of a kit are generally sterile and in sealed vials or other containers. Kits can be employed in diagnostic analysis or other methods for which antibodies are useful. A kit can contain instructions for use of the components in a method, e.g., a method in accordance with the present disclosure. Ancillary materials to assist in or to enable performing such a method may be included within a kit of the disclosure. O2-binding agents suitable for use in a kit include an anti-O2 antigen antibodies or antigen binding fragments thereof that comprise the heavy and light chain complementarity determining region (CDR) sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1. The CDR sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS30, and KPD1 antibodies as described in Tables 1 and 2 or comprise the variable light chain and variable heavy chain sequences of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS-G3), KPS30, and KPD1 antibodies as described in Tables 3 and 4.

The reactivities of antibodies or antigen-binding fragments thereof in a sample can be determined by any appropriate means. Radioimmunoassay (RIA) is one possibility. Radioactive labeled antigen is mixed with unlabeled antigen (the test sample) and allowed to bind to the antibody. Bound antigen is physically separated from unbound antigen and the amount of radioactive antigen bound to the antibody determined. The more antigen there is in the test sample the less radioactive antigen will bind to the antibody. A competitive binding assay can also be used with non-radioactive antigen, using antigen or an analogue linked to a reporter molecule. The reporter molecule can be a fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules can be enzymes which catalyze reactions that develop or change colors or cause changes in electrical properties, for example. They can be molecularly excitable, such that electronic transitions between energy states result in characteristic spectral absorptions or emissions. They can include chemical entities used in conjunction with biosensors. Biotin/avidin or biotin/streptavidin and alkaline phosphatase detection systems can be employed.

The signals generated by individual antibody-reporter conjugates can be used to derive quantifiable absolute or relative data of the relevant antibody binding in samples (normal and test).

The present disclosure also provides the use of an antigen-binding protein as described above for measuring antigen levels in a competition assay, including methods of measuring the level of O2 antigen or *Klebsiella* containing O2 antigen in a sample by employing an antigen-binding protein provided by the present disclosure in a competition assay. In some embodiments, the physical separation of bound from unbound antigen is not required. In some embodiments, a reporter molecule is linked to the antigen-binding protein so that a physical or optical change occurs on binding. The reporter molecule can directly or indirectly generate detectable, and preferably measurable, signals. In some embodiments, the linkage of reporter molecules is direct or indirect, or covalent, e.g., via a peptide bond or non-covalent interaction. Linkage via a peptide bond can be as a result of recombinant expression of a gene fusion encoding antibody and reporter molecule.

The present disclosure also provides methods of measuring levels of O2 antigen directly, by employing an antigen-binding protein (e.g., an anti-O2 antigen antibody or antigen-binding fragment thereof) according to the disclosure. In some embodiments, these methods utilize a biosensor system. In some embodiments, the methods comprise detecting O1 and O2 antigen by employing an antigen-binding protein (e.g., an anti-O2 antigen antibody or antigen-binding fragment thereof) according to the disclosure. In some embodiments, these methods utilize a biosensor system.

VI. Polynucleotides and Host Cells

In further aspects, the present disclosure provides an isolated nucleic acid comprising a nucleic acid sequence encoding an antigen-binding protein (e.g. an anti-O2 antigen antibody or antigen-binding fragment thereof), VH domain and/or VL domain according to the present disclosure. In some aspects the present disclosure provides methods of making or preparing an antigen-binding protein (e.g. an anti-O2 antigen antibody or antigen-binding fragment thereof), a VH domain and/or a VL domain described herein, comprising expressing said nucleic acid under conditions to bring about production of said antigen-binding protein, VH domain and/or VL domain and, optionally, recovering the antigen-binding protein, VH domain and/or VL domain.

A nucleic acid provided by the present disclosure includes DNA and/or RNA. In one aspect, the nucleic acid is cDNA. In one aspect, the present disclosure provides a nucleic acid which codes for a CDR or set of CDRs or VH domain or VL domain or antibody antigen-binding site or antibody, e.g., scFv, IgG1, or IgG2, as described above (see, e.g., Tables 1-4).

One aspect of the present disclosure provides a nucleic acid, generally isolated, optionally a cDNA, encoding a VH CDR or VL CDR sequence described herein. In some embodiments, the VH CDR sequence is selected from the SEQ ID NOs provided in Table 1. In some embodiments, the VL CDR sequence is selected from the SEQ ID NOs provided in Table 2. A nucleic acid encoding the KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 set of HCDRs and nucleic acid encoding the KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 set of LCDRs are also provided, as are nucleic acids encoding individual CDRs, HCDRs, LCDRs and sets of CDRs, HCDRs, LCDRs as described in Tables 1 and 2. In some embodiments, the nucleic acids of the present disclosure encode a VH and/or VL domain of KPN42, KPN42-v2016, KPN42-FR-GL-VH/KPN42-FR-GL-C105A-VL, KPS3, KPN70, KPN179, KPN179-FR-1-2-4-GL-N35S-VH/KPN179-FR-GL-C105A-VL, KPN179-FR-GL N35S-VH/KPN179-FR-GL-C105A-VL, KPN44, KPN17, 6F6, KPL26, KPS18, KPS24, KPS44, KPS44-W108F-VH/KPS44-D37N-S38Y-W107F-VL (KPS44-v2017), KPS44-D37N-S38Y-W107F-VL (KPS44-G1), KPS44-W108F-VH/KPS44-W107F-VL (KPS44-G2), KPS44-W108F-VH/KPS44-D37N-S38Y-VL (KPS44-G3), KPS30, or KPD1 as described in Tables 3 and 4.

The invention further provides a polynucleotide comprising a sequence selected from those shown in Tables 5 and 6 below.

TABLE 5

Variable heavy chain polynucleotide sequences

| Antibody | VH Polynucleotide Sequence (SEQ ID NO) |
|---|---|
| KPN42 | GAGGTGCAGCTGGTGGAGTCTGGGGGAGGCTTGGTAAAGCCGGGGGG<br>TCCCTTAGACTCTCCTGTGCAGCCTCTGGTTTCACTTTCAATGACGCCTGG<br>ATGAACTGGGTCCGCCAGGCTCCAGGAAAGGGGCTGGAGTGGGTCGCCC<br>GCATTAAAAAGAAACATGAAGGTGTTACGACAGACTACCCTGCATCCGT<br>GAGAGGCAGATTCACCATCTCAAGAGATGATTCTAAAAACACAGTGTAT<br>CTGCAGATGGGCAGACTGAGAATCGAGGACACTGCCATATATTACTGTA<br>CCACAAGGATAGTGACTACCAATGACTACTGGGGCCAGGGAACCCTGGT<br>CACCGTCTCCTCAG (SEQ ID NO: 136) |
| KPN42-v2016 | GAGGTGCAGCTGGTCGAATCTGGCGGGGGACTGGTGAAACCTGGCGGCT<br>CTCTGAGGCTGAGTTGCGCCGCTTCAGGCTTCACCTTCAACGACGCATGG<br>ATGAATTGGGTGCGACAGGCACCTGGAAAGGGACTGGAGTGGGTCGGCC<br>GGATCAAGAAAAAGCACGAAGGGGTGACCACAGATTACCCTGCTAGCGT<br>CCGGGGAAGATTCACTATTAGCAGAGACGATTCCAAAAACACCGTGTAT<br>CTGCAGATGGGCAGGCTGCGCATCGAGGACACCGCCATCTACTATTGTA<br>CTACCCGCATCGTGACAACTAATGATTACTGGGGCAGGGAACCCTGGT<br>GACAGTCAGCTCC (SEQ ID NO: 137) |
| KPN42-FR-GL-<br>VH/KPN42-FR-<br>GL-C105A-VL | GAGGTGCAGCTGGTCGAATCTGGCGGGGGACTGGTGAAGCCTGGCGGCT<br>CTCTGCGACTGAGTTGCGCCGCTTCAGGCTTCACCTTTAACGACGCTTGG<br>ATGAATTGGGTGAGGCAGGCACCTGGAAAGGGACTGGAGTGGGTGGGA<br>CGCATCAAGAAAAAGCACGAAGGGGTGACCACAGATTACGCAGCCCCT<br>GTCAAAGGCCGGTTCACAATTAGCAGAGACGATTCCAAGAACACTCTGT<br>ATCTGCAGATGAATAGCCTGAAAACCGAGGACACAGCCGTGTACTATTG<br>TACTACCAGAATCGTCACAACTAACGATTACTGGGGGCAGGGAACTCTG<br>GTGACCGTCAGCTCC (SEQ ID NO: 138) |
| KPS3 | CAGGGACAGTTGGTGGACTCTGGGGGAGGCGTGGTCCAGCGGGGGGGG<br>TCTCAGAGACTCTCCTGCGCAGCGTCTGGATTCAGCTTCAGAGACTATGG<br>CATGCACTGGGTCCGCCAGGCTCCAGGCAAGGGGCTGGAGTGGGTGGCC<br>TTTATATCATATGATGGGAGAGATCAATACTATGCAGACTCCGTGAAGG<br>GCCGATTCATCATCTCCAGAGACAATTCCAAGAACACGCTGTCTCTGCAA<br>ATGAACAGCCTGAGACCTGAGGACACGGCTGTCTATTACTGTGGGCCTTT<br>TTATAACCCCAGTCTCTACTACCCCCCCTGGGGCCACGGACTTCCGGTCA<br>TCGTCTCCTCAG (SEQ ID NO: 139) |
| KPN70 | CAGGTGCAGCTGCAGGAGTCGGGCCCGGGACTGGTGAAGCCTTCGGAGA<br>CCCTGTCTCTCACCTGCACTGTCTCTGGTGGCTCCATCAGTACTTACTACT<br>GGAACTGGATCCGGCAGTCCCCAGGGAAGGAATTGGAGTGGATTGCAAA<br>TATACATCAAAGTGGGACCACCTACTACAACCCCTCCCTCAAGAGTCGA<br>GTCACCATGTCAGTAGACACGTCCAAGAACCAGTTCTCCCTGAAGGTGA<br>TCTCTGTGACTGCTGCGGACACGGCCGTGTATTACTGTGCGAGAGAGTCC<br>GACGATGGCTACAAGTGGAACTACTTTGACTACTGGGGCCAGGGAACCC<br>TAGTCACCGTCTCCTCAG (SEQ ID NO: 140) |
| KPN179 | GAGGTGCAGGTGGTGGAGTCTGGGGGAGGCTTGGTAAAGCCGGGGGGG<br>TCCCTTAGACTCTCCTGTGCAGCCTCTGGTTTCACTTTCAATAACGCCTGG<br>ATGAACTGGGTCCGCCAGGCTCCAGGGAAGGGGCTGGAGTGGGTCGCCC<br>GTATTAAAAGGAAAGCTGATGGTGAGACAACAGACTACCCTGCATCCGT<br>GAAAGGCAGATTCACCGTCTCAAGAGATGATTCAAAAAACACAGATATAT<br>CTGCAGATGAACAGCCTGAAAACCGAGGACACAGCCATATATTACTGTA<br>CCACAAGGATAGTGACTACCAATGACTACTGGGGCCAGGGAACCCTGGT<br>CACCGTCTCCTCAG (SEQ ID NO: 141) |
| KPN179-FR-1-2-<br>4-GL-N35S-<br>VH/KPN179-FR-<br>GL-C105A-VL | GAGGTGCAGCTGGTCGAATCCGGCGGGGGACTGGTGAAACCTGGCGGCT<br>CTCTGCGACTGAGTTGCGCCGCTTCAGGCTTCACCTTTAGCAACGCATGG<br>ATGAATTGGGTGAGACAGGCACCTGGAAAGGGACTGGAGTGGGTCGGC<br>CGGATCAAGAGAAAACTGACGGGGAAACCACAGATTACCCTGCATCTG<br>TGAAGGGCAGGTTCACAGTCAGCCGCGACGATTCCAAAAACACTATCTA<br>CCTGCAGATGAATAGTCTGAAGACCGAGGACACAGCCATCTACTATTGT<br>ACTACCCGGATTGTGACAACTAACGATTACTGGGGGCAGGGAACTCTGG<br>TGACCGTCAGCTCC (SEQ ID NO: 193) |
| KPN179-FR-GL<br>N35S-<br>VH/KPN179-FR-<br>GL-C105A-VL | GAGGTGCAGCTGGTCGAATCTGGCGGGGGACTGGTGAAACCTGGCGGCT<br>CTCTGCGACTGAGTTGCGCCGCTTCAGGCTTCACCTTTAGCAACGCTTGG<br>ATGAATTGGGTGAGACAGGCACCTGGAAAGGGACTGGAGTGGGTGGGA<br>CGGATCAAGAGAAAAGCCGACGGGGAAACCACAGATTACGCAGCCCCT<br>GTGAAGGGCAGGTTCACAATTAGCCGCGACGATTCCAAAAACACTCTGT<br>ATCTGCAGATGAATAGCCTGAAGACCGAGGACACAGCCGTGTACTATTG<br>TACTACCCGGATCGTCACAACTAACGATTACTGGGGGCAGGGAACTCTG<br>GTGACCGTCAGCTCC (SEQ ID NO: 194) |
| KPN44 | CAGGTGCAGCTGCAGGAGTCGGGCCCGGGACTGGTGAAGCCTTCGGAGA<br>CCCTGTCTCTCACCTGCACTGTGTCCGGTGGCTCCACCAGTAGTTACTAC<br>TGGAACTGGATCCGGCAGGCCCCAGGGAAGCCATTGCAGTGGATTGCAA<br>ATATACATCACGGTGGGACCACTTATTACAACCCCTCCCTCAGGAGTCGG |

TABLE 5-continued

Variable heavy chain polynucleotide sequences

| Antibody | VH Polynucleotide Sequence (SEQ ID NO) |
|---|---|
|  | GTCACCATGTCTCTGGACACTTCCAATAACCAGTTCTCCCTGAAGCTGAC<br>CTCTGTGACTGCTGCGGACACGGCCGTCTATTTCTGTGCGAGAGAGTCCG<br>ACGATGGCTACAGGTGGAACTACTTTGACTACTGGGGCCAGGGAGTCCT<br>GGTCACCGTCTCCTCAG (SEQ ID NO: 142) |
| KPN17 | GAGGTGCAGCTGGTGGAGTCCGGGGGAGGCTTGGTTCAGCCTGGGGGGT<br>CCCTGAGACTCTCCTGTGCAGCCTCTGGATTCACCTTCAGTCACTTCTGG<br>ATGCACTGGGTCCGCCAAGCTCCAGGGCAGGGGCTGGTGTGGGTCGCAC<br>GTATTGATGGTTCTGTGACAAACTTGAGGTACGCGGGCTCCGTGGAGGG<br>GCGATTCACCATCTCCAGAGACAACGCCAAGAACACGCTGTATTTGCAA<br>ATGAACAGTCTGAGAGACGAGGACACGGCTGTATATTACTGTGCAAGAG<br>ATTTGGTAGGAATTGGCACGCCGGCCGGGTACGGTATGGACGTCTGGGG<br>CCAAGGGACCACGGTCACCGTCTCCTCAG (SEQ ID NO: 143) |
| 6F6 | CAGGTTCACCTACAACAGTCTGGTTCTGAACTGAGGAGTCCTGGGTCTTC<br>AGTAAAGCTTTCATGCAAGGATTTTGATTCAGACGTCTTCCCTATTGCTT<br>ATATGGGTTGGATTAGGCAGCAGCCTGGGCATGGATTTGACTGGATTGG<br>GGACATACTCCCAAATATTGGTAGAACAATCTATGGAGAGAAGTTTGAG<br>GACAAAGCCACACTGGATGCAGACACAGTGTCCAACACAGCCTACTTGG<br>AGCTCAGCAGTCTGACATCTGAGGACTCTGCTATCTACTATTGTGCAAGG<br>AGGGGGACGTCGGGGGCTATGGACTACTGGGGTCAAGGAACCTCAGTCA<br>CCGTCTCCTCA (SEQ ID NO: 144) |
| KPL26 | GAGGTGCAGCTGGTGGAGTCTGGGGGAGGCTTGGTCCAGTCGGGGGGT<br>CCCTGAGACTCTCCTGTGAAACCTCTGGATTCATTTTTGGTAGTTCTTGG<br>ATGACCTGGGTCCGCCAGGCTCCAGGGAAAGGGCTGGAGTGGGTGGCCA<br>CCATAAACCCTGATGGAAGTGCGACAAGCTATGAGGACTCTGTGAGGGG<br>CCGATTCGCCGTCTCCAGAGACAACGCCAAGAACTCAGTGTATCTGCAA<br>ATGAACAGCCTGAGAGCCGAGGACACGGCCGTGTACTTCTGTACAAGGA<br>ATAAGGCATACAATGCCCTTGACTACTGGGGCCAGGGAACCCTGGTCAC<br>CGTCTCCTCAG (SEQ ID NO: 145) |
| KPS18 | GAGGTTCGCCTGGTGGAGTCTGGGGGAGGCTTGGTAAAGCCTGGGGGGT<br>CCCTAAGACTCTCCTGTGCAGCCTCAGGATTCACTTTCAAAAACGCCTGG<br>ATGAGCTGGATCCGCCAGGCTCCAGGGAAGGGGCTGGAGTGGGTTGGCC<br>GTGTTAAAAACGAAGTTGATGGGGGGACAATAGACTACGGTGTGCCCGT<br>GAGAGGCAGATTCACCATCTCAAGAGACGATTCACAAGGCACGCTGTCT<br>CTGGAGATGAACAGCCTGAGAGAGGATGACACAGGGATTTATTACTGTC<br>GGGCTTTTTGGAGTGGTTTTCCTGCCGGATACTGGGGCCAGGGAACCCTG<br>GTCAGCGTCTCCTCAG (SEQ ID NO: 146) |
| KPS24 | GAGCTGCACCTGGTGGAGTCTGGGGGAGGCTTGGTAAAGCCTGGGGGGT<br>CCCTTAGACTCTCCTGTGCAGCCTCAGGATTCACTTTCAAAAACGCCTGG<br>ATGAGCTGGATCCGCCAGGCTCCAGGGAAGGGGCTGGAGTGGGTTGGCC<br>GTGTTAAAAGCGAAGTTGATGGGGGGACAACAGACTACGGTGTGCCCGT<br>GAGAGGCAGATTCACCATCTCAAGAGATGATTCACAAAGCACGCTGTCT<br>CTGGAGATGAGCAGCCTGCAAGACGATGACACAGGCGTTTATTACTGTC<br>GGGCTTTTTGGAGTGATTTTCAAACCGGCTACTGGGGCCAGGGAACCCT<br>GGTCACCGTCTCCTCAG (SEQ ID NO: 147) |
| KPS44 | GAGGTGCACCTGGTGGAGTCTGGGGGAGGCTTGGTAAAGCCTGGGGGGT<br>CCCTTAGACTCTCCTGTGCAGCCTCAGGATTCACTTTCAAAAACGCCTGG<br>ATGAGCTGGATCCGCCAGGCTCCAGGGAAGGGGCTGGAGTGGGTTGGCC<br>GTGTTAAAAGCGAAGTTGATGGGGGGACAATAGACTACGGTGTGCCCGT<br>GAGAGGCAGATTCACCATCTCAAGAGATGATTCACAAGGCACACTGTCT<br>CTGGAGATGAACAGCCTGAAAGACGATGACACAGGCGTTTATTATTGTC<br>GGGCTTTTTGGAGTGGTTTTCCTACCGGATACTGGGGCCAGGGAGCCCTG<br>GTCAGCGTCTCCTCAG (SEQ ID NO: 148) |
| KPS44-v2017 | GAGGTGCACCTGGTCGAATCCGGCGGGGGACTGGTGAAACCAGGCGGGT<br>CTCTGAGACTGAGTTGCGCCGCTTCAGGCTTCACCTTCAAGAACGCATGG<br>ATGAGCTGGATTAGACAGGCACCTGGGAAGGGACTGGAGTGGGTGGGC<br>CGCGTCAAATCTGAAGTGGATGGAGGCACCATCGACTACGGGTGCCTG<br>TCCGGGGAAGATTCACCATTAGCCGAGACGATTCCCAGGGCACACTGTC<br>TCTGGAGATGAATAGTCTGAAGGACGATGACACTGGGGTGTACTATTGT<br>AGAGCTTTCTTTTCAGGATTTCCTACCGGCTATTGGGGACAGGGGGCCCT<br>GGTGAGCGTCAGCTCC (SEQ ID NO: 206) |
| KPS44-G1 | GAGGTACACCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGGGGGGACGATAGATTACGGTGTTCCCG<br>TGCGCGGCAGATTCACGATAAGTCGAGACGACTCTCAGGGTACACTTAG<br>CCTCGAAATGAATAGCCTCAAAGACGATGATACAGGCGTTTATTATTGC<br>CGCGCATTCTGGAGTGGCTTCCCGACTGGGTACTGGGGGCAAGGTGCTC<br>TTGTCTCAGTGTCATCC (SEQ ID NO: 207) |

TABLE 5-continued

Variable heavy chain polynucleotide sequences

| Antibody | VH Polynucleotide Sequence (SEQ ID NO) |
| --- | --- |
| KPS44-G2 | GAGGTACACCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGGGGGACGATAGATTACGGTGTTCCCG<br>TGCGCGGCAGATTCACGATAAGTCGAGACGACTCTCAGGGTACACTTAG<br>CCTCGAAATGAATAGCCTCAAAGACGATGATACAGGCGTTTATTATTGC<br>CGCGCATTCTTTAGTGGCTTCCCGACTGGGTACTGGGGGCAAGGTGCTCT<br>TGTCTCAGTGTCATCC (SEQ ID NO: 208) |
| KPS44-G3 | GAGGTACACCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGGGGGACGATAGATTACGGTGTTCCCG<br>TGCGCGGCAGATTCACGATAAGTCGAGACGACTCTCAGGGTACACTTAG<br>CCTCGAAATGAATAGCCTCAAAGACGATGATACAGGCGTTTATTATTGC<br>CGCGCATTCTTTAGTGGCTTCCCGACTGGGTACTGGGGGCAAGGTGCTCT<br>TGTCTCAGTGTCATCC (SEQ ID NO: 208) |
| KPS30 | GAGATGCAGTTGGTAGAGTCTGGGGGAGGCTTGGTCCAGCCTGGGGTGT<br>CCCTGAGACTCTCCTGTGTAGACTCTGGATTCAGTTTTAGTACCTCTTGGT<br>TGGCCTGGGTCCGCCAGGCTCCAGGGAAGGGGCTGGAGTGGCTGGCCAA<br>CATAGATCCAGATGGAAGCACGAGAAATCATGTGGACTCTGTGAGGGGC<br>CGATTCACCATCTCCAGAGACAACGCCAAGAATTCACTGTATCTCCAGAT<br>GAACAGCCTGAGAGCCGAGGACACGGCCGTCTATTACTGTGCGAGAGAC<br>TATGCCTACAATCGCTTTGACTACTGGGGCCAGGGAACCATGGTCACCGT<br>CTCCTCAG (SEQ ID NO: 149) |
| KPD1 | CAGGTGCAGCTGCAGGAGTCGGACCCACGACTGGTGAAGCCTTCGGAGA<br>CCCTGTCCCTCACCTGTAGTGTCTCTGGTGTCTCCATCACCAGTAACACTT<br>ACTGGTGGGCCTGGATCCGCCAGCCCCCAGGGAAGAAACTGGAGTGGAT<br>TGGGAGTCTCTCTTACAGTGGGGACACCTACTACAACCCGTCCCTCACGA<br>GTCGCGTCACCATATCAAGAGATATCCATCAGAACCAATTTTTCCTGGAG<br>TTGAACTCTGTGACCGCCGCCGACACGGCCATGTATTACTGTGCGAGAG<br>ATCCCGACATCATTCGCAATTTCCAGTTTGACTACTGGGGCCGGGGAACC<br>CTGGTCACCGTCTCCTCGG (SEQ ID NO: 150) |
| KPL36 | GAGGTGCAGCTGGTGGAGTCTGGGGGAGGCGTGGTCCAGTCTGGGGGGT<br>CCCTGAGACTCTCCTGTGAGACTTCTGGATTCACCTTTATAAGTTCTTGG<br>ATGAGTTGGGTCCGCCAGGCTCCAGGGACAGGACTGGAGTGGGTGGCCA<br>CCATTAACCCTGATGGAACTGAGACACCCTACGCGGACTCGCTGAAGGG<br>CCGCTTCACCATCTCCAGAGACAACACCAAGAAGTCACTTTATCTGCAA<br>ATCCATAGCCTGAGAGCCGACGACACGGCCGTCTATTTCTGTGCAAGGA<br>ATAAGGCATACAATGCCCATGACTTCTGGGGCCAGGGAACCCTGGTCAC<br>CGTCTCCTCAG (SEQ ID NO: 195) |
| KPS44-G4 | CAGGTACAGCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGCCGGGACGATAGATTACGGTGTTCCCG<br>TGCGCGGCAGATTCACGATAAGTCGAGACGACTCTAAGAATACACTTTA<br>CCTCCAGATGAATAGCCTCAAAACCGAGGATACAGCCGTTTATTATTGCC<br>GCGCATTCTATAGTGGCTTCCCGACTGGGTACTGGGGGCAAGGTACTCTT<br>GTCACAGTGTCATCC (SEQ ID NO: 221) |
| KPS44-G6 | CAGGTACAGCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGCCGGGACGATAGATTACGGTGTTCCCG<br>TGCGCGGCAGATTCACGATAAGTCGAGACGACTCTAAGAATACACTTTA<br>CCTCCAGATGAATAGCCTCAAAACCGAGGATACAGCCGTTTATTATTGCC<br>GCGCATTCTATAGTGGCTTCCCGACTGGGTACTGGGGGCAAGGTACTCTT<br>GTCACAGTGTCATCC (SEQ ID NO: 231) |
| KPS44-G8 | CAGGTACAGCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGCCGGGACGATAGATTACGGTGTTCCCG<br>TGCGCGGCAGATTCACGATAAGTCGAGACGACTCTAAGAATACACTTTA<br>CCTCCAGATGAATAGCCTCAAAACCGAGGATACAGCCGTTTATTATTGCC<br>GCGCATTCTATAGTGGCTTCCCGACTGGGTACTGGGGGCAAGGTACTCTT<br>GTCACAGTGTCATCC (SEQ ID NO: 241) |
| KPS44-G10 | GAGGTACACCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA |

TABLE 5-continued

Variable heavy chain polynucleotide sequences

| Antibody | VH Polynucleotide Sequence (SEQ ID NO) |
|---|---|
| | CGAGTTAAGTCTGAGGTTGACGCGGGGACGATAGATTACGGTGTTCCCG<br>TGCGCGGCAGATTCACGATAAGTCGAGACGACTCTCAGGGTACACTTAG<br>CCTCGAAATGAATAGCCTCAAAGACGATGATACAGGCGTTTATTATTGC<br>CGCGCATTCTACAGTGGCTTCCCGACTGGGTACTGGGGGCAAGGTGCTCT<br>TGTCTCAGTGTCATCC (SEQ ID NO: 251) |
| KPS44-G11 | GAGGTACACCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGCGGGGACGATAGATTACGGTGTTCCCG<br>TGCGCGGCAGATTCACGATAAGTCGAGACGACTCTCAGGGTACACTTAG<br>CCTCGAAATGAATAGCCTCAAAGACGATGATACAGGCGTTTATTATTGC<br>CGCGCATTCTACAGTGGCTTCCCGACTGGGTACTGGGGGCAAGGTGCTCT<br>TGTCTCAGTGTCATCC (SEQ ID NO: 261) |
| KPS44-G14 | CAGGTACAGCTTGTAGAAAGTGGGGGTGGGCTTGTCAAGCCTGGGGGAA<br>GTTTGAGACTGAGTTGCGCCGCAAGTGGCTTCACGTTTAAGAACGCATG<br>GATGTCCTGGATTAGACAAGCCCCCGGTAAAGGTTTGGAATGGGTAGGA<br>CGAGTTAAGTCTGAGGTTGACGCCGGGACGATAGATTACGGTGTTCCCG<br>TGCGCGGCAGATTCACGATAAGTCGAGACGACTCTAAGAATACACTTTA<br>CCTCCAGATGAATAGCCTCAAAACCGAGGATACAGCCGTTTATTATTGCC<br>GCGCATTCTATAGTGGCTTCCCGACTGGGTACTGGGGGCAAGGTACTCTT<br>GTCACAGTGTCATCC (SEQ ID NO: 271) |

TABLE 6

Variable light chain polynucleotide sequences

| Antibody | VL Polynucleotide Sequence (SEQ ID NO) |
|---|---|
| KPN42 | CAGTCTGCCCTGACTCAGCCTCCCTCAGTGTCCGGGTCTCCTGGACAGTC<br>AGTCACCATCTCCTGCACTGGAACCAGCAGTGATGTTGGTGCTTACGACT<br>ATGTCTCCTGGTACCAACAGTACGCAGGCAAAGTCCCCAAACACATAAT<br>TTATGATGTCAATGAGCGGCCCTCAGGGGTCCCTGATCGCTTCTCTGGCT<br>CCAAGTCTGGCAACACGGCCGCCCTGACCATCTCTGGGCTCCAGGCTGA<br>GGATGAGGCTGATTATTATTGCTGCTCATATGCAGGCGGTGACATCTTTG<br>TCTTCGGAACTGGGACTCAGGTCACCGTCCTA (SEQ ID NO: 151) |
| KPN42-v2016 | CAGTCTGCCCTGACCCAGCCTAGGTCTGTGAGTGGGTCACCCGGACAGA<br>GTGTCACAATCTCATGCACCGGAACAAGCTCCGACGTGGGCGCTTACGA<br>TTATGTCTCTTGGTACCAGCAGCACCCCGGGAAGGCACCTAAACTGATG<br>ATCTACGACGTGAACAAGCGGCCAAGTGGCGTCCCCGATAGATTCAGCG<br>GCTCCAAATCTGGGAATACAGCTAGCCTGACTATCTCCGGCCTGCAGGC<br>AGAGGACGAAGCCGATTACTATTGTGCCAGCTACGCTGGCGGGGACATT<br>TTCGTGTTTGGAACTGGCACCAAGGTGACCGTCCTG (SEQ ID NO: 152) |
| KPN42-FR-GL-<br>VH/KPN42-FR-<br>GL-C105A-VL | CAGTCTGCCCTGACCCAGCCTAGGTCTGTGAGTGGGTCACCCGGACAGA<br>GTGTCACAATCTCATGCACCGGAACAAGCTCCGACGTGGGCGCTTACGA<br>TTATGTCTCTTGGTACCAGCAGCACCCCGGGAAGGCACCTAAACTGATG<br>ATCTACGACGTGAACAAGCGGCCAAGTGGCGTCCCCGATAGATTCAGCG<br>GCTCCAAATCTGGGAATACAGCTAGCCTGACTATCTCCGGCCTGCAGGC<br>AGAGGACGAAGCCGATTACTATTGTGCCAGCTACGCTGGCGGGGACATT<br>TTCGTGTTTGGAACTGGCACCAAGGTGACCGTCCTG (SEQ ID NO: 153) |
| KPS3 | GAGGTTGTCTTGACACAGTCTCCAGCCACTCTGTCTTTGTCTCCAGGGGA<br>AAGAGCCACCCTCTCCTGTAGGGCCAGTCAGAGCATTAGCAGCCAATTA<br>GCGTGGTACCAACAGAAACCTGGCCAGGCTCCCAGGCTCCTCATCCATG<br>ATGCATCCAACAGGGACACTGGCGTCCCAGACAGGTTCAGTGGCAGTGG<br>GTCTGGGACAGACTTCACTCTCACCATCAGCAGCCTAGAGCCTGAAGAT<br>TTTGCTATGTATTACTGTCTCCAGCGTAACAACTGGCCTCCGTGGACGTT<br>CGGCCAAGGGACCAAGGTGGAAATCAAAC (SEQ ID NO: 154) |
| KPN70 | GAAATTGTGTTGACACAGTCTCCAGCCTCCCTGTCTTTGTCTCCAGGGGA<br>AAGAGCCACCCTCTCCTGCAGGGCCAGTCAGATTGTTACCAACTACTTAG<br>CCTGGTATCAACATAAACCTGGCCAGGCTCCCAGGCTCCTCATCTTTGAT<br>ATGTCCATTAGGGCCGCTGGCATCCCAGCCAGGTTCAGTGGCAGTGGGT<br>CTGGGACAGACTTCACTCTCACCATCAGCAGCCTTGAGCCTGAAGATTTT<br>GCAGTTTATTACTGTCAACACCGTAGCAACTGGCCTCTATTCACTTTCGG<br>CCCTGGGACCAAAGTGGATATCAAAC (SEQ ID NO: 155) |
| KPN179 | CAGTCTGCCCTGACTCAGCCTCCCTCAGTGTCCGGGTCTCCTGGACAGTC<br>AGTCACCATCTCCTGCACTGGAACCAGCAGTGATGTTGGTTATTACGACT<br>ATGTCTCCTGGTACCAACAGCACCACCCAGGCAAAGCCCCCAAACACAT |

TABLE 6-continued

Variable light chain polynucleotide sequences

| Antibody | VL Polynucleotide Sequence (SEQ ID NO) |
|---|---|
| | GATTTATGATGTCAATAAGCGGCCCTCAGGGGTCCCTGATCGCTTCTCTG<br>GCTCCAAGTCTGGCAACACGGCCTCCCTGACCATCTCTGGGCTCCAGGCT<br>GAGGATGAGGCTGATTATTATTGCTGTTCATATGCAGGCGGTGACACTTT<br>TGTCTTCGGAACTGGGACCAAGGTCACCGTCCTAG (SEQ ID NO: 156) |
| KPN179-FR-1-2-<br>4-GL-N35S-<br>VH/KPN179-FR-<br>GL-C105A-VL | CAGTCTGCCCTGACTCAGCCTAGGTCTGTGAGTGGGTCACCCGGACAGA<br>GTGTCACAATCTCATGCACCGGAACAAGCTCCGACGTGGGCTACTATGA<br>TTACGTCTCTTGGTATCAGCAGCACCCCGGGAAGGCTCCTAAACTGATGA<br>TCTACGACGTGAACAAGCGGCCAAGTGGCGTCCCCGATAGATTCAGCGG<br>CTCCAAATCTGGGAATACAGCAAGCCTGACTATTTCCGGCCTGCAGGCA<br>GAGGACGAAGCCGATTACTATTGTGCCAGCTATGCTGGCGGGGACACCT<br>TCGTGTTTGGAACTGGCACCAAGGTGACAGTCCTG (SEQ ID NO: 196) |
| KPN179-FR-GL<br>N35S-<br>VH/KPN179-FR-<br>GL-C105A-VL | CAGTCTGCCCTGACTCAGCCTAGGTCTGTGAGTGGGTCACCCGGACAGA<br>GTGTCACAATCTCATGCACCGGAACAAGCTCCGACGTGGGCTACTATGA<br>TTACGTCTCTTGGTATCAGCAGCACCCCGGGAAGGCTCCTAAACTGATGA<br>TCTACGACGTGAACAAGCGGCCAAGTGGCGTCCCCGATAGATTCAGCGG<br>CTCCAAATCTGGGAATACAGCAAGCCTGACTATTTCCGGCCTGCAGGCA<br>GAGGACGAAGCCGATTACTATTGTGCCAGCTATGCTGGCGGGGACACCT<br>TCGTGTTTGGAACTGGCACCAAGGTGACAGTCCTG (SEQ ID NO: 197) |
| KPN44 | GAAATTGTGTTGACACAGTCTCCAGCCTCCCTGTCTTTGTCTCCAGGGGA<br>CAGAGCCACCCTCTCCTGCAGGGCCAGTCAGACGATTACCAACTACTTA<br>GCCTGGTACCAACATAAACCTGGCCAGGCTCCCAGACTCCTCATCTTTGA<br>TATGTCGAAAAGGGCCACTGGCATCCCAGCCAGGTTCAGTGGCAGTGGG<br>TCTGGGACAGACTTCACTCTCACCATCAGCAGCCTTGAGCCTGAAGATTT<br>TGCAGTTTACTACTGTCAACACCGTAGCAACTGGCCTCTATTCACTTTCG<br>GCCCTGGGACCAACGTGGATATCAAAC (SEQ ID NO: 157) |
| KPN17 | GACATCCAGTTGACCCAGTCTCCATCCTTCCTGTCTGCCTCTGTAGGAGA<br>CAGAGTCACCATCACTTGCCGGGCCAGTCAGGGCATTAGCACTTATTTAG<br>CCTGGTATCAACAAAAACCAGGGAAAGCCCCTAAGCTCCTGATCTATGC<br>TGCATCCACTTTGCAAAGTGGGGTCCCATCAAGGTTCAGCGGCAGTGGA<br>TCTGGGACAGAATTCACTCTCACAATCAACAGCCTGCAGTCTGAAGATTT<br>TGCAACTTACTACTGTCAGCAGCTTACTAGTCACCTCTACACTTTTGGCC<br>AGGGGACCAAGCTGGAGATCAAAC (SEQ ID NO: 158) |
| 6F6 | GATGTTGTGATGACCCAAACTCCACTCTTCCTGCCTGTCAGTCTTGGAGA<br>TCAAGCCTCCATCTCTTGCAGATCTAGTCAGGGCCTTGTACACAGTACTG<br>GAAACACCTTTTTACATTGGTACCTGCAGAAGCCAGGCCAGTCTCCAAA<br>GCTCCTGATCTACAAAGTTTCCAACCGATTTTCTGGGGTCCCAGACAGGT<br>TCAGTGGCAGTGGATCAGGGACAGATTTCACACTCAAGATCAGCAGAGT<br>GGAGGCTGAGGATCTGGGAATTTATTTCTGCTCTCAAAGTACACATATTC<br>CGTACACGTTCGGAGGGGGGACCAAGCTGGAAATAAAA (SEQ ID<br>NO: 159) |
| KPL26 | CAGTCTGCCCTGACTCAGCCTCCCTCCGCGTCCGGGTCTCCTGGACAATC<br>AGTCACCCTCTCCTGCACTGGAACCAGCAGTGACGTTGGTGGTAATAACT<br>ATGTCTCCTGGTACCAACAGCACCCAGGCAAAGCCCCCAAACTCATCAT<br>TTATGAGGTCAGTAAGCGGCCCTCAGGGGTCCCTAATCGTTTCTCTGGCT<br>CCAAGTCTGGCAACACGGCCTCCCTGACCGTCTCTGGGCTCCAGGCTGA<br>GGATGAGGCTGATTATTACTGCAGCTCATTTGGAGGTAGTAAGATGTTCG<br>GCGGAGGGACCAAGCTGACCGTCCTAG (SEQ ID NO: 160) |
| KPS18 | CAGTCTGTGTTGACGCAGCCGCCCTCACTGTCTGCGGCCCCAGGACAGA<br>CGGTCACCATCGCCTGCTCTGGAAGTAGATCCAACATTGGGAGTGATTCC<br>GTCTCCTGGTTCCAGCAGTTCCCAGGAACAGCCCCCAGAGTCCTCATGTA<br>TGACAATAATAAGCGACCCTCAGGCATTTCTGACCGATTCTCTGGCTCCA<br>AGTCTGGCACGTCAGTCACCCTGGACATCACCGGACTCCAGACTGGGGA<br>CGAGGCCGATTATTACTGCGCAACATGGGATAGCAGCCTGAGTGCTTAT<br>GTCTTCGGATCTGGGACCAAGGTCACCGTCCTAA (SEQ ID NO: 161) |
| KPS24 | CAGTCTGTGTTGACGCAGCCGCCCTCAGTGTCTGCGGCCCCAGGACAGA<br>CGGTCACCATCGCCTGCTCTGGAAGTAGCTCCAACATTGGGAGTGATTCC<br>GTATCCTGGTTCCAGCAGCTCCCAGGAACAGCCCCCAGAGTCCTCATGTA<br>TGAAAATAATAAGCGACCCTCAGGGATTTCTGACCGATTCTCTGGCTCCA<br>AGTCTGGCACGTCAGTCACCCTGGGCATCACCGGACTCCAGACTGGGGA<br>CGAGGCCGATTATTACTGCGCAGCATGGGATAGCAGCCTACGTGCTTAT<br>GTCTTCGGATCTGGGACCAAGGTCACCGTCCTAG (SEQ ID NO: 162) |
| KPS44 | CAGTCTGTGTTGACGCAGCCGCCCTCACTGTCTGCGGCCCCTGGACAGAC<br>GATCACCATCGCCTGCTCTGGAACTAGTTCCAACATTGGGAGTGATTCCG<br>TATCCTGGTTCCAGCAATTCCCAGGAACAGCCCCCAGAGTCCTCATATAT<br>GAGAATAATAAGCGACCCTCAGGCATTTCTGACCGATTCTCTGGCTCCAA |

TABLE 6-continued

Variable light chain polynucleotide sequences

| Antibody | VL Polynucleotide Sequence (SEQ ID NO) |
|---|---|
| | GTCTGGCACGTCAGTCACACTGGGCATCACCGGACTCCAGACTGGGGAC<br>GAGGCCGATTATTACTGCGCAACATGGGATAGCAGCCTGAGTGCTTATG<br>TCTTCGGATCTGGGACCAAGGTCACCGTCCTAG (SEQ ID NO: 163) |
| KPS44-v2017 | CAGAGCGTGCTGACACAGCCCCCTTCACTGAGCGCCGCTCCTGGACAGA<br>CCATCACAATTGCTTGCTCCGGCACTAGCTCCAACATCGGGTCCAATTAC<br>GTGTCTTGGTTCCAGCAGTTTCCAGGAACCGCACCCAGGGTCCTGATCTA<br>TGAGAACAATAAGCGGCCCTCAGGCATTAGCGACAGATTCTCCGGGTCT<br>AAAAGTGGAACTAGCGTGACCCTGGGAATTACCGGCCTGCAGACAGGCG<br>ACGAAGCAGATTACTATTGTGCCACCTTCGATTCTAGTCTGAGTGCCTAC<br>GTCTTTGGCTCTGGGACAAAAGTGACTGTCCTG (SEQ ID NO: 209) |
| KPS44-G1 | CAGTCCGTTTTGACGCAACCCCCGTCACTGAGTGCTGCGCCTGGGCAGAC<br>CATAACGATCGCCTGCTCAGGGACCAGCAGTAATATAGGCTCTAATTAT<br>GTATCATGGTTCCAGCAATTCCCTGGCACGGCACCTCGCGTACTGATCTA<br>CGAAAATAATAAGCGGCCCTCAGGCATTTCAGATAGGTTCTCTGGGAGC<br>AAGAGTGGTACAAGCGTAACGCTCGGTATCACCGGTCTCCAGACAGGTG<br>ATGAAGCTGATTACTACTGCGCTACTTTTGATAGCTCTCTTTCAGCTTAC<br>GTGTTTGGTTCCGGGACCAAAGTGACAGTCCTC (SEQ ID NO: 210) |
| KPS44-G2 | CAGTCCGTTTTGACGCAACCCCCGTCACTGAGTGCTGCGCCTGGGCAGAC<br>CATAACGATCGCCTGCTCAGGGACCAGCAGTAATATAGGCTCTGATTCT<br>GTATCATGGTTCCAGCAATTCCCTGGCACGGCACCTCGCGTACTGATCTA<br>CGAAAATAATAAGCGGCCCTCAGGCATTTCAGATAGGTTCTCTGGGAGC<br>AAGAGTGGTACAAGCGTAACGCTCGGTATCACCGGTCTCCAGACAGGTG<br>ATGAAGCTGATTACTACTGCGCTACTTTTGATAGCTCTCTTTCAGCTTAC<br>GTGTTTGGTTCCGGGACCAAAGTGACAGTCCTC (SEQ ID NO: 211) |
| KPS44-G3 | CAGTCCGTTTTGACGCAACCCCCGTCACTGAGTGCTGCGCCTGGGCAGAC<br>CATAACGATCGCCTGCTCAGGGACCAGCAGTAATATAGGCTCTAATTAT<br>GTATCATGGTTCCAGCAATTCCCTGGCACGGCACCTCGCGTACTGATCTA<br>CGAAAATAATAAGCGGCCCTCAGGCATTTCAGATAGGTTCTCTGGGAGC<br>AAGAGTGGTACAAGCGTAACGCTCGGTATCACCGGTCTCCAGACAGGTG<br>ATGAAGCTGATTACTACTGCGCTACTTGGGATAGCTCTCTTTCAGCTTAC<br>GTGTTTGGTTCCGGGACCAAAGTGACAGTCCTC (SEQ ID NO: 212) |
| KPS30 | CAGTCTGCCCTGACTCAGCCTCCCTCCGCGTCCGGGTCTCCTGGACAGTC<br>AGTCGTCATCTCCTGCACTGGAACCAGCAGTGACATTGGGGCTAATAAC<br>TATGTCTCCTGGTACCAACAACACCCAGGCAAAGCCCCCAAACTCTTGCT<br>TTATGAGGTCAATAAGCGGCCCTCAGGGGTCCCTGATCGCTTCTCTGCCT<br>CCAAGTCTGGCAACACGGCCTCCCTGACCGTCTCTGGGCTCCTGGCTGAG<br>GATGAGGCTGATTATTACTGCTGCGGATATGGAGGCGGGAGGGTGTTCG<br>GCGGAGGGACCAAGCTGACCGTCCTAC (SEQ ID NO: 164) |
| KPD1 | GAAATTGTGTTGACGCAGTCTCCAGGCATCCTGTCTTTGTCTCCAGGGGA<br>GAGAGCCACCCTCTCTTGCAGGGTCAGTCAGATTCTTTACATGTCTATT<br>TGGCCTGGTATCAGCATAAACCTGGACAGGCTCCCAGACTCCTCATCTAT<br>GGTGCGTCCATCAGGGCCACTGGCGTCCCAGACAGGTTCAGTGGCAGTG<br>GGTCCGGGACAGACTTCACTCTCACCATCAGCAGACTGGAGCCTGAAGA<br>TTTTGCAGTGTATTACTGTCAGCAGTATGGCGCCTCACCGACGTTCGGCC<br>AAGGGACAATGGTGGAAATCAAAC (SEQ ID NO: 165) |
| KPL36 | CAGTCTGCCCTGACTCAGCCTCCCTCCGCGTCCGGGTCTCCTGGACAATC<br>AGTCACCATCTCCTGCACTGGAACCAGTAGTGACGTAGGTGGTAATAAC<br>TTTGTCTCCTGGTACCAACAGTATCCAGGCAAAGCCCCCAAACTCATTAT<br>TTATGAGGTCAATAAGCGGCCCTCAGGGGTCCCTGATCGTTTCTCTGGCT<br>CCAAGTCTGGCAACACGGCCTCCCTGACCGTCTCTGGGCTCCAGGCTGA<br>GGATGAGGCTGATTATTACTGCGGCGCATTTGGAGGTAGCAAGATGTTC<br>GGCGGAGGGACCAAGCTGACCGTCCTAG (SEQ ID NO: 198) |
| KPS44-G4 | CAGTCCGTTTTGACGCAACCCCCGTCAGTGAGTGCTGCGCCTGGGCAGA<br>AGGTGACGATCGCCTGCTCAGGGACCAGCAGTAATATAGGCTCTGATGC<br>TGTATCATGGTTCCAGCAACTGCCTGGCACGGCACCTAAACTGCTGATCT<br>ACGAAAATAATAAGCGGCCCTCAGGCATTTCAGATAGGTTCTCTGGGAG<br>CAAGAGTGGTACAAGCGTAACGCTCGGTATCACCGGTCTCCAGACAGGT<br>GATGAAGCTGATTACTACTGCGCTACTTTTGAGAGCTCTCTTTCAGCTTA<br>CGTGTTTGGTACCGGGACCAAAGTGACAGTCCTC (SEQ ID NO: 222) |
| KPS44-G6 | CAGTCCGTTTTGACGCAACCCCCGTCAGTGAGTGCTGCGCCTGGGCAGA<br>AGGTGACGATCGCCTGCTCAGGGACCAGCAGTAATATAGGCTCTGAGTC<br>TGTATCATGGTTCCAGCAACTGCCTGGCACGGCACCTAAACTGCTGATCT<br>ACGAAAATAATAAGCGGCCCTCAGGCATTTCAGATAGGTTCTCTGGGAG<br>CAAGAGTGGTACAAGCGTAACGCTCGGTATCACCGGTCTCCAGACAGGT<br>GATGAAGCTGATTACTACTGCGCTACTTTTGAGAGCTCTCTTTCAGCTTA<br>CGTGTTTGGTACCGGGACCAAAGTGACAGTCCTC (SEQ ID NO: 232) |

TABLE 6-continued

Variable light chain polynucleotide sequences

| Antibody | VL Polynucleotide Sequence (SEQ ID NO) |
|---|---|
| KPS44-G8 | CAGTCCGTTTTGACGCAACCCCCGTCAGTGAGTGCTGCGCCTGGGCAGA<br>AGGTGACGATCGCCTGCTCAGGGACCAGCAGTAATATAGGCTCTGATTC<br>TGTATCATGGTTCCAGCAACTGCCTGGCACGGCACCTAAACTGCTGATCT<br>ACGAAAATAATAAGCGGCCCTCAGGCATTTCAGATAGGTTCTCTGGGAG<br>CAAGAGTGGTACAAGCGTAACGCTCGGTATCACCGGTCTCCAGACAGGT<br>GATGAAGCTGATTACTACTGCGCTACTTTTGAGAGCTCTCTTTCAGCTTA<br>CGTGTTTGGTACCGGGACCAAAGTGACAGTCCTC (SEQ ID NO: 242) |
| KPS44-G10 | CAGTCCGTTTTGACGCAACCCCCGTCACTGAGTGCTGCGCCTGGGCAGAC<br>CATAACGATCGCCTGCTCAGGGACCAGCAGTAATATAGGCTCTGATTCT<br>GTATCATGGTTCCAGCAATTCCCTGGCACGGCACCTCGCGTACTGATCTA<br>CGAAAATAATAAGCGGCCCTCAGGCATTTCAGATAGGTTCTCTGGGAGC<br>AAGAGTGGTACAAGCGTAACGCTCGGTATCACCGGTCTCCAGACAGGTG<br>ATGAAGCTGATTACTACTGCGCTACTTTTGAGAGCTCTCTTTCAGCTTAC<br>GTGTTTGGTTCCGGGACCAAAGTGACAGTCCTC (SEQ ID NO: 252) |
| KPS44-G11 | CAGTCCGTTTTGACGCAACCCCCGTCAGTGAGTGCTGCGCCTGGGCAGA<br>AGGTGACGATCGCCTGCTCAGGGACCAGCAGTAATATAGGCTCTGATTC<br>TGTATCATGGTTCCAGCAACTGCCTGGCACGGCACCTAAACTGCTGATCT<br>ACGAAAATAATAAGCGGCCCTCAGGCATTTCAGATAGGTTCTCTGGGAG<br>CAAGAGTGGTACAAGCGTAACGCTCGGTATCACCGGTCTCCAGACAGGT<br>GATGAAGCTGATTACTACTGCGCTACTTTTGAGAGCTCTCTTTCAGCTTA<br>CGTGTTTGGTACCGGGACCAAAGTGACAGTCCTC (SEQ ID NO: 262) |
| KPS44-G14 | CAGTCCGTTTTGACGCAACCCCCGTCACTGAGTGCTGCGCCTGGGCAGAC<br>CATAACGATCGCCTGCTCAGGGACCAGCAGTAATATAGGCTCTGATTCT<br>GTATCATGGTTCCAGCAATTCCCTGGCACGGCACCTCGCGTACTGATCTA<br>CGAAAATAATAAGCGGCCCTCAGGCATTTCAGATAGGTTCTCTGGGAGC<br>AAGAGTGGTACAAGCGTAACGCTCGGTATCACCGGTCTCCAGACAGGTG<br>ATGAAGCTGATTACTACTGCGCTACTTTTGAGAGCTCTCTTTCAGCTTAC<br>GTGTTTGGTTCCGGGACCAAAGTGACAGTCCTC (SEQ ID NO: 272) |

Also provided is a polynucleotide having at least about 95%, at least about 96%, at least about 97%, at least about 98%, or at least about 99% sequence identity to any one of the SEQ ID NOs provided in Table 5 or 6. Thus, in certain embodiments, the polynucleotide comprises (a) a polynucleotide having at least about 95% sequence identity to any one of the SEQ ID NOs provided in Table 5, and/or (b) a polynucleotide having at least about 95% sequence identity to any one of the SEQ ID NOs provided in Table 6. In certain embodiments, the polynucleotide comprises: (a) a polynucleotide having the sequence of a SEQ ID NO provided in Table 5; and/or (b) a polynucleotide having the sequence of a SEQ ID NO provided in Table 6.

The present disclosure provides an isolated polynucleotide or cDNA molecule sufficient for use as a hybridization probe, PCR primer or sequencing primer that is a fragment of a nucleic acid molecule disclosed herein or its complement. The nucleic acid molecule can, for example, be operably linked to a control sequence.

The present disclosure also provides constructs in the form of plasmids, vectors, transcription or expression cassettes which comprise at least one polynucleotide as described above (see, e.g., Tables 5 and 6).

The present disclosure also provides a recombinant host cell which comprises one or more nucleic acids, plasmids, vectors or as described above (see, e.g., Tables 5 and 6). A nucleic acid encoding any CDR or set of CDRs or VH domain or VL domain or antibody antigen-binding site, antibody, e.g., scFv, IgG1, or IgG2 as provided (see, e.g., Tables 1-4) itself forms an aspect of the present disclosure, as does a method of production of the encoded product, which method comprises expression from the nucleic acid encoding the product (e.g. the antigen binding protein, including, e.g., an anti-O2 antigen antibody or antigen-binding fragment thereof, disclosed herein). Expression can conveniently be achieved by culturing under appropriate conditions recombinant host cells containing a nucleic acid described herein. Following production by expression a CDR, set of CDRs, VH or VL domain, an antigen-binding protein can be isolated and/or purified using any suitable technique.

In some instances, the host cell is a mammalian host cell, such as a HEK293 cell, a HeLa cell, NS0 murine myeloma cell, a PER.C6® human cell, or a Chinese hamster ovary (CHO) cell.

Antigen-binding proteins, VH and/or VL domains and encoding nucleic acid molecules and vectors can be isolated and/or purified, e.g., from their natural environment, in substantially pure or homogeneous form, or, in the case of nucleic acid, free or substantially free of nucleic acid or genes origin other than the sequence encoding a polypeptide with the required function. Nucleic acids according to the present disclosure can comprise DNA or RNA and can be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, plant cells, yeast and baculovirus systems and transgenic plants and animals. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others. A common bacterial host is *E. coli*.

The expression of antibodies and antibody fragments in prokaryotic cells such as *E. coli* is well established in the art. For a review, see for example Plückthun, A. Bio/Technology 9: 545-551 (1991). Expression in eukaryotic cells in culture is also available to those skilled in the art as an option for production of an antigen-binding protein for example Chadd H E and Chamow S M (2001) 110 Current Opinion in Biotechnology 12: 188-194, Andersen D C and Krummen L (2002) Current Opinion in Biotechnology 13: 117, Larrick J W and Thomas D W (2001) Current opinion in Biotechnology 12:411-418.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual: 3rd edition*, Sambrook and Russell, 2001, Cold Spring Harbor Laboratory Press. Many known techniques and protocols for manipulation of nucleic acids, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1988, *Short Protocols in Molecular Biology: A Compendium of Methods from Current Protocols in Molecular Biology*, Ausubel et al. eds., John Wiley & Sons, $4^{th}$ edition 1999. The disclosures of Sambrook et al. and Ausubel et al. (both) are incorporated herein by reference.

Thus, a further aspect of the present disclosure provides a host cell containing nucleic acid as disclosed herein. For example, the disclosure provides a host cell transformed with nucleic acid comprising a nucleotide sequence (see, e.g., Tables 5 and 6) encoding an antigen-binding protein of the present disclosure or antibody CDR, set of CDRs, or VH and/or VL domain of an antigen-binding protein of the present disclosure (see, e.g., Tables 1-4). In some embodiments, the host cell comprises the expressed antigen-binding protein of the present disclosure or antibody CDR, set of CDRs, or VH and/or VL domain of an antigen-binding protein of the present disclosure (see, e.g., Tables 1-4).

Such a host cell can be in vitro and can be in culture. Such a host cell can be an isolated host cell. Such a host cell can be in vivo.

A still further aspect provided herein is a method comprising introducing such nucleic acid into a host cell. The introduction can employ any available technique. For eukaryotic cells, suitable techniques may include calcium phosphate transfection, DEAE-Dextran, electroporation, liposome-mediated transfection and transduction using retrovirus or other virus, e.g., vaccinia or, for insect cells, baculovirus. Introducing nucleic acid in the host cell, in particular a eukaryotic cell can use a viral or a plasmid based system. The plasmid system can be maintained episomally or may incorporated into the host cell or into an artificial chromosome. Incorporation can be either by random or targeted integration of one or more copies at single or multiple loci. For bacterial cells, suitable techniques may include calcium chloride transformation, electroporation, and transfection using bacteriophage.

The introduction can be followed by causing or allowing expression from the nucleic acid, e.g., by culturing host cells under conditions for expression of the gene.

In one embodiment, the nucleic acid of the present disclosure is integrated into the genome (e.g. chromosome) of the host cell. Integration can be promoted by inclusion of sequences which promote recombination with the genome, in accordance with standard techniques.

The present disclosure also provides a method which comprises using a construct (e.g. plasmid, vector, etc. as described above) in an expression system in order to express an antigen-binding protein or polypeptide as described above.

In another aspect, the disclosure provides a hybridoma producing the antigen-binding protein (e.g. anti-O2 antigen antibodies or antigen binding fragments thereof) of the disclosure.

A yet further aspect of the disclosure provides a method of production of an antibody binding protein (e.g. anti-O2 antigen antibodies or antigen binding fragments thereof) of the disclosure, the method including causing expression from encoding nucleic acid. Such a method can comprise culturing host cells under conditions suitable for production of said antigen-binding protein.

In some embodiments, the method of production further comprises isolating and/or purifying the antigen binding protein (including anti-O2 antigen antibodies or antigen binding fragments thereof) produced from the host cell or hybridoma.

EXAMPLES

Materials and Methods

Unless otherwise stated, all *K. pneumoniae* isolates were purchased from America Type Culture Collection, Eurofin collection, or IHMA collection, and cultures were maintained in 2×YT media at 37° C. supplemented with antibiotics when appropriate.

All statistical analysis was performed in GraphPad Prism version 6. For comparing bacterial burden, anti-O2 antigen antibody treated animals were compared with human isotype control antibody treated animals by unpaired t test. Survival results were plotted as Kaplan-Meier curves and analyzed as Log-rank (Mental-Cox) tests.

Unless otherwise specified, all antibodies used in the examples were in the human IgG1 format.

Example 1: Expansion of O2 Serotype in Multi-Drug Resistant (MDR) Strains

Highly purified LPS was generated from *Klebsiella pneumoniae* LPS serotype reference strains (Staten Serum Institute), which do not express capsular polysaccharides. SDS-PAGE analysis followed by Silver Stain confirmed the purity of LPS. Human antibodies against O2 serotypes were then identified based on the reactivity of human B cells against the respective purified LPS. The anti-O2 LPS antibodies (such as KPD1) showed cross-reactivity with O1 LPS, likely due to the common D-galactan I subunit shared between O1 and O2 LPS. (FIG. 1A).

Western blots were performed on 709 *Klebsiella* clinical isolates collected between 2012 and 2014 from various geographical locations spanning six continents and various sites of infection. The KPD1 antibody was used to assess the propensity of O2 isolates. Contrary to historical literature demonstrating the propensity of O1 isolates (Trautmann, M, et. al. 2004. O antigen seroepidemiology of *Klebsiella* clinical isolates and implications for immunoprophylaxis of *Klebsiella* infections. Vaccine. 22: 818-821.), O2 was the most prevalent LPS serotype (35.8%, FIG. 1B). Isolates were further categorized into three different drug susceptibility groups to determine if the increased incidence of O2 may be attributed to an overall increase in multi-drug resistant (MDR) isolates. The susceptibility groups were based on minimum inhibitory concentration (MIC) information provided by IHMA. Extended spectrum beta-lactamase producing (ESBL) strains are resistant to ceftazidime, but susceptible to carbanpenem. Carbapenem-Resistant Enterobacteriaceae (CRE) strains are resistant to carbanpenems. Interestingly, steady increases were observed in the O2 prevalence in multi-drug resistant isolates. The increases of O2 serotype were even more pronounced in CRE strains, suggesting the unique expansion of O2 MDR strains (see FIG. 1B).

Example 2: Isolation of *K. pneumoniae* O2 Specific Hybridomas

BALB/c mice were immunized weekly with O2 lipopolysaccharide (LPS) via subcutaneous route for four weeks. At the end of the immunization, lymph node and splenic B cells were harvested and fused with P3X myelomas. Supernatants from the resulting hybridomas were then screened for binding to *Klebsiella pneumoniae* 43816DM by whole bacterial enzyme-linked immunosorbent assay (ELISA). Positive hybridomas were sub-cultured in antibiotic-free medium, and the supernatants were subjected to ELISA binding and opsonophagocytic killing (OPK) assay to select for potentially protective hybridomas against *K. pneumoniae* O2 LPS. The 6F6 antibody was obtained from this method.

Example 3: Isolation of *K. pneumoniae* O2 Specific Antibodies from Tonsil and Patient B Cells Peripheral blood mononuclear cells (PBMC) and sera were separated from buffy coats from healthy blood donors or convalescent patients after *K. pneumoniae* infection as described in Beltramello M. et al., *Cell Host Microbe.* 8, 271-283 (2010). PMBC were stored in liquid nitrogen whereas the plasma was stored at 4° C. Alternatively lymphocytes were obtained from tonsils or adenoids after tissue homogenization in the presence of DNAaseI and collagenase. Memory B cells were isolated from cryopreserved PMBC or from lymphocytes isolated from tonsils or adenoids using CD19 microbeads, followed by depletion of cells carrying IgM, IgD, and IgA by cell sorting. Memory B cells were immortalized as described in Traggiai, E. et al., *Nature Medicine* 10: 871-875 (2004).

For PBMC donor selection the corresponding plasmas were diluted in PBS and used to determine the presence of antibodies binding to different pools of bacterial strains or to purified bacterial antigens (e.g. LPS or other polysaccharides, bacterial proteins) by ELISA.

For tonsil and adenoid donor selection, tonsillar lymphocytes were polyclonally stimulated as described in Pinna, D., et al., *European Journal of Immunology* 39: 1260-1270 (2009). Supernatants containing polyclonal antibody mixtures were used to determine the presence of antibodies binding to different pools of bacterial strains or to purified bacterial antigens (e.g. LPS or other polysaccharides, bacterial proteins) by enzyme-linked immunosorbent assay (ELISA).

The antibody KPD1 was isolated by screening B cells from peripheral blood mononuclear cells (PBMC) of a healthy donor in ELISA with plates coated with different *K. pneumoniae* strains. In secondary screenings, KPD1 showed binding to LPS-O1 and O2, neutralized LPS-O1 and O2, and showed OPK activity against an O2 capsule mutant. KPD1 was isolated as a human IgG2 antibody.

The antibodies KPS3, KPS24, KPS18, KPS30, and KPS44 were obtained by screening B cells of a convalescent donor in ELISA with plates coated with LPS-O2. In secondary screening KPS30 bound LPS-O1 and-O2, whereas KPS3, KPS18 and KPS24 bound specifically to LPS-O2. KPS3, 18, 24, 30, and 44 showed strong OPK activity against an O2 capsule mutant strain, but not the O1 capsule mutant strain. KPS3, KPS24, KPS18 neutralized LPSO2, KPS30 neutralized both LPS-O1 and LPS-O2. KPS3, KPS18, KPS24, KPS30 and KPS44 were isolated as human IgG2 antibodies.

The antibodies KPN17, KPN42, KPN44, KPN70, and KPN179 were isolated by interrogating sorted IgG2 B cells from tonsil 21 in ELISA with LPS-O2. KPN17, KPN42, KPN44 and KPN179 were shown to bind LPS-O1 and-O2 in secondary screening by ELISA. KPN17 and KPN42 neutralize LPS-O2, KPN44 and KPN70 neutralize both LPS-O2 and LPS-O1. KPN179 did not show LPS-neutralizing activity. KPN17, KPN42 and KPN44 showed OPK activity against an O2 capsule mutant.

The antibodies KPL26 and KPL36 were isolated by interrogating sorted IgG2 B cells from tonsil 14 in high content flow cytometry for binding to O2 strains. In secondary screening they were confirmed to bind to LPS-O1 and LPS-O2 in ELISA and KPL26 to neutralize LPS-O1 and LPS-O2, KPL36 to neutralize LPS-O2. KPL26 showed OPK activity against O1 and O2 capsule mutants.

Example 4: Summary of Three Classes of O2 LPS mAbs

As described in more detail in below, anti-O2 LPS mAbs were tested for: 1) binding to O1 and O2 LPS (see Example 5); 2) LPS neutralization (LPS-Neut) against O1 and O2 LPS (see Example 7); 3) OPK against capsule mutant strain 43816ΔcpsB lux (O1) and 8570ΔcpsB lux (O2) (see Example 8); and 4) protective activity in pneumonia models (see Example 9). O2 LPS mAbs were subsequently divided into three classes based on their in vitro activities. Class I mAbs were characterized as Binding (O1+O2+)/OPK (O1−O2+); Class 2 mAbs were characterized as Binding (O1+O2+)/OPK (O1+O2+); and Class III mAbs were characterized as Binding (O1±O2+)/OPK (O1−O2+). Table 7 summarizes the binding characteristics of the three classes of Anti-O2 LPS mAbs.

TABLE 7

Summary of Anti-O2 Antigen Antibodies.

| Catagory | mAb | Original Isotype | LPS binding | LPS Neut O1 | LPS Neut O2 | D Capsule OPK O1 | D Capsule OPK O2 | Mouse protection models |
|---|---|---|---|---|---|---|---|---|
| Class I | KPD1 | Hu rIgG2 | O1/O2 | ++ | ++ | − | ++ | − (O1/O2) |
|  | 6F6 | Ms IgM |  | NT | NT | − | + | − (O2) |

TABLE 7-continued

Summary of Anti-O2 Antigen Antibodies.

| Catagory | mAb | Original Isotype | LPS binding | LPS Neut O1 | LPS Neut O2 | D Capsule OPK O1 | D Capsule OPK O2 | Mouse protection models |
|---|---|---|---|---|---|---|---|---|
| | KPN17 | Hu rIgG2 | | − | +/− | − | + | − (O2) |
| | KPN70 | Hu rIgG2 | | ++ | ++ | − | +++ | +/− (O1/O2) |
| | KPS30 | Hu rIgG2 | | ++ | ++ | − | +++ | NT |
| Class II | KPL26 | Hu rIgG2 | O1/O2 | + | + | + | + | + (O1) |
| | KPL36 | Hu rIgG2 | | − | + | + | + | NT |
| Class III | KPN42 | Hu rIgG2 | O2, | − | +/− | − | +++ | +++ (O2) |
| | KPN179 | Hu rIgG2 | weak O1 | − | +/− | − | +++ | +++ (O2) |
| | KPS3 | Hu rIgG2 | | − | +/− | − | +++ | NT |
| | KPS18 | Hu rIgG2 | | − | +/− | − | +++ | NT |
| | KPS24 | Hu rIgG2 | | − | +/− | − | +++ | NT |
| | KPS44v2017 | Hu rIgG2 | | − | +/− | − | +++ | +++ (O2) |
| | KPS44 | Hu rIgG2 | | − | +/− | − | +++ | +++ (O2) |

NT: not tested
+++: Strongly positive activity
+: Positive activity
+/−: Somewhat positive depending upon the test conditions Notably, significant LPS neutralization activity is not required for high levels of in vivo protection.

Example 5: Enzyme-Linked Immunosorbent Assay (ELISA)

For screening by ELISA, spectraplate-384 with high protein binding treatment (custom made from Perkin Elmer, CUSG83093) were coated overnight at 4° C. with 5 µg/ml O1 or O2 LPS in phosphate-buffered saline (PBS), pH 7.2, and plates were subsequently blocked with PBS-B, i.e. PBS supplemented with 1% endotoxin free BSA (Sigma, #A9430). The coated plates were incubated with cell culture supernatants from polyclonally stimulated lymphocytes (AMBRA) or from monoclonal immortalized B cells (donor interrogations) containing fully human antibodies or with diluted plasma samples (PB MC donor selections) for 1 hour at room temperature. The plates were then washed with PBS containing 0.1% Tween-20 (PBS-T). Secondary antibody was added; either Alkaline Phosphatase-conjugated Goat Anti-Human IgG-AP (Southern Biotech, 2040-04, 1:1000 in PBS-B) or Peroxidase AffiniPure F(ab')$_2$ Fragment Goat Anti-Human IgG, Fcγ Fragment Specific (Jackson ImmunoResearch #309 036 098, 1:5000 in PBS-B) were used. Secondary antibodies were typically incubated for 1 h. Plates were washed three times with PBS-T, and P-NitroPhenyl Phosphate (pNPP, Sigma-Aldrich, cat #N2765-100TAB) or Sureblue (KPL, 53-00-03) substrates were added and incubated for 10 min or until the development of a colorimetric reaction. In the case of the HRP substrate Sureblue, the reaction was stopped by adding an equal volume of 0.2N HCl. The absorbance at 405 nm (pNPP) or 450 nm (Sureblue) was measured by a microplate reader (Biotek, Elx808).

To determine binding EC50 values ELISA was performed in 96 well plates (Maxi sorp, Nunc #442404) coated overnight at 4° C. with 5 µg/ml O1 or O2 LPS in phosphate-buffered saline (PBS), pH 7.2, and plates were subsequently blocked with PBS-B, i.e. PBS supplemented with 1% endotoxin free BSA (Sigma, #A9430). The coated plates were incubated with serial dilutions of the monoclonal antibodies for 1 hour at room temperature. The plates were then washed with PBS containing 0.1% Tween-20 (PBS-T). Alkaline Phosphatase-conjugated Goat Anti-Human IgG (Southern Biotech, 2040-04, 1:1000 in PBS-B) was added. The secondary antibody reactions were incubated for 1 h. Plates were washed three times with PBS-T, and P-NitroPhenyl Phosphate (pNPP, Sigma-Aldrich, cat #N2765-100TAB) substrate was added and incubated for 30 min or until the development of a colorimetric reaction. The absorbance at 405 nm was measured by a microplate reader (Biotek, Elx808). The data was plotted with Graphpad Prism software. Representative mAbs from each class were tested for their binding to O1 LPS (FIG. 2A) and O2 LPS (FIG. 2B), and EC50 values were obtained (FIG. 2C). The majority of the anti-O2 LPS mAbs bound to both O1 and O2 LPS by ELISA. Among these, KPN42 showed lower affinity to O1 than O2. None of these LPS mAbs bound to the O3, O4, O5, O7, or O12 LPS serotypes (see e.g., FIG. 1A).

Example 6: Octet Binding Assay with Anti-O2 mAbs

Figure 3G:
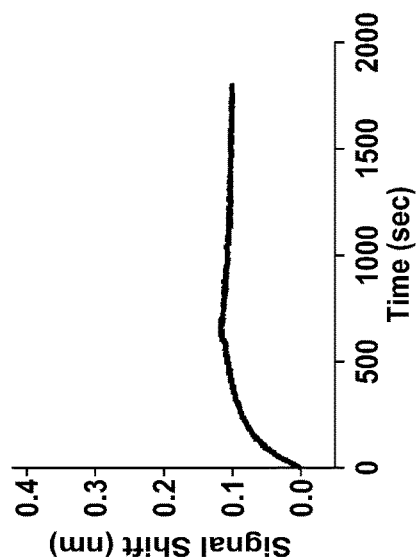
Figure 3H:
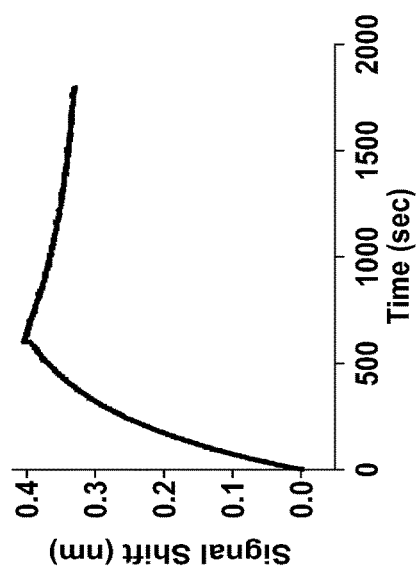
Figure 3I:
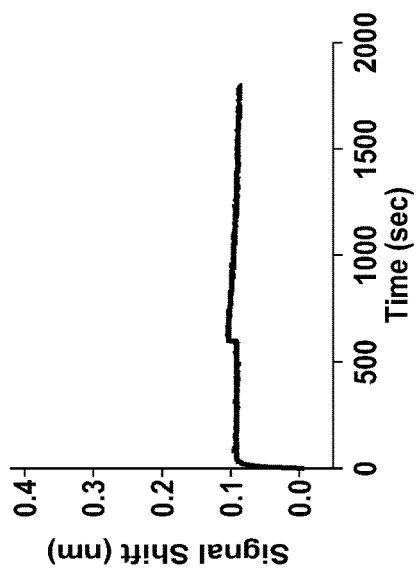
Figure 3J:
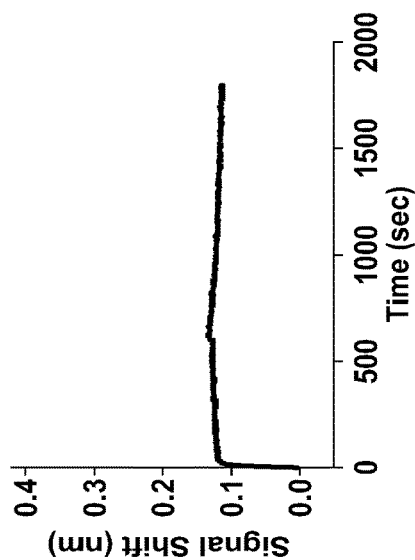
Figure 3K:
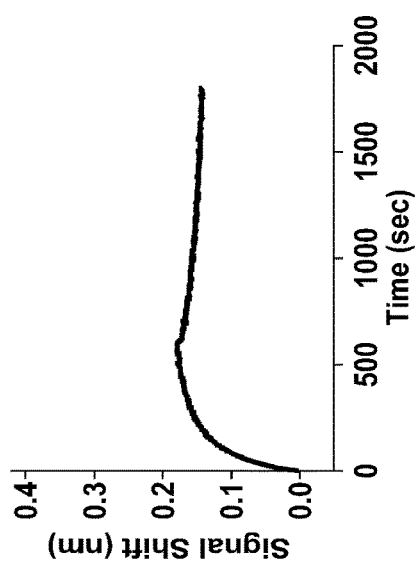
Figure 3L:
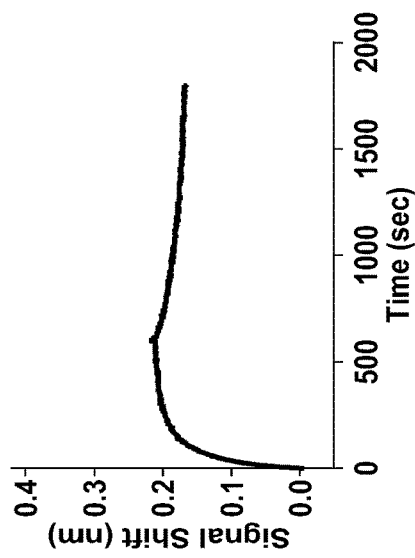

The interaction of anti-O2 LPS mAbs with O1 and O2 LPS was further tested in solution phase by Octet platform. This platform provides a powerful tool to measure the rate of biomolecular complex formation and complex stability in a more biologically meaningful setting. Briefly, Protein A coated sensors were coated with 0.2 µg/mL anti-O2 LPS mAbs for 10 minutes before being dipped into solution containing 2 µg/mL O1 or O2 LPS in Kinetics buffer (ForteBio, dilute 10× to 1× with PBS). Changes in the number of molecules bound to the biosensor caused a shift in the interference pattern that was recorded in real time. As shown in FIGS. 3A and 3B, Class I and Class II mAbs bound to both O1 and O2 LPS, while Class III mAb (KPN42) showed no binding to O1 LPS. The affinity constant ($K_D$) of Class III mAbs to O2 LPS was calculated based on the on-rate and off-rate from Octet sensorgram. Both KPN42 and KPN179 showed comparable affinity constant at the average of 4.8E-09 and 7.98E-09M, respectively (FIG. 3C).

Example 7: LPS Neutralization Assays

Activation of TLR4 receptors by bacterial LPS leads to downstream activation of the NF-κB transcriptional regulator. A decrease in induction of NF-κB-responsive luciferase activity was used to quantify LPS neutralization activity by LPS mAbs. A murine RAW264.7 macrophage cell line was engineered to carry a firefly luciferase reporter gene under the control of an NF-κB-responsive promoter (RAW264.7-lux). Serially diluted antibody stocks were mixed with LPS in a 1:1 ratio and incubated at 4° C. for 1 hr. Antibody/LPS mixtures were then diluted 1:10 into assay plates containing pre-seeded RAW264.7-lux cells (4e5 cells/well), which were then placed at 37° C. with 5% CO2 for 2.5 hours. Following incubations, Steady Glo solution (Promega) was added to each well and incubated for another 20 min protected from light. The relative light units (RLUs) were measured using a multi-mode microplate reader (Synergy 2, Biotek or envision multilabel plate reader, Perkin Elmer). The percentage of inhibition was determined by comparing RLU derived from assays with no antibodies to RLU derived from assays with anti-*K. pneumoniae* mAbs and assays performed with a negative control mAb. Results from these neutralization assays are shown in FIG. 4. The KPD1, KPN44, KPN70, and KPL26 blocked O1 and O2 LPS activation of NF-κB, while KPN42, KPN17, KPL36, KPS3, KPS18, KPS24, and KPS44 showed moderate neutralizing activity against O2 LPS, but no activity against O1 LPS. All mAbs were tested in human IgG1 format.

Example 8: OPK Activity of Selected O2 mAbs

Figure 5A:
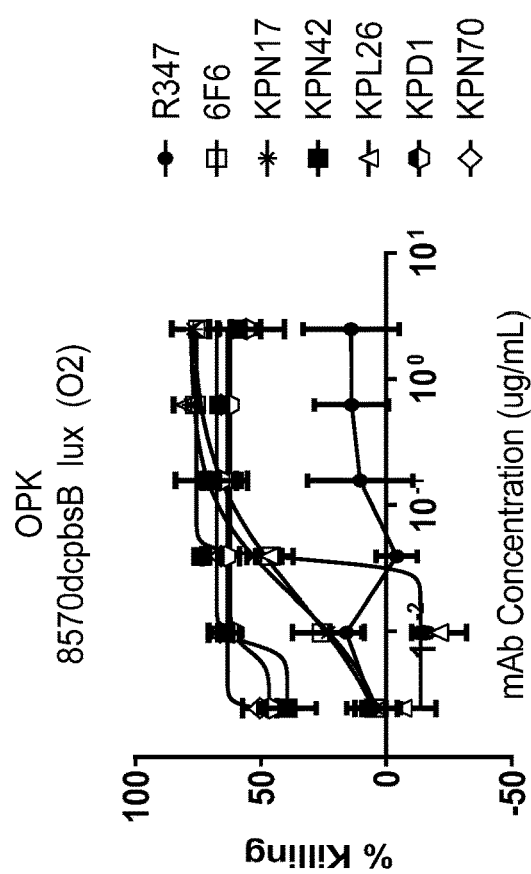
FIGS. 5A-5B show the opsonophagocytic killing (OPK) activity of selected anti-O2 monoclonal antibodies (mAbs). The OPK of these mAbs against an O1 strain of *K. pneumoniae* is shown in FIG. 5A, and the OPK of these mAbs against an O2 strain of *K. pneumoniae* is shown in FIG. 5B.
Figure 5B:
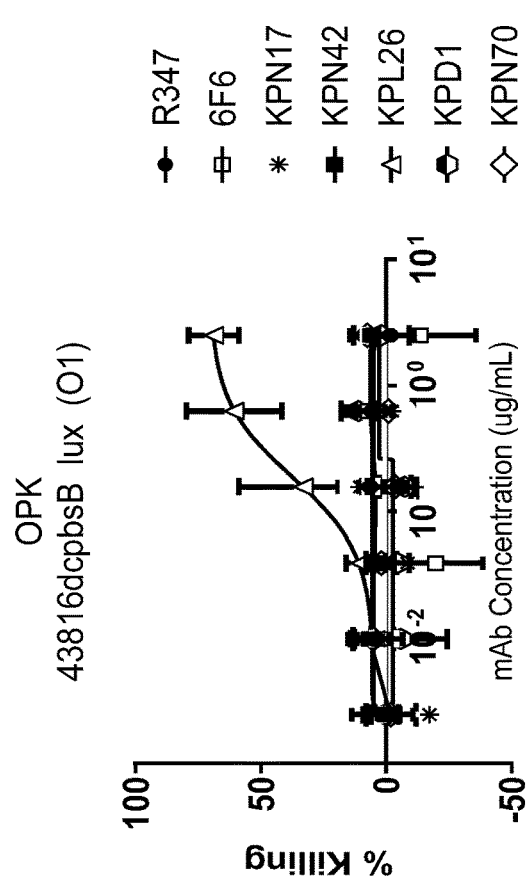

OPK activity of anti-O2 LPS mAbs was tested against O1 and O2 strains. Briefly, log phase cultures of luminescent *K. pneumoniae* strains 8570ΔcpsBLux (O2) and 43816ΔcpsBLux (O1) were diluted to ~2×10$^6$ cells/ml. *K. pneumoniae* cells, 5e5/well dimethylformamide (DMF) differentiated HL-60 cells, cleared baby rabbit serum (1:10 Cedarlane), and a series dilution of antibodies (2 ng-2.5 μg/mL) were mixed in 96-well plates and incubated at 37° C. for two hours with shaking (250 rpm). The relative light units (RLUs) were then measured using a multi-mode microplate reader (Synergy 2, Biotek or envision multilabel plate reader, Perkin Elmer). The percentage of killing was determined by comparing RLU derived from assays with no antibodies to RLU derived from assays with anti-*K. pneumoniae* mAbs and assays performed with a negative control mAb. Positive killing was determined where the percentage of killing is above 40%. All anti-O2 IgG1 mAbs tested showed strong OPK activity (80-100% killing) against O2 capsule mutant strains (FIG. 5 and FIG. 10). KPL26 induced OPK activity to both O1 and O2 strains (FIG. 5).

Example 9: Class III mAbs Protect in Lethal Pneumonia Models

C57/BL6 mice were obtained from Jackson Laboratories and maintained in a special pathogen-free facility. All animal experiments were conducted in accordance with Institutional Animal Care and Use Committee (IACUC) protocol and guidance. *K. pneumoniae* strains were grown on agar plates overnight and diluted in saline at proper concentration. The inoculum titer was determined by plating a serial dilution of bacteria onto agar plates prior to and post challenge. In acute pneumonia models, C57/BL6 mice were inoculated with 1e4 to 2e8 colony-forming units (CFU) of *K. pneumoniae* clinical isolates in 50 μl saline intranasally. Anti-*K. pneumoniae* monoclonal antibodies (mAbs) and human IgG1 control antibodies were given 1-24 hour post bacterial challenge (therapeutic dosing). Mouse survival was monitored daily until up to day 8. Survival data of representative experiments were plotted in Graphpad Prism software.

Figure 6A:
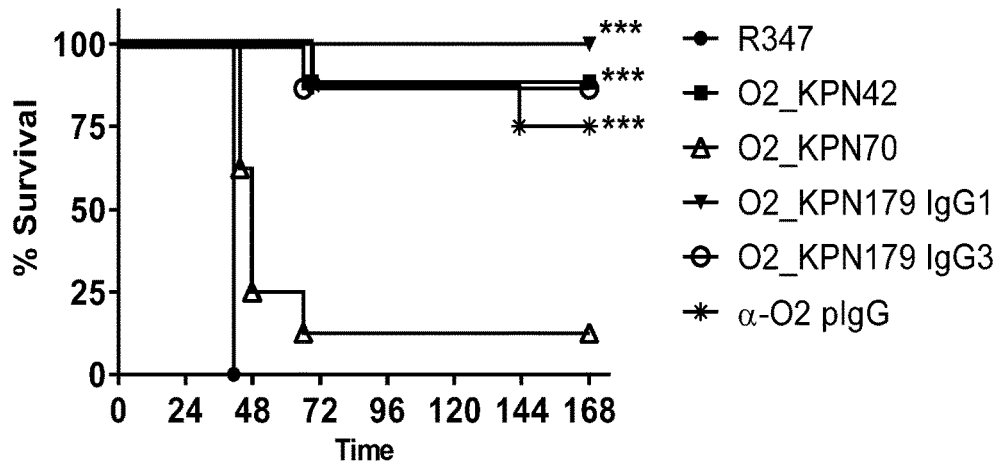
FIGS. 6A-6B show the protection conferred by Class III monoclonal antibodies (mAbs) in lethal pneumonia models. The % survival of mice challenged with *K. pneumoniae* Carbanpenemase (KPC) strain Kp961842_O2 is shown in FIG. 6A, and the % survival of mice challenged with KPC strain Kp977778_O2 is shown in FIG. 6B.
Figure 6B:
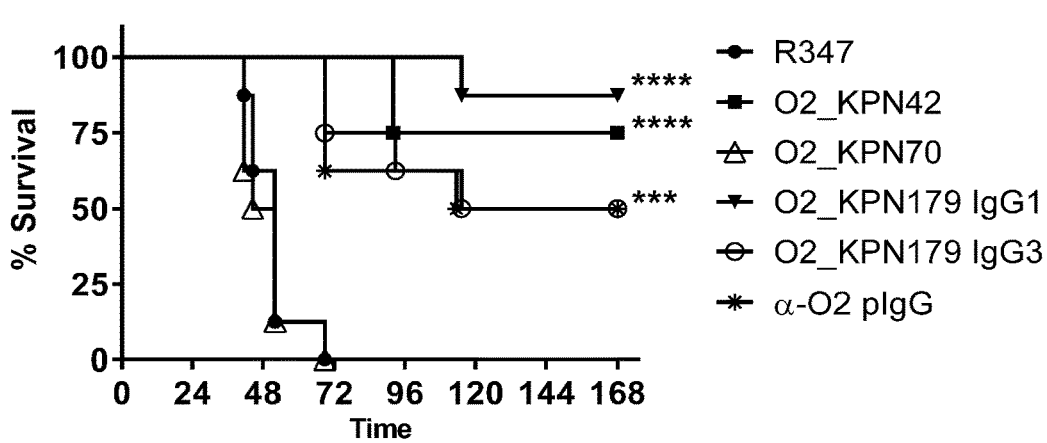

Mice were challenged with 2e8 CFU of *Klebsiella pneumoniae* Carbanpenemase (KPC) strain Kp961842_O2 or with 3e8 CFU of KPC strain Kp977778_O2, followed by the administration of anti-O2 mAbs. When administered at a concentration of 2 mg/kg 1 hour post bacterial infection, Class III anti-O2 LPS mAbs KPN42, KPN179-IgG1, and KPS44v2017 protected mice from lethal bacterial challenge with the multi-drug resistant KPC strains Kp961842_O2 (FIG. 6, left panel, and FIG. 10) and Kp977778_O2 (FIG. 6B, right panel). KPN179-IgG3 also conferred protection, while the Class I mAb KPN70-hIgG1 or KPD1-IgG1 did not protect in these two models. Class II mAb KPL26 conferred moderate protection in a lethal O1 pneumonia model, while did not show protection in Kp961842_O2 pneumonia model.

Example 10: Anti-O2 LPS mAbs KPN42 and KPN179 Show Strong Synergy with Antibiotic Meropenem in Lethal Pneumonia Model The lethal pneumonia model as described in Example 9 was used to assess the activity of anti-O2 LPS antibodies in combination with an antibiotic. Both antibiotic and antibody were administered 1 hour after bacterial infection. The combination of meropenem human equivalent dosage (50 mpk) with sub-therapeutic dosages (0.2 mpk) of KPN42 or KPN179 showed significantly improved protection compared to antibody or antibiotic monotherapy (FIG. 7). These results illustrate that administration of an anti-O2 antibody, including KPN42 or KPN179, sensitizes antibiotic resistant *Klebsiella pneumoniae* strains to antibiotic therapy and that sub-therapeutic doses of the anti-O2 antibodies KPN42 or KPN179 show strong synergy with antibiotics in antibiotic resistant *Klebsiella pneumoniae* strains.

Example 11: KPN42 Protects Up to 6 Hour Post Infection in Conjunction with Meropenem 50 mg/kg of meropenem and 2 mg/kg of antibody were administered at 1, 2, 4, 6, and 24 hour after bacterial infection, as described for the antibody and antibiotic combination studies in Examples 9 and 10. The combination of meropenem and KPN42 showed significantly better protection than a combination of a control mAb and meropenem up to 6 hours post infection (FIG. 8). The combination of KPN179 and meropenem conferred better protection than a combination of a control mAb and meropenem up to 4 hours post infection (FIG. 8). Together with Example 10, these results illustrate the efficacy of administering an anti-O2 antibody, including KPN42 or KPN179, after bacterial infection (i.e., therapeutic administration).

Example 12: KPN42 and KPN179 Sequence Optimization

In order to reduce sequence liability for mAb development and potential anti-drug antibody, an unpaired cysteine in the light chain CDR3 of KPN42 was exchanged with alanine (see FIG. 9, antibody A (KPN42-FR-GL-VH/KPN42-FR-GL-C105A-VL) and antibody B (KPN42-FR-1-2-4-GL-VH/KPN42-FR-GL-C105A-VL)), and somatic mutations in the frameworks of KPN42 (see FIG. 9, antibody A) or in the frameworks 1, 2, and 4 of KPN42 (see FIG. 9, antibody B) were replace with germline residues. Similarly an unpaired cysteine in the light chain CDR3 of KPN179 was exchanged with alanine, and an asparagine residue forming a deamidation motif in the KPN179 heavy chain CDR1 was replaced with the germline residue serine (see FIG. 9, antibody C (KPN179-FR-GL-N35S-VH/ KPN179-FR-GL-C105A-VL) and antibody D (KPN179-FR-1-2-4-GL-N35S-VH/KPN179-FR-GL-C105A-VL)), somatic mutations in the frameworks of KPN179 (see FIG. 9, antibody C) or in frameworks 1, 2 and 4 of KPN179 were replaced with germline residues (see FIG. 9, antibody D). Replacement of all somatic mutations in KPN179 VH and VL frameworks with germline residues (see FIG. 9, antibody C) significantly reduced binding to O2 LPS. The rest of the mutations showed comparable binding to parent antibodies (see, e.g., FIG. 9, antibodies A, B and D).

Example 13: Anti-O2 Antigen Antibodies Bind to Clinically Relevant *Klebsiella*

In order to determine if anti-O2 antigen antibodies bind to clinically relevant *Klebsiella* strains, the binding of anti-O2 mAbs to clinical isolates was determined by western blot assay. Briefly, purified LPS or bacterial lysates were subjected to sodium dodecyl sulfate-polyacryalminde gel electrophoresis (SDS-PAGE). Separated proteins and LPS were transferred from gels to nitrocellulose membranes with an iBlot apparatus based on the manufacturer's recommendation. (Life Technology). Membranes were then blocked with Casein blocking buffer before being probed with O2 (KPD1) monoclonal antibodies or antibodies specific for other LPS serotypes. After three washes with 0.05% Tween in PBS buffer (PBS-T), blots were incubated with IRDye680 or 800 fluorescent $2^{nd}$ antibodies (Licor). Blots were visualized with an Odyssey Image Station. Distinct laddering patterns were observed for LPS blots. Assays were repeated at least twice. In some circumstances, bacterial lysates were treated with Protease K to remove protein components before the western blot analysis. Strains that bind to KPD1, but not to other LPS serotype specific mAbs were characterized as O2 strains. A summary of the clinically relevant *Klebsiella* strains to which anti-O2 mAbs KPD1 and KPN42 bind is shown in Table 8.

TABLE 8

Summary of clinical *Klebsiella* strains to which anti-O2 mAbs bind.

| | Region | Country | IHMA Number | Body Location | Facility Name | Molecular Summary |
|---|---|---|---|---|---|---|
| 1 | Latin America | Chile | 847204 | INT: Wound | Surgery General | SHV-11(b); TEM-1(b); KPC-2; |
| 2 | Latin America | Argentina | 847378 | Respiratory: Endotracheal aspirate | Medicine ICU | KPC-2; |
| 3 | Latin America | Argentina | 847383 | Respiratory: Bronchoalveolar lavage | Medicine ICU | SHV-11(b); TEM-1(b); CTX-M-15; NDM-1; |
| 4 | Latin America | Argentina | 847387 | Respiratory: Bronchoalveolar lavage | Medicine ICU | SHV-11(b); TEM-1(b); CTX-M-15; NDM-1; |
| 5 | Latin America | Argentina | 847694 | Unknown | Medicine ICU | SHV-11(b); KPC-2; |
| 6 | Latin America | Argentina | 847747 | Respiratory: Endotracheal aspirate | Medicine ICU | SHV-11(b); KPC-2; |
| 7 | Europe | Greece | 848832 | Respiratory: Sputum | General Unspecified ICU | SHV-1(b); CTX-M-15; KPC-2; |
| 8 | Europe | Greece | 848844 | Respiratory: Sputum | General Unspecified ICU | SHV-12(e); KPC-2; |
| 9 | Europe | Greece | 848876 | Respiratory: Bronchial brushing | Medicine General | SHV-1(b); TEM-1(b); CTX-M-2; |
| 10 | Middle East | Israel | 849156 | Bodily Fluids: Peritoneal | Medicine General | SHV-1(b); TEM-1(b); CTX-M-2; |
| 11 | Middle East | Israel | 849584 | INT: Abscess | Pediatric ICU | SHV- 11(b); TEM- 1(b); KPC-3; |
| 12 | Middle East | Israel | 849585 | INT: Wound | Medicine General | SHV-1(b); KPC-3; |
| 13 | North America | United States | 854022 | Respiratory: Endotracheal aspirate | General Unspecified ICU | SHV-11(b); TEM-1(b); CTX-M-15; OXA-48(c) |
| 14 | North America | United States | 857973 | Respiratory: Endotracheal aspirate | Other | SHV-11(b); TEM-1(b); CTX-M-15; OXA-48(c) |
| 15 | North America | United States | 857978 | Respiratory: Endotracheal aspirate | Medicine General | SHV-11(b); TEM-1(b); CTX-M-15; |
| 16 | North America | United States | 863890 | INT: Decubitus | None Given | SHV-11(b); TEM-1(b); KPC-2; |
| 17 | North America | United States | 863930 | Bodily Fluids: Peritoneal | Surgery ICU | SHV-11(b); TEM-1(b); KPC-2; |
| 18 | Europe | Italy | 867822 | Bodily Fluids: Peritoneal | Surgery General | SHV-11(b); TEM-1(b); KPC-3; |
| 19 | Middle East | Israel | 869311 | Respiratory: Bronchial brushing | Medicine ICU | SHV-11(b); KPC-3; |
| 20 | Europe | Romania | 869918 | Respiratory: Sputum | General Unspecified ICU | SHV-11(b); TEM-1(b); KPC-2; |
| 21 | Europe | Russia | 874316 | Respiratory: Sputum | General Unspecified ICU | SHV-11(b); CTX-M-55; OXA-48(c) |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 22 | Europe | Russia | 874329 | Respiratory: Other | General Unspecified ICU | |
| 23 | Europe | Russia | 874876 | Respiratory: Sputum | Pediatric ICU | SHV-11(b); TEM-1(b); CTX-M-15; KPC-2; |
| 24 | Europe | Belgium | 875655 | Respiratory: Endotracheal aspirate | General Unspecified ICU | SHV-28(e); TEM-1(b); CTX-M-15; KPC-3; |
| 25 | Europe | Italy | 875926 | Respiratory: Sputum | Medicine General | SHV-11(b); KPC-3; |
| 26 | Europe | Italy | 875928 | Respiratory: Endotracheal aspirate | Medicine ICU | SHV-2(e); |
| 27 | Europe | Italy | 875931 | Respiratory: Bronchoalveolar lavage | Medicine General | SHV-11(b); KPC-3; |
| 28 | Latin America | Brazil | 900678 | Respiratory: Endotracheal aspirate | Medicine ICU | SHV-OSBL(u); TEM-OSBL(u); VEB-2; KPC-2; |
| 29 | Europe | Italy | 918904 | Respiratory: Bronchoalveolar lavage | Medicine General | SHV-OSBL(u); TEM-OSBL(u); KPC-3; |
| 30 | Europe | Greece | 921185 | Respiratory: Sputum | Medicine General | SHV-12(e); KPC-2; |
| 31 | Europe | Turkey | 926871 | Respiratory: Endotracheal aspirate | General Unspecified ICU | SHV-OSBL(u); CTX-M-15; OXA-48(c) |
| 32 | Europe | Turkey | 926901 | Respiratory: Sputum | Medicine General | SHV-OSBL(u); CTX-M-15; OXA-48(c) |
| 33 | Europe | Greece | 927850 | Respiratory: Endotracheal aspirate | Medicine ICU | SHV-OSBL(u); OXA-48(c) |
| 34 | Europe | Greece | 927897 | Respiratory: Endotracheal aspirate | General Unspecified ICU | SHV-OSBL(u); TEM-OSBL(u); CTX-M-2; |
| 35 | Europe | Greece | 927898 | Respiratory: Endotracheal aspirate | General Unspecified ICU | SHV-OSBL(u); KPC-2; |
| 36 | Europe | Greece | 927915 | Respiratory: Endotracheal aspirate | General Unspecified ICU | |
| 37 | Europe | Greece | 927952 | Respiratory: Endotracheal aspirate | General Unspecified ICU | |
| 38 | Europe | Greece | 927963 | Respiratory: Endotracheal aspirate | General Unspecified ICU | |
| 39 | Europe | Greece | 927964 | Respiratory: Endotracheal aspirate | General Unspecified ICU | TEM-OSBL(u); CTX-M-15; CTX-M-27; NDM-1; |
| 40 | Middle East | Israel | 937433 | Respiratory: Sputum | Medicine General | SHV-OSBL(u); KPC-3; |
| 41 | Europe | Romania | 938940 | INT: Wound | Medicine General | SHV-OSBL(u); TEM-OSBL(u); KPC-2; |
| 42 | Europe | Romania | 939003 | Respiratory: Endotracheal aspirate | Medicine ICU | SHV-OSBL(u); TEM-OSBL(u); KPC-2; |
| 43 | Latin America | Argentina | 939866 | Respiratory: Lungs | Surgery ICU | SHV-OSBL(u); TEM-OSBL(u); CTX-M-15; OXA-48(c) |
| 44 | Latin America | Argentina | 939929 | Respiratory: Bronchial brushing | General Unspecified ICU | SHV-12(e); TEM-OSBL(u); KPC-2; |
| 45 | Latin America | Argentina | 939943 | Respiratory: Bronchial brushing | General Unspecified ICU | SHV-12(e); TEM-OSBL(u); KPC-2; |
| 46 | Europe | Italy | 946889 | Respiratory: Bronchoalveolar lavage | General Unspecified ICU | SHV-OSBL(u); TEM-OSBL(u); KPC-2; |
| 47 | Europe | Italy | 946897 | Respiratory: Bronchial brushing | Medicine General | SHV-OSBL(u); KPC-3; |
| 48 | Europe | Italy | 946900 | Respiratory: Bronchial brushing | Surgery General | SHV-OSBL(u); TEM-OSBL(u); KPC-3; |
| 49 | Europe | Italy | 947475 | Respiratory: Lungs | Medicine General | SHV-OSBL(u); TEM-OSBL(u); CTX-M-65; KPC-2; |
| 50 | Latin America | Colombia | 960228 | INT: Wound | Medicine General | SHV-OSBL(u); TEM-OSBL(u); KPC-2; |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 51 | Latin America | Colombia | 960249 | Respiratory: Other | Medicine General | SHV-OSBL(u); KPC-2; |
| 52 | North America | United States | 961842 | Respiratory: Bronchoalveolar lavage | Medicine ICU | SHV-12(e); TEM-OSBL(u); CTX-M-65; KPC-2; |
| 53 | Africa | South Africa | 963278 | Respiratory: Endotracheal aspirate | Medicine ICU | SHV-12(e); KPC-2; |
| 54 | South Pacific | Philippines | 966426 | Respiratory: Sputum | Medicine General | SHV-12(e); TEM-OSBL(u); CTX-M-15; NDM-7; |
| 55 | Europe | Italy | 971222 | Respiratory: Bronchial brushing | Medicine General | SHV-OSBL(u); TEM-OSBL(u); KPC-3; |
| 56 | Europe | Russia | 975977 | Respiratory: Endotracheal aspirate | Surgery ICU | SHV-12(e); TEM-OSBL(u); KPC-2; |
| 57 | Europe | Russia | 976037 | Respiratory: Endotracheal aspirate | Surgery ICU | SHV-OSBL(u); TEM-OSBL(u); CTX-M-15; OXA-244(c) |
| 58 | Europe | Russia | 976078 | Respiratory: Endotracheal aspirate | Surgery ICU | SHV-12(e); TEM-OSBL(u); KPC-2; |
| 59 | Latin America | Argentina | 977128 | INT: Wound | Medicine General | SHV-12(e); TEM-OSBL(u); KPC-2; |
| 60 | Latin America | Argentina | 977314 | Bodily Fluids: Peritoneal | Medicine General | SHV-12(e); KPC-2; |
| 61 | North America | United States | 977778 | GI: Abscess | Medicine General | SHV-OSBL(u); KPC-3; |
| 62 | North America | United States | 978960 | INT: Wound | Medicine General | SHV-12(e); TEM-OSBL(u); KPC-3; |
| 63 | North America | United States | 978971 | Respiratory: Sputum | Medicine ICU | SHV-OSBL(u); TEM-OSBL(u); KPC-3; |
| 64 | North America | United States | 979049 | Respiratory: Sputum | Medicine General | CTX-M-12; KPC-2; |
| 65 | North America | United States | 979288 | Respiratory: Sputum | Surgery General | SHV-OSBL(u); KPC-3; |
| 66 | North America | United States | 979290 | Respiratory: Sputum | Medicine ICU | SHV-12(e); TEM-OSBL(u); KPC-3; |
| 67 | Latin America | Brazil | 990976 | Bodily Fluids: Peritoneal | None Given | SHV-OSBL(u); CTX-M-2; KPC-2; |
| 68 | Latin America | Brazil | 991499 | Respiratory: Endotracheal aspirate | Medicine ICU | SHV-OSBL(u); TEM-OSBL(u); CTX-M-15; NDM-1; |
| 69 | Middle East | Israel | 994039 | Respiratory: Endotracheal aspirate | Medicine General | SHV-OSBL(u); CTX-M-15; NDM-1; |
| 70 | Asia | China | 995976 | Respiratory: Sputum | Pediatric ICU | SHV-OSBL(u); TEM-OSBL(u); CTX-M-15; OXA-48(c) |
| 71 | Europe | Greece | 1013421 | Respiratory: Sputum | Medicine General | |
| 72 | Europe | Greece | 1013442 | INT: Skin Ulcer | General Unspecified ICU | SHV-OSBL(u); CTX-M-15; OXA-48(c) |
| 73 | Africa | Nigeria | 1043242 | INT: Wound | Medicine General | SHV-55(e); TEM-OSBL(u); CTX-M-15; NDM-1; |
| 74 | Europe | Russia | 1049163 | Respiratory: Endotracheal aspirate | Medicine ICU | SHV-OSBL(u); TEM-OSBL(u); CTX-M-15; |
| 75 | Europe | Russia | 1049391 | Respiratory: Bronchoalveolar lavage | Surgery ICU | SHV-12(e); TEM-OSBL(u); KPC-2; |
| 76 | Europe | Russia | 1049400 | Respiratory: Bronchoalveolar lavage | Surgery ICU | SHV-OSBL(u); TEM-OSBL(u); CTX-M-15; |
| 77 | Europe | Russia | 1049474 | Respiratory: Bronchoalveolar lavage | Surgery General | SHV-12(e); TEM-OSBL(u); KPC-2; |
| 78 | Europe | Russia | 1049592 | Respiratory: Sputum | Medicine ICU | SHV-OSBL(u); CTX-M-3; OXA-48(c) |
| 79 | Europe | Spain | 1073956 | Respiratory: Bronchial brushing | Medicine ICU | SHV-OSBL(u); TEM-OSBL(u); KPC-3; |
| 80 | South Pacific | Philippines | 1079540 | CVS: Blood | Pediatric ICU | SHV-12(e); TEM-OSBL(u); KPC-3; |
| 81 | South Pacific | Philippines | 1079544 | Respiratory: Endotracheal aspirate | Medicine ICU | TEM-OSBL(u); KPC-3; |
| 82 | Europe | Italy | 1081144 | Respiratory: Sputum | Medicine ICU | |
| 83 | Europe | Greece | 1081949 | CVS: Blood | Medicine General | |
| 84 | Europe | Greece | 1081956 | CVS: Blood | Surgery General | SHV-OSBL(u); TEM-OSBL(u); KPC-3; |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 85 | Europe | Greece | 1081997 | Respiratory: Bronchoalveolar lavage | General Unspecified ICU | SHV-OSBL(u); TEM-OSBL(u); KPC-3; |
| 86 | Europe | Greece | 1082051 | Respiratory: Bronchoalveolar lavage | General Unspecified ICU | SHV-12(e); TEM-OSBL(u); KPC-2; |
| 87 | Europe | Greece | 1082058 | CVS: Blood | Other | |
| 88 | Europe | Greece | 1082074 | CVS: Blood | General Unspecified ICU | |
| 89 | Europe | Greece | 1082098 | CVS: Blood | General Unspecified ICU | |
| 90 | Asia | Korea, South | 1085601 | Respiratory: Sputum | Medicine General | SHV-12(e); TEM-OSBL(u); KPC-2; |
| 91 | Europe | Hungary | 1090072 | Bodily Fluids: Peritoneal | Surgery General | |
| 92 | Africa | South Africa | 1093894 | Bodily Fluids: Peritoneal | General Unspecified ICU | SHV-OSBL(u); CTX-M-15; |
| 93 | Latin America | Argentina | 1093960 | Respiratory: Bronchoalveolar lavage | Medicine ICU | SHV-OSBL(u); CTX-M-15; KPC-2; |
| 94 | Latin America | Argentina | 1093976 | Respiratory: Bronchoalveolar lavage | Medicine ICU | SHV-OSBL(u); KPC-2; |
| 95 | Latin America | Argentina | 1093980 | Bodily Fluids: Peritoneal | Emergency Room | |
| 96 | North America | United States | 1105534 | Respiratory: Bronchoalveolar lavage | Medicine General | SHV-OSBL(u); TEM-OSBL(u); KPC-2; |
| 97 | North America | United States | 1105547 | Respiratory: Bronchoalveolar lavage | Medicine General | |
| 98 | Latin America | Colombia | 1109216 | Bodily Fluids: Peritoneal | Surgery General | SHV-OSBL(u); KPC-3; |
| 99 | Europe | Czech Republic | 1120042 | Respiratory: Sputum | Medicine ICU | SHV-OSBL(u); TEM-OSBL(u); CTX-M-15; |
| 100 | Europe | Austria | 1127552 | INT: Wound | Medicine ICU | |
| 101 | Europe | Italy | 1137983 | GI: Abscess | Surgery General | SHV-OSBL(u); |
| 102 | Europe | Italy | 1137984 | Respiratory: Bronchial brushing | Medicine ICU | SHV-12(e); TEM-OSBL(u); KPC-2; |
| 103 | Europe | Italy | 1137991 | Bodily Fluids: Peritoneal | Surgery General | |
| 104 | Latin America | Chile | 969740 | INT: Wound | Surgery General | SHV-OSBL(u); TEM-OSBL(u); CTX-M-15; |
| 105 | Latin America | Chile | 969743 | Respiratory: Endotracheal aspirate | Medicine General | SHV-OSBL(u); TEM-OSBL(u); CTX-M-15; CTX-M-2; |
| 106 | Latin America | Argentina | 977113 | Respiratory: Endotracheal aspirate | Medicine ICU | |
| 107 | North America | United States | 1094435 | INT: Wound | Medicine General | |
| 108 | North America | United States | 1147894 | Respiratory: Endotracheal aspirate | Medicine ICU | |
| 109 | Europe | Italy | 947566 | GU: Urine | Medicine General | SHV-12(e); VIM-New V ariant; |
| 110 | Latin America | Argentina | 847700 | GU: Urine | Medicine General | TEM-1(b); KPC-2; |
| 111 | Latin America | Argentina | 847708 | GU: Urine | Medicine ICU | SHV-11(b); TEM-1(b); KPC-2; |
| 112 | Europe | Greece | 848827 | GU: Urine | Emergency Room | SHV-11(b); TEM-1(b); KPC-2; |
| 113 | Europe | Greece | 848828 | GU: Urine | General Unspecified ICU | SHV-11(b); TEM-1(b); KPC-2; |
| 114 | Europe | Greece | 848829 | GU: Urine | Other | SHV-11(b); KPC-2; |
| 115 | Europe | Greece | 848843 | GU: Urine | Medicine General | SHV-11(b); TEM-1(b); KPC-2; |
| 116 | Middle East | Israel | 869317 | GU: Urine | Other | SHV-11(b); TEM-1(b); KPC-3; |
| 117 | North America | United States | 872020 | GU: Urine | Medicine ICU | SHV-28(e); TEM-1(b); CTX-M-15; KPC-2; |
| 118 | Europe | Turkey | 889939 | GU: Urine | Surgery ICU | SHV-1(b); OXA-48(c) |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 119 | North America | United States | 897067 | GU: Urine | Surgery ICU | SHV-11(b); KPC-3; |
| 120 | Latin America | Brazil | 900687 | GU: Urine | Surgery General | TEM-1(b); CTX-M-14; KPC-2; |
| 121 | Latin America | Brazil | 900765 | GU: Urine | Emergency Room | SHV-11(b); TEM-1(b); CTX-M-14; KPC-2; |
| 122 | Europe | Greece | 921177 | GU: Ureter | Medicine General | SHV-12(e); TEM-OSBL(u); CMY-13; KPC-2; VIM-1; |
| 123 | Europe | Greece | 927901 | GU: Urine | Medicine General | SHV-12(e); |
| 124 | Europe | Greece | 927949 | GU: Urine | Medicine General | SHV-12(e); TEM-OSBL(u); KPC-2; |
| 125 | Europe | Greece | 927981 | GU: Urine | Medicine General | SHV-12(e); TEM-OSBL(u); KPC-2; |
| 126 | Europe | Greece | 928020 | GU: Urine | Pediatric General | SHV-12(e); TEM-OSBL(u); KPC-2; |
| 127 | Europe | Russia | 976026 | GU: Urine | Surgery ICU | SHV-OSBL(u); TEM-OSBL(u); CTX-M-15; OXA-244(c) |
| 128 | North America | United States | 978959 | GU: Urine | Medicine General | SHV-OSBL(u); TEM-OSBL(u); KPC-3; |
| 129 | Europe | Belgium | 979620 | GU: Urine | Medicine General | SHV-OSBL(u); NDM-1; OXA-232(c) |
| 130 | Latin America | Brazil | 990975 | GU: Urine | Medicine General | SHV-OSBL(u); TEM-OSBL(u); CTX-M-15; KPC-2; |
| 131 | Latin America | Brazil | 991020 | GU: Urine | Medicine ICU | SHV-OSBL(u); TEM-OSBL(u); KPC-2; |
| 132 | Latin America | Brazil | 991969 | GU: Urine | Medicine ICU | SHV-OSBL(u); KPC-2; |
| 133 | Latin America | Colombia | 960227 | GU: Urine | Medicine General | SHV-OSBL(u); TEM-OSBL(u); KPC-3; |
| 134 | South Pacific | Australia | 1035778 | GU: Urine | Surgery General | SHV-OSBL(u); TEM-OSBL(u); IMP-4; |
| 135 | Europe | Russia | 1048991 | GU: Urine | Surgery General | SHV-OSBL(u); TEM-OSBL(u); CTX-M-15; OXA-48(c) |
| 136 | Latin America | Colombia | 1109206 | GU: Urine | Other | |
| 137 | Latin America | Mexico | 1138246 | GU: Urine | Medicine General | |
| 138 | Africa | Nigeria | 1143069 | GU: Urine | Emergency Room | |
| 139 | Africa | Nigeria | 1143099 | GU: Urine | Medicine General | |
| 140 | Middle East | Kuwait | 1143576 | GU: Urine | Emergency Room | |
| 141 | South Pacific | Philippines | 850792 | Bodily Fluids: Abcess/Pus | Other | SHV-1(b); TEM-1(b); CTX-M-15; |
| 142 | South Pacific | Philippines | 845353 | Respiratory: Sputum | Other | SHV-1(b); CTX-M-15; |
| 143 | South Pacific | Philippines | 845587 | Respiratory: Sputum | Medicine General | SHV-31(e); |
| 144 | Europe | Italy | 848597 | Respiratory: Sputum | Surgery ICU | SHV-12(e); |
| 145 | Europe | Czech Republic | 851661 | Respiratory: Sputum | Medicine ICU | SHV-5(e); |
| 146 | North America | United States | 851698 | GI: Stomach | Surgery General | SHV-11(b); DHA-1; |
| 147 | North America | United States | 851702 | GI: Small Colon | Surgery General | SHV-12(e); TEM-1(b); |
| 148 | Latin America | Mexico | 854739 | Respiratory: Other | Pediatric General | SHV-11(b); TEM-1(b); CTX-M-15; DHA-1; |
| 149 | South Pacific | Philippines | 855930 | Respiratory: Endotracheal aspirate | Surgery General | SHV-11(b); TEM-1(b); CTX-M-15; |
| 150 | Latin America | Venezuela | 858492 | Respiratory: Sputum | Emergency Room | SHV-5(e); CTX-M-3; |
| 151 | Latin America | Venezuela | 866356 | Bodily Fluids: Peritoneal | None Given | SHV-5(e); CTX-M-15; |
| 152 | Middle East | Israel | 869315 | GU: Urethra | Medicine General | SHV-11(b); TEM-1(b); CTX-M-15; |
| 153 | Europe | Russia | 870216 | Respiratory: Sputum | Medicine General | SHV-11(b); TEM-1(b); CTX-M-14; |
| 154 | Europe | Russia | 870245 | Respiratory: Sputum | Medicine General | SHV-11(b); TEM-1(b); CTX-M-15; |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 155 | Europe | Russia | 870258 | INT: Wound | Surgery General | SHV-11(b); CTX-M-55; |
| 156 | Asia | China | 871354 | Respiratory: Sputum | Other | SHV-11(b); TEM-1(b); CTX-M-15; |
| 157 | North America | United States | 873464 | Respiratory: Endotracheal aspirate | Medicine General | SHV-1(b); TEM-1(b); CTX-M-15; |
| 158 | Europe | Russia | 874317 | Respiratory: Sputum | General Unspecified ICU | SHV-11(b); TEM-1(b); CTX-M-28; |
| 159 | Europe | Russia | 874882 | Respiratory: Bronchoalveolar lavage | Medicine ICU | SHV-1(b); TEM-1(b); CTX-M-15; |
| 160 | Europe | Russia | 874899 | Respiratory: Bronchoalveolar lavage | Surgery General | SHV-11(b); CTX-M-15; |
| 161 | Europe | Russia | 874907 | Respiratory: Bronchoalveolar lavage | Medicine General | SHV-11(b); TEM-1(b); CTX-M-15; CMY-2; |
| 162 | Europe | Russia | 874921 | Respiratory: Bronchoalveolar lavage | Medicine ICU | SHV-12(e); |
| 163 | Africa | South Africa | 884275 | Respiratory: Endotracheal aspirate | Pediatric ICU | SHV-11(b); TEM-1(b); CTX-M-15; CTX-M-2; |
| 164 | Africa | South Africa | 884335 | Respiratory: Sputum | Medicine General | SHV-OSBL(u); TEM-OSBL(u); CTX-M-15; |
| 165 | Latin America | Brazil | 900685 | Respiratory: Endotracheal aspirate | Medicine ICU | SHV-OSBL(u); TEM-12(e); CTX-M-15; |
| 166 | Europe | Greece | 921041 | INT: Wound | Medicine General | SHV-12(e); |
| 167 | Europe | France | 921564 | Respiratory: Endotracheal aspirate | Surgery ICU | SHV-OSBL(u); TEM-OSBL(u); CTX-M-15; |
| 168 | North America | United States | 928335 | Respiratory: Bronchoalveolar lavage | Medicine ICU | SHV-OSBL(u); TEM-OSBL(u); CTX-M-15; |
| 169 | North America | United States | 928336 | Respiratory: Bronchoalveolar lavage | Medicine ICU | SHV-OSBL(u); TEM-OSBL(u); CTX-M-15; |
| 170 | Europe | Portugal | 938166 | Respiratory: Sputum | Surgery General | SHV-OSBL(u); TEM-OSBL(u); CTX-M-15; OXA-48(c) |
| 171 | Europe | Portugal | 938170 | Respiratory: Endotracheal aspirate | Surgery ICU | SHV-12(e); TEM-OSBL(u); CTX-M-14; |
| 172 | Europe | Romania | 938937 | INT: Wound | Medicine General | SHV-OSBL(u); TEM-OSBL(u); CTX-M-15; |
| 173 | Asia | Taiwan | 949399 | Respiratory: Other | Medicine ICU | SHV-12(e); |
| 174 | Latin America | Mexico | 950099 | Respiratory: Sputum | Medicine General | SHV-12(e); |
| 175 | Latin America | Mexico | 950104 | Respiratory: Endotracheal aspirate | Surgery General | SHV-12(e); |
| 176 | South Pacific | Philippines | 957823 | Respiratory: Endotracheal aspirate | Medicine ICU | SHV-OSBL(u); TEM-OSBL(u); CTX-M-15; |
| 177 | South Pacific | Philippines | 957905 | Respiratory: Endotracheal aspirate | Medicine General | SHV-12(e); TEM-OSBL(u); CTX-M-15; DHA-1; |
| 178 | South Pacific | Philippines | 957920 | Respiratory: Endotracheal aspirate | Medicine ICU | SHV-OSBL(u); TEM-OSBL(u); CTX-M-15; |
| 179 | South Pacific | Philippines | 957921 | Respiratory: Sputum | Medicine General | SHV-OSBL(u); TEM-OSBL(u); CTX-M-15; |
| 180 | Asia | Taiwan | 958118 | Respiratory: Bronchoalveolar lavage | Medicine ICU | SHV-OSBL(u); TEM-OSBL(u); CTX-M-15; |
| 181 | Europe | Russia | 975237 | Respiratory: Bronchoalveolar lavage | Surgery ICU | SHV-OSBL(u); TEM-OSBL(u); CTX-M-15; |
| 182 | Europe | Russia | 975238 | Respiratory: Bronchoalveolar lavage | Pediatric ICU | SHV-5(e); CTX-M-15; |
| 183 | Europe | Russia | 975905 | Respiratory: Bronchoalveolar lavage | Surgery ICU | SHV-OSBL(u); TEM-OSBL(u); CTX-M-15; DHA-1; |
| 184 | Europe | Russia | 975906 | Respiratory: Bronchoalveolar lavage | Surgery ICU | SHV-12(e); |
| 185 | Europe | Russia | 977430 | GU: Urine | Surgery General | SHV-OSBL(u); TEM-OSBL(u); CTX-M-15; |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 186 | Europe | Poland | 985195 | Respiratory: Sputum | Medicine General | SHV-12(e); TEM-OSBL(u); |
| 187 | Asia | Korea, South | 990759 | Respiratory: Sputum | Medicine General | SHV-OSBL(u); TEM-OSBL(u); CTX-M-15; |
| 188 | Asia | Korea, South | 990778 | Respiratory: Sputum | Medicine ICU | SHV-OSBL(u); |
| 189 | Asia | Malaysia | 993593 | GU: Urine | Pediatric General | SHV-OSBL(u); TEM-OSBL(u); CTX-M-15; |
| 190 | Middle East | Israel | 1007663 | Respiratory: Endotracheal aspirate | Medicine General | SHV-OSBL(u); TEM-OSBL(u); CTX-M-15; |
| 191 | Middle East | Israel | 1007677 | Bodily Fluids: Peritoneal | Surgery General | SHV-OSBL(u); TEM-OSBL(u); CTX-M-15; |
| 192 | Europe | Russia | 1049171 | Respiratory: Endotracheal aspirate | Medicine ICU | SHV-OSBL(u); TEM-OSBL(u); CTX-M-15; |
| 193 | Europe | Russia | 1049223 | Respiratory: Bronchoalveolar lavage | Surgery General | SHV-OSBL(u); CTX-M-15; |
| 194 | Europe | Russia | 1049540 | Respiratory: Sputum | Medicine General | |
| 195 | Europe | Russia | 1049545 | Respiratory: Bronchoalveolar lavage | Surgery General | |
| 196 | Europe | Russia | 1049870 | Respiratory: Bronchoalveolar lavage | Medicine General | SHV-2A(e); TEM-1(b); CTX-M-15; |
| 197 | Latin America | Venezuela | 1073801 | Respiratory: Endotracheal aspirate | Medicine ICU | SHV-36(u); |
| 198 | Asia | Korea, South | 1085618 | Respiratory: Sputum | Medicine General | CTX-M-15; |
| 199 | North America | United States | 873460 | Respiratory: Sputum | Medicine General | SHV-11(b); CTX-M-15; |
| 200 | Europe | Russia | 874383 | Respiratory: Endotracheal aspirate | General Unspecified ICU | SHV-28(e); TEM-1(b); CTX-M-15; DHA-1; |
| 201 | Europe | Russia | 875080 | Respiratory: Sputum | Surgery ICU | SHV-12(e); TEM-OSBL(u); |
| 202 | North America | United States | 882753 | INT: Wound | Medicine General | SHV-OSBL(u); TEM-OSBL(u); CTX-M-15; |
| 203 | Asia | Taiwan | 894334 | Respiratory: Other | Medicine ICU | SHV-12(e); |
| 204 | Europe | Czech Republic | 923859 | Respiratory: Endotracheal aspirate | Surgery ICU | SHV-12(e); |
| 205 | Europe | Portugal | 938167 | Bodily Fluids: Peritoneal | Emergency Room | SHV-OSBL(u); TEM-OSBL(u); CTX-M-15; |
| 206 | Latin America | Mexico | 950100 | Respiratory: Bronchoalveolar lavage | Medicine ICU | SHV-OSBL(u); CTX-M-14; |
| 207 | Latin America | Mexico | 950102 | Respiratory: Endotracheal aspirate | Surgery ICU | SHV-OSBL(u); TEM-OSBL(u); CTX-M-15; |
| 208 | Latin America | Mexico | 950107 | Respiratory: Endotracheal aspirate | Medicine ICU | SHV-OSBL(u); TEM-OSBL(u); CTX-M-15; |
| 209 | Latin America | Mexico | 951241 | Respiratory: Bronchial brushing | Pediatric ICU | SHV-OSBL(u); TEM-OSBL(u); CTX-M-15; |
| 210 | South Pacific | Philippines | 957918 | Respiratory: Sputum | Medicine ICU | |
| 211 | South Pacific | Philippines | 966430 | Respiratory: Sputum | Medicine General | |
| 212 | Europe | Russia | 975841 | Respiratory: Sputum | Surgery ICU | SHV-OSBL(u); TEM-OSBL(u); CTX-M-15; |
| 213 | Latin America | Mexico | 979791 | Respiratory: Bronchial brushing | Surgery ICU | SHV-OSBL(u); TEM-OSBL(u); CTX-M-15; |
| 214 | North America | United States | 981436 | Respiratory: Endotracheal aspirate | Medicine ICU | SHV-OSBL(u); TEM-OSBL(u); CTX-M-15; |
| 215 | Europe | Russia | 1049468 | Respiratory: Bronchoalveolar lavage | Medicine General | SHV-110(u); CTX-M-15; |
| 216 | Europe | Russia | 1050019 | INT: Wound | Surgery ICU | SHV-OSBL(u); TEM-OSBL(u); CTX-M-15; |
| 217 | Europe | Russia | 1050029 | INT: Wound | General Unspecified ICU | |
| 218 | Europe | Russia | 1050038 | INT: Wound | Medicine General | |
| 219 | Europe | Russia | 1050052 | Respiratory: Bronchoalveolar lavage | Medicine ICU | |

TABLE 8-continued

Summary of clinical *Klebsiella* strains to which anti-O2 mAbs bind.

| | Region | Country | IHMA Number | Body Location | Facility Name | Molecular Summary |
|---|---|---|---|---|---|---|
| 220 | North America | United States | 1073361 | Respiratory: Sputum | Medicine General | TEM-1(b); CTX-M-15; |
| 221 | Europe | Spain | 1073953 | Respiratory: Sputum | Medicine General | SHV-11(b); CTX-M-15; |
| 222 | Europe | United Kingdom | 1081745 | Respiratory: Endotracheal aspirate | Medicine ICU | SHV-11(b); TEM-1(b); CTX-M-15; |
| 223 | Latin America | Mexico | 950095 | Respiratory: Endotracheal aspirate | Surgery ICU | SHV-12(e); DHA-1; |
| 224 | Europe | Russia | 870321 | Respiratory: Other | Surgery General | SHV-OSBL(u); |
| 225 | Europe | Russia | 1050017 | INT: Wound | Surgery ICU | |
| 226 | Europe | Russia | 1050053 | Respiratory: Bronchoalveolar lavage | Medicine ICU | |
| 227 | Europe | Greece | 848879 | Respiratory: Sputum | General Unspecified ICU | |
| 228 | North America | United States | 855499 | INT: Wound | Outpatient | |
| 229 | Latin America | Colombia | 860723 | GI: Abscess | General Unspecified ICU | |
| 230 | Asia | Taiwan | 862260 | Respiratory: Sputum | Surgery General | |
| 231 | North America | United States | 863922 | GI: Gall Bladder | Other | |
| 232 | Latin America | Venezuela | 866365 | GU: Urine | Medicine ICU | |
| 233 | Europe | Austria | 896420 | INT: Wound | Surgery ICU | |
| 234 | North America | United States | 920265 | GI: Stomach | Medicine ICU | |
| 235 | Asia | Thailand | 949027 | Respiratory: Sputum | Medicine General | |
| 236 | Latin America | Brazil | 991831 | GU: Urine | Emergency Room | |
| 237 | Asia | Malaysia | 996710 | GI: Abscess | Surgery General | |
| 238 | North America | United States | 1072091 | GU: Urine | Medicine ICU | |
| 239 | Europe | United Kingdom | 1087502 | Respiratory: Sputum | Surgery General | |
| 240 | Africa | South Africa | 1088186 | INT: Wound | Medicine ICU | |
| 241 | Europe | Belgium | 1089861 | GU: Urine | Medicine General | |
| 242 | Europe | Czech Republic | 1097531 | Respiratory: Endotracheal aspirate | Medicine ICU | |
| 243 | Europe | Spain | 1098542 | INT: Wound | Medicine General | |
| 244 | Asia | Japan | 1132015 | Respiratory: Sputum | Medicine General | |
| 245 | Europe | France | 1149311 | Bodily Fluids: Peritoneal | Medicine ICU | |
| 246 | Asia | Hong Kong | 1151042 | GU: Urine | Medicine General | |
| 247 | South Pacific | Philippines | 845578 | INT: Wound | Medicine General | |
| 248 | Europe | Portugal | 845918 | INT: Wound | Medicine General | |
| 249 | Latin America | Chile | 847189 | GI: Abscess | Surgery ICU | |
| 250 | Latin America | Argentina | 847386 | GI: Abscess | Surgery General | |
| 251 | North America | United States | 857611 | Respiratory: Sputum | Surgery ICU | |
| 252 | Latin America | Colombia | 860724 | Respiratory: Sputum | Medicine General | |
| 253 | Latin America | Venezuela | 866345 | Respiratory: Sputum | Medicine General | |
| 254 | Latin America | Argentina | 867249 | Respiratory: Endotracheal aspirate | Surgery ICU | |

The isolates in rows 1-140 of Table 8 are *Klebsiella pneumoniae* carbapenamase (KPC) strains. The isolates in rows 141-226 of Table 8 are extended spectrum beta lactamase (ESBL) strains, and the isolates in rows 227-254 of Table 8 are antibiotic-susceptible strains.

These results demonstrate that anti-O2 mAbs bind not only to a large and diverse group of clinical strains, but also to antibiotic resistant clinically relevant strains. These results suggest that anti-O2 mAbs can be useful as a therapeutic and/or diagnostic as described herein, for example, for one or more of the *Klebsiella* strains disclosed in Table 8.

Example 14: Anti-O2 Antigen Antibodies Bind to O2 *Klebsiella* Strains Regardless of gml Gene Expression Monoclonal antibodies that recognized Gal III structure have been reported to bind to gml+*Klebsiella* ST258 strains. We obtained whole genome sequences from a number of O2 *Klebsiella* clinical isolates and performed experiments to (i) whether these strains express the gml gene; and (ii) whether anti-O2 mAbs bind to these strains by fluorescence activated cell sorting (FACS) or western blot analysis. In addition, we analyzed multi locus sequence type (MLST) and gml locus based on whole genome sequences. Table 9 lists FACS binding, MLST, and gml expression data of 31 O2 *Klebsiella* clinical isolates.

TABLE 9

Anti-O2 monoclonal antibodies binding to gml+ and gml− Klebsiella clinical isolates.

| | KPN42 | KPN70 | KPN179 | MLST | gml | comments |
|---|---|---|---|---|---|---|
| ARC2698 | + | + | + | 258 | + | |
| ARC2708 | + | + | + | 258 | + | |
| ARC2712 | + | + | + | 258 | + | |
| ARC2929 | + | + | + | 258 | + | |
| ARC2945 | + | + | + | 258 | + | |
| ARC3516 | + | + | + | 45 | | |
| ARC3797 | + | + | + | 147 | | |
| ARC4771 | + | + | + | 45 | | |
| ARC4773 | +/− | +/− | +/− | 45 | | KPN42+ by Western |
| ARC4778 | + | + | + | 70 | + | |
| ARC4780 | + | + | + | 11 | + | |
| ARC4784 | + | + | + | 218 | + | |
| ARC5109 | + | + | + | 258 | + | |
| ARC5113 | + | + | + | 1728 | | KPN42+ by Western |
| ARC5115 | + | + | + | 34 | | |
| ARC5116 | + | + | + | 258 | + | |
| ARC5117 | + | + | + | 258 | + | |
| ARC5121 | + | ++ | + | 258 | + | |
| ARC5372 | + | + | + | 258 | + | KPN42+ by Western |
| ARC5411 | + | + | + | 258 | + | |
| ARC5449 | + | + | + | 11* | | KPN42+ by Western |
| ARC6084 | + | + | + | 17 | + | KPN42+ by Western |
| ARC6086 | + | + | + | 11 | + | |
| ARC6093 | + | + | + | 11 | | |
| ARC6095 | + | + | + | 258 | + | KPN42+ by Western |
| ARC6099 | + | + | + | 437* | | |
| ARC6100 | + | + | + | 340 | | |
| ARC6102 | + | + | + | 20 | + | KPN42+ by Western |
| ARC6106 | + | + | + | 641 | | |

TABLE 9-continued

Anti-O2 monoclonal antibodies binding to gml+ and gml− Klebsiella clinical isolates.

| | KPN42 | KPN70 | KPN179 | MLST | gml | comments |
|---|---|---|---|---|---|---|
| ARC6114 | + | + | + | 45 | | |
| ARC6118 | + | + | + | 512 | + | |

As shown in Table 9, multiple ST types, including ST258, were present in this collection. Twelve of the non-ST258 strains did not express the gml gene. KPN42 bound to 92% (11/12) gml− and 100% (19/19) gml+ *Klebsiella* strains. These data suggest that anti-O2 antibodies such as KPN42 bind to O2 antigen, but do not bind to a Gal III epitope. Thus, such O2 antibodies confer broader coverage against O2 strains than Gal III-binding antibodies.

Example 15: KPS44 Sequence Optimization

In order to reduce sequence liability for mAb development, a tryptophan in the heavy chain CDR3 of KPS44 was exchanged with a phenylalanine (see heavy chain of KPS44-v2017, SEQ ID NO: 202, also known as KPS44-v2017-W108F-VH). Additionally, a tryptophan in the light chain CDR1 of KPS44 was exchanged with a phenylalanine, and an aspartic acid and a serine in the light chain CDR3 of KPS44 were substituted for an asparagine and a tyrosine, respectively (see light chain of KPS44v-2017, SEQ ID NO: 203, also known as KPS44-v2017-D37N-S38Y-W107F-VL). Collectively, this resulted in KPS44-v2017 (also known as KPS44-W108F-VH/KPS44-D37N-S38Y-W107F-VL.)

Combinations of the heavy chain CDRs and light chain CDRs of parental KPS44 and KPS44-v2017 were made, resulting in KPS44-D37N-S38Y-W107F-VL (KPS44-G1), KPS44-W108F-VH/KPS44-W107F-VL (KPS44-G2), and KPS44-W108F-VH/KPS44-D37N-S38Y-VL (KPS44-G3).

The foregoing description of the specific embodiments will so fully reveal the general nature of the disclosure that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An isolated antigen binding protein that specifically binds to *Klebsiella pneumoniae* 02 antigen comprising a set of Complementarity-Determining Regions (CDRs): HCDR1, HCDR2, HCDR3, LCDR1, LCDR2, and LCDR3 wherein the HCDR1, HCDR2, HCDR3, LCDR1, LCDR2, and LCDR3 comprise the amino acid sequences of:
SEQ. ID. NOs: 109-112, 113, and 115, respectively.

2. The isolated antigen binding protein of claim 1, wherein said antigen binding protein comprises a VH and VL comprising:
SEQ. ID. NO: 116 and SEQ ID NO:117, respectively.

3. An isolated antigen binding protein that specifically binds to the same epitope in the *Klebsiella pneumoniae* 02 antigen as an antibody comprising a VH and a VL comprising:
SEQ. ID. NO: 116 and SEQ ID NO:117, respectively.

4. An isolated antigen binding protein that competitively inhibits the binding to *Klebsiella pneumoniae* 02 antigen of an antibody comprising a VH and a VL comprising:
SEQ. ID. NO: 116 and SEQ ID NO:117, respectively.

5. The antigen binding protein of claim 1, wherein said antigen binding protein is an antibody or an antigen binding fragment of an antibody.

6. The antigen binding protein of claim 5, wherein the antigen binding fragment comprises a Fab, Fab', F(ab')2, Fd, single chain Fv, disulfide linked Fv, (scFv)2, or scFv-Fc.

7. The antigen binding protein of claim 1, which binds to *Klebsiella* 02 antigen with an affinity constant of about 4.5E-09 or about 7.8E-09M.

8. The antigen binding protein of claim 1, wherein said antigen binding protein neutralizes lipopolysaccharide (LPS); or inhibits, reduces, or prevents nuclear factor kappa B (NF-kB) activation induced by LPS.

9. The antigen binding protein of claim 1, wherein said antigen binding protein inhibits, reduces, or prevents NF-kB activation induced by both *Klebsiella pneumoniae* O1 LPS and *Klebsiella pneumoniae* 02 LPS, or wherein said antigen binding protein inhibits, reduces, or prevents NF-kB activation induced by *Klebsiella pneumoniae* 02 LPS, but does not inhibit, reduce, or prevent NF-kB activation induced by *Klebsiella pneumoniae* O1 LPS.

10. The antigen binding protein of claim 1, wherein the antigen binding protein comprises i) a heavy chain immunoglobulin constant domain selected from the group consisting of:
(a) an IgA constant domain;
(b) an IgD constant domain;
(c) an IgE constant domain;
(d) an IgG1 constant domain;
(e) an IgG2 constant domain;
an IgG3 constant domain;
(g) an IgG4 constant domain; and
(h) an IgM constant domain; and/or
ii) a light chain immunoglobulin constant domain selected from the group consisting of: (a) an Ig kappa constant domain; and
(b) an Ig lambda constant domain.

11. A pharmaceutical composition comprising the antigen binding protein according to claim 1 and a pharmaceutically acceptable excipient.

12. The antigen binding protein of claim 5, wherein said antigen binding protein is a murine, non-human, humanized, or chimeric, antibody or antigen binding fragment of an antibody.

13. A pharmaceutical composition comprising the antigen binding protein according to claim 2, and a pharmaceutically acceptable excipient.

14. The isolated antigen binding protein of claim 1, wherein said antigen binding protein is an IgG1 antibody or an antigen-binding fragment thereof.

15. The isolated antigen binding protein of claim 14, wherein said antigen binding protein is an IgG1 antibody.

16. A pharmaceutical composition comprising the antigen binding protein according to claim 15, and a pharmaceutically acceptable excipient.

17. The isolated antigen binding protein of claim 2, wherein said antigen binding protein is an IgG1 antibody or an antigen-binding fragment thereof.

18. The isolated antigen binding protein of claim 17, wherein said antigen binding protein is an IgG1 antibody.

19. A pharmaceutical composition comprising the antigen binding protein according to claim 18, and a pharmaceutically acceptable excipient.

20. The isolated antigen binding protein of claim 1, wherein the LCDR2 comprises the amino acid sequences of SEQ. ID. NO: 114.

21. A pharmaceutical composition comprising the antigen binding protein according to claim 20, and a pharmaceutically acceptable excipient.

* * * * *